US009895436B2

(12) United States Patent
Long et al.

(10) Patent No.: US 9,895,436 B2
(45) Date of Patent: *Feb. 20, 2018

(54) VACCINES AGAINST HERPES SIMPLEX VIRUS TYPE 2: COMPOSITIONS AND METHODS FOR ELICITING AN IMMUNE RESPONSE

(71) Applicant: Genocea Biosciences, Inc., Cambridge, MA (US)

(72) Inventors: Deborah Long, Monroe, NY (US); Jessica Flechtner, Sudbury, MA (US); Mojca Skoberne, Cambridge, MA (US); George R. Siber, New York, NY (US)

(73) Assignee: Genocea Biosciences, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/077,676

(22) Filed: Nov. 12, 2013

(65) Prior Publication Data

US 2014/0227307 A1   Aug. 14, 2014

Related U.S. Application Data

(63) Continuation of application No. 12/786,425, filed on May 24, 2010, now Pat. No. 8,617,564.

(60) Provisional application No. 61/180,784, filed on May 22, 2009, provisional application No. 61/235,628, filed on Aug. 20, 2009, provisional application No. 61/240,587, filed on Sep. 8, 2009, provisional application No. 61/240,626, filed on Sep. 8, 2009, provisional application No. 61/305,918, filed on Feb. 18, 2010.

(51) Int. Cl.
*A61K 39/245* (2006.01)
*A61K 39/12* (2006.01)
*A61K 39/00* (2006.01)

(52) U.S. Cl.
CPC ............ *A61K 39/245* (2013.01); *A61K 39/12* (2013.01); *A61K 2039/54* (2013.01); *A61K 2039/541* (2013.01); *A61K 2039/55566* (2013.01); *A61K 2039/55577* (2013.01); *C12N 2710/16634* (2013.01)

(58) Field of Classification Search
None
See application file for complete search history.

(56) References Cited

U.S. PATENT DOCUMENTS

| 4,818,694 | A | 4/1989 | Watson et al. |
| 5,149,529 | A | 9/1992 | Ho et al. |
| 5,612,041 | A | 3/1997 | Burke et al. |
| 5,648,079 | A | 7/1997 | Burke et al. |
| 5,654,174 | A | 8/1997 | Cohen et al. |
| 5,656,457 | A | 8/1997 | Parkes et al. |
| 5,679,348 | A | 10/1997 | Nesburn et al. |
| 5,750,114 | A | 5/1998 | Burke et al. |
| 5,763,406 | A | 6/1998 | Pedersen et al. |
| 5,795,579 | A | 8/1998 | Burke et al. |
| 5,807,557 | A | 9/1998 | Dubin |
| 5,851,533 | A | 12/1998 | Berman et al. |
| 5,876,923 | A | 3/1999 | Leopardi et al. |
| 5,955,088 | A | 9/1999 | Ghiasi et al. |
| 5,958,895 | A | 9/1999 | Pachuk et al. |
| 5,962,428 | A | 10/1999 | Carrano et al. |
| 6,027,730 | A | 2/2000 | Francotte et al. |
| 6,156,319 | A * | 12/2000 | Cohen et al. ............ 424/196.11 |
| 6,197,497 | B1 | 3/2001 | Goade et al. |
| 6,207,168 | B1 | 3/2001 | Aurelian |
| 6,352,697 | B1 * | 3/2002 | Cox et al. .................. 424/278.1 |
| 6,413,518 | B1 | 7/2002 | Koelle et al. |
| 6,468,982 | B1 | 10/2002 | Weiner et al. |
| 6,537,555 | B2 | 3/2003 | Hosken et al. |
| 6,635,258 | B2 | 10/2003 | Burke et al. |
| 6,682,892 | B2 | 1/2004 | Noma et al. |
| 6,692,752 | B1 | 2/2004 | Slaoui et al. |
| 6,814,969 | B2 | 11/2004 | Koelle et al. |
| 6,867,000 | B2 | 3/2005 | Mishkin et al. |
| 6,932,972 | B2 | 8/2005 | Stephenne et al. |
| 6,936,255 | B1 | 8/2005 | Wettendorff |
| 6,962,709 | B2 | 11/2005 | Koelle et al. |
| 7,037,509 | B2 | 5/2006 | Koelle et al. |
| 7,078,041 | B2 * | 7/2006 | Koelle ................. A61K 39/245 424/204.1 |
| 7,094,767 | B2 | 8/2006 | Armstrong et al. |
| 7,157,437 | B2 | 1/2007 | Van Nest |
| 7,196,066 | B1 | 3/2007 | Swain et al. |

(Continued)

FOREIGN PATENT DOCUMENTS

EP        0139417 B2 *  2/1985
WO     WO-94/29456 A2   12/1994
(Continued)

OTHER PUBLICATIONS

Genbank CAB06713.1 (May 29, 2002).*
Genbank BAA01264.1 (Nov. 14, 2006).*
Skoberne et al., J. Virol., 2013, 87(7):3930-3942.*
Dolan, A., Human herpesvirus 2, complete genome. NCBI Reference Sequence: NC_001798. Dep. Apr. 3, 2000.
Dolan, A., RS1 [human herpesvirus 2]. NCBI Reference Sequence: NC_044530.1. Dep. Apr. 3, 2000.
Dolan, A., Virion glycoprotein D [Human herpesvirus 2]. NCBI Reference Sequence: NC_044536.1. Dep. Apr. 3, 2000.

(Continued)

*Primary Examiner* — Stacy B Chen
(74) *Attorney, Agent, or Firm* — Choate, Hall & Stewart, LLP; Brenda Herschbach Jarrell; Rolando Medina

(57) ABSTRACT

Herpes Simplex Virus-2 (HSV-2) infection is a major health concern. The present disclosure provides, inter alia, certain highly effective vaccines and immunogenic compositions against HSV-2. The antigens can be used therapeutically or prophylactically.

69 Claims, 6 Drawing Sheets

(56) References Cited

U.S. PATENT DOCUMENTS

| | | |
|---|---|---|
| 7,264,817 B1 | 9/2007 | Berman et al. |
| 7,267,940 B2 | 9/2007 | Chen et al. |
| 7,569,218 B2 | 8/2009 | Weiner et al. |
| 7,628,993 B2 | 12/2009 | Vilalta et al. |
| 7,666,434 B2 | 2/2010 | Koelle et al. |
| 7,744,903 B2 | 6/2010 | Koelle et al. |
| 8,197,824 B2 | 6/2012 | Koelle et al. |
| 8,313,894 B2 | 11/2012 | Flechtner et al. |
| 2002/0058021 A1 | 5/2002 | Audonnet et al. |
| 2003/0017174 A1 | 1/2003 | Burke et al. |
| 2003/0165537 A1 | 9/2003 | Fehler et al. |
| 2003/0165819 A1 | 9/2003 | McGowan et al. |
| 2004/0220076 A1 | 11/2004 | Aurelian et al. |
| 2007/0196389 A1 | 8/2007 | Caligiuri et al. |
| 2008/0145375 A1 | 6/2008 | Bembridge et al. |
| 2008/0299140 A1 | 12/2008 | Georges et al. |
| 2009/0148467 A1 | 6/2009 | Friedman et al. |
| 2010/0203073 A1 | 8/2010 | Koelle |
| 2010/0330112 A1 | 12/2010 | Long et al. |
| 2011/0293664 A1 | 12/2011 | Cohane et al. |
| 2012/0135025 A1 | 5/2012 | Flechtner et al. |
| 2013/0171234 A1 | 7/2013 | Fairman et al. |
| 2013/0337000 A1 | 12/2013 | Long et al. |
| 2014/0328870 A1 | 11/2014 | Long et al. |

FOREIGN PATENT DOCUMENTS

| | | | | |
|---|---|---|---|---|
| WO | WO-95/06055 A1 | 3/1995 | | |
| WO | WO 95/16779 | * 3/1995 | ............. | C12N 15/38 |
| WO | WO-1995/16779 A1 | 6/1995 | | |
| WO | WO-982/0016 A1 | 5/1998 | | |
| WO | WO-00/77043 A2 | 12/2000 | | |
| WO | WO-01/44477 A1 | 6/2001 | | |
| WO | WO-2002/002131 A2 | 1/2002 | | |
| WO | WO-03/020108 A2 | 3/2003 | | |
| WO | WO-2003/086308 A2 | 10/2003 | | |
| WO | WO-2003/099860 A2 | 12/2003 | | |
| WO | WO-2004/009021 A2 | 1/2004 | | |
| WO | WO-2005/028496 A2 | 3/2005 | | |
| WO | WO-2007/106404 A2 | 9/2007 | | |
| WO | WO-2008/011609 A2 | 1/2008 | | |
| WO | WO-2008/027394 A2 | 3/2008 | | |
| WO | WO-2008/030560 A2 | 3/2008 | | |
| WO | WO-2008/085486 A1 | 7/2008 | | |
| WO | WO-2008/140478 A2 | 11/2008 | | |
| WO | WO-2009/006618 A2 | 1/2009 | | |
| WO | WO-2009/006680 A1 | 1/2009 | | |
| WO | WO-2010/02326 A1 | 1/2010 | | |
| WO | WO-2010/103017 A2 | 9/2010 | | |
| WO | WO-2010/135747 A1 | 11/2010 | | |
| WO | WO-2011/112717 A1 | 9/2011 | | |

OTHER PUBLICATIONS

Dolan, A., Virion glycoprotein L [Human herpesvirus 2]. NCBI Reference Sequence: NC_044470.1. Dep. Apr. 3, 2000.
World Health Organization (WHO), Status of Vaccine Research and Development of Vaccines for Herpes Simplex Virus Prepared for WHO PD-VAC, <http://www.who.int/immunization/research/meetings_workshops/HSV_vaccineRD_Sept2014.pdf> Pub. Sep. 24, 2014.
Ashley, R. et al., Humoral Immune Response to Herpes Simplex Virus Type 2 Glycoproteins in Patients Receiving a Glycoprotein Subunit Vaccine, Journal of Virology, 56(2):475-481 (1985).
Braun, R.P. et al., Characterization of the IFN-γ T-cell responses to immediate early antigens in humans with genital herpes, Virology Journal, 3(54):1-15 (2006).
Cattamanchi, A. et al., Phase I Study of a Herpes Simplex Virus Type 2 (HSV-2) DNA Vaccine Administered to Healthy, HSV-2-Seronegative Adults by a Needle-Free Injection System, Clinical and Vaccine Immunology, 15(11):1638-1643 (2008).
Dasgupta, G. et al., New Concepts in Herpes Simplex Virus Vaccine Development: Notes from the Battlefield, Expert Rev. Vaccines, 8(8):1023-1035 (2009).
Extended European Search Report for EP 10778532.1, 9 pages (dated Jun. 28, 2013).
Genbank BAA01264.1 (May 29, 2002).
Genbank CAB06713.1 (Nov. 14, 2006).
GenBank Direct Submission UniProtKB/Swiss-Prot: P28278.1, Envelope glycoprotein L; Short=gL; Flags: Precursor (2010).
International Search Report for PCT/US11/62120, 6 pages (dated Jul. 10, 2012).
International Search Report for PCT/US2010/035998, 7 pages (dated Oct. 26, 2010).
International Search Report for PCT/US2010/036000, 7 pages (dated Sep. 7, 2010).
Jones, C.A. et al., Vaccination strategies to prevent genital herpes and neonatal herpes simplex virus (HSV) disease, The Journal of the IHMF (England), 11(1):12-7 (2004). Abstract only.
Koelle, D.M. et al., Antigenic Specificities of Human CD4+ T-Cell Clones Recovered from Recurrent Genital Herpes Simplex Virus Type 2 Lesions, Journal of Virology, 68(5):2803-2810 (1994).
Koelle, D.M. et al., Immunodominance among herpes simplex virus-specific CD8 T cells expressing a tissue-specific homing receptor, PNAS, 100(22):12899-12904 (2003).
Langenberg, A.G.M. et al., A Recombinant Glycoprotein Vaccine for Herpes Simplex Type 2: Safety and Efficacy, Annals of Internal Medicine, 122(12):889-898 (1995).
Liljeqvist, J.A. et al., Monoclonal antibodies and human sera directed to the secreted glycoprotein G of herpes simplex virus type 2 recognize type-specific antigenic determinants, Journal of General Virology, 83:157-165 (2002).
Mertz, G.J. Asymptomatic Shedding of Herpes Simplex Virus 1 and 2: Implications for Prevention of Transmission, The Journal of Infectious Diseases, 198:1-2 (2008).
Meseda, C.A. et al., A Prime-Boost Immunization with DNA and Modified Vaccinia Virus Ankara Vectors Expressing Herpes Simplex Virus-2 Glycoprotein D Elicits Greater Specific Antibody and Cytokine Responses than DNA Vaccine Alone, The Journal of Infectious Diseases, 186:1065-1073 (2002).
Rajaguru, S.C., Inhibition of Herpes Simplex Virus Replication Using Small Interfering RNA That Target ICP4 Gene of Herpes Simplex Type 2, Master of Science Thesis, University of Florida (2004).
Sedlackova, L. et al., Herpes Simplex Virus Type 1 Immediate-Early Protein ICP27 Is Required for Efficient Incorporation of ICP0 and ICP4 into Virions, Journal of Virology, 82(1):268-277 (2008).
Shlapobersky, M. et al., Vaxfectin-adjuvanted plasmid DNA vaccine improves protection and immunogenecity in a murine model of genital herpes infection, Journal of General Virology, 93:1305-1315 (2012).
Strasser, J.E. et al., Herpes Simplex Virus DNA Vaccine Efficacy: Effect of Glycoprotein D Plasmid Constructs, The Journal of Infectious Diseases, 182:1304-1310 (2000).
Tigges, M.A. et al., Human CD8+ Herpes Simplex Virus-Specific Cytotoxic T-Lymphocyte Clones Recognize Diverse Virion Protein Antigens, Journal of Virology, 66(3):1622-1634 (1992).
Watari, E. et al., A synthetic peptide induces long-term protection from lethal infection with herpes simplex virus 2, The Journal of Experimental Medicine, 165:459-470 (1987).
Written Opinion for PCT/US11/62120, 9 pages (dated Jul. 10, 2012).
Yang, Huilan et al., High effective expression of gD2 gene of herpes virus in *Escherichia coli*, Chinese Journal of Dermatology, 3:157-159 (1997).
Zhou, J. et al., Research Progress of Envelope Glycoprotein gG-2 of HSV, Foreign Medical Sciences, 11(4):123-126 (2004). (English Abstract).
Baccari, A. et al., Both HSV-2 and HSV-1 neutralizing antibody titers are boosted in subjects with genital herpes after vaccination with GEN-0003, a novel HSV-2 immunotherapy, Paper Poster Session 1, Abstract, P0279 (2015).
Bowie, J.U. et al., Deciphering the message in protein sequences: tolerance to amino acid substitutions, Science, 247(4948): 1306-1310 (1990).
Fife, K.H. et al., An International, Randomized, Double-Blind, Placebo-Controlled, Study of Valacyclovir for the Suppression of

(56) References Cited

OTHER PUBLICATIONS

Herpes Simplex Virus Type 2 Genital Herpes in Newly Diagnosed Patients, Sexually Transmitted Diseases 35(7): 668-673 (2008).
Freeman, E.F. et al., Herpes simplex virus 2 infection increases HIV acquisition in men and women: systematic review and meta-analysis of longitudinal studies, AIDS, 73-83 (2006).
Garland, S.M. et al., Genital herpes, Best Practice & Research Clinical Obstetrics and Gynaecology, 28: 1095-110 (2014).
Genocea Biosciences, Genocea Announces Positive Durability Data from 6-Month Analysis of Phase 2 Clinical Trial of Genital Herpes Immunotherapy GEN-003, Business Wire, Cambridge, MA, 3 pages (Oct. 7, 2015).
Knipe, D.M. et al., HSV-2 vaccine: Current state and insights into development of a vaccine that targets genital mucosal protection, Vaccine, 32: 1561-1562 (2014).
Roth, K. et al., HSV-2 vaccine: Current state and insights into development of a vaccine that targets genital mucosal protection, Microbiol Pathogenesis, 1-10 (2012).
Schiffer, J.T. et al., Herpes simplex virus-2 transmission probability estimates based on quantity of viral shedding, Journal of the Royal Society Interface, 1-12 (2014).
Bernstein, D.J. et al., Effects of herpes simplex virus type 2 glycoprotein vaccines and CLDC adjuvant on genital herpes infection in the guinea pig, Vaccine, 29: 2071-2078 (2011).
Boursnell, M. et al., A Genetically Inactivated Herpes Simplex Virus Type 2 (HSV-2) Vaccine Provides Effective Protection against Primary and Recurrent HSV-2 Disease, The Journal of Infectious Diseases, 175(1): 16-25 (1997).
Braun, R.P. et al., Multi-antigenic DNA immunization using herpes simplex virus type 2 genomic fragments, Human Vaccines, 4(1): 36-43 (2008).
Database EMBL P28278 (GL_HHV2H), Jan. 12, 1992 (McGeoch et al., J. Gen. Virol., 72:3057-3075 (1991) [retrieved on Sep. 1, 2013]. Retrieved from the internet: <URL:http//www.uniprot.org/uniprot/P28278>).
Database EMBL Q69467 (GD_HHV2H), Jan. 11, 1996 (Dolan et al., J. Virol., 72(3):2010-2021 (1998) [retrieved on Sep. 1, 2013]. Retrieved from the internet: <URL:http//www.uniprot.org/uniprot/Q69467>).
Dolan, A., Herpes simplex virus type 2 (strain HG52), complete genome, GenBank Acc No. Z86099.2, Dep. Mar. 5, 1997, Rev. Nov. 14, 2006.
Dolan, et al., The Genome Sequence of Herpes Simplex Virus Type 2, J. Virol., 72(3):2010-2021 (1998).
Fló, J., Co-immunization with plasmids coding the full length and a soluble form of glycoprotein D of HSV-2 induces protective cellular and humoral immune response in mice, Vaccine, 21(11-12): 1239-1245 (2003).
Fló, J., et al., Superiority of intramuscular route and full length glycoprotein D for DNA vaccination against herpes simplex 2. Enhancement of protection by the co-delivery of the GM-CSF gene. Vaccine, 18(28): 3242-3253 (2000).
GenBank ABU45435.1, glycoprotein D [Human herpesvirus 2] (Nov. 29, 2007).
Grabowska, A.M. et al., Immunisation with Phage Displaying Peptides Representing Single Epitopes of the Glycoprotein G can give rise to Partial Protective Immunity to HSV-2, Virology, 269: 47-53 (2000).
International Search Report for PCT/US2012/066241, dated Feb. 28, 2013, published as WO 2013/078299 (2 pages).
Lasky, L.A. et al., DNA Sequence Analysis of the Type-Common Glycoprotein-D Genes of Herpes Simplex Virus Types 1 and 2, DNA, 3(1): 23-29 (1984).
McClements, W.L. et al., Immunization with DNA vaccines encoding glycoprotein D or glycoprotein B, alone or in combination, induces protective immunity in animal models of herpes simplex virus-2 disease, Proceedings of the National Academy of Sciences, National Academy of Sciences, 93(21): 11414-11420 (1996).
McGeoch et al., Database EMBL P28278, J. Gen. Virol., 71:3057-3075 (1991) (retrieved from the internet: <URL:http://www.uniprot.org/uniprot/P28278>).
Mikloaska, Z. et al., Monophosphoryl Lipid A and QS21 Increase CD8 T Lymphocyte Cytotoxicity to Herpes implex Virus-2 Infected Cell Proteins 4 and 27 Through IFN-g and IL-12 Production, J. Immuno., 164: 5167-5176 (2000).
Posavad, C.M. et al., Detailed characterization of T cell responses to herpes simplex virus-2 in immune seronegative persons, J. Immunol., 184(4): 3250-3259 (2010).
Sin, J-I. et al., DNA vaccines encoding interleukin-8 and RANTES enhance antigen-specific Th1-type CD4(+) T-cell-mediated protective immunity against herpes simplex virus type 2 in vivo, Journal of Virology, 74(23): 11173-11180 (2000).
Sin, J-I. et al., IL-12 gene as a DNA vaccine adjuvant in a herpes mouse model: 7-15 IL-12 enhances Th1-type CD4+ T cell-mediated protective immunity against herpes simplex virus-2 challenge, The Journal of Immunology, 162(5): 2912-2921 (1999).
Written Opinion for PCT/US2012/066241, dated Feb. 28, 2013, published as WO 2013/078299 (3 pages).
Sojikul, P. et al., A plant signal peptide-hepatitis B surface antigen fusion protein with enhanced stability and immunogenicity expressed in plant cells, PNAS, 100(5): 2209-2214 (2003).

\* cited by examiner

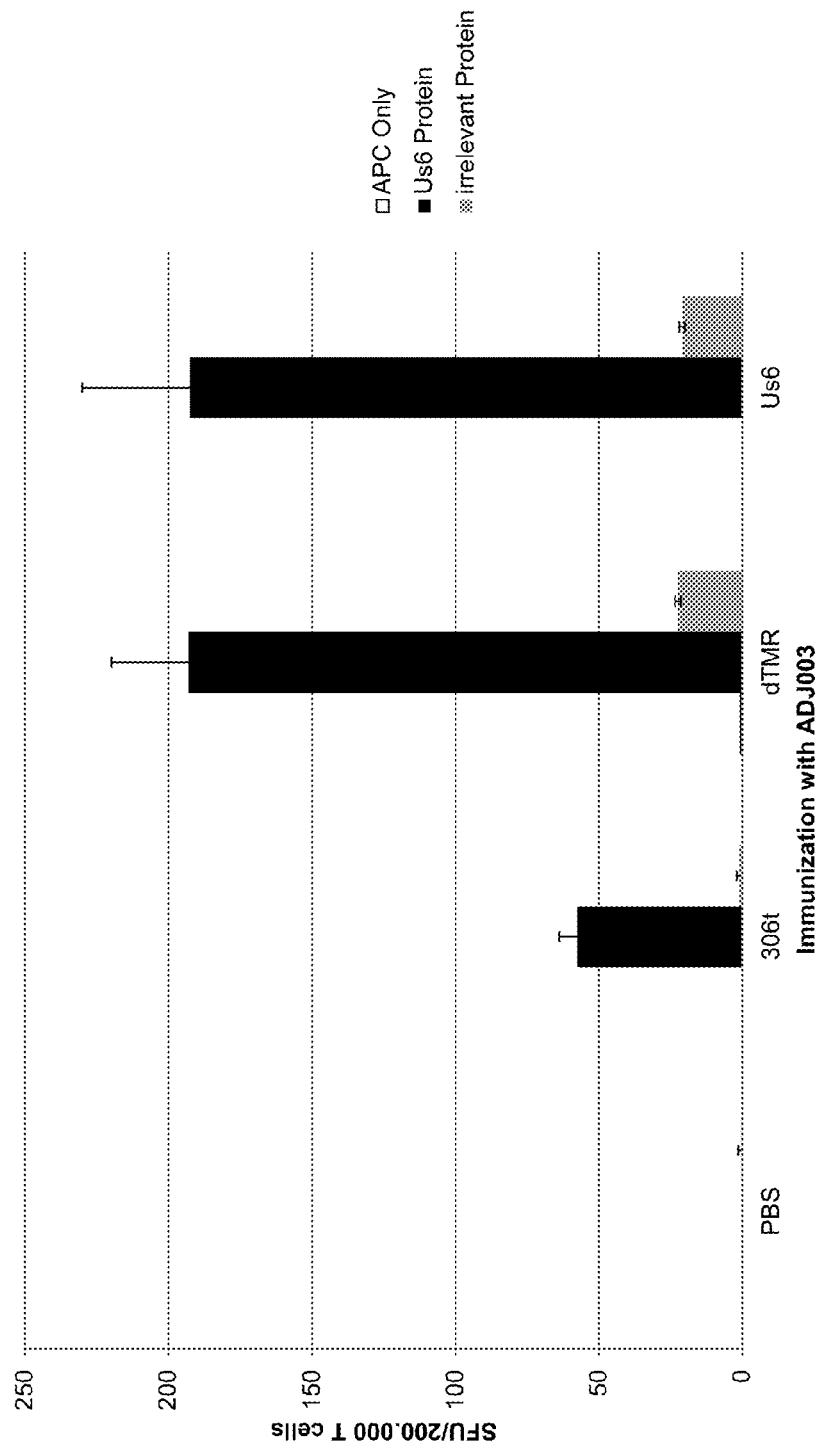

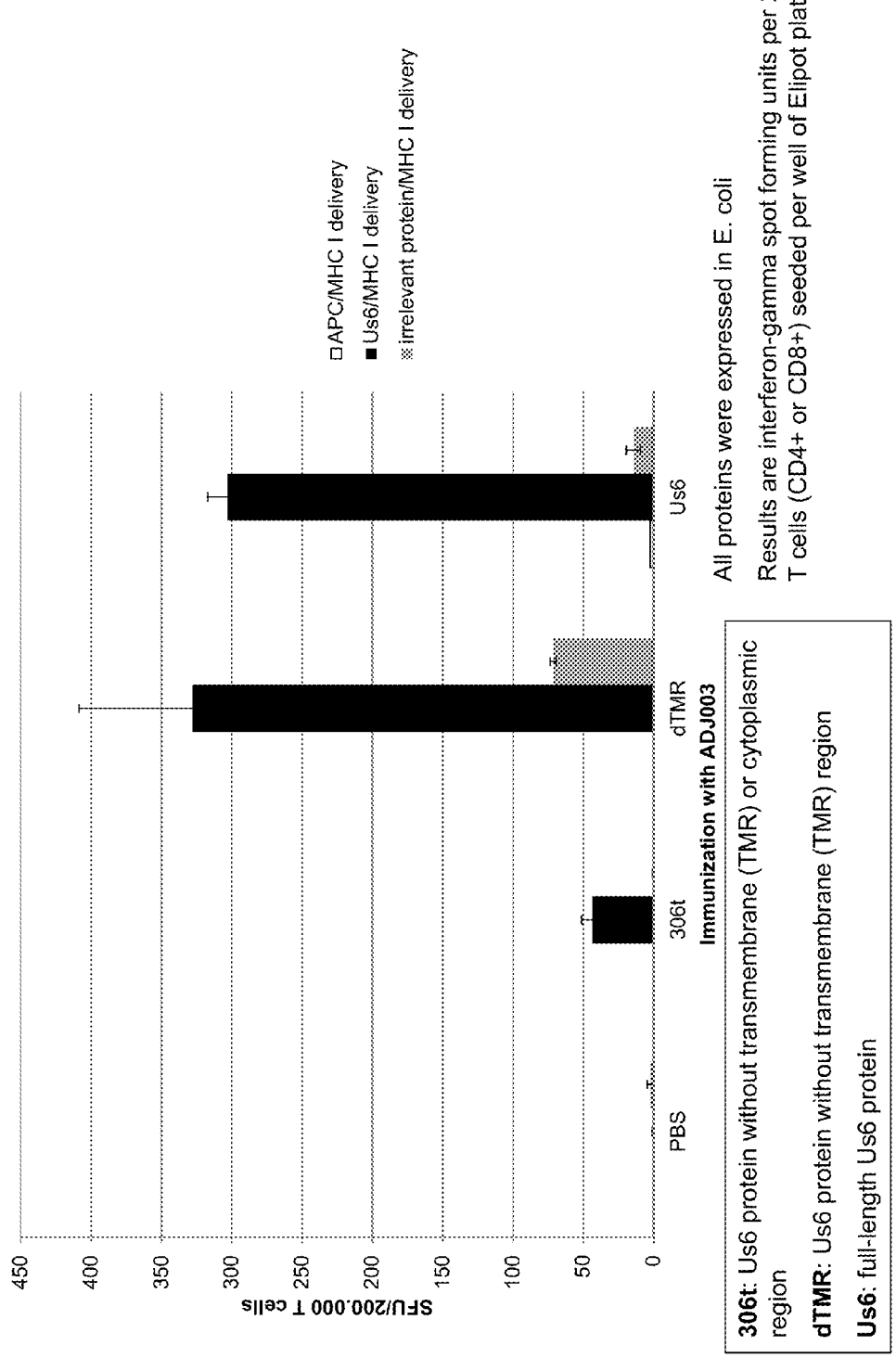

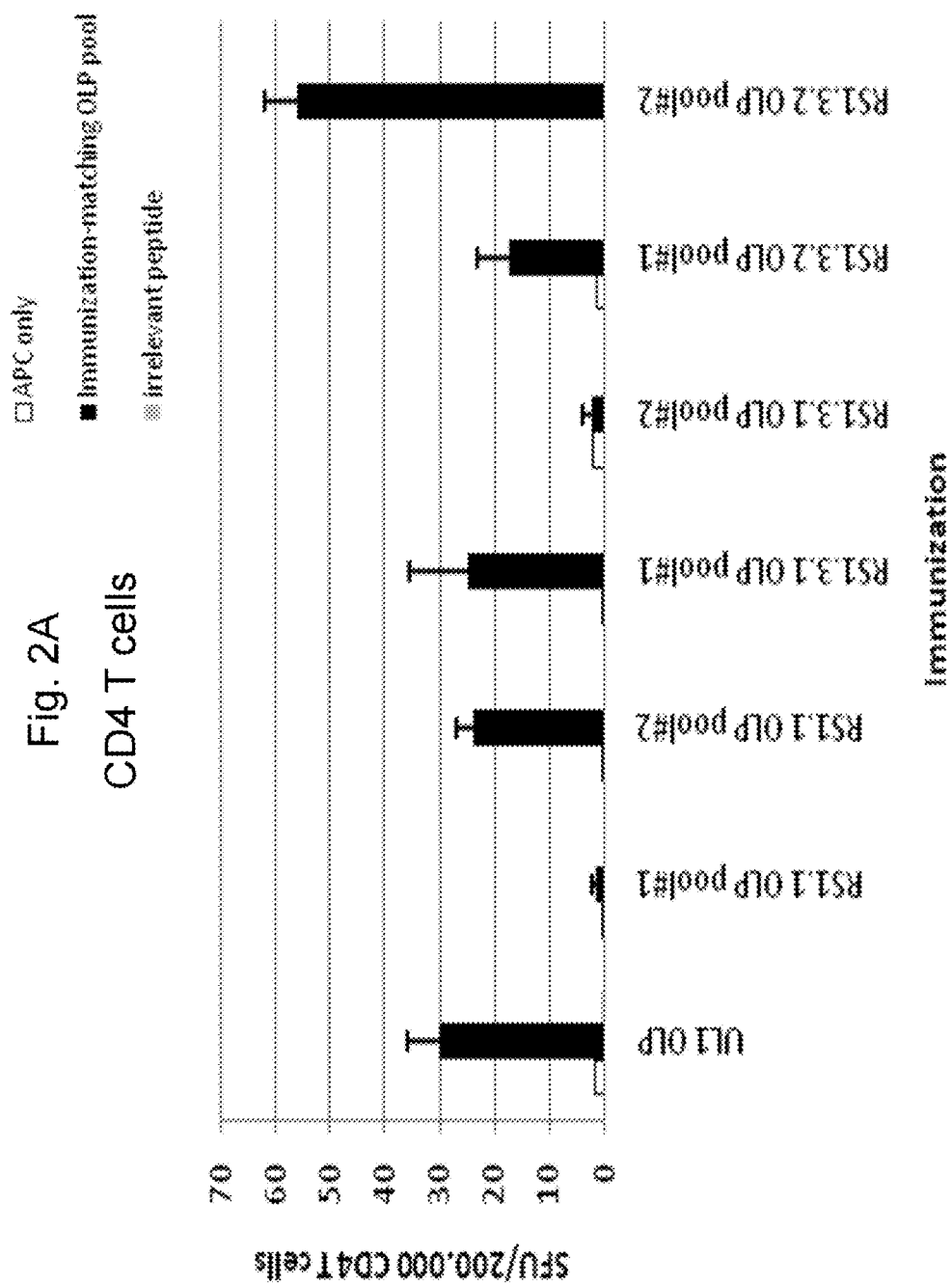

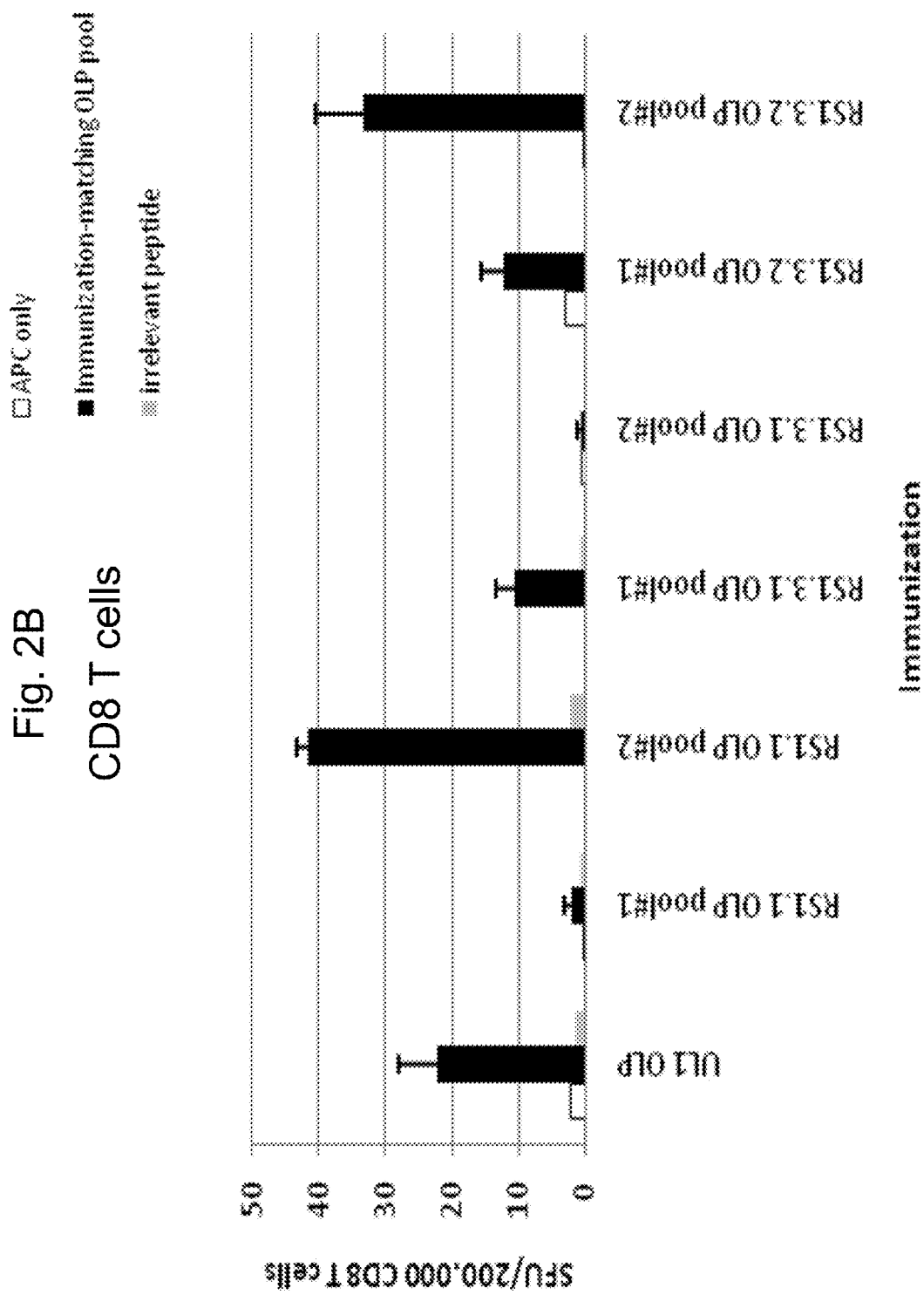

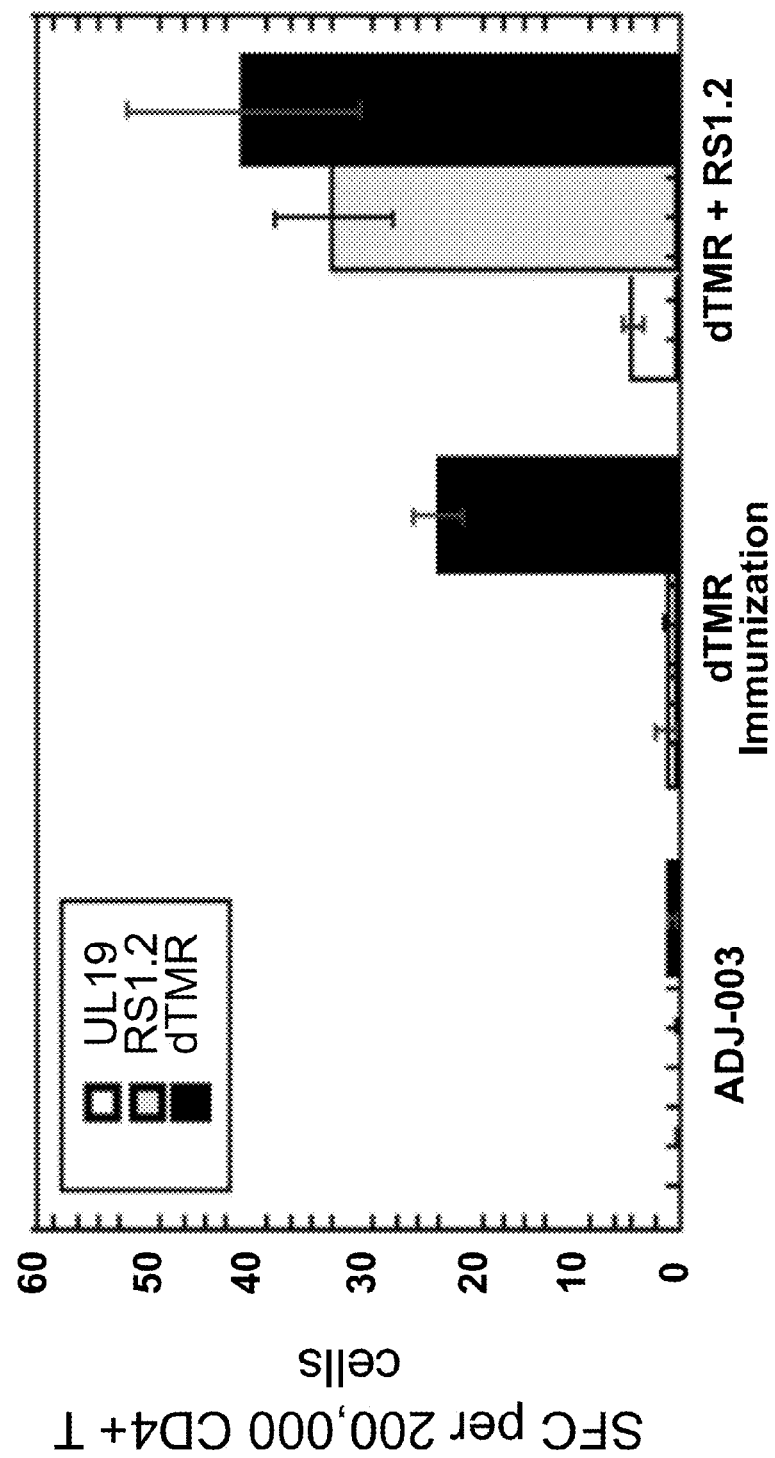

SEQUENCE LISTING

<160> NUMBER OF SEQ ID NOS: 137

<210> SEQ ID NO 1
<211> LENGTH: 1317
<212> TYPE: PRT
<213> ORGANISM: Human herpesvirus 2

<400> SEQUENCE: 1

Ser Ala Glu Gln Arg Lys Lys Lys Lys Thr Thr Thr Thr Thr Gln Gly
1               5                   10                  15

-continued

```
Arg Gly Ala Glu Val Ala Met Ala Asp Glu Asp Gly Arg Leu Arg
            20                  25                  30
Ala Ala Ala Glu Thr Thr Gly Gly Pro Gly Ser Pro Asp Pro Ala Asp
        35                  40                  45
Gly Pro Pro Thr Pro Asn Pro Asp Arg Arg Pro Ala Ala Arg Pro
 50                  55                  60
Gly Phe Gly Trp His Gly Pro Glu Glu Asn Glu Asp Glu Ala Asp
 65                  70                  75                  80
Asp Ala Ala Ala Asp Ala Asp Ala Asp Glu Ala Pro Ala Ser Gly
                85                  90                  95
Glu Ala Val Asp Glu Pro Ala Ala Asp Gly Val Val Ser Pro Arg Gln
                100                 105                 110
Leu Ala Leu Leu Ala Ser Met Val Asp Glu Ala Val Arg Thr Ile Pro
            115                 120                 125
Ser Pro Pro Pro Glu Arg Asp Gly Ala Gln Glu Glu Ala Ala Arg Ser
            130                 135                 140
Pro Ser Pro Pro Arg Thr Pro Ser Met Arg Ala Asp Tyr Gly Glu Glu
145                 150                 155                 160
Asn Asp Asp Asp Asp Asp Asp Asp Asp Asp Arg Asp Ala Gly
                165                 170                 175
Arg Trp Val Arg Gly Pro Glu Thr Thr Ser Ala Val Arg Gly Ala Tyr
            180                 185                 190
Pro Asp Pro Met Ala Ser Leu Ser Pro Arg Pro Ala Pro Arg Arg
            195                 200                 205
His His His His His His Arg Arg Arg Ala Pro Arg Arg Arg
            210                 215                 220
Ser Ala Ala Ser Asp Ser Ser Lys Ser Gly Ser Ser Ser Ala Ser
225                 230                 235                 240
Ser Ala Ser Ser Ser Ala Ser Ser Ser Ser Ala Ser Ala Ser Ser
                245                 250                 255
Ser Asp Asp Asp Asp Asp Asp Ala Ala Arg Ala Pro Ala Ser Ala
            260                 265                 270
Ala Asp His Ala Ala Gly Gly Thr Leu Gly Ala Asp Asp Glu Glu Ala
            275                 280                 285
Gly Val Pro Ala Arg Ala Pro Gly Ala Ala Pro Arg Pro Ser Pro Pro
            290                 295                 300
Arg Ala Glu Pro Ala Pro Ala Arg Thr Pro Ala Ala Thr Ala Gly Arg
305                 310                 315                 320
Leu Glu Arg Arg Arg Ala Arg Ala Ala Val Ala Gly Arg Asp Ala Thr
                325                 330                 335
Gly Arg Phe Thr Ala Gly Arg Pro Arg Arg Val Glu Leu Asp Ala Asp
            340                 345                 350
Ala Ala Ser Gly Ala Phe Tyr Ala Arg Tyr Arg Asp Gly Tyr Val Ser
            355                 360                 365
Gly Glu Pro Trp Pro Gly Ala Gly Pro Pro Pro Gly Arg Val Leu
            370                 375                 380
Tyr Gly Gly Leu Gly Asp Ser Arg Pro Gly Leu Trp Gly Ala Pro Glu
385                 390                 395                 400
Ala Glu Glu Ala Arg Ala Arg Phe Glu Ala Ser Gly Ala Pro Ala Pro
                405                 410                 415
Val Trp Ala Pro Glu Leu Gly Asp Ala Ala Gln Gln Tyr Ala Leu Ile
            420                 425                 430
Thr Arg Leu Leu Tyr Thr Pro Asp Ala Glu Ala Met Gly Trp Leu Gln
```

```
                435                 440                 445
Asn Pro Arg Val Ala Pro Gly Asp Val Ala Leu Asp Gln Ala Cys Phe
450                 455                 460
Arg Ile Ser Gly Ala Ala Arg Asn Ser Ser Phe Ile Ser Gly Ser
465                 470                 475                 480
Val Ala Arg Ala Val Pro His Leu Gly Tyr Ala Met Ala Ala Gly Arg
                485                 490                 495
Phe Gly Trp Gly Leu Ala His Val Ala Ala Val Ala Met Ser Arg
                500                 505                 510
Arg Tyr Asp Arg Ala Gln Lys Gly Phe Leu Leu Thr Ser Leu Arg Arg
                515                 520                 525
Ala Tyr Ala Pro Leu Leu Ala Arg Glu Asn Ala Ala Leu Thr Gly Ala
                530                 535                 540
Arg Thr Pro Asp Asp Gly Gly Asp Ala Asn Arg His Asp Gly Asp Asp
545                 550                 555                 560
Ala Arg Gly Lys Pro Ala Ala Ala Ala Pro Leu Pro Ser Ala Ala
                        565                 570                 575
Ala Ser Pro Ala Asp Glu Arg Ala Val Pro Ala Gly Tyr Gly Ala Ala
                580                 585                 590
Gly Val Leu Ala Ala Leu Gly Arg Leu Ser Ala Ala Pro Ala Ser Ala
                595                 600                 605
Pro Ala Gly Ala Asp Asp Asp Asp Asp Asp Gly Ala Gly Gly Gly
610                 615                 620
Gly Gly Gly Arg Arg Ala Glu Ala Gly Arg Val Ala Val Glu Cys Leu
625                 630                 635                 640
Ala Ala Cys Arg Gly Ile Leu Glu Ala Leu Ala Glu Gly Phe Asp Gly
                        645                 650                 655
Asp Leu Ala Ala Val Pro Gly Leu Ala Gly Ala Arg Pro Ala Ala Pro
                660                 665                 670
Pro Arg Pro Gly Pro Ala Gly Ala Ala Ala Pro Pro His Ala Asp Ala
                675                 680                 685
Pro Arg Leu Arg Ala Trp Leu Arg Glu Leu Arg Phe Val Arg Asp Ala
                690                 695                 700
Leu Val Leu Met Arg Leu Arg Gly Asp Leu Arg Val Ala Gly Gly Ser
705                 710                 715                 720
Glu Ala Ala Val Ala Val Arg Ala Val Ser Leu Val Ala Gly Ala
                        725                 730                 735
Leu Gly Pro Ala Leu Pro Arg Ser Pro Arg Leu Leu Ser Ser Ala Ala
                740                 745                 750
Ala Ala Ala Ala Asp Leu Leu Phe Gln Asn Gln Ser Leu Arg Pro Leu
                755                 760                 765
Leu Ala Asp Thr Val Ala Ala Asp Ser Leu Ala Ala Pro Ala Ser
                770                 775                 780
Ala Pro Arg Glu Ala Arg Lys Arg Lys Ser Pro Ala Pro Ala Arg Ala
785                 790                 795                 800
Pro Pro Gly Gly Ala Pro Arg Pro Lys Lys Ser Arg Ala Asp Ala
                        805                 810                 815
Pro Arg Pro Ala Ala Pro Ala Gly Ala Ala Pro Ala
                820                 825                 830
Pro Thr Pro Pro Arg Pro Arg Pro Ala Ala Leu Thr Arg Arg
                835                 840                 845
Pro Ala Glu Gly Pro Asp Pro Gln Gly Gly Trp Arg Arg Gln Pro Pro
                850                 855                 860
```

```
Gly Pro Ser His Thr Pro Ala Pro Ser Ala Ala Ala Leu Glu Ala Tyr
865                 870                 875                 880

Cys Ala Pro Arg Ala Val Ala Glu Leu Thr Asp His Pro Leu Phe Pro
                885                 890                 895

Ala Pro Trp Arg Pro Ala Leu Met Phe Asp Pro Arg Ala Leu Ala Ser
            900                 905                 910

Leu Ala Ala Arg Cys Ala Pro Pro Gly Gly Ala Pro Ala Ala
            915                 920                 925

Phe Gly Pro Leu Arg Ala Ser Gly Pro Leu Arg Arg Ala Ala Ala Trp
            930                 935                 940

Met Arg Gln Val Pro Asp Pro Glu Asp Val Arg Val Val Ile Leu Tyr
945                 950                 955                 960

Ser Pro Leu Pro Gly Glu Asp Leu Ala Ala Gly Arg Ala Gly Gly Gly
                965                 970                 975

Pro Pro Pro Glu Trp Ser Ala Glu Arg Gly Gly Leu Ser Cys Leu Leu
            980                 985                 990

Ala Ala Leu Gly Asn Arg Leu Cys Gly Pro Ala Thr Ala Ala Trp Ala
            995                 1000                1005

Gly Asn Trp Thr Gly Ala Pro Asp Val Ser Ala Leu Gly Ala Gln
    1010                1015                1020

Gly Val Leu Leu Leu Ser Thr Arg Asp Leu Ala Phe Ala Gly Ala
    1025                1030                1035

Val Glu Phe Leu Gly Leu Leu Ala Gly Ala Cys Asp Arg Arg Leu
    1040                1045                1050

Ile Val Val Asn Ala Val Arg Ala Ala Asp Trp Pro Ala Asp Gly
    1055                1060                1065

Pro Val Val Ser Arg Gln His Ala Tyr Leu Ala Cys Glu Val Leu
    1070                1075                1080

Pro Ala Val Gln Cys Ala Val Arg Trp Pro Ala Ala Arg Asp Leu
    1085                1090                1095

Arg Arg Thr Val Leu Ala Ser Gly Arg Val Phe Gly Pro Gly Val
    1100                1105                1110

Phe Ala Arg Val Glu Ala Ala His Ala Arg Leu Tyr Pro Asp Ala
    1115                1120                1125

Pro Pro Leu Arg Leu Cys Arg Gly Ala Asn Val Arg Tyr Arg Val
    1130                1135                1140

Arg Thr Arg Phe Gly Pro Asp Thr Leu Val Pro Met Ser Pro Arg
    1145                1150                1155

Glu Tyr Arg Arg Ala Val Leu Pro Ala Leu Asp Gly Arg Ala Ala
    1160                1165                1170

Ala Ser Gly Ala Gly Asp Ala Met Ala Pro Gly Ala Pro Asp Phe
    1175                1180                1185

Cys Glu Asp Glu Ala His Ser His Arg Ala Cys Ala Arg Trp Gly
    1190                1195                1200

Leu Gly Ala Pro Leu Arg Pro Val Tyr Val Ala Leu Gly Arg Asp
    1205                1210                1215

Ala Val Arg Gly Gly Pro Ala Glu Leu Arg Gly Pro Arg Arg Glu
    1220                1225                1230

Phe Cys Ala Arg Ala Leu Leu Glu Pro Asp Gly Asp Ala Pro Pro
    1235                1240                1245

Leu Val Leu Arg Asp Asp Ala Asp Ala Gly Pro Pro Pro Gln Ile
    1250                1255                1260
```

```
Arg Trp Ala Ser Ala Ala Gly Arg Ala Gly Thr Val Leu Ala Ala
    1265                1270                1275

Ala Gly Gly Gly Val Glu Val Val Gly Thr Ala Ala Gly Leu Ala
1280                1285                1290

Thr Pro Pro Arg Arg Glu Pro Val Asp Met Asp Ala Glu Leu Glu
    1295                1300                1305

Asp Asp Asp Asp Gly Leu Phe Gly Glu
    1310                1315

<210> SEQ ID NO 2
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Val Leu Tyr Gly Gly Leu Gly Asp Ser Arg Pro Gly Leu Trp Gly
1               5                   10                  15

Ala Pro Glu Ala Glu Glu Ala Arg Ala Arg Phe Glu Ala Ser Gly Ala
            20                  25                  30

Pro Ala Pro Val Trp Ala Pro Glu Leu Gly Asp Ala Ala Gln Gln Tyr
        35                  40                  45

Ala Leu Ile Thr Arg Leu Leu Tyr Thr Pro Asp Ala Glu Ala Met Gly
    50                  55                  60

Trp Leu Gln Asn Pro Arg Val Ala Pro Gly Asp Val Ala Leu Asp Gln
65                  70                  75                  80

Ala Cys Phe Arg Ile Ser Gly Ala Ala Arg Asn Ser Ser Ser Phe Ile
                85                  90                  95

Ser Gly Ser Val Ala Arg Ala Val Pro His Leu Gly Tyr Ala Met Ala
            100                 105                 110

Ala Gly Arg Phe Gly Trp Gly Leu Ala His Val Ala Ala Ala Val Ala
        115                 120                 125

Met Ser Arg Arg Tyr Asp Arg Ala Gln Lys Gly Phe Leu Leu Thr Ser
    130                 135                 140

Leu Arg Arg Ala Tyr Ala Pro Leu Leu Ala Arg Glu Asn Ala Ala Leu
145                 150                 155                 160

Thr Gly Ala Arg Thr Pro Asp Asp Gly Gly Asp Ala Asn Arg Arg Asp
                165                 170                 175

Gly Asp Asp Ala Arg Gly Lys Pro Ala Ala Ala Ala Pro Leu Pro
            180                 185                 190

Ser Ala Ala Ser Pro Ala Asp Glu Arg Ala Val Pro Ala Gly Tyr
        195                 200                 205

Gly Ala Ala Gly Val Leu Ala Ala Leu Gly Arg Leu Ser Ala Ala Pro
    210                 215                 220

Ala Ser Ala Pro Ala Gly Ala Asp Asp Asp Asp Asp Asp Asp Gly
225                 230                 235                 240

Ala Gly Gly Gly Gly Gly Gly Gly Gly Gly Gly Arg Arg Ala
                245                 250                 255

Glu Ala Gly Arg Val Ala Val Glu Cys Leu Ala Ala Cys Arg Gly Ile
            260                 265                 270

Leu Glu Ala Leu Ala Glu Gly Phe Asp Gly Asp Leu Ala Ala Val Pro
        275                 280                 285

Gly Leu Ala Gly Ala Arg Pro Ala Ala Pro Pro Arg Pro Gly Pro Ala
    290                 295                 300
```

Gly Ala Ala Ala Pro Pro His Ala Asp Ala Pro Arg Leu Arg Ala Trp
305                 310                 315                 320

Leu Arg Glu Leu Arg Phe Val Arg Asp Ala Leu Val Leu Met Arg Leu
            325                 330                 335

Arg Gly Asp Leu Arg Val Ala Gly Gly Ser Glu Ala Ala Val Ala Ala
        340                 345                 350

Val Arg Ala Val Ser Leu Val Ala Gly Ala Leu Gly Pro Ala Leu Pro
        355                 360                 365

Arg Ser Pro Arg Leu Leu Ser Ser Ala Ala Ala Ala Ala Ala Asp Leu
    370                 375                 380

Leu Phe Gln Asn Gln Ser Leu
385                 390

<210> SEQ ID NO 3
<211> LENGTH: 224
<212> TYPE: PRT
<213> ORGANISM: Human herpesvirus 2

<400> SEQUENCE: 3

Met Gly Phe Val Cys Leu Phe Gly Leu Val Val Met Gly Ala Trp Gly
1               5                   10                  15

Ala Trp Gly Gly Ser Gln Ala Thr Glu Tyr Val Leu Arg Ser Val Ile
            20                  25                  30

Ala Lys Glu Val Gly Asp Ile Leu Arg Val Pro Cys Met Arg Thr Pro
        35                  40                  45

Ala Asp Asp Val Ser Trp Arg Tyr Glu Ala Pro Ser Val Ile Asp Tyr
    50                  55                  60

Ala Arg Ile Asp Gly Ile Phe Leu Arg Tyr His Cys Pro Gly Leu Asp
65                  70                  75                  80

Thr Phe Leu Trp Asp Arg His Ala Gln Arg Ala Tyr Leu Val Asn Pro
                85                  90                  95

Phe Leu Phe Ala Ala Gly Phe Leu Glu Asp Leu Ser His Ser Val Phe
            100                 105                 110

Pro Ala Asp Thr Gln Glu Thr Thr Thr Arg Arg Ala Leu Tyr Lys Glu
        115                 120                 125

Ile Arg Asp Ala Leu Gly Ser Arg Lys Gln Ala Val Ser His Ala Pro
    130                 135                 140

Val Arg Ala Gly Cys Val Asn Phe Asp Tyr Ser Arg Thr Arg Arg Cys
145                 150                 155                 160

Val Gly Arg Arg Asp Leu Arg Pro Ala Asn Thr Thr Ser Thr Trp Glu
                165                 170                 175

Pro Pro Val Ser Ser Asp Asp Glu Ala Ser Ser Gln Ser Lys Pro Leu
            180                 185                 190

Ala Thr Gln Pro Pro Val Leu Ala Leu Ser Asn Ala Pro Pro Arg Arg
        195                 200                 205

Val Ser Pro Thr Arg Gly Arg Arg Arg His Thr Arg Leu Arg Arg Asn
    210                 215                 220

<210> SEQ ID NO 4
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Asn Arg Trp Lys Tyr Ala Leu Ala Asp Pro Ser Leu Lys Met Ala Asp
1               5                   10                  15

Pro Asn Arg Phe Arg Gly Lys Asn Leu Pro Val Leu Asp Gln Leu Thr
            20                  25                  30

Asp Pro Pro Gly Val Lys Arg Val Tyr His Ile Gln Pro Ser Leu Glu
        35                  40                  45

Asp Pro Phe Gln Pro Pro Ser Ile Pro Ile Thr Val Tyr Tyr Ala Val
50                  55                  60

Leu Glu Arg Ala Cys Arg Ser Val Leu Leu His Ala Pro Ser Glu Ala
65                  70                  75                  80

Pro Gln Ile Val Arg Gly Ala Ser Asp Glu Ala Arg Lys His Thr Tyr
                85                  90                  95

Asn Leu Thr Ile Ala Trp Tyr Arg Met Gly Asp Asn Cys Ala Ile Pro
            100                 105                 110

Ile Thr Val Met Glu Tyr Thr Glu Cys Pro Tyr Asn Lys Ser Leu Gly
        115                 120                 125

Val Cys Pro Ile Arg Thr Gln Pro Arg Trp Ser Tyr Tyr Asp Ser Phe
    130                 135                 140

Ser Ala Val Ser Glu Asp Asn Leu Gly Phe Leu Met His Ala Pro Ala
145                 150                 155                 160

Phe Glu Thr Ala Gly Thr Tyr Leu Arg Leu Val Lys Ile Asn Asp Trp
                165                 170                 175

Thr Glu Ile Thr Gln Phe Ile Leu Glu His Arg Ala Arg Ala Ser Cys
            180                 185                 190

Lys Tyr Ala Leu Pro Leu Arg Ile Pro Pro Ala Ala Cys Leu Thr Ser
        195                 200                 205

Lys Ala Tyr Gln Gln Gly Val Thr Val Asp Ser Ile Gly Met Leu Pro
    210                 215                 220

Arg Phe Ile Pro Glu Asn Gln Arg Thr Val Ala Leu Tyr Ser Leu Lys
225                 230                 235                 240

Ile Ala Gly Trp His Gly Pro Lys Pro Pro Tyr Thr Ser Thr Leu Leu
                245                 250                 255

Pro Pro Glu Leu Ser Asp Thr Thr Asn Ala Thr Gln Pro Glu Leu Val
            260                 265                 270

Pro Glu Asp Pro Glu Asp Ser Ala Leu Leu Glu Asp Pro Ala Gly Thr
        275                 280                 285

Val Ser Ser Gln Ile Pro Pro Asn Trp His Ile Pro Ser Ile Gln Asp
    290                 295                 300

Val Ala Pro His His Ala Pro Ala Ala Pro Ser Asn Pro Arg Arg Arg
305                 310                 315                 320

Ala Gln Met Ala Pro Lys Arg Leu Arg Leu Pro His Ile Arg Asp Asp
                325                 330                 335

Asp Ala Pro Pro Ser His Gln Pro Leu Phe Tyr
            340                 345

<210> SEQ ID NO 5
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Gly Arg Leu Thr Ser Gly Val Gly Thr Ala Ala Leu Leu Val Val
```

```
              1               5                  10                 15
            Ala Val Gly Leu Arg Val Cys Ala Lys Tyr Ala Leu Ala Asp Pro
                           20                  25                  30

Ser Leu Lys Met Ala Asp Pro Asn Arg Phe Arg Gly Lys Asn Leu Pro
                           35                  40                  45

Val Leu Asp Gln Leu Thr Asp Pro Pro Gly Val Lys Arg Val Tyr His
                           50                  55                  60

Ile Gln Pro Ser Leu Glu Asp Pro Phe Gln Pro Ser Ile Pro Ile
            65                  70                  75                  80

Thr Val Tyr Tyr Ala Val Leu Glu Arg Ala Cys Arg Ser Val Leu Leu
                           85                  90                  95

His Ala Pro Ser Glu Ala Pro Gln Ile Val Arg Gly Ala Ser Asp Glu
                           100                 105                 110

Ala Arg Lys His Thr Tyr Asn Leu Thr Ile Ala Trp Tyr Arg Met Gly
                           115                 120                 125

Asp Asn Cys Ala Ile Pro Ile Thr Val Met Glu Tyr Thr Glu Cys Pro
                           130                 135                 140

Tyr Asn Lys Ser Leu Gly Val Cys Pro Ile Arg Thr Gln Pro Arg Trp
            145                 150                 155                 160

Ser Tyr Tyr Asp Ser Phe Ser Ala Val Ser Glu Asp Asn Leu Gly Phe
                           165                 170                 175

Leu Met His Ala Pro Ala Phe Glu Thr Ala Gly Thr Tyr Leu Arg Leu
                           180                 185                 190

Val Lys Ile Asn Asp Trp Thr Glu Ile Thr Gln Phe Ile Leu Glu His
                           195                 200                 205

Arg Ala Arg Ala Ser Cys Lys Tyr Ala Leu Pro Leu Arg Ile Pro Pro
                           210                 215                 220

Ala Ala Cys Leu Thr Ser Lys Ala Tyr Gln Gln Gly Val Thr Val Asp
            225                 230                 235                 240

Ser Ile Gly Met Leu Pro Arg Phe Ile Pro Glu Asn Gln Arg Thr Val
                           245                 250                 255

Ala Leu Tyr Ser Leu Lys Ile Ala Gly Trp His Gly Pro Lys Pro Pro
                           260                 265                 270

Tyr Thr Ser Thr Leu Leu Pro Pro Glu Leu Ser Asp Thr Thr Asn Ala
                           275                 280                 285

Thr Gln Pro Glu Leu Val Pro Glu Asp Pro Glu Asp Ser Ala Leu Leu
                           290                 295                 300

Glu Asp Pro Ala Gly Thr Val Ser Ser Gln Ile Pro Pro Asn Trp His
            305                 310                 315                 320

Ile Pro Ser Ile Gln Asp Val Ala Pro His His Ala Pro Ala Ala Pro
                           325                 330                 335

Ser Asn Pro Gly Leu Ile Ile Gly Ala Leu Ala Gly Ser Thr Leu Ala
                           340                 345                 350

Val Leu Val Ile Gly Gly Ile Ala Phe Trp Val Arg Arg Arg Ala Gln
                           355                 360                 365

Met Ala Pro Lys Arg Leu Arg Leu Pro His Ile Arg Asp Asp Asp Ala
                           370                 375                 380

Pro Pro Ser His Gln Pro Leu Phe Tyr
            385                 390

<210> SEQ ID NO 6
<211> LENGTH: 261
<212> TYPE: PRT
<213> ORGANISM: Human herpesvirus 2
```

```
<400> SEQUENCE: 6

Met Ser Arg Arg Arg Gly Pro Arg Arg Gly Pro Arg Arg Pro
1               5                   10                  15

Arg Pro Gly Ala Pro Ala Val Pro Arg Pro Gly Ala Pro Ala Val Pro
            20                  25                  30

Arg Pro Gly Ala Leu Pro Thr Ala Asp Ser Gln Met Val Pro Ala Tyr
            35                  40                  45

Asp Ser Gly Thr Ala Val Glu Ser Ala Pro Ala Ala Ser Ser Leu Leu
        50                  55                  60

Arg Arg Trp Leu Leu Val Pro Gln Ala Asp Asp Ser Asp Asp Ala Asp
65              70                  75                  80

Tyr Ala Gly Asn Asp Asp Ala Glu Trp Ala Asn Ser Pro Pro Ser Glu
                85                  90                  95

Gly Gly Gly Lys Ala Pro Glu Ala Pro His Ala Ala Pro Ala Ala Ala
                100                 105                 110

Cys Pro Pro Pro Pro Arg Lys Glu Arg Gly Pro Gln Arg Pro Leu
            115                 120                 125

Pro Pro His Leu Ala Leu Arg Leu Arg Thr Thr Thr Glu Tyr Leu Ala
    130                 135                 140

Arg Leu Ser Leu Arg Arg Arg Pro Pro Ala Ser Pro Pro Ala Asp
145             150                 155                 160

Ala Pro Arg Gly Lys Val Cys Phe Ser Pro Arg Val Gln Val Arg His
                165                 170                 175

Leu Val Ala Trp Glu Thr Ala Ala Arg Leu Ala Arg Arg Gly Ser Trp
            180                 185                 190

Ala Arg Glu Arg Ala Asp Arg Asp Arg Phe Arg Arg Val Ala Ala
            195                 200                 205

Ala Glu Ala Val Ile Gly Pro Cys Leu Glu Pro Glu Ala Arg Ala Arg
        210                 215                 220

Ala Arg Ala Arg Ala Arg Ala His Glu Asp Gly Gly Pro Ala Glu Glu
225                 230                 235                 240

Glu Glu Ala Ala Ala Ala Arg Gly Ser Ser Ala Ala Ala Gly Pro
                245                 250                 255

Gly Arg Arg Ala Val
            260

<210> SEQ ID NO 7
<211> LENGTH: 825
<212> TYPE: PRT
<213> ORGANISM: Human herpesvirus 2

<400> SEQUENCE: 7

Met Glu Pro Arg Pro Gly Thr Ser Ser Arg Ala Asp Pro Gly Pro Glu
1               5                   10                  15

Arg Pro Pro Arg Gln Thr Pro Gly Thr Gln Pro Ala Ala Pro His Ala
            20                  25                  30

Trp Gly Met Leu Asn Asp Met Gln Trp Leu Ala Ser Ser Asp Ser Glu
            35                  40                  45

Glu Glu Thr Glu Val Gly Ile Ser Asp Asp Asp Leu His Arg Asp Ser
        50                  55                  60

Thr Ser Glu Ala Gly Ser Thr Asp Thr Glu Met Phe Glu Ala Gly Leu
65              70                  75                  80

Met Asp Ala Ala Thr Pro Pro Ala Arg Pro Pro Ala Glu Arg Gln Gly
                85                  90                  95
```

-continued

```
Ser Pro Thr Pro Ala Asp Ala Gln Gly Ser Cys Gly Gly Pro Val
            100                 105                 110

Gly Glu Glu Glu Ala Glu Ala Gly Gly Gly Asp Val Cys Ala Val
            115                 120                 125

Cys Thr Asp Glu Ile Ala Pro Pro Leu Arg Cys Gln Ser Phe Pro Cys
            130                 135                 140

Leu His Pro Phe Cys Ile Pro Cys Met Lys Thr Trp Ile Pro Leu Arg
145                 150                 155                 160

Asn Thr Cys Pro Leu Cys Asn Thr Pro Val Ala Tyr Leu Ile Val Gly
                165                 170                 175

Val Thr Ala Ser Gly Ser Phe Ser Thr Ile Pro Ile Val Asn Asp Pro
            180                 185                 190

Arg Thr Arg Val Glu Ala Glu Ala Ala Val Arg Ala Gly Thr Ala Val
            195                 200                 205

Asp Phe Ile Trp Thr Gly Asn Pro Arg Thr Ala Pro Arg Ser Leu Ser
            210                 215                 220

Leu Gly Gly His Thr Val Arg Ala Leu Ser Pro Thr Pro Pro Trp Pro
225                 230                 235                 240

Gly Thr Asp Asp Glu Asp Asp Asp Leu Ala Asp Val Asp Tyr Val Pro
                245                 250                 255

Pro Ala Pro Arg Arg Ala Pro Arg Arg Gly Gly Gly Gly Ala Gly Ala
            260                 265                 270

Thr Arg Gly Thr Ser Gln Pro Ala Ala Thr Arg Pro Ala Pro Pro Gly
            275                 280                 285

Ala Pro Arg Ser Ser Ser Ser Gly Gly Ala Pro Leu Arg Ala Gly Val
            290                 295                 300

Gly Ser Gly Ser Gly Gly Gly Pro Ala Val Ala Ala Val Val Pro Arg
305                 310                 315                 320

Val Ala Ser Leu Pro Pro Ala Ala Gly Gly Gly Arg Ala Gln Ala Arg
                325                 330                 335

Arg Val Gly Glu Asp Ala Ala Ala Glu Gly Arg Thr Pro Pro Ala
            340                 345                 350

Arg Gln Pro Arg Ala Ala Gln Glu Pro Pro Ile Val Ile Ser Asp Ser
            355                 360                 365

Pro Pro Pro Ser Pro Arg Arg Pro Ala Gly Pro Gly Pro Leu Ser Phe
            370                 375                 380

Val Ser Ser Ser Ala Gln Val Ser Ser Gly Pro Gly Gly Gly Gly
385                 390                 395                 400

Leu Pro Gln Ser Ser Gly Arg Ala Ala Arg Pro Arg Ala Ala Val Ala
                405                 410                 415

Pro Arg Val Arg Ser Pro Pro Arg Ala Ala Ala Pro Val Val Ser
            420                 425                 430

Ala Ser Ala Asp Ala Ala Gly Pro Ala Pro Pro Ala Val Pro Val Asp
            435                 440                 445

Ala His Arg Ala Pro Arg Ser Arg Met Thr Gln Ala Gln Thr Asp Thr
            450                 455                 460

Gln Ala Gln Ser Leu Gly Arg Ala Gly Ala Thr Asp Ala Arg Gly Ser
465                 470                 475                 480

Gly Gly Pro Gly Ala Glu Gly Pro Gly Val Pro Arg Gly Thr Asn
                485                 490                 495

Thr Pro Gly Ala Ala Pro His Ala Ala Glu Gly Ala Ala Ala Arg Pro
            500                 505                 510
```

```
Arg Lys Arg Arg Gly Ser Asp Ser Gly Pro Ala Ala Ser Ser Ala
            515                 520                 525

Ser Ser Ser Ala Ala Pro Arg Ser Pro Leu Ala Pro Gln Gly Val Gly
        530                 535                 540

Ala Lys Arg Ala Ala Pro Arg Arg Ala Pro Asp Ser Asp Ser Gly Asp
545                 550                 555                 560

Arg Gly His Gly Pro Leu Ala Pro Ala Ser Gly Ala Ala Pro Pro
                565                 570                 575

Ser Ala Ser Pro Ser Ser Gln Ala Ala Val Ala Ala Ala Ser Ser Ser
            580                 585                 590

Ser Ala Ser Ser Ser Ser Ala Ser Ser Ser Ala Ser Ser Ser Ser
        595                 600                 605

Ala Ser Ser Ser Ser Ala Ser Ser Ser Ala Ser Ser Ser Ala
    610                 615                 620

Ser Ser Ser Ala Gly Gly Ala Gly Gly Ser Val Ala Ser Ala Ser Gly
625                 630                 635                 640

Ala Gly Glu Arg Arg Glu Thr Ser Leu Gly Pro Arg Ala Ala Ala Pro
                645                 650                 655

Arg Gly Pro Arg Lys Cys Ala Arg Lys Thr Arg His Ala Glu Gly Gly
                660                 665                 670

Pro Glu Pro Gly Ala Arg Asp Pro Ala Pro Gly Leu Thr Arg Tyr Leu
            675                 680                 685

Pro Ile Ala Gly Val Ser Ser Val Val Ala Leu Ala Pro Tyr Val Asn
        690                 695                 700

Lys Thr Val Thr Gly Asp Cys Leu Pro Val Leu Asp Met Glu Thr Gly
705                 710                 715                 720

His Ile Gly Ala Tyr Val Val Leu Val Asp Gln Thr Gly Asn Val Ala
                725                 730                 735

Asp Leu Leu Arg Ala Ala Ala Pro Ala Trp Ser Arg Arg Thr Leu Leu
            740                 745                 750

Pro Glu His Ala Arg Asn Cys Val Arg Pro Pro Asp Tyr Pro Thr Pro
        755                 760                 765

Pro Ala Ser Glu Trp Asn Ser Leu Trp Met Thr Pro Val Gly Asn Met
770                 775                 780

Leu Phe Asp Gln Gly Thr Leu Val Gly Ala Leu Asp Phe His Gly Leu
785                 790                 795                 800

Arg Ser Arg His Pro Trp Ser Arg Glu Gln Gly Ala Pro Ala Pro Ala
                805                 810                 815

Gly Asp Ala Pro Ala Gly His Gly Glu
            820                 825

<210> SEQ ID NO 8
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ser Ala Glu Gln Arg Lys Lys Lys Thr Thr Thr Thr Thr Gln
1               5                   10                  15

Gly Arg Gly Ala Glu Val Ala Met Ala Asp Glu Asp Gly Gly Arg Leu
            20                  25                  30

Arg Ala Ala Ala Glu Thr Thr Gly Gly Pro Gly Ser Pro Asp Pro Ala
        35                  40                  45
```

Asp Gly Pro Pro Pro Thr Pro Asn Pro Asp Arg Arg Pro Ala Ala Arg
 50                  55                  60

Pro Gly Phe Gly Trp His Gly Gly Pro Glu Glu Asn Glu Asp Glu Ala
 65                  70                  75                  80

Asp Asp Ala Ala Ala Asp Ala Asp Ala Asp Glu Ala Ala Pro Ala Ser
                 85                  90                  95

Gly Glu Ala Val Asp Glu Pro Ala Ala Asp Gly Val Val Ser Pro Arg
                100                 105                 110

Gln Leu Ala Leu Leu Ala Ser Met Val Asp Glu Ala Val Arg Thr Ile
            115                 120                 125

Pro Ser Pro Pro Pro Glu Arg Asp Gly Ala Gln Glu Glu Ala Ala Arg
            130                 135                 140

Ser Pro Ser Pro Pro Arg Thr Pro Ser Met Arg Ala Asp Tyr Gly Glu
145                 150                 155                 160

Glu Asn Asp Asp Asp Asp Asp Asp Asp Asp Asp Arg Asp Ala
                165                 170                 175

Gly Arg Trp Val Arg Gly Pro Glu Thr Thr Ser Ala Val Arg Gly Ala
                180                 185                 190

Tyr Pro Asp Pro Met Ala Ser Leu Ser Pro Arg Pro Ala Pro Arg
            195                 200                 205

Arg His His His His His His Arg Arg Arg Ala Pro Arg Arg
210                 215                 220

Arg Ser Ala Ala Ser Asp Ser Ser Lys Ser Gly Ser Ser Ser Ser Ala
225                 230                 235                 240

Ser Ser Ala Ser Ser Ala Ser Ser Ser Ser Ala Ser Ala Ser
                245                 250                 255

Ser Ser Asp Asp Asp Asp Asp Asp Ala Ala Arg Ala Pro Ala Ser
                260                 265                 270

Ala Ala Asp His Ala Ala Gly Gly Thr Leu Gly Ala Asp Asp Glu Glu
            275                 280                 285

Ala Gly Val Pro Ala Arg Ala Pro Gly Ala Ala Pro Arg Pro Ser Pro
            290                 295                 300

Pro Arg Ala Glu Pro Ala Pro Ala Arg Thr Pro Ala Ala Thr Ala Gly
305                 310                 315                 320

Arg Leu Glu Arg Arg Ala Arg Ala Ala Val Ala Gly Arg Asp Ala
                325                 330                 335

Thr Gly Arg Phe Thr Ala Gly Arg Pro Arg Arg Val Glu Leu Asp Ala
                340                 345                 350

Asp Ala Ala Ser Gly Ala Phe Tyr Ala Arg Tyr Arg Asp Gly Tyr Val
            355                 360                 365

Ser Gly Glu Pro Trp Pro Gly Ala Gly Pro Pro Pro Gly Arg Val
            370                 375                 380

Leu Tyr Gly Gly Leu Gly Asp Ser Arg Pro Gly Leu Trp Gly Ala Pro
385                 390                 395                 400

<210> SEQ ID NO 9
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ser Ser Ala Ala Ala Ala Ala Ala Asp Leu Leu Phe Gln Asn Gln Ser

```
   1               5                  10                 15
Leu Arg Pro Leu Leu Ala Asp Thr Val Ala Ala Asp Ser Leu Ala
                20                 25                 30

Ala Pro Ala Ser Ala Pro Arg Glu Ala Arg Lys Arg Lys Ser Pro Ala
                35                 40                 45

Pro Ala Arg Ala Pro Pro Gly Ala Pro Arg Pro Lys Lys Ser
                50                 55                 60

Arg Ala Asp Ala Pro Arg Pro Ala Ala Pro Pro Ala Gly Ala Ala
65                  70                 75                 80

Pro Pro Ala Pro Pro Thr Pro Pro Arg Pro Pro Arg Pro Ala Ala
                    85                 90                 95

Leu Thr Arg Arg Pro Ala Glu Gly Pro Asp Pro Gln Gly Gly Trp Arg
                100                105                110

Arg Gln Pro Pro Gly Pro Ser His Thr Pro Ala Pro Ser Ala Ala Ala
                115                120                125

Leu Glu Ala Tyr Cys Ala Pro Arg Ala Val Ala Glu Leu Thr Asp His
                130                135                140

Pro Leu Phe Pro Ala Pro Trp Arg Pro Ala Leu Met Phe Asp Pro Arg
145                 150                155                160

Ala Leu Ala Ser Leu Ala Ala Arg Cys Ala Ala Pro Pro Gly Gly
                165                170                175

Ala Pro Ala Ala Phe Gly Pro Leu Arg Ala Ser Gly Pro Leu Arg Arg
                180                185                190

Ala Ala Ala Trp Met Arg Gln Val Pro Asp Pro Glu Asp Val Arg Val
                195                200                205

Val Ile Leu Tyr Ser Pro Leu Pro Gly Glu Asp Leu Ala Ala Gly Arg
                210                215                220

Ala Gly Gly Gly Pro Pro Glu Trp Ser Ala Glu Arg Gly Gly Leu
225                 230                235                240

Ser Cys Leu Leu Ala Ala Leu Gly Asn Arg Leu Cys Gly Pro Ala Thr
                245                250                255

Ala Ala Trp Ala Gly Asn Trp Thr Gly Ala Pro Asp Val Ser Ala Leu
                260                265                270

Gly Ala Gln
        275

<210> SEQ ID NO 10
<211> LENGTH: 311
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Trp Ala Gly Asn Trp Thr Gly Ala Pro Asp Val Ser Ala Leu Gly Ala
1               5                  10                 15

Gln Gly Val Leu Leu Ser Thr Arg Asp Leu Ala Phe Ala Gly Ala
                20                 25                 30

Val Glu Phe Leu Gly Leu Leu Ala Gly Ala Cys Asp Arg Arg Leu Ile
                35                 40                 45

Val Val Asn Ala Val Arg Ala Ala Asp Trp Pro Ala Asp Gly Pro Val
                50                 55                 60

Val Ser Arg Gln His Ala Tyr Leu Ala Cys Glu Val Leu Pro Ala Val
65                  70                 75                 80
```

```
Gln Cys Ala Val Arg Trp Pro Ala Ala Arg Asp Leu Arg Arg Thr Val
             85                  90                  95

Leu Ala Ser Gly Arg Val Phe Gly Pro Gly Val Phe Ala Arg Val Glu
            100                 105                 110

Ala Ala His Ala Arg Leu Tyr Pro Asp Ala Pro Pro Leu Arg Leu Cys
            115                 120                 125

Arg Gly Ala Asn Val Arg Tyr Arg Val Arg Thr Arg Phe Gly Pro Asp
        130                 135                 140

Thr Leu Val Pro Met Ser Pro Arg Glu Tyr Arg Ala Val Leu Pro
145                 150                 155                 160

Ala Leu Asp Gly Arg Ala Ala Ser Gly Ala Gly Asp Ala Met Ala
                165                 170                 175

Pro Gly Ala Pro Asp Phe Cys Glu Asp Glu Ala His Ser His Arg Ala
            180                 185                 190

Cys Ala Arg Trp Gly Leu Gly Ala Pro Leu Arg Pro Val Tyr Val Ala
        195                 200                 205

Leu Gly Arg Asp Ala Val Arg Gly Gly Pro Ala Glu Leu Arg Gly Pro
        210                 215                 220

Arg Arg Glu Phe Cys Ala Arg Ala Leu Leu Glu Pro Asp Gly Asp Ala
225                 230                 235                 240

Pro Pro Leu Val Leu Arg Asp Asp Ala Asp Ala Gly Pro Pro Pro Gln
                245                 250                 255

Ile Arg Trp Ala Ser Ala Ala Gly Arg Ala Gly Thr Val Leu Ala Ala
            260                 265                 270

Ala Gly Gly Gly Val Glu Val Val Gly Thr Ala Ala Gly Leu Ala Thr
        275                 280                 285

Pro Pro Arg Arg Glu Pro Val Asp Met Asp Ala Glu Leu Glu Asp Asp
        290                 295                 300

Asp Asp Gly Leu Phe Gly Glu
305                 310

<210> SEQ ID NO 11
<211> LENGTH: 569
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ser Ser Ala Ala Ala Ala Ala Asp Leu Leu Phe Gln Asn Gln Ser
1               5                  10                  15

Leu Arg Pro Leu Leu Ala Asp Thr Val Ala Ala Ala Asp Ser Leu Ala
            20                  25                  30

Ala Pro Ala Ser Ala Pro Arg Glu Ala Arg Lys Arg Lys Ser Pro Ala
        35                  40                  45

Pro Ala Arg Ala Pro Pro Gly Gly Ala Pro Arg Pro Pro Lys Lys Ser
    50                  55                  60

Arg Ala Asp Ala Pro Arg Pro Ala Ala Pro Pro Ala Gly Ala Ala
65              70                  75                  80

Pro Pro Ala Pro Pro Thr Pro Pro Arg Pro Arg Pro Ala Ala
                85                  90                  95

Leu Thr Arg Arg Pro Ala Glu Gly Pro Asp Pro Gln Gly Gly Trp Arg
            100                 105                 110

Arg Gln Pro Pro Gly Pro Ser His Thr Pro Ala Pro Ser Ala Ala Ala
        115                 120                 125
```

```
Leu Glu Ala Tyr Cys Ala Pro Arg Ala Val Ala Glu Leu Thr Asp His
    130                 135                 140
Pro Leu Phe Pro Ala Pro Trp Arg Pro Ala Leu Met Phe Asp Pro Arg
145                 150                 155                 160
Ala Leu Ala Ser Leu Ala Ala Arg Cys Ala Ala Pro Pro Gly Gly
                165                 170                 175
Ala Pro Ala Ala Phe Gly Pro Leu Arg Ala Ser Gly Pro Leu Arg Arg
                180                 185                 190
Ala Ala Ala Trp Met Arg Gln Val Pro Asp Pro Glu Asp Val Arg Val
            195                 200                 205
Val Ile Leu Tyr Ser Pro Leu Pro Gly Glu Asp Leu Ala Ala Gly Arg
    210                 215                 220
Ala Gly Gly Pro Pro Glu Trp Ser Ala Glu Arg Gly Gly Leu
225                 230                 235                 240
Ser Cys Leu Leu Ala Ala Leu Gly Asn Arg Leu Cys Gly Pro Ala Thr
                245                 250                 255
Ala Ala Trp Ala Gly Asn Trp Thr Gly Ala Pro Asp Val Ser Ala Leu
            260                 265                 270
Gly Ala Gln Gly Val Leu Leu Leu Ser Thr Arg Asp Leu Ala Phe Ala
    275                 280                 285
Gly Ala Val Glu Phe Leu Gly Leu Leu Ala Gly Ala Cys Asp Arg Arg
290                 295                 300
Leu Ile Val Val Asn Ala Val Arg Ala Ala Asp Trp Pro Ala Asp Gly
305                 310                 315                 320
Pro Val Val Ser Arg Gln His Ala Tyr Leu Ala Cys Glu Val Leu Pro
                325                 330                 335
Ala Val Gln Cys Ala Val Arg Trp Pro Ala Ala Arg Asp Leu Arg Arg
            340                 345                 350
Thr Val Leu Ala Ser Gly Arg Val Phe Gly Pro Gly Val Phe Ala Arg
    355                 360                 365
Val Glu Ala Ala His Ala Arg Leu Tyr Pro Asp Ala Pro Pro Leu Arg
370                 375                 380
Leu Cys Arg Gly Ala Asn Val Arg Tyr Arg Val Arg Thr Arg Phe Gly
385                 390                 395                 400
Pro Asp Thr Leu Val Pro Met Ser Pro Arg Glu Tyr Arg Arg Ala Val
                405                 410                 415
Leu Pro Ala Leu Asp Gly Arg Ala Ala Ser Gly Ala Gly Asp Ala
            420                 425                 430
Met Ala Pro Gly Ala Pro Asp Phe Cys Glu Asp Glu Ala His Ser His
    435                 440                 445
Arg Ala Cys Ala Arg Trp Gly Leu Gly Ala Pro Leu Arg Pro Val Tyr
450                 455                 460
Val Ala Leu Gly Arg Asp Ala Val Arg Gly Gly Pro Ala Glu Leu Arg
465                 470                 475                 480
Gly Pro Arg Arg Glu Phe Cys Ala Arg Ala Leu Leu Glu Pro Asp Gly
                485                 490                 495
Asp Ala Pro Pro Leu Val Leu Arg Asp Asp Ala Asp Ala Gly Pro Pro
            500                 505                 510
Pro Gln Ile Arg Trp Ala Ser Ala Ala Gly Arg Ala Gly Thr Val Leu
    515                 520                 525
Ala Ala Ala Gly Gly Gly Val Glu Val Val Gly Thr Ala Ala Gly Leu
530                 535                 540
```

-continued

Ala Thr Pro Pro Arg Arg Glu Pro Val Asp Met Asp Ala Glu Leu Glu
545                 550                 555                 560

Asp Asp Asp Asp Gly Leu Phe Gly Glu
            565

<210> SEQ ID NO 12
<211> LENGTH: 543
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Thr Ala Gly Arg Pro Arg Arg Val Glu Leu Asp Ala Asp Ala Ala Ser
1               5                   10                  15

Gly Ala Phe Tyr Ala Arg Tyr Arg Asp Gly Tyr Val Ser Gly Glu Pro
            20                  25                  30

Trp Pro Gly Ala Gly Pro Pro Pro Gly Arg Val Leu Tyr Gly Gly
        35                  40                  45

Leu Gly Asp Ser Arg Pro Gly Leu Trp Gly Ala Pro Glu Ala Glu Glu
50                  55                  60

Ala Arg Ala Arg Phe Glu Ala Ser Gly Ala Pro Ala Pro Val Trp Ala
65                  70                  75                  80

Pro Glu Leu Gly Asp Ala Ala Gln Gln Tyr Ala Leu Ile Thr Arg Leu
                85                  90                  95

Leu Tyr Thr Pro Asp Ala Glu Ala Met Gly Trp Leu Gln Asn Pro Arg
            100                 105                 110

Val Ala Pro Gly Asp Val Ala Leu Asp Gln Ala Cys Phe Arg Ile Ser
        115                 120                 125

Gly Ala Ala Arg Asn Ser Ser Ser Phe Ile Ser Gly Ser Val Ala Arg
130                 135                 140

Ala Val Pro His Leu Gly Tyr Ala Met Ala Ala Gly Arg Phe Gly Trp
145                 150                 155                 160

Gly Leu Ala His Val Ala Ala Val Ala Met Ser Arg Arg Tyr Asp
                165                 170                 175

Arg Ala Gln Lys Gly Phe Leu Leu Thr Ser Leu Arg Arg Ala Tyr Ala
            180                 185                 190

Pro Leu Leu Ala Arg Glu Asn Ala Ala Leu Thr Gly Ala Arg Thr Pro
        195                 200                 205

Asp Asp Gly Gly Asp Ala Asn Arg His Asp Gly Asp Ala Arg Gly
210                 215                 220

Lys Pro Ala Ala Ala Ala Pro Leu Pro Ser Ala Ala Ala Ser Pro
225                 230                 235                 240

Ala Asp Glu Arg Ala Val Pro Ala Gly Tyr Gly Ala Ala Gly Val Leu
                245                 250                 255

Ala Ala Leu Gly Arg Leu Ser Ala Ala Pro Ala Ser Ala Pro Ala Gly
            260                 265                 270

Ala Asp Asp Asp Asp Asp Asp Gly Ala Gly Gly Gly Gly Gly
        275                 280                 285

Arg Arg Ala Glu Ala Gly Arg Val Ala Val Glu Cys Leu Ala Ala Cys
290                 295                 300

Arg Gly Ile Leu Glu Ala Leu Ala Glu Gly Phe Asp Gly Asp Leu Ala
305                 310                 315                 320

Ala Val Pro Gly Leu Ala Gly Ala Arg Pro Ala Ala Pro Pro Arg Pro
                325                 330                 335

-continued

```
Gly Pro Ala Gly Ala Ala Pro Pro His Ala Asp Ala Pro Arg Leu
            340                 345                 350

Arg Ala Trp Leu Arg Glu Leu Arg Phe Val Arg Asp Ala Leu Val Leu
        355                 360                 365

Met Arg Leu Arg Gly Asp Leu Arg Val Ala Gly Gly Ser Glu Ala Ala
370                 375                 380

Val Ala Ala Val Arg Ala Val Ser Leu Val Ala Gly Ala Leu Gly Pro
385                 390                 395                 400

Ala Leu Pro Arg Ser Pro Arg Leu Leu Ser Ala Ala Ala Ala Ala
            405                 410                 415

Ala Asp Leu Leu Phe Gln Asn Gln Ser Leu Arg Pro Leu Leu Ala Asp
            420                 425                 430

Thr Val Ala Ala Asp Ser Leu Ala Ala Pro Ala Ser Ala Pro Arg
            435                 440                 445

Glu Ala Arg Lys Arg Lys Ser Pro Ala Pro Ala Arg Ala Pro Pro Gly
450                 455                 460

Gly Ala Pro Arg Pro Pro Lys Lys Ser Arg Ala Asp Ala Pro Arg Pro
465                 470                 475                 480

Ala Ala Ala Pro Pro Ala Gly Ala Ala Pro Pro Ala Pro Pro Thr Pro
            485                 490                 495

Pro Pro Arg Pro Pro Arg Pro Ala Ala Leu Thr Arg Arg Pro Ala Glu
            500                 505                 510

Gly Pro Asp Pro Gln Gly Gly Trp Arg Arg Gln Pro Pro Gly Pro Ser
            515                 520                 525

His Thr Pro Ala Pro Ser Ala Ala Leu Glu Ala Tyr Cys Ala
            530                 535                 540

<210> SEQ ID NO 13
<211> LENGTH: 544
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Ala Ala Asp Ser Leu Ala Ala Pro Ala Ser Ala Pro Arg Glu Ala
1               5                   10                  15

Arg Lys Arg Lys Ser Pro Ala Pro Ala Arg Ala Pro Pro Gly Gly Ala
            20                  25                  30

Pro Arg Pro Pro Lys Lys Ser Arg Ala Asp Ala Pro Arg Pro Ala Ala
        35                  40                  45

Ala Pro Pro Ala Gly Ala Ala Pro Pro Ala Pro Pro Thr Pro Pro Pro
50                  55                  60

Arg Pro Pro Arg Pro Ala Ala Leu Thr Arg Arg Pro Ala Glu Gly Pro
65                  70                  75                  80

Asp Pro Gln Gly Gly Trp Arg Arg Gln Pro Pro Gly Pro Ser His Thr
                85                  90                  95

Pro Ala Pro Ser Ala Ala Leu Glu Ala Tyr Cys Ala Pro Arg Ala
            100                 105                 110

Val Ala Glu Leu Thr Asp His Pro Leu Phe Pro Ala Pro Trp Arg Pro
        115                 120                 125

Ala Leu Met Phe Asp Pro Arg Ala Leu Ala Ser Leu Ala Ala Arg Cys
    130                 135                 140

Ala Ala Pro Pro Pro Gly Gly Ala Pro Ala Ala Phe Gly Pro Leu Arg
```

```
            145                 150                 155                 160
Ala Ser Gly Pro Leu Arg Arg Ala Ala Ala Trp Met Arg Gln Val Pro
                165                 170                 175

Asp Pro Glu Asp Val Arg Val Val Ile Leu Tyr Ser Pro Leu Pro Gly
            180                 185                 190

Glu Asp Leu Ala Ala Gly Arg Ala Gly Gly Pro Pro Glu Trp
        195                 200                 205

Ser Ala Glu Arg Gly Gly Leu Ser Cys Leu Leu Ala Ala Leu Gly Asn
    210                 215                 220

Arg Leu Cys Gly Pro Ala Thr Ala Ala Trp Ala Gly Asn Trp Thr Gly
225                 230                 235                 240

Ala Pro Asp Val Ser Ala Leu Gly Ala Gln Gly Val Leu Leu Leu Ser
                245                 250                 255

Thr Arg Asp Leu Ala Phe Ala Gly Ala Val Glu Phe Leu Gly Leu Leu
                260                 265                 270

Ala Gly Ala Cys Asp Arg Arg Leu Ile Val Val Asn Ala Val Arg Ala
            275                 280                 285

Ala Asp Trp Pro Ala Asp Gly Pro Val Val Ser Arg Gln His Ala Tyr
        290                 295                 300

Leu Ala Cys Glu Val Leu Pro Ala Val Gln Cys Ala Val Arg Trp Pro
305                 310                 315                 320

Ala Ala Arg Asp Leu Arg Arg Thr Val Leu Ala Ser Gly Arg Val Phe
                325                 330                 335

Gly Pro Gly Val Phe Ala Arg Val Glu Ala Ala His Ala Arg Leu Tyr
            340                 345                 350

Pro Asp Ala Pro Pro Leu Arg Leu Cys Arg Gly Ala Asn Val Arg Tyr
        355                 360                 365

Arg Val Arg Thr Arg Phe Gly Pro Asp Thr Leu Val Pro Met Ser Pro
370                 375                 380

Arg Glu Tyr Arg Arg Ala Val Leu Pro Ala Leu Asp Gly Arg Ala Ala
385                 390                 395                 400

Ala Ser Gly Ala Gly Asp Ala Met Ala Pro Gly Ala Pro Asp Phe Cys
                405                 410                 415

Glu Asp Glu Ala His Ser His Arg Ala Cys Ala Arg Trp Gly Leu Gly
            420                 425                 430

Ala Pro Leu Arg Pro Val Tyr Val Ala Leu Gly Arg Asp Ala Val Arg
        435                 440                 445

Gly Gly Pro Ala Glu Leu Arg Gly Pro Arg Arg Glu Phe Cys Ala Arg
    450                 455                 460

Ala Leu Leu Glu Pro Asp Gly Asp Ala Pro Leu Val Leu Arg Asp
465                 470                 475                 480

Asp Ala Asp Ala Gly Pro Pro Gln Ile Arg Trp Ala Ser Ala Ala
                485                 490                 495

Gly Arg Ala Gly Thr Val Leu Ala Ala Gly Gly Val Glu Val
            500                 505                 510

Val Gly Thr Ala Ala Gly Leu Ala Thr Pro Pro Arg Arg Glu Pro Val
        515                 520                 525

Asp Met Asp Ala Glu Leu Glu Asp Asp Asp Gly Leu Phe Gly Glu
    530                 535                 540

<210> SEQ ID NO 14
<211> LENGTH: 1109
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 14

His His His His His His Arg Arg Arg Ala Pro Arg Arg
1               5                   10                  15

Ser Ala Ala Ser Asp Ser Ser Lys Ser Gly Ser Ser Ser Ala Ser
            20                  25                  30

Ser Ala Ser Ser Ser Ala Ser Ser Ser Ser Ala Ser Ala Ser Ser
        35                  40                  45

Ser Asp Asp Asp Asp Asp Asp Ala Ala Arg Ala Pro Ala Ser Ala
    50                  55                  60

Ala Asp His Ala Ala Gly Gly Thr Leu Gly Ala Asp Glu Glu Ala
65                  70                  75                  80

Gly Val Pro Ala Arg Ala Pro Gly Ala Ala Pro Arg Pro Ser Pro Pro
                85                  90                  95

Arg Ala Glu Pro Ala Pro Ala Arg Thr Pro Ala Ala Thr Ala Gly Arg
            100                 105                 110

Leu Glu Arg Arg Arg Ala Arg Ala Ala Val Ala Gly Arg Asp Ala Thr
        115                 120                 125

Gly Arg Phe Thr Ala Gly Arg Pro Arg Arg Val Glu Leu Asp Ala Asp
    130                 135                 140

Ala Ala Ser Gly Ala Phe Tyr Ala Arg Tyr Arg Asp Gly Tyr Val Ser
145                 150                 155                 160

Gly Glu Pro Trp Pro Gly Ala Gly Pro Pro Pro Gly Arg Val Leu
                165                 170                 175

Tyr Gly Gly Leu Gly Asp Ser Arg Pro Gly Leu Trp Gly Ala Pro Glu
            180                 185                 190

Ala Glu Glu Ala Arg Ala Arg Phe Glu Ala Ser Gly Ala Pro Ala Pro
        195                 200                 205

Val Trp Ala Pro Glu Leu Gly Asp Ala Ala Gln Gln Tyr Ala Leu Ile
    210                 215                 220

Thr Arg Leu Leu Tyr Thr Pro Asp Ala Glu Ala Met Gly Trp Leu Gln
225                 230                 235                 240

Asn Pro Arg Val Ala Pro Gly Asp Val Ala Leu Asp Gln Ala Cys Phe
                245                 250                 255

Arg Ile Ser Gly Ala Ala Arg Asn Ser Ser Phe Ile Ser Gly Ser
            260                 265                 270

Val Ala Arg Ala Val Pro His Leu Gly Tyr Ala Met Ala Ala Gly Arg
        275                 280                 285

Phe Gly Trp Gly Leu Ala His Val Ala Ala Val Ala Met Ser Arg
290                 295                 300

Arg Tyr Asp Arg Ala Gln Lys Gly Phe Leu Leu Thr Ser Leu Arg Arg
305                 310                 315                 320

Ala Tyr Ala Pro Leu Leu Ala Arg Glu Asn Ala Ala Leu Thr Gly Ala
                325                 330                 335

Arg Thr Pro Asp Asp Gly Gly Asp Ala Asn Arg His Asp Gly Asp Asp
            340                 345                 350

Ala Arg Gly Lys Pro Ala Ala Ala Ala Pro Leu Pro Ser Ala Ala
        355                 360                 365

Ala Ser Pro Ala Asp Glu Arg Ala Val Pro Ala Gly Tyr Gly Ala Ala
    370                 375                 380

Gly Val Leu Ala Ala Leu Gly Arg Leu Ser Ala Ala Pro Ala Ser Ala
```

```
            385                 390                 395                 400
        Pro Ala Gly Ala Asp Asp Asp Asp Asp Gly Ala Gly Gly
                        405                 410                 415
        Gly Gly Gly Arg Arg Ala Glu Ala Gly Arg Val Ala Val Glu Cys Leu
                        420                 425                 430
        Ala Ala Cys Arg Gly Ile Leu Glu Ala Leu Ala Glu Gly Phe Asp Gly
                        435                 440                 445
        Asp Leu Ala Ala Val Pro Gly Leu Ala Gly Ala Arg Pro Ala Ala Pro
                        450                 455                 460
        Pro Arg Pro Gly Pro Ala Gly Ala Ala Pro Pro His Ala Asp Ala
        465                 470                 475                 480
        Pro Arg Leu Arg Ala Trp Leu Arg Glu Leu Arg Phe Val Arg Asp Ala
                        485                 490                 495
        Leu Val Leu Met Arg Leu Arg Gly Asp Leu Arg Val Ala Gly Gly Ser
                        500                 505                 510
        Glu Ala Ala Val Ala Ala Val Arg Ala Val Ser Leu Val Ala Gly Ala
                        515                 520                 525
        Leu Gly Pro Ala Leu Pro Arg Ser Pro Arg Leu Leu Ser Ser Ala Ala
        530                 535                 540
        Ala Ala Ala Ala Asp Leu Leu Phe Gln Asn Gln Ser Leu Arg Pro Leu
        545                 550                 555                 560
        Leu Ala Asp Thr Val Ala Ala Ala Asp Ser Leu Ala Ala Pro Ala Ser
                        565                 570                 575
        Ala Pro Arg Glu Ala Arg Lys Arg Lys Ser Pro Ala Pro Ala Arg Ala
                        580                 585                 590
        Pro Pro Gly Gly Ala Pro Arg Pro Pro Lys Lys Ser Arg Ala Asp Ala
                        595                 600                 605
        Pro Arg Pro Ala Ala Ala Pro Pro Ala Gly Ala Ala Pro Pro Ala Pro
                        610                 615                 620
        Pro Thr Pro Pro Pro Arg Pro Pro Arg Pro Ala Ala Leu Thr Arg Arg
        625                 630                 635                 640
        Pro Ala Glu Gly Pro Asp Pro Gln Gly Gly Trp Arg Arg Gln Pro Pro
                        645                 650                 655
        Gly Pro Ser His Thr Pro Ala Pro Ser Ala Ala Ala Leu Glu Ala Tyr
                        660                 665                 670
        Cys Ala Pro Arg Ala Val Ala Glu Leu Thr Asp His Pro Leu Phe Pro
                        675                 680                 685
        Ala Pro Trp Arg Pro Ala Leu Met Phe Asp Pro Arg Ala Leu Ala Ser
                        690                 695                 700
        Leu Ala Ala Arg Cys Ala Ala Pro Pro Gly Gly Ala Pro Ala Ala
        705                 710                 715                 720
        Phe Gly Pro Leu Arg Ala Ser Gly Pro Leu Arg Ala Ala Ala Trp
                        725                 730                 735
        Met Arg Gln Val Pro Asp Pro Glu Asp Val Arg Val Val Ile Leu Tyr
                        740                 745                 750
        Ser Pro Leu Pro Gly Glu Asp Leu Ala Ala Gly Arg Ala Gly Gly Gly
                        755                 760                 765
        Pro Pro Pro Glu Trp Ser Ala Glu Arg Gly Gly Leu Ser Cys Leu Leu
                        770                 775                 780
        Ala Ala Leu Gly Asn Arg Leu Cys Gly Pro Ala Thr Ala Ala Trp Ala
        785                 790                 795                 800
        Gly Asn Trp Thr Gly Ala Pro Asp Val Ser Ala Leu Gly Ala Gln Gly
                        805                 810                 815
```

Val Leu Leu Leu Ser Thr Arg Asp Leu Ala Phe Ala Gly Ala Val Glu
            820                 825                 830

Phe Leu Gly Leu Leu Ala Gly Ala Cys Asp Arg Arg Leu Ile Val Val
            835                 840                 845

Asn Ala Val Arg Ala Ala Asp Trp Pro Ala Asp Gly Pro Val Val Ser
850                 855                 860

Arg Gln His Ala Tyr Leu Ala Cys Glu Val Leu Pro Ala Val Gln Cys
865                 870                 875                 880

Ala Val Arg Trp Pro Ala Arg Asp Leu Arg Arg Thr Val Leu Ala
            885                 890                 895

Ser Gly Arg Val Phe Gly Pro Gly Val Phe Ala Arg Val Glu Ala Ala
            900                 905                 910

His Ala Arg Leu Tyr Pro Asp Ala Pro Pro Leu Arg Leu Cys Arg Gly
            915                 920                 925

Ala Asn Val Arg Tyr Arg Val Arg Thr Arg Phe Gly Pro Asp Thr Leu
            930                 935                 940

Val Pro Met Ser Pro Arg Glu Tyr Arg Arg Ala Val Leu Pro Ala Leu
945                 950                 955                 960

Asp Gly Arg Ala Ala Ser Gly Ala Gly Asp Ala Met Ala Pro Gly
            965                 970                 975

Ala Pro Asp Phe Cys Glu Asp Glu Ala His Ser His Arg Ala Cys Ala
            980                 985                 990

Arg Trp Gly Leu Gly Ala Pro Leu Arg Pro Val Tyr Val Ala Leu Gly
            995                 1000                1005

Arg Asp Ala Val Arg Gly Gly Pro Ala Glu Leu Arg Gly Pro Arg
            1010                1015                1020

Arg Glu Phe Cys Ala Arg Ala Leu Leu Glu Pro Asp Gly Asp Ala
            1025                1030                1035

Pro Pro Leu Val Leu Arg Asp Ala Asp Ala Gly Pro Pro Pro
            1040                1045                1050

Gln Ile Arg Trp Ala Ser Ala Ala Gly Arg Ala Gly Thr Val Leu
            1055                1060                1065

Ala Ala Ala Gly Gly Gly Val Glu Val Val Gly Thr Ala Ala Gly
            1070                1075                1080

Leu Ala Thr Pro Pro Arg Arg Glu Pro Val Asp Met Asp Ala Glu
            1085                1090                1095

Leu Glu Asp Asp Asp Asp Gly Leu Phe Gly Glu
            1100                1105

<210> SEQ ID NO 15
<211> LENGTH: 1164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Ser Ala Glu Gln Arg Lys Lys Lys Thr Thr Thr Thr Thr Gln
1               5                   10                  15

Gly Arg Gly Ala Glu Val Ala Met Ala Asp Glu Asp Gly Gly Arg Leu
            20                  25                  30

Arg Ala Ala Ala Glu Thr Thr Gly Gly Pro Gly Ser Pro Asp Pro Ala
        35                  40                  45

Asp Gly Pro Pro Pro Thr Pro Asn Pro Asp Arg Arg Pro Ala Ala Arg

```
                50                  55                  60
Pro Gly Phe Gly Trp His Gly Gly Pro Glu Glu Asn Glu Asp Glu Ala
65                  70                  75                  80

Asp Asp Ala Ala Ala Asp Ala Asp Ala Asp Glu Ala Ala Pro Ala Ser
                    85                  90                  95

Gly Glu Ala Val Asp Glu Pro Ala Ala Asp Gly Val Val Ser Pro Arg
                    100                 105                 110

Gln Leu Ala Leu Leu Ala Ser Met Val Asp Glu Ala Val Arg Thr Ile
                    115                 120                 125

Pro Ser Pro Pro Pro Glu Arg Asp Gly Ala Gln Glu Glu Ala Ala Arg
                    130                 135                 140

Ser Pro Ser Pro Pro Arg Thr Pro Ser Met Arg Ala Asp Tyr Gly Glu
145                 150                 155                 160

Glu Asn Asp Asp Asp Asp Asp Asp Asp Asp Asp Asp Arg Asp Ala
                    165                 170                 175

Gly Arg Trp Val Arg Gly Pro Glu Thr Thr Ser Ala Val Arg Gly Ala
                    180                 185                 190

Tyr Pro Asp Pro Met Ala Ser Leu Ser Pro Arg Pro Ala Pro Arg
                    195                 200                 205

Arg His His His His His His Arg Arg Arg Ala Pro Arg Arg
                    210                 215                 220

Arg Ser Ala Ala Ser Asp Ser Ser Lys Ser Gly Ser Ser Ser Ala
225                 230                 235                 240

Ser Ser Ala Ser Ser Ser Ala Ser Ser Ser Ser Ala Ser Ala Ser
                    245                 250                 255

Ser Ser Asp Asp Asp Asp Asp Ala Ala Arg Ala Pro Ala Ser
                    260                 265                 270

Ala Ala Asp His Ala Ala Gly Gly Thr Leu Gly Ala Asp Asp Glu Glu
                    275                 280                 285

Ala Gly Val Pro Ala Arg Ala Pro Gly Ala Ala Pro Arg Pro Ser Pro
                    290                 295                 300

Pro Arg Ala Glu Pro Ala Pro Ala Arg Thr Pro Ala Ala Thr Ala Gly
305                 310                 315                 320

Arg Leu Glu Arg Arg Arg Ala Arg Ala Ala Val Ala Gly Arg Asp Ala
                    325                 330                 335

Thr Gly Arg Phe Thr Ala Gly Arg Pro Arg Arg Val Glu Leu Asp Ala
                    340                 345                 350

Asp Ala Ala Ser Gly Ala Phe Tyr Ala Arg Tyr Arg Asp Gly Tyr Val
                    355                 360                 365

Ser Gly Glu Pro Trp Pro Gly Ala Gly Pro Pro Pro Gly Arg Val
                    370                 375                 380

Leu Tyr Gly Gly Leu Gly Ala Arg Thr Pro Asp Gly Gly Asp Ala
385                 390                 395                 400

Asn Arg His Asp Gly Asp Asp Ala Arg Gly Lys Pro Ala Ala Ala
                    405                 410                 415

Ala Pro Leu Pro Ser Ala Ala Ser Pro Ala Asp Glu Arg Ala Val
                    420                 425                 430

Pro Ala Gly Tyr Gly Ala Ala Gly Val Leu Ala Ala Leu Gly Arg Leu
                    435                 440                 445

Ser Ala Ala Pro Ala Ser Ala Pro Ala Gly Ala Asp Asp Asp Asp
                    450                 455                 460

Asp Asp Gly Ala Gly Gly Gly Gly Gly Arg Arg Ala Glu Ala Gly
465                 470                 475                 480
```

```
Arg Val Ala Val Glu Cys Leu Ala Ala Cys Arg Gly Ile Leu Glu Ala
                485                 490                 495

Leu Ala Glu Gly Phe Asp Gly Asp Leu Ala Ala Val Pro Gly Leu Ala
            500                 505                 510

Gly Ala Arg Pro Ala Ala Pro Pro Arg Pro Gly Pro Ala Gly Ala Ala
        515                 520                 525

Ala Pro Pro His Ala Asp Ala Pro Arg Leu Arg Ala Trp Leu Arg Glu
    530                 535                 540

Leu Arg Phe Val Arg Asp Ala Leu Val Leu Met Arg Leu Arg Gly Asp
545                 550                 555                 560

Leu Arg Val Ala Gly Gly Ser Glu Ala Ala Val Ala Ala Val Arg Ala
                565                 570                 575

Val Ser Leu Val Ala Gly Ala Leu Gly Pro Ala Leu Pro Arg Ser Pro
            580                 585                 590

Arg Leu Leu Ser Ser Ala Ala Ala Ala Ala Asp Leu Leu Phe Gln
        595                 600                 605

Asn Gln Ser Leu Arg Pro Leu Leu Ala Asp Thr Val Ala Ala Ala Asp
    610                 615                 620

Ser Leu Ala Ala Pro Ala Ser Ala Pro Arg Glu Ala Arg Lys Arg Lys
625                 630                 635                 640

Ser Pro Ala Pro Ala Arg Ala Pro Pro Gly Ala Pro Arg Pro Pro
                645                 650                 655

Lys Lys Ser Arg Ala Asp Ala Pro Arg Pro Ala Ala Ala Pro Pro Ala
            660                 665                 670

Gly Ala Ala Pro Pro Ala Pro Pro Thr Pro Pro Arg Pro Pro Arg
        675                 680                 685

Pro Ala Ala Leu Thr Arg Arg Pro Ala Glu Gly Pro Asp Pro Gln Gly
    690                 695                 700

Gly Trp Arg Arg Gln Pro Pro Gly Pro Ser His Thr Pro Ala Pro Ser
705                 710                 715                 720

Ala Ala Ala Leu Glu Ala Tyr Cys Ala Pro Arg Ala Val Ala Glu Leu
                725                 730                 735

Thr Asp His Pro Leu Phe Pro Ala Pro Trp Arg Pro Ala Leu Met Phe
            740                 745                 750

Asp Pro Arg Ala Leu Ala Ser Leu Ala Ala Arg Cys Ala Ala Pro Pro
        755                 760                 765

Pro Gly Gly Ala Pro Ala Ala Phe Gly Pro Leu Arg Ala Ser Gly Pro
    770                 775                 780

Leu Arg Arg Ala Ala Ala Trp Met Arg Gln Val Pro Asp Pro Glu Asp
785                 790                 795                 800

Val Arg Val Val Ile Leu Tyr Ser Pro Leu Pro Gly Glu Asp Leu Ala
                805                 810                 815

Ala Gly Arg Ala Gly Gly Pro Pro Glu Trp Ser Ala Glu Arg
            820                 825                 830

Gly Gly Leu Ser Cys Leu Leu Ala Leu Gly Asn Arg Leu Cys Gly
        835                 840                 845

Pro Ala Thr Ala Ala Trp Ala Gly Asn Trp Thr Gly Ala Pro Asp Val
    850                 855                 860

Ser Ala Leu Gly Ala Gln Gly Val Leu Leu Ser Thr Arg Asp Leu
865                 870                 875                 880

Ala Phe Ala Gly Ala Val Glu Phe Leu Gly Leu Leu Ala Gly Ala Cys
                885                 890                 895
```

Asp Arg Arg Leu Ile Val Val Asn Ala Val Arg Ala Ala Asp Trp Pro
            900                 905                 910

Ala Asp Gly Pro Val Val Ser Arg Gln His Ala Tyr Leu Ala Cys Glu
        915                 920                 925

Val Leu Pro Ala Val Gln Cys Ala Val Arg Trp Pro Ala Ala Arg Asp
    930                 935                 940

Leu Arg Arg Thr Val Leu Ala Ser Gly Arg Val Phe Gly Pro Gly Val
945                 950                 955                 960

Phe Ala Arg Val Glu Ala Ala His Ala Arg Leu Tyr Pro Asp Ala Pro
                965                 970                 975

Pro Leu Arg Leu Cys Arg Gly Ala Asn Val Arg Tyr Arg Val Arg Thr
            980                 985                 990

Arg Phe Gly Pro Asp Thr Leu Val Pro Met Ser Pro Arg Glu Tyr Arg
        995                 1000                1005

Arg Ala Val Leu Pro Ala Leu Asp Gly Arg Ala Ala Ala Ser Gly
    1010                1015                1020

Ala Gly Asp Ala Met Ala Pro Gly Ala Pro Asp Phe Cys Glu Asp
    1025                1030                1035

Glu Ala His Ser His Arg Ala Cys Ala Arg Trp Gly Leu Gly Ala
    1040                1045                1050

Pro Leu Arg Pro Val Tyr Val Ala Leu Gly Arg Asp Ala Val Arg
    1055                1060                1065

Gly Gly Pro Ala Glu Leu Arg Gly Pro Arg Arg Glu Phe Cys Ala
    1070                1075                1080

Arg Ala Leu Leu Glu Pro Asp Gly Asp Ala Pro Pro Leu Val Leu
    1085                1090                1095

Arg Asp Asp Ala Asp Ala Gly Pro Pro Pro Gln Ile Arg Trp Ala
    1100                1105                1110

Ser Ala Ala Gly Arg Ala Gly Thr Val Leu Ala Ala Ala Gly Gly
    1115                1120                1125

Gly Val Glu Val Val Gly Thr Ala Ala Gly Leu Ala Thr Pro Pro
    1130                1135                1140

Arg Arg Glu Pro Val Asp Met Asp Ala Glu Leu Glu Asp Asp Asp
    1145                1150                1155

Asp Gly Leu Phe Gly Glu
    1160

<210> SEQ ID NO 16
<211> LENGTH: 1234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Ser Ala Glu Gln Arg Lys Lys Lys Thr Thr Thr Thr Thr Gln
1               5                   10                  15

Gly Arg Gly Ala Glu Val Ala Met Ala Asp Glu Asp Gly Gly Arg Leu
                20                  25                  30

Arg Ala Ala Ala Glu Thr Thr Gly Gly Pro Gly Ser Pro Asp Pro Ala
            35                  40                  45

Asp Gly Pro Pro Pro Thr Pro Asn Pro Asp Arg Pro Ala Ala Arg
        50                  55                  60

Pro Gly Phe Gly Trp His Gly Gly Pro Glu Glu Asn Glu Asp Glu Ala
65                  70                  75                  80

-continued

```
Asp Asp Ala Ala Ala Asp Ala Asp Ala Asp Glu Ala Pro Ala Ser
                85                  90                  95

Gly Glu Ala Val Asp Glu Pro Ala Ala Asp Gly Val Val Ser Pro Arg
                100                 105                 110

Gln Leu Ala Leu Leu Ala Ser Met Val Asp Glu Ala Val Arg Thr Ile
            115                 120                 125

Pro Ser Pro Pro Pro Glu Arg Asp Gly Ala Gln Glu Glu Ala Ala Arg
    130                 135                 140

Ser Pro Ser Pro Pro Arg Thr Pro Ser Met Arg Ala Asp Tyr Gly Glu
145                 150                 155                 160

Glu Asn Asp Asp Asp Asp Asp Asp Asp Asp Asp Arg Asp Ala
                165                 170                 175

Gly Arg Trp Val Arg Gly Pro Glu Thr Thr Ser Ala Val Arg Gly Ala
            180                 185                 190

Tyr Pro Asp Pro Met Ala Ser Leu Ser Pro Arg Pro Pro Ala Pro Arg
        195                 200                 205

Arg His His His His His His Arg Arg Arg Arg Ala Pro Arg Arg
    210                 215                 220

Arg Ser Ala Ala Ser Asp Ser Ser Lys Ser Gly Ser Ser Ser Ser Ala
225                 230                 235                 240

Ser Ser Ala Ser Ser Ser Ala Ser Ser Ser Ser Ala Ser Ala Ser
                245                 250                 255

Ser Ser Asp Asp Asp Asp Asp Asp Ala Ala Arg Ala Pro Ala Ser
                260                 265                 270

Ala Ala Asp His Ala Ala Gly Gly Thr Leu Gly Ala Asp Asp Glu Glu
            275                 280                 285

Ala Gly Val Pro Ala Arg Ala Pro Gly Ala Ala Pro Arg Pro Ser Pro
    290                 295                 300

Pro Arg Ala Glu Pro Ala Pro Ala Arg Thr Pro Ala Ala Thr Ala Gly
305                 310                 315                 320

Arg Leu Glu Arg Arg Arg Ala Arg Ala Ala Val Ala Gly Arg Asp Ala
                325                 330                 335

Thr Gly Arg Phe Thr Ala Gly Arg Pro Arg Arg Val Glu Leu Asp Ala
            340                 345                 350

Asp Ala Ala Ser Gly Ala Phe Tyr Ala Arg Tyr Arg Asp Gly Tyr Val
        355                 360                 365

Ser Gly Glu Pro Trp Pro Gly Ala Gly Pro Pro Pro Gly Arg Val
370                 375                 380

Leu Tyr Gly Gly Leu Gly Asp Ser Arg Pro Gly Leu Trp Gly Ala Pro
385                 390                 395                 400

Glu Ala Glu Glu Ala Arg Ala Arg Phe Glu Ala Ser Gly Ala Pro Ala
                405                 410                 415

Pro Val Trp Ala Pro Glu Leu Gly Asp Ala Gln Gln Tyr Ala Leu
            420                 425                 430

Ile Thr Arg Leu Leu Tyr Thr Pro Asp Ala Glu Ala Met Gly Trp Leu
        435                 440                 445

Gln Asn Pro Arg Val Ala Pro Gly Asp Val Ala Leu Asp Gln Ala Cys
    450                 455                 460

Phe Arg Ile Ser Gly Ala Ala Arg Asn Ser Ser Ser Phe Ile Ser Gly
465                 470                 475                 480

Ser Val Ala Arg Ala Val Pro His Leu Gly Tyr Ala Met Ala Ala Gly
                485                 490                 495
```

-continued

```
Arg Phe Gly Trp Gly Leu Ala His Val Ala Ala Val Ala Met Ser
                500                 505                 510
Arg Arg Tyr Asp Arg Ala Gln Lys Gly Phe Leu Leu Thr Ser Leu Arg
        515                 520                 525
Arg Ala Tyr Ala Pro Leu Leu Ala Arg Glu Asn Ala Ala Leu Thr Gly
    530                 535                 540
Ala Arg Thr Pro Asp Asp Gly Asp Ala Asn Arg His Asp Gly Asp
545                 550                 555                 560
Asp Ala Arg Gly Lys Pro Ala Ala Ala Pro Leu Pro Ser Ala
                565                 570                 575
Ala Ala Ser Pro Ala Asp Glu Arg Ala Val Pro Ala Gly Tyr Gly Ala
            580                 585                 590
Ala Gly Val Leu Ala Ala Leu Gly Arg Leu Ser Ala Ala Pro Ala Ser
        595                 600                 605
Ala Pro Ala Gly Ala Asp Asp Asp Asp Asp Asp Gly Ala Gly Gly
    610                 615                 620
Gly Gly Gly Gly Arg Arg Ala Glu Ala Gly Arg Val Ala Val Glu Cys
625                 630                 635                 640
Leu Ala Ala Cys Arg Gly Ile Leu Glu Ala Leu Ala Glu Gly Phe Asp
                645                 650                 655
Gly Asp Leu Ala Ala Val Pro Gly Leu Ala Gly Ala Arg Pro Ala Ala
            660                 665                 670
Pro Pro Arg Pro Gly Pro Ala Gly Ala Ala Pro His Ala Asp
        675                 680                 685
Ala Pro Arg Leu Arg Ala Trp Leu Arg Glu Leu Arg Phe Val Arg Asp
    690                 695                 700
Ala Leu Val Leu Met Arg Leu Arg Gly Asp Leu Arg Val Ala Gly Gly
705                 710                 715                 720
Ser Glu Ala Ala Val Ala Ala Val Arg Ala Val Ser Leu Val Ala Gly
                725                 730                 735
Ala Leu Gly Pro Ala Leu Pro Arg Ser Pro Arg Leu Leu Ser Ser Ala
            740                 745                 750
Ala Ala Ala Ala Ala Asp Leu Leu Phe Gln Asn Gln Ser Leu Arg Pro
        755                 760                 765
Leu Leu Ala Asp Thr Val Ala Ala Asp Ser Leu Ala Ala Pro Ala
    770                 775                 780
Ser Thr Pro Ala Pro Ser Ala Ala Ala Leu Glu Ala Tyr Cys Ala Pro
785                 790                 795                 800
Arg Ala Val Ala Glu Leu Thr Asp His Pro Leu Phe Pro Ala Pro Trp
                805                 810                 815
Arg Pro Ala Leu Met Phe Asp Pro Arg Ala Leu Ala Ser Leu Ala Ala
            820                 825                 830
Arg Cys Ala Ala Pro Pro Gly Gly Ala Pro Ala Ala Phe Gly Pro
        835                 840                 845
Leu Arg Ala Ser Gly Pro Leu Arg Arg Ala Ala Ala Trp Met Arg Gln
    850                 855                 860
Val Pro Asp Pro Glu Asp Val Arg Val Val Ile Leu Tyr Ser Pro Leu
865                 870                 875                 880
Pro Gly Glu Asp Leu Ala Ala Gly Arg Ala Gly Gly Pro Pro
                885                 890                 895
Glu Trp Ser Ala Glu Arg Gly Gly Leu Ser Cys Leu Leu Ala Ala Leu
                900                 905                 910
Gly Asn Arg Leu Cys Gly Pro Ala Thr Ala Ala Trp Ala Gly Asn Trp
```

```
                    915                 920                 925
Thr Gly Ala Pro Asp Val Ser Ala Leu Gly Ala Gln Gly Val Leu Leu
            930                 935                 940

Leu Ser Thr Arg Asp Leu Ala Phe Ala Gly Ala Val Glu Phe Leu Gly
945                 950                 955                 960

Leu Leu Ala Gly Ala Cys Asp Arg Arg Leu Ile Val Val Asn Ala Val
                965                 970                 975

Arg Ala Ala Asp Trp Pro Ala Asp Gly Pro Val Val Ser Arg Gln His
            980                 985                 990

Ala Tyr Leu Ala Cys Glu Val Leu Pro Ala Val Gln Cys Ala Val Arg
        995                 1000                1005

Trp Pro Ala Ala Arg Asp Leu Arg Arg Thr Val Leu Ala Ser Gly
    1010                1015                1020

Arg Val Phe Gly Pro Gly Val Phe Ala Arg Val Glu Ala Ala His
    1025                1030                1035

Ala Arg Leu Tyr Pro Asp Ala Pro Pro Leu Arg Leu Cys Arg Gly
    1040                1045                1050

Ala Asn Val Arg Tyr Arg Val Arg Thr Arg Phe Gly Pro Asp Thr
    1055                1060                1065

Leu Val Pro Met Ser Pro Arg Glu Tyr Arg Arg Ala Val Leu Pro
    1070                1075                1080

Ala Leu Asp Gly Arg Ala Ala Ser Gly Ala Gly Asp Ala Met
    1085                1090                1095

Ala Pro Gly Ala Pro Asp Phe Cys Glu Asp Glu Ala His Ser His
    1100                1105                1110

Arg Ala Cys Ala Arg Trp Gly Leu Gly Ala Pro Leu Arg Pro Val
    1115                1120                1125

Tyr Val Ala Leu Gly Arg Asp Ala Val Arg Gly Gly Pro Ala Glu
    1130                1135                1140

Leu Arg Gly Pro Arg Arg Glu Phe Cys Ala Arg Ala Leu Leu Glu
    1145                1150                1155

Pro Asp Gly Asp Ala Pro Pro Leu Val Leu Arg Asp Asp Ala Asp
    1160                1165                1170

Ala Gly Pro Pro Pro Gln Ile Arg Trp Ala Ser Ala Ala Gly Arg
    1175                1180                1185

Ala Gly Thr Val Leu Ala Ala Gly Gly Gly Val Glu Val Val
    1190                1195                1200

Gly Thr Ala Ala Gly Leu Ala Thr Pro Pro Arg Arg Glu Pro Val
    1205                1210                1215

Asp Met Asp Ala Glu Leu Glu Asp Asp Asp Gly Leu Phe Gly
    1220                1225                1230

Glu

<210> SEQ ID NO 17
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Phe Ser Ala Ser Thr Thr Pro Glu Gln Pro Leu Gly Leu Ser Gly
1               5                   10                  15

Asp Ala Thr Pro Pro Leu Pro Thr Ser Val Pro Leu Asp Trp Ala Ala
```

-continued

```
                20                  25                  30
Phe Arg Arg Ala Phe Leu Ile Asp Asp Ala Trp Arg Pro Leu Leu Glu
            35                  40                  45
Pro Glu Leu Ala Asn Pro Leu Thr Ala Arg Leu Leu Ala Glu Tyr Asp
        50                  55                  60
Arg Arg Cys Gln Thr Glu Val Leu Pro Arg Glu Asp Val Phe
65                  70                  75                  80
Ser Trp Thr Arg Tyr Cys Thr Pro Asp Val Arg Val Ile Ile
                85                  90                  95
Gly Gln Asp Pro Tyr His His Pro Gly Gln Ala His Gly Leu Ala Phe
            100                 105                 110
Ser Val Arg Ala Asp Val Pro Val Pro Pro Ser Leu Arg Asn Val Leu
        115                 120                 125
Ala Ala Val Lys Asn Cys Tyr Pro Asp Ala Arg Met Ser Gly Arg Gly
        130                 135                 140
Cys Leu Glu Lys Trp Ala Arg Asp Gly Val Leu Leu Leu Asn Thr Thr
145                 150                 155                 160
Leu Thr Val Lys Arg Gly Ala Ala Ala Ser His Ser Lys Leu Gly Trp
                165                 170                 175
Asp Arg Phe Val Gly Gly Val Val Gln Arg Leu Ala Ala Arg Arg Pro
            180                 185                 190
Gly Leu Val Phe Met Leu Trp Gly Ala His Ala Gln Asn Ala Ile Arg
        195                 200                 205
Pro Asp Pro Arg Gln His Tyr Val Leu Lys Phe Ser His Pro Ser Pro
    210                 215                 220
Leu Ser Lys Val Pro Phe Gly Thr Cys Gln His Phe Leu Ala Ala Asn
225                 230                 235                 240
Arg Tyr Leu Glu Thr Arg Asp Ile Met Pro Ile Asp Trp Ser Val
                245                 250                 255

<210> SEQ ID NO 18
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Gly Leu Ala Phe Ser Gly Ala Arg Pro Cys Cys Arg His Asn
1               5                   10                  15
Val Ile Thr Thr Asp Gly Gly Glu Val Val Ser Leu Thr Ala His Glu
                20                  25                  30
Phe Asp Val Val Asp Ile Glu Ser Glu Glu Gly Asn Phe Tyr Val
            35                  40                  45
Pro Pro Asp Val Arg Val Thr Arg Ala Pro Gly Pro Gln Tyr Arg
        50                  55                  60
Arg Ala Ser Asp Pro Pro Ser Arg His Thr Arg Arg Asp Pro Asp
65                  70                  75                  80
Val Ala Arg Pro Pro Ala Thr Leu Thr Pro Pro Leu Ser Asp Ser Glu
                85                  90                  95

<210> SEQ ID NO 19
<211> LENGTH: 226
<212> TYPE: PRT
<213> ORGANISM: Human herpesvirus 2
```

<400> SEQUENCE: 19

Asn Arg Trp Gly Phe Val Cys Leu Phe Gly Leu Val Val Met Gly Ala
1               5                   10                  15

Trp Gly Ala Trp Gly Gly Ser Gln Ala Thr Glu Tyr Val Leu Arg Ser
            20                  25                  30

Val Ile Ala Lys Glu Val Gly Asp Ile Leu Arg Val Pro Cys Met Arg
        35                  40                  45

Thr Pro Ala Asp Asp Val Ser Trp Arg Tyr Glu Ala Pro Ser Val Ile
    50                  55                  60

Asp Tyr Ala Arg Ile Asp Gly Ile Phe Leu Arg Tyr His Cys Pro Gly
65                  70                  75                  80

Leu Asp Thr Phe Leu Trp Asp Arg His Ala Gln Arg Ala Tyr Leu Val
                85                  90                  95

Asn Pro Phe Leu Phe Ala Ala Gly Phe Leu Glu Asp Leu Ser His Ser
            100                 105                 110

Val Phe Pro Ala Asp Thr Gln Glu Thr Thr Thr Arg Arg Ala Leu Tyr
        115                 120                 125

Lys Glu Ile Arg Asp Ala Leu Gly Ser Arg Lys Gln Ala Val Ser His
    130                 135                 140

Ala Pro Val Arg Ala Gly Cys Val Asn Phe Asp Tyr Ser Arg Thr Arg
145                 150                 155                 160

Arg Cys Val Gly Arg Arg Asp Leu Arg Pro Ala Asn Thr Thr Ser Thr
                165                 170                 175

Trp Glu Pro Pro Val Ser Ser Asp Asp Glu Ala Ser Ser Gln Ser Lys
            180                 185                 190

Pro Leu Ala Thr Gln Pro Pro Val Leu Ala Leu Ser Asn Ala Pro Pro
        195                 200                 205

Arg Arg Val Ser Pro Thr Arg Gly Arg Arg Arg His Thr Arg Leu Arg
210                 215                 220

Arg Asn
225

<210> SEQ ID NO 20
<211> LENGTH: 1388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Tyr Asp Ile Pro Thr Thr Glu Asn Leu Tyr Phe Gln Gly Met Ala
1               5                   10                  15

Ala Pro Ala Arg Asp Pro Pro Gly Tyr Arg Tyr Ala Ala Ala Met Val
            20                  25                  30

Pro Thr Gly Ser Ile Leu Ser Thr Ile Glu Val Ala Ser His Arg Arg
        35                  40                  45

Leu Phe Asp Phe Phe Ala Arg Val Arg Ser Asp Glu Asn Ser Leu Tyr
    50                  55                  60

Asp Val Glu Phe Asp Ala Leu Leu Gly Ser Tyr Cys Asn Thr Leu Ser
65                  70                  75                  80

Leu Val Arg Phe Leu Glu Leu Gly Leu Ser Val Ala Cys Val Cys Thr
                85                  90                  95

Lys Phe Pro Glu Leu Ala Tyr Met Asn Glu Gly Arg Val Gln Phe Glu
            100                 105                 110

Val His Gln Pro Leu Ile Ala Arg Asp Gly Pro His Pro Val Glu Gln
            115                 120                 125

Pro Val His Asn Tyr Met Thr Lys Val Ile Asp Arg Arg Ala Leu Asn
        130                 135                 140

Ala Ala Phe Ser Leu Ala Thr Glu Ala Ile Ala Leu Leu Thr Gly Glu
145                 150                 155                 160

Ala Leu Asp Gly Thr Gly Ile Ser Leu His Arg Gln Leu Arg Ala Ile
                165                 170                 175

Gln Gln Leu Ala Arg Asn Val Gln Ala Val Leu Gly Ala Phe Glu Arg
            180                 185                 190

Gly Thr Ala Asp Gln Met Leu His Val Leu Glu Lys Ala Pro Pro
        195                 200                 205

Leu Ala Leu Leu Leu Pro Met Gln Arg Tyr Leu Asp Asn Gly Arg Leu
210                 215                 220

Ala Thr Arg Val Ala Arg Ala Thr Leu Val Ala Glu Leu Lys Arg Ser
225                 230                 235                 240

Phe Cys Asp Thr Ser Phe Phe Leu Gly Lys Ala Gly His Arg Arg Glu
                245                 250                 255

Ala Ile Glu Ala Trp Leu Val Asp Leu Thr Thr Ala Thr Gln Pro Ser
            260                 265                 270

Val Ala Val Pro Arg Leu Thr His Ala Asp Thr Arg Gly Arg Pro Val
        275                 280                 285

Asp Gly Val Leu Val Thr Thr Ala Ala Ile Lys Gln Arg Leu Leu Gln
290                 295                 300

Ser Phe Leu Lys Val Glu Asp Thr Glu Ala Asp Val Pro Val Thr Tyr
305                 310                 315                 320

Gly Glu Met Val Leu Asn Gly Ala Asn Leu Val Thr Ala Leu Val Met
                325                 330                 335

Gly Lys Ala Val Arg Ser Leu Asp Asp Val Gly Arg His Leu Leu Glu
            340                 345                 350

Met Gln Glu Glu Gln Leu Glu Ala Asn Arg Glu Thr Leu Asp Glu Leu
        355                 360                 365

Glu Ser Ala Pro Gln Thr Thr Arg Val Arg Ala Asp Leu Val Ala Ile
370                 375                 380

Gly Asp Arg Leu Val Phe Leu Glu Ala Leu Glu Lys Arg Ile Tyr Ala
385                 390                 395                 400

Ala Thr Asn Val Pro Tyr Pro Leu Val Gly Ala Met Asp Leu Thr Phe
                405                 410                 415

Val Leu Pro Leu Gly Leu Phe Asn Pro Ala Met Glu Arg Phe Ala Ala
            420                 425                 430

His Ala Gly Asp Leu Val Pro Ala Pro Gly His Pro Glu Pro Arg Ala
        435                 440                 445

Phe Pro Pro Arg Gln Leu Phe Phe Trp Gly Lys Asp His Gln Val Leu
450                 455                 460

Arg Leu Ser Met Glu Asn Ala Val Gly Thr Val Cys His Pro Ser Leu
465                 470                 475                 480

Met Asn Ile Asp Ala Ala Val Gly Gly Val Asn His Asp Pro Val Glu
                485                 490                 495

Ala Ala Asn Pro Tyr Gly Ala Tyr Val Ala Ala Pro Ala Gly Pro Gly
            500                 505                 510

Ala Asp Met Gln Gln Arg Phe Leu Asn Ala Trp Arg Gln Arg Leu Ala
        515                 520                 525

His Gly Arg Val Arg Trp Val Ala Glu Cys Gln Met Thr Ala Glu Gln

```
              530                 535                 540
Phe Met Gln Pro Asp Asn Ala Asn Leu Ala Leu Glu Leu His Pro Ala
545                 550                 555                 560

Phe Asp Phe Phe Ala Gly Val Ala Asp Val Glu Leu Pro Gly Gly Glu
                565                 570                 575

Val Pro Pro Ala Gly Pro Gly Ala Ile Gln Ala Thr Trp Arg Val Val
                580                 585                 590

Asn Gly Asn Leu Pro Leu Ala Leu Cys Pro Val Ala Phe Arg Asp Ala
            595                 600                 605

Arg Gly Leu Glu Leu Gly Val Gly Arg His Ala Met Ala Pro Ala Thr
            610                 615                 620

Ile Ala Ala Val Arg Gly Ala Phe Glu Asp Arg Ser Tyr Pro Ala Val
625                 630                 635                 640

Phe Tyr Leu Leu Gln Ala Ala Ile His Gly Ser Glu His Val Phe Cys
                645                 650                 655

Ala Leu Ala Arg Leu Val Thr Gln Cys Ile Thr Ser Tyr Trp Asn Asn
                660                 665                 670

Thr Arg Cys Ala Ala Phe Val Asn Asp Tyr Ser Leu Val Ser Tyr Ile
            675                 680                 685

Val Thr Tyr Leu Gly Gly Asp Leu Pro Glu Glu Cys Met Ala Val Tyr
            690                 695                 700

Arg Asp Leu Val Ala His Val Glu Ala Leu Ala Gln Leu Val Asp Asp
705                 710                 715                 720

Phe Thr Leu Pro Gly Pro Glu Leu Gly Gly Gln Ala Gln Ala Glu Leu
                725                 730                 735

Asn His Leu Met Arg Asp Pro Ala Leu Leu Pro Pro Leu Val Trp Asp
                740                 745                 750

Cys Asp Gly Leu Met Arg His Ala Ala Leu Asp Arg His Arg Asp Cys
            755                 760                 765

Arg Ile Asp Ala Gly Glu His Glu Pro Val Tyr Ala Ala Ala Cys Asn
            770                 775                 780

Val Ala Thr Ala Asp Phe Asn Arg Asn Asp Gly Arg Leu Leu His Asn
785                 790                 795                 800

Thr Gln Ala Arg Ala Ala Asp Ala Ala Asp Asp Arg Pro His Arg Pro
                805                 810                 815

Ala Asp Trp Thr Val His His Lys Ile Tyr Tyr Tyr Val Leu Val Pro
                820                 825                 830

Ala Phe Ser Arg Gly Arg Cys Cys Thr Ala Gly Val Arg Phe Asp Arg
            835                 840                 845

Val Tyr Ala Thr Leu Gln Asn Met Val Val Pro Glu Ile Ala Pro Gly
            850                 855                 860

Glu Glu Cys Pro Ser Asp Pro Val Thr Asp Pro Ala His Pro Leu His
865                 870                 875                 880

Pro Ala Asn Leu Val Ala Asn Thr Val Asn Ala Met Phe His Asn Gly
                885                 890                 895

Arg Val Val Val Asp Gly Pro Ala Met Leu Thr Leu Gln Val Leu Ala
                900                 905                 910

His Asn Met Ala Glu Arg Thr Thr Ala Leu Leu Cys Ser Ala Ala Pro
            915                 920                 925

Asp Ala Gly Ala Asn Thr Ala Ser Thr Ala Asn Met Arg Ile Phe Asp
            930                 935                 940

Gly Ala Leu His Ala Gly Val Leu Leu Met Ala Pro Gln His Leu Asp
945                 950                 955                 960
```

```
His Thr Ile Gln Asn Gly Glu Tyr Phe Tyr Val Leu Pro Val His Ala
                965                 970                 975

Leu Phe Ala Gly Ala Asp His Val Ala Asn Ala Pro Asn Phe Pro Pro
            980                 985                 990

Ala Leu Arg Asp Leu Ala Arg His  Val Pro Leu Val Pro  Pro Ala Leu
        995                 1000                1005

Gly Ala  Asn Tyr Phe Ser Ser  Ile Arg Gln Pro Val  Val Gln His
    1010                 1015                 1020

Ala Arg  Glu Ser Ala Ala Gly  Glu Asn Ala Leu Thr  Tyr Ala Leu
    1025                 1030                 1035

Met Ala  Gly Tyr Phe Lys Met  Ser Pro Val Ala Leu  Tyr His Gln
    1040                 1045                 1050

Leu Lys  Thr Gly Leu His Pro  Gly Phe Gly Phe Thr  Val Val Arg
    1055                 1060                 1065

Gln Asp  Arg Phe Val Thr Glu  Asn Val Leu Phe Ser  Glu Arg Ala
    1070                 1075                 1080

Ser Glu  Ala Tyr Phe Leu Gly  Gln Leu Gln Val Ala  Arg His Glu
    1085                 1090                 1095

Thr Gly  Gly Gly Val Ser Phe  Thr Leu Thr Gln Pro  Arg Gly Asn
    1100                 1105                 1110

Val Asp  Leu Gly Val Gly Tyr  Thr Ala Val Ala Ala  Thr Ala Thr
    1115                 1120                 1125

Val Arg  Asn Pro Val Thr Asp  Met Gly Asn Leu Pro  Gln Asn Phe
    1130                 1135                 1140

Tyr Leu  Gly Arg Gly Ala Pro  Pro Leu Leu Asp Asn  Ala Ala Ala
    1145                 1150                 1155

Val Tyr  Leu Arg Asn Ala Val  Val Ala Gly Asn Arg  Leu Gly Pro
    1160                 1165                 1170

Ala Gln  Pro Leu Pro Val Phe  Gly Cys Ala Gln Val  Pro Arg Arg
    1175                 1180                 1185

Ala Gly  Met Asp His Gly Gln  Asp Ala Val Cys Glu  Phe Ile Ala
    1190                 1195                 1200

Thr Pro  Val Ala Thr Asp Ile  Asn Tyr Phe Arg Arg  Pro Cys Asn
    1205                 1210                 1215

Pro Arg  Gly Arg Ala Ala Gly  Gly Val Tyr Ala Gly  Asp Lys Glu
    1220                 1225                 1230

Gly Asp  Val Ile Ala Leu Met  Tyr Asp His Gly Gln  Ser Asp Pro
    1235                 1240                 1245

Ala Arg  Pro Phe Ala Ala Thr  Ala Asn Pro Trp Ala  Ser Gln Arg
    1250                 1255                 1260

Phe Ser  Tyr Gly Asp Leu Leu  Tyr Asn Gly Ala Tyr  His Leu Asn
    1265                 1270                 1275

Gly Ala  Ser Pro Val Leu Ser  Pro Cys Phe Lys Phe  Phe Thr Ala
    1280                 1285                 1290

Ala Asp  Ile Thr Ala Lys His  Arg Cys Leu Glu Arg  Leu Ile Val
    1295                 1300                 1305

Glu Thr  Gly Ser Ala Val Ser  Thr Ala Thr Ala Ala  Ser Asp Val
    1310                 1315                 1320

Gln Phe  Lys Arg Pro Pro Gly  Cys Arg Glu Leu Val  Glu Asp Pro
    1325                 1330                 1335

Cys Gly  Leu Phe Gln Glu Ala  Tyr Pro Ile Thr Cys  Ala Ser Asp
    1340                 1345                 1350
```

```
Pro Ala Leu Leu Arg Ser Ala Arg Asp Gly Glu Ala His Ala Arg
    1355                1360                1365

Glu Thr His Phe Thr Gln Tyr Leu Ile Tyr Asp Ala Ser Pro Leu
1370                1375                1380

Lys Gly Leu Ser Leu
    1385

<210> SEQ ID NO 21
<211> LENGTH: 1374
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Ala Ala Pro Ala Arg Asp Pro Pro Gly Tyr Arg Tyr Ala Ala Ala
1               5                   10                  15

Met Val Pro Thr Gly Ser Ile Leu Ser Thr Ile Glu Val Ala Ser His
            20                  25                  30

Arg Arg Leu Phe Asp Phe Phe Ala Arg Val Arg Ser Asp Glu Asn Ser
        35                  40                  45

Leu Tyr Asp Val Glu Phe Asp Ala Leu Leu Gly Ser Tyr Cys Asn Thr
    50                  55                  60

Leu Ser Leu Val Arg Phe Leu Glu Leu Gly Leu Ser Val Ala Cys Val
65                  70                  75                  80

Cys Thr Lys Phe Pro Glu Leu Ala Tyr Met Asn Glu Gly Arg Val Gln
                85                  90                  95

Phe Glu Val His Gln Pro Leu Ile Ala Arg Asp Gly Pro His Pro Val
            100                 105                 110

Glu Gln Pro Val His Asn Tyr Met Thr Lys Val Ile Asp Arg Arg Ala
        115                 120                 125

Leu Asn Ala Ala Phe Ser Leu Ala Thr Glu Ala Ile Ala Leu Leu Thr
    130                 135                 140

Gly Glu Ala Leu Asp Gly Thr Gly Ile Ser Leu His Arg Gln Leu Arg
145                 150                 155                 160

Ala Ile Gln Gln Leu Ala Arg Asn Val Gln Ala Val Leu Gly Ala Phe
                165                 170                 175

Glu Arg Gly Thr Ala Asp Gln Met Leu His Val Leu Glu Lys Ala
            180                 185                 190

Pro Pro Leu Ala Leu Leu Pro Met Gln Arg Tyr Leu Asp Asn Gly
        195                 200                 205

Arg Leu Ala Thr Arg Val Ala Arg Ala Thr Leu Val Ala Glu Leu Lys
    210                 215                 220

Arg Ser Phe Cys Asp Thr Ser Phe Phe Leu Gly Lys Ala Gly His Arg
225                 230                 235                 240

Arg Glu Ala Ile Glu Ala Trp Leu Val Asp Leu Thr Thr Ala Thr Gln
                245                 250                 255

Pro Ser Val Ala Val Pro Arg Leu Thr His Ala Asp Thr Arg Gly Arg
            260                 265                 270

Pro Val Asp Gly Val Leu Val Thr Thr Ala Ala Ile Lys Gln Arg Leu
        275                 280                 285

Leu Gln Ser Phe Leu Lys Val Glu Asp Thr Glu Ala Asp Val Pro Val
    290                 295                 300

Thr Tyr Gly Glu Met Val Leu Asn Gly Ala Asn Leu Val Thr Ala Leu
305                 310                 315                 320
```

-continued

Val Met Gly Lys Ala Val Arg Ser Leu Asp Asp Val Gly Arg His Leu
            325                 330                 335

Leu Glu Met Gln Glu Gln Leu Glu Ala Asn Arg Glu Thr Leu Asp
            340                 345                 350

Glu Leu Glu Ser Ala Pro Gln Thr Thr Arg Val Arg Ala Asp Leu Val
            355                 360                 365

Ala Ile Gly Asp Arg Leu Val Phe Leu Glu Ala Leu Glu Lys Arg Ile
370                 375                 380

Tyr Ala Ala Thr Asn Val Pro Tyr Pro Leu Val Gly Ala Met Asp Leu
385                 390                 395                 400

Thr Phe Val Leu Pro Leu Gly Leu Phe Asn Pro Ala Met Glu Arg Phe
            405                 410                 415

Ala Ala His Ala Gly Asp Leu Val Pro Ala Pro Gly His Pro Glu Pro
            420                 425                 430

Arg Ala Phe Pro Pro Arg Gln Leu Phe Phe Trp Gly Lys Asp His Gln
            435                 440                 445

Val Leu Arg Leu Ser Met Glu Asn Ala Val Gly Thr Val Cys His Pro
450                 455                 460

Ser Leu Met Asn Ile Asp Ala Ala Val Gly Gly Val Asn His Asp Pro
465                 470                 475                 480

Val Glu Ala Ala Asn Pro Tyr Gly Ala Tyr Val Ala Ala Pro Ala Gly
            485                 490                 495

Pro Gly Ala Asp Met Gln Gln Arg Phe Leu Asn Ala Trp Arg Gln Arg
            500                 505                 510

Leu Ala His Gly Arg Val Arg Trp Val Ala Glu Cys Gln Met Thr Ala
            515                 520                 525

Glu Gln Phe Met Gln Pro Asp Asn Ala Asn Leu Ala Leu Glu Leu His
            530                 535                 540

Pro Ala Phe Asp Phe Phe Ala Gly Val Ala Asp Val Glu Leu Pro Gly
545                 550                 555                 560

Gly Glu Val Pro Pro Ala Gly Pro Gly Ala Ile Gln Ala Thr Trp Arg
            565                 570                 575

Val Val Asn Gly Asn Leu Pro Leu Ala Leu Cys Pro Val Ala Phe Arg
            580                 585                 590

Asp Ala Arg Gly Leu Glu Leu Gly Val Gly Arg His Ala Met Ala Pro
            595                 600                 605

Ala Thr Ile Ala Ala Val Arg Gly Ala Phe Glu Asp Arg Ser Tyr Pro
            610                 615                 620

Ala Val Phe Tyr Leu Leu Gln Ala Ala Ile His Gly Ser Glu His Val
625                 630                 635                 640

Phe Cys Ala Leu Ala Arg Leu Val Thr Gln Cys Ile Thr Ser Tyr Trp
            645                 650                 655

Asn Asn Thr Arg Cys Ala Ala Phe Val Asn Asp Tyr Ser Leu Val Ser
            660                 665                 670

Tyr Ile Val Thr Tyr Leu Gly Gly Asp Leu Pro Glu Cys Met Ala
            675                 680                 685

Val Tyr Arg Asp Leu Val Ala His Val Glu Ala Leu Ala Gln Leu Val
            690                 695                 700

Asp Asp Phe Thr Leu Pro Gly Pro Glu Leu Gly Gln Ala Gln Ala
705                 710                 715                 720

Glu Leu Asn His Leu Met Arg Asp Pro Ala Leu Leu Pro Pro Leu Val
            725                 730                 735

```
Trp Asp Cys Asp Gly Leu Met Arg His Ala Ala Leu Asp Arg His Arg
            740                 745                 750

Asp Cys Arg Ile Asp Ala Gly Glu His Glu Pro Val Tyr Ala Ala Ala
            755                 760                 765

Cys Asn Val Ala Thr Ala Asp Phe Asn Arg Asn Asp Gly Arg Leu Leu
            770                 775                 780

His Asn Thr Gln Ala Arg Ala Ala Asp Ala Ala Asp Asp Arg Pro His
785                 790                 795                 800

Arg Pro Ala Asp Trp Thr Val His His Lys Ile Tyr Tyr Tyr Val Leu
            805                 810                 815

Val Pro Ala Phe Ser Arg Gly Arg Cys Cys Thr Ala Gly Val Arg Phe
            820                 825                 830

Asp Arg Val Tyr Ala Thr Leu Gln Asn Met Val Val Pro Glu Ile Ala
            835                 840                 845

Pro Gly Glu Glu Cys Pro Ser Asp Pro Val Thr Asp Pro Ala His Pro
            850                 855                 860

Leu His Pro Ala Asn Leu Val Ala Asn Thr Val Asn Ala Met Phe His
865                 870                 875                 880

Asn Gly Arg Val Val Asp Gly Pro Ala Met Leu Thr Leu Gln Val
            885                 890                 895

Leu Ala His Asn Met Ala Glu Arg Thr Thr Ala Leu Leu Cys Ser Ala
            900                 905                 910

Ala Pro Asp Ala Gly Ala Asn Thr Ala Ser Thr Ala Asn Met Arg Ile
            915                 920                 925

Phe Asp Gly Ala Leu His Ala Gly Val Leu Leu Met Ala Pro Gln His
            930                 935                 940

Leu Asp His Thr Ile Gln Asn Gly Glu Tyr Phe Tyr Val Leu Pro Val
945                 950                 955                 960

His Ala Leu Phe Ala Gly Ala Asp His Val Ala Asn Ala Pro Asn Phe
            965                 970                 975

Pro Pro Ala Leu Arg Asp Leu Ala Arg His Val Pro Leu Val Pro Pro
            980                 985                 990

Ala Leu Gly Ala Asn Tyr Phe Ser  Ser Ile Arg Gln Pro  Val Val Gln
            995                 1000                1005

His Ala  Arg Glu Ser Ala Ala  Gly Glu Asn Ala Leu  Thr Tyr Ala
            1010                1015                1020

Leu Met  Ala Gly Tyr Phe Lys  Met Ser Pro Val Ala  Leu Tyr His
            1025                1030                1035

Gln Leu  Lys Thr Gly Leu His  Pro Gly Phe Gly Phe  Thr Val Val
            1040                1045                1050

Arg Gln  Asp Arg Phe Val Thr  Glu Asn Val Leu Phe  Ser Glu Arg
            1055                1060                1065

Ala Ser  Glu Ala Tyr Phe Leu  Gly Gln Leu Gln Val  Ala Arg His
            1070                1075                1080

Glu Thr  Gly Gly Gly Val Ser  Phe Thr Leu Thr Gln  Pro Arg Gly
            1085                1090                1095

Asn Val  Asp Leu Gly Val Gly  Tyr Thr Ala Val Ala  Ala Thr Ala
            1100                1105                1110

Thr Val  Arg Asn Pro Val Thr  Asp Met Gly Asn Leu  Pro Gln Asn
            1115                1120                1125

Phe Tyr  Leu Gly Arg Gly Ala  Pro Pro Leu Leu Asp  Asn Ala Ala
            1130                1135                1140

Ala Val  Tyr Leu Arg Asn Ala  Val Val Ala Gly Asn  Arg Leu Gly
```

```
            1145                1150                1155

Pro Ala Gln Pro Leu Pro Val Phe Gly Cys Ala Gln Val Pro Arg
        1160                1165                1170

Arg Ala Gly Met Asp His Gly Gln Asp Ala Val Cys Glu Phe Ile
    1175                1180                1185

Ala Thr Pro Val Ala Thr Asp Ile Asn Tyr Phe Arg Arg Pro Cys
1190                1195                1200

Asn Pro Arg Gly Arg Ala Ala Gly Gly Val Tyr Ala Gly Asp Lys
        1205                1210                1215

Glu Gly Asp Val Ile Ala Leu Met Tyr Asp His Gly Gln Ser Asp
    1220                1225                1230

Pro Ala Arg Pro Phe Ala Ala Thr Ala Asn Pro Trp Ala Ser Gln
1235                1240                1245

Arg Phe Ser Tyr Gly Asp Leu Leu Tyr Asn Gly Ala Tyr His Leu
        1250                1255                1260

Asn Gly Ala Ser Pro Val Leu Ser Pro Cys Phe Lys Phe Phe Thr
    1265                1270                1275

Ala Ala Asp Ile Thr Ala Lys His Arg Cys Leu Glu Arg Leu Ile
1280                1285                1290

Val Glu Thr Gly Ser Ala Val Ser Thr Ala Thr Ala Ala Ser Asp
        1295                1300                1305

Val Gln Phe Lys Arg Pro Pro Gly Cys Arg Glu Leu Val Glu Asp
    1310                1315                1320

Pro Cys Gly Leu Phe Gln Glu Ala Tyr Pro Ile Thr Cys Ala Ser
1325                1330                1335

Asp Pro Ala Leu Leu Arg Ser Ala Arg Asp Gly Glu Ala His Ala
        1340                1345                1350

Arg Glu Thr His Phe Thr Gln Tyr Leu Ile Tyr Asp Ala Ser Pro
    1355                1360                1365

Leu Lys Gly Leu Ser Leu
        1370

<210> SEQ ID NO 22
<211> LENGTH: 3122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Ile Pro Ala Ala Leu Pro His Pro Thr Met Lys Arg Gln Gly Asp
1               5                   10                  15

Arg Asp Ile Val Val Thr Gly Val Arg Asn Gln Phe Ala Thr Asp Leu
            20                  25                  30

Glu Pro Gly Gly Ser Val Ser Cys Met Arg Ser Ser Leu Ser Phe Leu
        35                  40                  45

Ser Leu Leu Phe Asp Val Gly Pro Arg Asp Val Leu Ser Ala Glu Ala
    50                  55                  60

Ile Glu Gly Cys Leu Val Glu Gly Gly Glu Trp Thr Arg Ala Ala Ala
65                  70                  75                  80

Gly Ser Gly Pro Pro Arg Met Cys Ser Ile Ile Glu Leu Pro Asn Phe
                85                  90                  95

Leu Glu Tyr Pro Ala Ala Arg Gly Gly Leu Arg Cys Val Phe Ser Arg
            100                 105                 110
```

-continued

```
Val Tyr Gly Glu Val Gly Phe Phe Gly Glu Pro Thr Ala Gly Leu Leu
            115                 120                 125
Glu Thr Gln Cys Pro Ala His Thr Phe Phe Ala Gly Pro Trp Ala Met
130                 135                 140
Arg Pro Leu Ser Tyr Thr Leu Leu Thr Ile Gly Pro Leu Gly Met Gly
145                 150                 155                 160
Leu Tyr Arg Asp Gly Asp Thr Ala Tyr Leu Phe Asp Pro His Gly Leu
                165                 170                 175
Pro Ala Gly Thr Pro Ala Phe Ile Ala Lys Val Arg Ala Gly Asp Val
            180                 185                 190
Tyr Pro Tyr Leu Thr Tyr Tyr Ala His Asp Arg Pro Lys Val Arg Trp
        195                 200                 205
Ala Gly Ala Met Val Phe Phe Val Pro Ser Gly Pro Gly Ala Val Ala
    210                 215                 220
Pro Ala Asp Leu Thr Ala Ala Ala Leu His Leu Tyr Gly Ala Ser Glu
225                 230                 235                 240
Thr Tyr Leu Gln Asp Glu Pro Phe Val Glu Arg Arg Val Ala Ile Thr
                245                 250                 255
His Pro Leu Arg Gly Glu Ile Gly Gly Leu Gly Ala Leu Phe Val Gly
            260                 265                 270
Val Val Pro Arg Gly Asp Gly Glu Gly Ser Gly Pro Val Val Pro Ala
        275                 280                 285
Leu Pro Ala Pro Thr His Val Gln Thr Pro Gly Ala Asp Arg Pro Pro
    290                 295                 300
Glu Ala Pro Arg Gly Ala Ser Gly Pro Pro Asp Thr Pro Gln Ala Gly
305                 310                 315                 320
His Pro Asn Arg Pro Pro Asp Asp Val Trp Ala Ala Ala Leu Glu Gly
                325                 330                 335
Thr Pro Pro Ala Lys Pro Ser Ala Pro Asp Ala Ala Ala Ser Gly Pro
            340                 345                 350
Pro His Ala Ala Pro Pro Gln Thr Pro Ala Gly Asp Ala Ala Glu
        355                 360                 365
Glu Ala Glu Asp Leu Arg Val Leu Glu Val Gly Ala Val Pro Val Gly
    370                 375                 380
Arg His Arg Ala Arg Tyr Ser Thr Gly Leu Pro Lys Arg Arg Arg Pro
385                 390                 395                 400
Thr Trp Thr Pro Pro Ser Ser Val Glu Asp Leu Thr Ser Gly Glu Arg
                405                 410                 415
Pro Ala Pro Lys Ala Pro Pro Ala Lys Ala Lys Lys Ser Ala Pro
            420                 425                 430
Lys Lys Lys Ala Pro Val Ala Ala Glu Val Pro Ala Ser Ser Pro Thr
        435                 440                 445
Pro Ile Ala Ala Thr Val Pro Pro Ala Pro Asp Thr Pro Pro Gln Ser
    450                 455                 460
Gly Gln Gly Gly Gly Asp Asp Gly Pro Ala Ser Pro Ser Ser Pro Ser
465                 470                 475                 480
Val Leu Glu Thr Leu Gly Ala Arg Arg Pro Glu Pro Pro Gly Ala
                485                 490                 495
Asp Leu Ala Gln Leu Phe Glu Val His Pro Asn Val Ala Ala Thr Ala
            500                 505                 510
Val Arg Leu Ala Ala Arg Asp Ala Ala Leu Ala Arg Glu Val Ala Ala
        515                 520                 525
Cys Ser Gln Leu Thr Ile Asn Ala Leu Arg Ser Pro Tyr Pro Ala His
```

```
                    530                 535                 540
Pro Gly Leu Leu Glu Leu Cys Val Ile Phe Phe Glu Arg Val Leu
545                 550                 555                 560

Ala Phe Leu Ile Glu Asn Gly Ala Arg Thr His Thr Gln Ala Gly Val
                565                 570                 575

Ala Gly Pro Ala Ala Leu Leu Asp Phe Thr Leu Arg Met Leu Pro
            580                 585                 590

Arg Lys Thr Ala Val Gly Asp Phe Leu Ala Ser Thr Arg Met Ser Leu
                595                 600                 605

Ala Asp Val Ala Ala His Arg Pro Leu Ile Gln His Val Leu Asp Glu
            610                 615                 620

Asn Ser Gln Ile Gly Arg Leu Ala Leu Ala Lys Leu Val Leu Val Ala
625                 630                 635                 640

Arg Asp Val Ile Arg Glu Thr Asp Ala Phe Tyr Gly Asp Leu Ala Asp
                645                 650                 655

Leu Asp Leu Gln Leu Arg Ala Ala Pro Pro Ala Asn Leu Tyr Ala Arg
                660                 665                 670

Leu Gly Glu Trp Leu Leu Glu Arg Ser Arg Ala His Pro Asn Thr Leu
                675                 680                 685

Phe Ala Pro Ala Thr Pro Thr His Pro Glu Pro Leu Leu His Arg Ile
690                 695                 700

Gln Ala Leu Ala Gln Phe Ala Arg Gly Glu Glu Met Arg Val Glu Ala
705                 710                 715                 720

Glu Ala Arg Glu Met Arg Glu Ala Leu Asp Ala Leu Ala Arg Gly Val
                725                 730                 735

Asp Ser Val Ser Gln Arg Ala Gly Pro Leu Thr Val Met Pro Val Pro
                740                 745                 750

Ala Ala Pro Gly Ala Gly Gly Arg Ala Pro Cys Pro Pro Ala Leu Gly
            755                 760                 765

Pro Glu Ala Ile Gln Ala Arg Leu Glu Asp Val Arg Ile Gln Ala Arg
            770                 775                 780

Arg Ala Ile Glu Ser Ala Val Lys Glu Tyr Phe His Arg Gly Ala Val
785                 790                 795                 800

Tyr Ser Ala Lys Ala Leu Gln Ala Ser Asp Ser His Asp Cys Arg Phe
                805                 810                 815

His Val Ala Ser Ala Ala Val Val Pro Met Val Gln Leu Leu Glu Ser
            820                 825                 830

Leu Pro Ala Phe Asp Gln His Thr Arg Asp Val Ala Gln Arg Ala Ala
            835                 840                 845

Leu Pro Pro Pro Pro Leu Ala Thr Ser Pro Gln Ala Ile Leu Leu
850                 855                 860

Arg Asp Leu Leu Gln Arg Gly Gln Pro Leu Ala Pro Glu Asp Leu
865                 870                 875                 880

Ala Ala Trp Leu Ser Val Leu Thr Asp Ala Thr Gln Gly Leu Ile
                885                 890                 895

Glu Arg Lys Pro Leu Glu Glu Leu Ala Arg Ser Ile His Gly Ile Asn
                900                 905                 910

Asp Gln Gln Ala Arg Arg Ser Ser Gly Leu Ala Glu Leu Gln Arg Phe
            915                 920                 925

Asp Ala Leu Asp Ala Ala Leu Ala Gln Gln Leu Asp Ser Asp Ala Ala
            930                 935                 940

Phe Val Pro Ala Thr Gly Pro Ala Pro Tyr Val Asp Gly Gly Gly Leu
945                 950                 955                 960
```

-continued

```
Ser Pro Glu Ala Thr Arg Met Ala Glu Asp Ala Leu Arg Gln Ala Arg
            965                 970                 975

Ala Met Glu Ala Ala Lys Met Thr Ala Glu Leu Ala Pro Glu Ala Arg
            980                 985                 990

Ser Arg Leu Arg Glu Arg Ala His Ala Leu Glu Ala Met Leu Asn Asp
        995                 1000                1005

Ala Arg Glu Arg Ala Lys Val Ala His Asp Ala Arg Glu Lys Phe
    1010                1015                1020

Leu His Lys Leu Gln Gly Val Leu Arg Pro Leu Pro Asp Phe Val
    1025                1030                1035

Gly Leu Lys Ala Cys Pro Ala Val Leu Ala Thr Leu Arg Ala Ser
    1040                1045                1050

Leu Pro Ala Gly Trp Thr Asp Leu Ala Asp Ala Val Arg Gly Pro
    1055                1060                1065

Pro Pro Glu Val Thr Ala Ala Leu Arg Ala Asp Leu Trp Gly Leu
    1070                1075                1080

Leu Gly Gln Tyr Arg Glu Ala Leu Glu His Pro Thr Pro Asp Thr
    1085                1090                1095

Ala Thr Ala Leu Ala Gly Leu His Pro Ala Phe Val Val Val Leu
    1100                1105                1110

Lys Thr Leu Phe Ala Asp Ala Pro Glu Thr Pro Val Leu Val Gln
    1115                1120                1125

Phe Phe Ser Asp His Ala Pro Thr Ile Ala Lys Ala Val Ser Asn
    1130                1135                1140

Ala Ile Asn Ala Gly Ser Ala Ala Val Ala Thr Ala Ser Pro Ala
    1145                1150                1155

Ala Thr Val Asp Ala Ala Val Arg Ala His Gly Ala Leu Ala Asp
    1160                1165                1170

Ala Val Ser Ala Leu Gly Ala Ala Ala Arg Asp Pro Ala Ser Pro
    1175                1180                1185

Leu Ser Phe Leu Ala Val Leu Ala Asp Ser Ala Ala Gly Tyr Val
    1190                1195                1200

Lys Ala Thr Arg Leu Ala Leu Glu Ala Arg Gly Ala Ile Asp Glu
    1205                1210                1215

Leu Thr Thr Leu Gly Ser Ala Ala Ala Asp Leu Val Val Gln Ala
    1220                1225                1230

Arg Arg Ala Cys Ala Gln Pro Glu Gly Asp His Ala Ala Leu Ile
    1235                1240                1245

Asp Ala Ala Ala Arg Ala Thr Thr Ala Ala Arg Glu Ser Leu Ala
    1250                1255                1260

Gly His Glu Ala Gly Phe Gly Gly Leu Leu His Ala Glu Gly Thr
    1265                1270                1275

Ala Gly Asp His Ser Pro Ser Gly Arg Ala Leu Gln Glu Leu Gly
    1280                1285                1290

Lys Val Ile Gly Ala Thr Arg Arg Arg Ala Asp Glu Leu Glu Ala
    1295                1300                1305

Ala Val Ala Asp Leu Thr Ala Lys Met Ala Ala Gln Arg Ala Arg
    1310                1315                1320

Gly Ser Ser Glu Arg Trp Ala Ala Gly Val Glu Ala Ala Leu Asp
    1325                1330                1335

Arg Val Glu Asn Arg Ala Glu Phe Asp Val Val Glu Leu Arg Arg
    1340                1345                1350
```

| | | | | | | | | | | | |
|---|---|---|---|---|---|---|---|---|---|---|---|
|Leu|Gln|Ala|Leu|Ala|Gly|Thr|His|Gly|Tyr|Asn|Pro|Arg|Asp|Phe|
|   |1355|   |   |   |   |1360|   |   |   |   |1365|   |   |   |

Leu Gln Ala Leu Ala Gly Thr His Gly Tyr Asn Pro Arg Asp Phe
    1355                1360                1365

Arg Lys Arg Ala Glu Gln Ala Leu Ala Ala Asn Ala Glu Ala Val
    1370                1375                1380

Thr Leu Ala Leu Asp Thr Ala Phe Ala Phe Asn Pro Tyr Thr Pro
    1385                1390                1395

Glu Asn Gln Arg His Pro Met Leu Pro Pro Leu Ala Ala Ile His
    1400                1405                1410

Arg Leu Gly Trp Ser Ala Ala Phe His Ala Ala Ala Glu Thr Tyr
    1415                1420                1425

Ala Asp Met Phe Arg Val Asp Ala Glu Pro Leu Ala Arg Leu Leu
    1430                1435                1440

Arg Ile Ala Glu Gly Leu Leu Glu Met Ala Gln Ala Gly Asp Gly
    1445                1450                1455

Phe Ile Asp Tyr His Glu Ala Val Gly Arg Leu Ala Asp Asp Met
    1460                1465                1470

Thr Ser Val Pro Gly Leu Arg Arg Tyr Val Pro Phe Phe Gln His
    1475                1480                1485

Gly Tyr Ala Asp Tyr Val Glu Leu Arg Asp Arg Leu Asp Ala Ile
    1490                1495                1500

Arg Ala Asp Val His Arg Ala Leu Gly Gly Val Pro Leu Asp Leu
    1505                1510                1515

Ala Ala Ala Glu Gln Ile Ser Ala Ala Arg Asn Asp Pro Glu
    1520                1525                1530

Ala Thr Ala Glu Leu Val Arg Thr Gly Val Thr Leu Pro Cys Pro
    1535                1540                1545

Ser Glu Asp Ala Leu Val Ala Cys Ala Ala Ala Leu Glu Arg Val
    1550                1555                1560

Asp Gln Ser Pro Val Lys Asn Thr Ala Tyr Ala Glu Tyr Val Ala
    1565                1570                1575

Phe Val Thr Arg Gln Asp Thr Ala Glu Thr Lys Asp Ala Val Val
    1580                1585                1590

Arg Ala Lys Gln Gln Arg Ala Glu Ala Thr Glu Arg Val Met Ala
    1595                1600                1605

Gly Leu Arg Glu Ala Leu Ala Ala Arg Glu Arg Ala Gln Ile
    1610                1615                1620

Glu Ala Glu Gly Leu Ala Asn Leu Lys Thr Met Leu Lys Val Val
    1625                1630                1635

Ala Val Pro Ala Thr Val Ala Lys Thr Leu Asp Gln Ala Arg Ser
    1640                1645                1650

Val Ala Glu Ile Ala Asp Gln Val Glu Val Leu Leu Asp Gln Thr
    1655                1660                1665

Glu Lys Thr Arg Glu Leu Asp Val Pro Ala Val Ile Trp Leu Glu
    1670                1675                1680

His Ala Gln Arg Thr Phe Glu Thr His Pro Leu Ser Ala Ala Arg
    1685                1690                1695

Gly Asp Gly Pro Gly Pro Leu Ala Arg His Ala Gly Arg Leu Gly
    1700                1705                1710

Ala Leu Phe Asp Thr Arg Arg Val Asp Ala Leu Arg Arg Ser
    1715                1720                1725

Leu Glu Glu Ala Glu Ala Glu Trp Asp Glu Val Trp Gly Arg Phe
    1730                1735                1740

Gly Arg Val Arg Gly Gly Ala Trp Lys Ser Pro Glu Gly Phe Arg

```
             1745                1750                1755

Ala Met His Glu Gln Leu Arg Ala Leu Gln Asp Thr Thr Asn Thr
    1760                1765                1770

Val Ser Gly Leu Arg Ala Gln Pro Ala Tyr Glu Arg Leu Ser Ala
    1775                1780                1785

Arg Tyr Gln Gly Val Leu Gly Ala Lys Gly Ala Glu Arg Ala Glu
    1790                1795                1800

Ala Val Glu Glu Leu Gly Ala Arg Val Thr Lys His Thr Ala Leu
    1805                1810                1815

Cys Ala Arg Leu Arg Asp Glu Val Val Arg Arg Val Pro Trp Glu
    1820                1825                1830

Met Asn Phe Asp Ala Leu Gly Gly Leu Leu Ala Glu Phe Asp Ala
    1835                1840                1845

Ala Ala Ala Asp Leu Ala Pro Trp Ala Val Glu Glu Phe Arg Gly
    1850                1855                1860

Ala Arg Glu Leu Ile Gln Tyr Arg Met Gly Leu Tyr Ser Ala Tyr
    1865                1870                1875

Ala Arg Ala Gly Gly Gln Thr Gly Ala Gly Ala Glu Ser Ala Pro
    1880                1885                1890

Ala Pro Leu Leu Val Asp Leu Arg Ala Leu Asp Ala Arg Ala Arg
    1895                1900                1905

Ala Ser Ser Ser Pro Glu Gly His Glu Val Asp Pro Gln Leu Leu
    1910                1915                1920

Arg Arg Arg Gly Glu Ala Tyr Leu Arg Ala Gly Gly Asp Pro Gly
    1925                1930                1935

Pro Leu Val Leu Arg Glu Ala Val Ser Ala Leu Asp Leu Pro Phe
    1940                1945                1950

Ala Thr Ser Phe Leu Ala Pro Asp Gly Thr Pro Leu Gln Tyr Ala
    1955                1960                1965

Leu Cys Phe Pro Ala Val Thr Asp Lys Leu Gly Ala Leu Leu Met
    1970                1975                1980

Arg Pro Glu Ala Ala Cys Val Arg Pro Pro Leu Pro Thr Asp Val
    1985                1990                1995

Leu Glu Ser Ala Pro Thr Val Thr Ala Met Tyr Val Leu Thr Val
    2000                2005                2010

Val Asn Arg Leu Gln Leu Ala Leu Ser Asp Ala Gln Ala Ala Asn
    2015                2020                2025

Phe Gln Leu Phe Gly Arg Phe Val Arg His Arg Gln Ala Thr Trp
    2030                2035                2040

Gly Ala Ser Met Asp Ala Ala Glu Leu Tyr Val Ala Leu Val
    2045                2050                2055

Ala Thr Thr Leu Thr Arg Glu Phe Gly Cys Arg Trp Ala Gln Leu
    2060                2065                2070

Gly Trp Ala Ser Gly Ala Ala Pro Arg Pro Pro Gly Pro
    2075                2080                2085

Arg Gly Ser Gln Arg His Cys Val Ala Phe Asn Glu Asn Asp Val
    2090                2095                2100

Leu Val Ala Leu Val Ala Gly Val Pro Glu His Ile Tyr Asn Phe
    2105                2110                2115

Trp Arg Leu Asp Leu Val Arg Gln His Glu Tyr Met His Leu Thr
    2120                2125                2130

Leu Glu Arg Ala Phe Glu Asp Ala Ala Glu Ser Met Leu Phe Val
    2135                2140                2145
```

-continued

```
Gln Arg Leu Thr Pro His Pro Asp Ala Arg Ile Arg Val Leu Pro
2150                2155                2160

Thr Phe Leu Asp Gly Gly Pro Pro Thr Arg Gly Leu Leu Phe Gly
2165                2170                2175

Thr Arg Leu Ala Asp Trp Arg Arg Gly Lys Leu Ser Glu Thr Asp
2180                2185                2190

Pro Leu Ala Pro Trp Arg Ser Ala Leu Glu Leu Gly Thr Gln Arg
2195                2200                2205

Arg Asp Val Pro Ala Leu Gly Lys Leu Ser Pro Ala Gln Ala Leu
2210                2215                2220

Ala Ala Val Ser Val Leu Gly Arg Met Cys Leu Pro Ser Ala Ala
2225                2230                2235

Leu Ala Ala Leu Trp Thr Cys Met Phe Pro Asp Asp Tyr Thr Glu
2240                2245                2250

Tyr Asp Ser Phe Asp Ala Leu Leu Ala Ala Arg Leu Glu Ser Gly
2255                2260                2265

Gln Thr Leu Gly Pro Ala Gly Gly Arg Glu Ala Ser Leu Pro Glu
2270                2275                2280

Ala Pro His Ala Leu Tyr Arg Pro Thr Gly Gln His Val Ala Val
2285                2290                2295

Leu Ala Ala Thr His Arg Thr Pro Ala Ala Arg Val Thr Ala
2300                2305                2310

Met Asp Leu Val Leu Ala Ala Val Leu Leu Gly Ala Pro Val Val
2315                2320                2325

Val Ala Leu Arg Asn Thr Thr Ala Phe Ser Arg Glu Ser Glu Leu
2330                2335                2340

Glu Leu Cys Leu Thr Leu Phe Asp Ser Arg Pro Gly Gly Pro Asp
2345                2350                2355

Ala Ala Leu Arg Asp Val Val Ser Ser Asp Ile Glu Thr Trp Ala
2360                2365                2370

Val Gly Leu Leu His Thr Asp Leu Asn Pro Ile Glu Asn Ala Cys
2375                2380                2385

Leu Ala Ala Gln Leu Pro Arg Leu Ser Ala Leu Ile Ala Glu Arg
2390                2395                2400

Pro Leu Ala Asp Gly Pro Pro Cys Leu Val Leu Val Asp Ile Ser
2405                2410                2415

Met Thr Pro Val Ala Val Leu Trp Glu Ala Pro Glu Pro Pro Gly
2420                2425                2430

Pro Pro Asp Val Arg Phe Val Gly Ser Glu Ala Thr Glu Glu Leu
2435                2440                2445

Pro Phe Val Ala Thr Ala Gly Asp Val Leu Ala Ala Ser Ala Ala
2450                2455                2460

Asp Ala Asp Pro Phe Phe Ala Arg Ala Ile Leu Gly Arg Pro Phe
2465                2470                2475

Asp Ala Ser Leu Leu Thr Gly Glu Leu Phe Pro Gly His Pro Val
2480                2485                2490

Tyr Gln Arg Pro Leu Ala Asp Glu Ala Gly Pro Ser Ala Pro Thr
2495                2500                2505

Ala Ala Arg Asp Pro Arg Asp Leu Ala Gly Gly Asp Gly Gly Ser
2510                2515                2520

Gly Pro Glu Asp Pro Ala Ala Pro Pro Ala Arg Gln Ala Asp Pro
2525                2530                2535
```

```
Gly Val Leu Ala Pro Thr Leu Leu Thr Asp Ala Thr Thr Gly Glu
    2540                2545                2550

Pro Val Pro Pro Arg Met Trp Ala Trp Ile His Gly Leu Glu Glu
2555                2560                2565

Leu Ala Ser Asp Asp Ala Gly Gly Pro Thr Pro Asn Pro Ala Pro
    2570                2575                2580

Ala Leu Leu Pro Pro Pro Ala Thr Asp Gln Ser Val Pro Thr Ser
2585                2590                2595

Gln Tyr Ala Pro Arg Pro Ile Gly Pro Ala Ala Thr Ala Arg Glu
    2600                2605                2610

Thr Arg Pro Ser Val Pro Pro Gln Gln Asn Thr Gly Arg Val Pro
2615                2620                2625

Val Ala Pro Arg Asp Asp Pro Arg Pro Ser Pro Pro Thr Pro Ser
    2630                2635                2640

Pro Pro Ala Asp Ala Ala Leu Pro Pro Pro Ala Phe Ser Gly Ser
2645                2650                2655

Ala Ala Ala Phe Ser Ala Ala Val Pro Arg Val Arg Arg Ser Arg
    2660                2665                2670

Arg Thr Arg Ala Lys Ser Arg Ala Pro Arg Ala Ser Ala Pro Pro
2675                2680                2685

Glu Gly Trp Arg Pro Pro Ala Leu Pro Ala Pro Val Ala Pro Val
    2690                2695                2700

Ala Ala Ser Ala Arg Pro Pro Asp Gln Pro Pro Thr Pro Glu Ser
2705                2710                2715

Ala Pro Pro Ala Trp Val Ser Ala Leu Pro Leu Pro Pro Gly Pro
    2720                2725                2730

Ala Ser Ala Arg Gly Ala Phe Pro Ala Pro Thr Leu Ala Pro Ile
2735                2740                2745

Pro Pro Pro Pro Ala Glu Gly Ala Val Val Pro Gly Gly Asp Arg
    2750                2755                2760

Arg Arg Gly Arg Arg Gln Thr Thr Ala Gly Pro Ser Pro Thr Pro
2765                2770                2775

Pro Arg Gly Pro Ala Ala Gly Pro Pro Arg Arg Leu Thr Arg Pro
    2780                2785                2790

Ala Val Ala Ser Leu Ser Ala Ser Leu Asn Ser Leu Pro Ser Pro
2795                2800                2805

Arg Asp Pro Ala Asp His Ala Ala Val Ser Ala Ala Ala Ala
    2810                2815                2820

Ala Val Pro Pro Ser Pro Gly Leu Ala Pro Pro Thr Ser Ala Val
2825                2830                2835

Gln Thr Ser Pro Pro Pro Leu Ala Pro Gly Pro Val Ala Pro Ser
    2840                2845                2850

Glu Pro Leu Cys Gly Trp Val Val Pro Gly Gly Pro Val Ala Arg
2855                2860                2865

Arg Pro Pro Pro Gln Ser Pro Ala Thr Lys Pro Ala Ala Arg Thr
    2870                2875                2880

Arg Ile Arg Ala Arg Ser Val Pro Gln Pro Pro Leu Pro Gln Pro
2885                2890                2895

Pro Leu Pro Gln Pro Pro Leu Pro Gln Pro Pro Leu Pro Gln Pro
    2900                2905                2910

Pro Leu Pro Gln Pro Pro Leu Pro Gln Pro Pro Leu Pro Gln Pro
2915                2920                2925

Pro Leu Pro Gln Pro Pro Leu Pro Gln Pro Pro Leu Pro Gln Pro
```

-continued

```
                      2930                2935                2940

Pro Leu Pro Pro Val Thr Arg Thr Leu Thr Pro Gln Ser Arg Asp
            2945                2950                2955

Ser Val Pro Thr Pro Glu Ser Pro Thr His Thr Asn Thr His Leu
    2960                2965                2970

Pro Val Ser Ala Val Thr Ser Trp Ala Ser Ser Leu Ala Leu His
    2975                2980                2985

Val Asp Ser Ala Pro Pro Ala Ser Leu Leu Gln Thr Leu His
    2990                2995                3000

Ile Ser Ser Asp Asp Glu His Ser Asp Ala Asp Ser Leu Arg Phe
    3005                3010                3015

Ser Asp Ser Asp Asp Thr Glu Ala Leu Asp Pro Leu Pro Pro Glu
    3020                3025                3030

Pro His Leu Pro Pro Ala Asp Glu Pro Pro Gly Pro Leu Ala Ala
    3035                3040                3045

Asp His Leu Gln Ser Pro His Ser Gln Phe Gly Pro Leu Pro Val
    3050                3055                3060

Gln Ala Asn Ala Val Leu Ser Arg Arg Tyr Val Arg Ser Thr Gly
    3065                3070                3075

Arg Ser Ala Leu Ala Val Leu Ile Arg Ala Cys Arg Arg Ile Gln
    3080                3085                3090

Gln Gln Leu Gln Arg Thr Arg Arg Ala Leu Phe Gln Arg Ser Asn
    3095                3100                3105

Ala Val Leu Thr Ser Leu His His Val Arg Met Leu Leu Gly
    3110                3115                3120

<210> SEQ ID NO 23
<211> LENGTH: 964
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Ala Gln Arg Ala Arg Gly Ser Ser Glu Arg Trp Ala Ala Gly Val
1               5                   10                  15

Glu Ala Ala Leu Asp Arg Val Glu Asn Arg Ala Glu Phe Asp Val Val
                20                  25                  30

Glu Leu Arg Arg Leu Gln Ala Leu Ala Gly Thr His Gly Tyr Asn Pro
            35                  40                  45

Arg Asp Phe Arg Lys Arg Ala Glu Gln Ala Leu Ala Ala Asn Ala Glu
        50                  55                  60

Ala Val Thr Leu Ala Leu Asp Thr Ala Phe Ala Phe Asn Pro Tyr Thr
65                  70                  75                  80

Pro Glu Asn Gln Arg His Pro Met Leu Pro Pro Leu Ala Ala Ile His
                85                  90                  95

Arg Leu Gly Trp Ser Ala Ala Phe His Ala Ala Ala Glu Thr Tyr Ala
            100                 105                 110

Asp Met Phe Arg Val Asp Ala Glu Pro Leu Ala Arg Leu Leu Arg Ile
        115                 120                 125

Ala Glu Gly Leu Leu Glu Met Ala Gln Ala Gly Asp Gly Phe Ile Asp
    130                 135                 140

Tyr His Glu Ala Val Gly Arg Leu Ala Asp Asp Met Thr Ser Val Pro
145                 150                 155                 160
```

```
Gly Leu Arg Arg Tyr Val Pro Phe Phe Gln His Gly Tyr Ala Asp Tyr
                165                 170                 175

Val Glu Leu Arg Asp Arg Leu Asp Ala Ile Arg Ala Asp Val His Arg
            180                 185                 190

Ala Leu Gly Gly Val Pro Leu Asp Leu Ala Ala Ala Ala Glu Gln Ile
        195                 200                 205

Ser Ala Ala Arg Asn Asp Pro Glu Ala Thr Ala Glu Leu Val Arg Thr
    210                 215                 220

Gly Val Thr Leu Pro Cys Pro Ser Glu Asp Ala Leu Val Ala Cys Ala
225                 230                 235                 240

Ala Ala Leu Glu Arg Val Asp Gln Ser Pro Val Lys Asn Thr Ala Tyr
                245                 250                 255

Ala Glu Tyr Val Ala Phe Val Thr Arg Gln Asp Thr Ala Glu Thr Lys
            260                 265                 270

Asp Ala Val Val Arg Ala Lys Gln Gln Arg Ala Glu Ala Thr Glu Arg
        275                 280                 285

Val Met Ala Gly Leu Arg Glu Ala Leu Ala Ala Arg Glu Arg Arg Ala
    290                 295                 300

Gln Ile Glu Ala Glu Gly Leu Ala Asn Leu Lys Thr Met Leu Lys Val
305                 310                 315                 320

Val Ala Val Pro Ala Thr Val Ala Lys Thr Leu Asp Gln Ala Arg Ser
                325                 330                 335

Val Ala Glu Ile Ala Asp Gln Val Glu Val Leu Leu Asp Gln Thr Glu
            340                 345                 350

Lys Thr Arg Glu Leu Asp Val Pro Ala Val Ile Trp Leu Glu His Ala
        355                 360                 365

Gln Arg Thr Phe Glu Thr His Pro Leu Ser Ala Arg Gly Asp Gly
    370                 375                 380

Pro Gly Pro Leu Ala Arg His Ala Gly Arg Leu Gly Ala Leu Phe Asp
385                 390                 395                 400

Thr Arg Arg Arg Val Asp Ala Leu Arg Arg Ser Leu Glu Glu Ala Glu
                405                 410                 415

Ala Glu Trp Asp Glu Val Trp Gly Arg Phe Gly Arg Val Arg Gly Gly
            420                 425                 430

Ala Trp Lys Ser Pro Glu Gly Phe Arg Ala Met His Glu Gln Leu Arg
        435                 440                 445

Ala Leu Gln Asp Thr Thr Asn Thr Val Ser Gly Leu Arg Ala Gln Pro
    450                 455                 460

Ala Tyr Glu Arg Leu Ser Ala Arg Tyr Gln Gly Val Leu Gly Ala Lys
465                 470                 475                 480

Gly Ala Glu Arg Ala Glu Ala Val Glu Glu Leu Gly Ala Arg Val Thr
                485                 490                 495

Lys His Thr Ala Leu Cys Ala Arg Leu Arg Asp Glu Val Val Arg Arg
            500                 505                 510

Val Pro Trp Glu Met Asn Phe Asp Ala Leu Gly Gly Leu Leu Ala Glu
        515                 520                 525

Phe Asp Ala Ala Ala Asp Leu Ala Pro Trp Ala Val Glu Glu Phe
    530                 535                 540

Arg Gly Ala Arg Glu Leu Ile Gln Tyr Arg Met Gly Leu Tyr Ser Ala
545                 550                 555                 560

Tyr Ala Arg Ala Gly Gly Gln Thr Gly Ala Gly Ala Glu Ser Ala Pro
                565                 570                 575

Ala Pro Leu Leu Val Asp Leu Arg Ala Leu Asp Ala Arg Ala Arg Ala
```

```
            580                 585                 590
Ser Ser Ser Pro Glu His Glu Val Asp Pro Gln Leu Leu Arg Arg
            595                 600                 605
Arg Gly Glu Ala Tyr Leu Arg Ala Gly Gly Asp Pro Gly Pro Leu Val
            610                 615                 620
Leu Arg Glu Ala Val Ser Ala Leu Asp Leu Pro Phe Ala Thr Ser Phe
625                 630                 635                 640
Leu Ala Pro Asp Gly Thr Pro Leu Gln Tyr Ala Leu Cys Phe Pro Ala
                    645                 650                 655
Val Thr Asp Lys Leu Gly Ala Leu Leu Met Arg Pro Glu Ala Ala Cys
                660                 665                 670
Val Arg Pro Pro Leu Pro Thr Asp Val Leu Glu Ser Ala Pro Thr Val
                675                 680                 685
Thr Ala Met Tyr Val Leu Thr Val Val Asn Arg Leu Gln Leu Ala Leu
                690                 695                 700
Ser Asp Ala Gln Ala Ala Asn Phe Gln Leu Phe Gly Arg Phe Val Arg
705                 710                 715                 720
His Arg Gln Ala Thr Trp Gly Ala Ser Met Asp Ala Ala Ala Glu Leu
                    725                 730                 735
Tyr Val Ala Leu Val Ala Thr Thr Leu Thr Arg Glu Phe Gly Cys Arg
                    740                 745                 750
Trp Ala Gln Leu Gly Trp Ala Ser Gly Ala Ala Pro Arg Pro Pro
                755                 760                 765
Pro Gly Pro Arg Gly Ser Gln Arg His Cys Val Ala Phe Asn Glu Asn
            770                 775                 780
Asp Val Leu Val Ala Leu Val Ala Gly Val Pro Glu His Ile Tyr Asn
785                 790                 795                 800
Phe Trp Arg Leu Asp Leu Val Arg Gln His Glu Tyr Met His Leu Thr
                    805                 810                 815
Leu Glu Arg Ala Phe Glu Asp Ala Ala Glu Ser Met Leu Phe Val Gln
                820                 825                 830
Arg Leu Thr Pro His Pro Asp Ala Arg Ile Arg Val Leu Pro Thr Phe
                835                 840                 845
Leu Asp Gly Gly Pro Pro Thr Arg Gly Leu Leu Phe Gly Thr Arg Leu
850                 855                 860
Ala Asp Trp Arg Arg Gly Lys Leu Ser Glu Thr Asp Pro Leu Ala Pro
865                 870                 875                 880
Trp Arg Ser Ala Leu Glu Leu Gly Thr Gln Arg Arg Asp Val Pro Ala
                885                 890                 895
Leu Gly Lys Leu Ser Pro Ala Gln Ala Leu Ala Ala Val Ser Val Leu
                900                 905                 910
Gly Arg Met Cys Leu Pro Ser Ala Ala Leu Ala Ala Leu Trp Thr Cys
                915                 920                 925
Met Phe Pro Asp Asp Tyr Thr Glu Tyr Asp Ser Phe Asp Ala Leu Leu
            930                 935                 940
Ala Ala Arg Leu Glu Ser Gly Gln Thr Leu Gly Pro Ala Gly Gly Arg
945                 950                 955                 960
Glu Ala Ser Leu

<210> SEQ ID NO 24
<211> LENGTH: 870
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 24

```
Glu Tyr Asp Ser Phe Asp Ala Leu Leu Ala Ala Arg Leu Glu Ser Gly
1               5                   10                  15

Gln Thr Leu Gly Pro Ala Gly Gly Arg Glu Ala Ser Leu Pro Glu Ala
            20                  25                  30

Pro His Ala Leu Tyr Arg Pro Thr Gly Gln His Val Ala Val Leu Ala
        35                  40                  45

Ala Ala Thr His Arg Thr Pro Ala Ala Arg Val Thr Ala Met Asp Leu
    50                  55                  60

Val Leu Ala Ala Val Leu Leu Gly Ala Pro Val Val Ala Leu Arg
65                  70                  75                  80

Asn Thr Thr Ala Phe Ser Arg Glu Ser Glu Leu Glu Leu Cys Leu Thr
                85                  90                  95

Leu Phe Asp Ser Arg Pro Gly Gly Pro Asp Ala Ala Leu Arg Asp Val
            100                 105                 110

Val Ser Ser Asp Ile Glu Thr Trp Ala Val Gly Leu Leu His Thr Asp
        115                 120                 125

Leu Asn Pro Ile Glu Asn Ala Cys Leu Ala Ala Gln Leu Pro Arg Leu
    130                 135                 140

Ser Ala Leu Ile Ala Glu Arg Pro Leu Ala Asp Gly Pro Pro Cys Leu
145                 150                 155                 160

Val Leu Val Asp Ile Ser Met Thr Pro Val Ala Val Leu Trp Glu Ala
                165                 170                 175

Pro Glu Pro Pro Gly Pro Pro Asp Val Arg Phe Val Gly Ser Glu Ala
            180                 185                 190

Thr Glu Glu Leu Pro Phe Val Ala Thr Ala Gly Asp Val Leu Ala Ala
        195                 200                 205

Ser Ala Ala Asp Ala Asp Pro Phe Phe Ala Arg Ala Ile Leu Gly Arg
    210                 215                 220

Pro Phe Asp Ala Ser Leu Leu Thr Gly Glu Leu Phe Pro Gly His Pro
225                 230                 235                 240

Val Tyr Gln Arg Pro Leu Ala Asp Glu Ala Gly Pro Ser Ala Pro Thr
                245                 250                 255

Ala Ala Arg Asp Pro Arg Asp Leu Ala Gly Gly Asp Gly Gly Ser Gly
            260                 265                 270

Pro Glu Asp Pro Ala Ala Pro Ala Arg Gln Ala Asp Pro Gly Val
        275                 280                 285

Leu Ala Pro Thr Leu Leu Thr Asp Ala Thr Thr Gly Glu Pro Val Pro
    290                 295                 300

Pro Arg Met Trp Ala Trp Ile His Gly Leu Glu Leu Ala Ser Asp
305                 310                 315                 320

Asp Ala Gly Gly Pro Thr Pro Asn Pro Ala Pro Ala Leu Leu Pro Pro
                325                 330                 335

Pro Ala Thr Asp Gln Ser Val Pro Thr Ser Gln Tyr Ala Pro Arg Pro
            340                 345                 350

Ile Gly Pro Ala Ala Thr Ala Arg Glu Thr Arg Pro Ser Val Pro Pro
        355                 360                 365

Gln Gln Asn Thr Gly Arg Val Pro Val Ala Pro Arg Asp Asp Pro Arg
    370                 375                 380

Pro Ser Pro Pro Thr Pro Ser Pro Pro Ala Asp Ala Ala Leu Pro Pro
385                 390                 395                 400
```

-continued

```
Pro Ala Phe Ser Gly Ser Ala Ala Phe Ser Ala Ala Val Pro Arg
            405                 410                 415

Val Arg Arg Ser Arg Arg Thr Arg Ala Lys Ser Arg Ala Pro Arg Ala
            420                 425                 430

Ser Ala Pro Pro Glu Gly Trp Arg Pro Ala Leu Pro Ala Pro Val
            435                 440                 445

Ala Pro Val Ala Ala Ser Ala Arg Pro Asp Gln Pro Pro Thr Pro
    450                 455                 460

Glu Ser Ala Pro Pro Ala Trp Val Ser Ala Leu Pro Leu Pro Pro Gly
465                 470                 475                 480

Pro Ala Ser Ala Arg Gly Ala Phe Pro Ala Pro Thr Leu Ala Pro Ile
                485                 490                 495

Pro Pro Pro Pro Ala Glu Gly Ala Val Val Pro Gly Gly Asp Arg Arg
                500                 505                 510

Arg Gly Arg Arg Gln Thr Thr Ala Gly Pro Ser Pro Thr Pro Pro Arg
            515                 520                 525

Gly Pro Ala Ala Gly Pro Pro Arg Arg Leu Thr Arg Pro Ala Val Ala
            530                 535                 540

Ser Leu Ser Ala Ser Leu Asn Ser Leu Pro Ser Pro Arg Asp Pro Ala
545                 550                 555                 560

Asp His Ala Ala Ala Val Ser Ala Ala Ala Ala Val Pro Pro Ser
                565                 570                 575

Pro Gly Leu Ala Pro Pro Thr Ser Ala Val Gln Thr Ser Pro Pro Pro
                580                 585                 590

Leu Ala Pro Gly Pro Val Ala Pro Ser Glu Pro Leu Cys Gly Trp Val
                595                 600                 605

Val Pro Gly Gly Pro Val Ala Arg Arg Pro Pro Gln Ser Pro Ala
            610                 615                 620

Thr Lys Pro Ala Ala Arg Thr Arg Ile Arg Ala Arg Ser Val Pro Gln
625                 630                 635                 640

Pro Pro Leu Pro Gln Pro Pro Leu Pro Gln Pro Pro Leu Pro Gln Pro
                645                 650                 655

Pro Leu Pro Gln Pro Pro Leu Pro Gln Pro Pro Leu Pro Gln Pro Pro
                660                 665                 670

Leu Pro Gln Pro Pro Leu Pro Gln Pro Pro Leu Pro Gln Pro Pro Leu
            675                 680                 685

Pro Gln Pro Pro Leu Pro Pro Val Thr Arg Thr Leu Thr Pro Gln Ser
            690                 695                 700

Arg Asp Ser Val Pro Thr Pro Glu Ser Pro Thr His Thr Asn Thr His
705                 710                 715                 720

Leu Pro Val Ser Ala Val Thr Ser Trp Ala Ser Ser Leu Ala Leu His
                725                 730                 735

Val Asp Ser Ala Pro Pro Ala Ser Leu Leu Gln Thr Leu His Ile
                740                 745                 750

Ser Ser Asp Asp Glu His Ser Asp Ala Asp Ser Leu Arg Phe Ser Asp
                755                 760                 765

Ser Asp Asp Thr Glu Ala Leu Asp Pro Leu Pro Glu Pro His Leu
770                 775                 780

Pro Pro Ala Asp Glu Pro Pro Gly Pro Leu Ala Ala Asp His Leu Gln
785                 790                 795                 800

Ser Pro His Ser Gln Phe Gly Pro Leu Pro Val Gln Ala Asn Ala Val
                805                 810                 815
```

```
Leu Ser Arg Arg Tyr Val Arg Ser Thr Gly Arg Ser Ala Leu Ala Val
            820                 825                 830

Leu Ile Arg Ala Cys Arg Arg Ile Gln Gln Gln Leu Gln Arg Thr Arg
            835                 840                 845

Arg Ala Leu Phe Gln Arg Ser Asn Ala Val Leu Thr Ser Leu His His
        850                 855                 860

Val Arg Met Leu Leu Gly
865             870

<210> SEQ ID NO 25
<211> LENGTH: 337
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Asp Pro Ala Val Ser Pro Ala Ser Thr Asp Pro Leu Asp Thr His
1               5                   10                  15

Ala Ser Gly Ala Gly Ala Ala Pro Ile Pro Val Cys Pro Thr Pro Glu
            20                  25                  30

Arg Tyr Phe Tyr Thr Ser Gln Cys Pro Asp Ile Asn His Leu Arg Ser
        35                  40                  45

Leu Ser Ile Leu Asn Arg Trp Leu Glu Thr Glu Leu Val Phe Val Gly
    50                  55                  60

Asp Glu Glu Asp Val Ser Lys Leu Ser Glu Gly Leu Gly Phe Tyr
65                  70                  75                  80

Arg Phe Leu Phe Ala Phe Leu Ser Ala Ala Asp Leu Val Thr Glu
                85                  90                  95

Asn Leu Gly Gly Leu Ser Gly Leu Phe Glu Gln Lys Asp Ile Leu His
            100                 105                 110

Tyr Tyr Val Glu Gln Glu Cys Ile Glu Val Val His Ser Arg Val Tyr
        115                 120                 125

Asn Ile Ile Gln Leu Val Leu Phe His Asn Asn Asp Gln Ala Arg Arg
    130                 135                 140

Ala Tyr Val Ala Arg Thr Ile Asn His Pro Ala Ile Arg Val Lys Val
145                 150                 155                 160

Asp Trp Leu Glu Ala Arg Val Arg Glu Cys Asp Ser Ile Pro Glu Lys
                165                 170                 175

Phe Ile Leu Met Ile Leu Ile Glu Gly Val Phe Phe Ala Ala Ser Phe
            180                 185                 190

Ala Ala Ile Ala Tyr Leu Arg Thr Asn Asn Leu Leu Arg Val Thr Cys
        195                 200                 205

Gln Ser Asn Asp Leu Ile Ser Arg Asp Glu Ala Val His Thr Thr Ala
    210                 215                 220

Ser Cys Tyr Ile Tyr Asn Asn Tyr Leu Gly Gly His Ala Lys Pro Glu
225                 230                 235                 240

Ala Ala Arg Val Tyr Arg Leu Phe Arg Glu Ala Val Asp Ile Glu Ile
                245                 250                 255

Gly Phe Ile Arg Ser Gln Ala Pro Thr Asp Ser Ser Ile Leu Ser Pro
            260                 265                 270

Gly Ala Leu Ala Ala Ile Glu Asn Tyr Val Arg Phe Ser Ala Asp Arg
        275                 280                 285

Leu Leu Gly Leu Ile His Met Gln Pro Leu Tyr Ser Ala Pro Ala Pro
    290                 295                 300
```

```
Asp Ala Ser Phe Pro Leu Ser Leu Met Ser Thr Asp Lys His Thr Asn
305                 310                 315                 320

Phe Phe Glu Cys Arg Ser Thr Ser Tyr Ala Gly Ala Val Val Asn Asp
                325                 330                 335

Leu

<210> SEQ ID NO 26
<211> LENGTH: 86
<212> TYPE: PRT
<213> ORGANISM: Human herpesvirus 2

<400> SEQUENCE: 26

Met Ser Trp Ala Leu Lys Thr Thr Asp Met Phe Leu Asp Ser Ser Arg
1               5                   10                  15

Cys Thr His Arg Thr Tyr Gly Asp Val Cys Ala Glu Ile His Lys Arg
            20                  25                  30

Glu Arg Glu Asp Arg Glu Ala Ala Arg Thr Ala Val Thr Asp Pro Glu
        35                  40                  45

Leu Pro Leu Leu Cys Pro Pro Asp Val Arg Ser Asp Pro Ala Ser Arg
    50                  55                  60

Asn Pro Thr Gln Gln Thr Arg Gly Cys Ala Arg Ser Asn Glu Arg Gln
65                  70                  75                  80

Asp Arg Val Leu Ala Pro
                85

<210> SEQ ID NO 27
<211> LENGTH: 467
<212> TYPE: PRT
<213> ORGANISM: Human herpesvirus 2

<400> SEQUENCE: 27

Met Gly Arg Arg Ala Pro Arg Gly Ser Pro Glu Ala Ala Pro Gly Ala
1               5                   10                  15

Asp Val Ala Pro Gly Ala Arg Ala Ala Trp Trp Val Trp Cys Val Gln
            20                  25                  30

Val Ala Thr Phe Ile Val Ser Ala Ile Cys Val Val Gly Leu Leu Val
        35                  40                  45

Leu Ala Ser Val Phe Arg Asp Arg Phe Pro Cys Leu Tyr Ala Pro Ala
    50                  55                  60

Thr Ser Tyr Ala Lys Ala Asn Ala Thr Val Glu Val Arg Gly Gly Val
65                  70                  75                  80

Ala Val Pro Leu Arg Leu Asp Thr Gln Ser Leu Leu Ala Thr Tyr Ala
                85                  90                  95

Ile Thr Ser Thr Leu Leu Leu Ala Ala Ala Val Tyr Ala Ala Val Gly
            100                 105                 110

Ala Val Thr Ser Arg Tyr Glu Arg Ala Leu Asp Ala Ala Arg Arg Leu
        115                 120                 125

Ala Ala Ala Arg Met Ala Met Pro His Ala Thr Leu Ile Ala Gly Asn
    130                 135                 140

Val Cys Ala Trp Leu Leu Gln Ile Thr Val Leu Leu Leu Ala His Arg
145                 150                 155                 160

Ile Ser Gln Leu Ala His Leu Ile Tyr Val Leu His Phe Ala Cys Leu
                165                 170                 175

Val Tyr Leu Ala Ala His Phe Cys Thr Arg Gly Val Leu Ser Gly Thr
            180                 185                 190
```

```
Tyr Leu Arg Gln Val His Gly Leu Ile Asp Pro Ala Pro Thr His His
            195                 200                 205
Arg Ile Val Gly Pro Val Arg Ala Val Met Thr Asn Ala Leu Leu Leu
            210                 215                 220
Gly Thr Leu Leu Cys Thr Ala Ala Ala Val Ser Leu Asn Thr Ile
225                 230                 235                 240
Ala Ala Leu Asn Phe Asn Phe Ser Ala Pro Ser Met Leu Ile Cys Leu
                245                 250                 255
Thr Thr Leu Phe Ala Leu Leu Val Ser Leu Leu Leu Val Val Glu
                260                 265                 270
Gly Val Leu Cys His Tyr Val Arg Val Leu Val Gly Pro His Leu Gly
            275                 280                 285
Ala Ile Ala Ala Thr Gly Ile Val Gly Leu Ala Cys Glu His Tyr His
            290                 295                 300
Thr Gly Gly Tyr Tyr Val Val Glu Gln Gln Trp Pro Gly Ala Gln Thr
305                 310                 315                 320
Gly Val Arg Val Ala Leu Ala Leu Val Ala Ala Phe Ala Leu Ala Met
                325                 330                 335
Ala Val Leu Arg Cys Thr Arg Ala Tyr Leu Tyr His Arg Arg His His
                340                 345                 350
Thr Lys Phe Phe Val Arg Met Arg Asp Thr Arg His Arg Ala His Ser
            355                 360                 365
Ala Leu Arg Arg Val Arg Ser Ser Met Arg Gly Ser Arg Arg Gly Gly
            370                 375                 380
Pro Pro Gly Asp Pro Gly Tyr Ala Glu Thr Pro Tyr Ala Ser Val Ser
385                 390                 395                 400
His His Ala Glu Ile Asp Arg Tyr Gly Asp Ser Asp Gly Asp Pro Ile
                405                 410                 415
Tyr Asp Glu Val Ala Pro Asp His Glu Ala Glu Leu Tyr Ala Arg Val
                420                 425                 430
Gln Arg Pro Gly Pro Val Pro Asp Ala Glu Pro Ile Tyr Asp Thr Val
            435                 440                 445
Glu Gly Tyr Ala Pro Arg Ser Ala Gly Glu Pro Val Tyr Ser Thr Val
450                 455                 460
Arg Arg Trp
465

<210> SEQ ID NO 28
<211> LENGTH: 734
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Phe Gly Gln Gln Leu Ala Ser Asp Val Gln Gln Tyr Leu Glu Arg
1               5                   10                  15
Leu Glu Lys Gln Arg Gln Gln Lys Val Gly Val Asp Glu Ala Ser Ala
            20                  25                  30
Gly Leu Thr Leu Gly Gly Asp Ala Leu Arg Val Pro Phe Leu Asp Phe
        35                  40                  45
Ala Thr Ala Thr Pro Lys Arg His Gln Thr Val Val Pro Gly Val Gly
    50                  55                  60
Thr Leu His Asp Cys Cys Glu His Ser Pro Leu Phe Ser Ala Val Ala
65                  70                  75                  80
```

```
Arg Arg Leu Leu Phe Asn Ser Leu Val Pro Ala Gln Leu Arg Gly Arg
                85                  90                  95

Asp Phe Gly Gly Asp His Thr Ala Lys Leu Glu Phe Leu Ala Pro Glu
            100                 105                 110

Leu Val Arg Ala Val Ala Arg Leu Arg Phe Arg Glu Cys Ala Pro Glu
            115                 120                 125

Asp Ala Val Pro Gln Arg Asn Ala Tyr Tyr Ser Val Leu Asn Thr Phe
130                 135                 140

Gln Ala Leu His Arg Ser Glu Ala Phe Arg Gln Leu Val His Phe Val
145                 150                 155                 160

Arg Asp Phe Ala Gln Leu Leu Lys Thr Ser Phe Arg Ala Ser Ser Leu
            165                 170                 175

Ala Glu Thr Thr Gly Pro Pro Lys Lys Arg Ala Lys Val Asp Val Ala
            180                 185                 190

Thr His Gly Gln Thr Tyr Gly Thr Leu Glu Leu Phe Gln Lys Met Ile
            195                 200                 205

Leu Met His Ala Thr Tyr Phe Leu Ala Ala Val Leu Leu Gly Asp His
    210                 215                 220

Ala Glu Gln Val Asn Thr Phe Leu Arg Leu Val Phe Glu Ile Pro Leu
225                 230                 235                 240

Phe Ser Asp Thr Ala Val Arg His Phe Arg Gln Arg Ala Thr Val Phe
            245                 250                 255

Leu Val Pro Arg Arg His Gly Lys Thr Trp Phe Leu Val Pro Leu Ile
            260                 265                 270

Ala Leu Ser Leu Ala Ser Phe Arg Gly Ile Lys Ile Gly Tyr Thr Ala
            275                 280                 285

His Ile Arg Lys Ala Thr Glu Pro Val Phe Asp Glu Ile Asp Ala Cys
    290                 295                 300

Leu Arg Gly Trp Phe Gly Ser Ser Arg Val Asp His Val Lys Gly Glu
305                 310                 315                 320

Thr Ile Ser Phe Ser Phe Pro Asp Gly Ser Arg Ser Thr Ile Val Phe
            325                 330                 335

Ala Ser Ser His Asn Thr Asn Gly Ile Arg Gly Gln Asp Phe Asn Leu
            340                 345                 350

Leu Phe Val Asp Glu Ala Asn Phe Ile Arg Pro Asp Ala Val Gln Thr
            355                 360                 365

Ile Met Gly Phe Leu Asn Gln Ala Asn Cys Lys Ile Ile Phe Val Ser
    370                 375                 380

Ser Thr Asn Thr Gly Lys Ala Ser Thr Ser Phe Leu Tyr Asn Leu Arg
385                 390                 395                 400

Gly Ala Ala Asp Glu Leu Leu Asn Val Val Thr Tyr Ile Cys Asp Asp
            405                 410                 415

His Met Pro Arg Val Val Thr His Thr Asn Ala Thr Ala Cys Ser Cys
            420                 425                 430

Tyr Ile Leu Asn Lys Pro Val Phe Ile Thr Met Asp Gly Ala Val Arg
            435                 440                 445

Arg Thr Ala Asp Leu Phe Leu Pro Asp Ser Phe Met Gln Glu Ile Ile
    450                 455                 460

Gly Gly Gln Ala Arg Glu Thr Gly Asp Asp Arg Pro Val Leu Thr Lys
465                 470                 475                 480

Ser Ala Gly Glu Arg Phe Leu Leu Tyr Arg Pro Ser Thr Thr Thr Asn
            485                 490                 495
```

```
Ser Gly Leu Met Ala Pro Glu Leu Tyr Val Tyr Val Asp Pro Ala Phe
            500                 505                 510

Thr Ala Asn Thr Arg Ala Ser Gly Thr Gly Ile Ala Val Val Gly Arg
        515                 520                 525

Tyr Arg Asp Asp Phe Ile Ile Phe Ala Leu Glu His Phe Phe Leu Arg
    530                 535                 540

Ala Leu Thr Gly Ser Ala Pro Ala Asp Ile Ala Arg Cys Val Val His
545                 550                 555                 560

Ser Leu Ala Gln Val Leu Ala Leu His Pro Gly Ala Phe Arg Ser Val
                565                 570                 575

Arg Val Ala Val Glu Gly Asn Ser Ser Gln Asp Ser Ala Val Ala Ile
            580                 585                 590

Ala Thr His Val His Thr Glu Met His Arg Ile Leu Ala Ser Ala Gly
        595                 600                 605

Ala Asn Gly Pro Gly Pro Glu Leu Leu Phe Tyr His Cys Glu Pro Pro
    610                 615                 620

Gly Gly Ala Val Leu Tyr Pro Phe Phe Leu Leu Asn Lys Gln Lys Thr
625                 630                 635                 640

Pro Ala Phe Glu Tyr Phe Ile Lys Lys Phe Asn Ser Gly Gly Val Met
                645                 650                 655

Ala Ser Gln Glu Leu Val Ser Val Thr Val Arg Leu Gln Thr Asp Pro
            660                 665                 670

Val Glu Tyr Leu Ser Glu Gln Leu Asn Asn Leu Ile Glu Thr Val Ser
        675                 680                 685

Pro Asn Thr Asp Val Arg Met Tyr Ser Gly Lys Arg Asn Gly Ala Ala
    690                 695                 700

Asp Asp Leu Met Val Ala Val Ile Met Ala Ile Tyr Leu Ala Ala Pro
705                 710                 715                 720

Thr Gly Ile Pro Pro Ala Phe Phe Pro Ile Thr Arg Thr Ser
                725                 730

<210> SEQ ID NO 29
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Asn Pro Val Ser Ala Ser Gly Ala Pro Ala Pro Pro Pro Pro Gly
1               5                   10                  15

Asp Gly Ser Tyr Leu Trp Ile Pro Ala Ser His Tyr Asn Gln Leu Val
            20                  25                  30

Thr Gly Gln Ser Ala Pro Arg His Pro Pro Leu Thr Ala Cys Gly Leu
        35                  40                  45

Pro Ala Ala Gly Thr Val Ala Tyr Gly His Pro Gly Ala Gly Pro Ser
    50                  55                  60

Pro His Tyr Pro Pro Pro Ala His Pro Tyr Pro Gly Met Leu Phe
65                  70                  75                  80

Ala Gly Pro Ser Pro Leu Glu Ala Gln Ile Ala Ala Leu Val Gly Ala
                85                  90                  95

Ile Ala Ala Asp Arg Gln Ala Gly Gly Leu Pro Ala Ala Ala Gly Asp
            100                 105                 110

His Gly Ile Arg Gly Ser Ala Lys Arg Arg His Glu Val Glu Gln
        115                 120                 125
```

```
Pro Glu Tyr Asp Cys Gly Arg Asp Glu Pro Asp Arg Asp Phe Pro Tyr
            130                 135                 140

Tyr Pro Gly Glu Ala Arg Pro Glu Pro Arg Pro Val Asp Ser Arg Arg
145                 150                 155                 160

Ala Ala Arg Gln Ala Ser Gly Pro His Glu Thr Ile Thr Ala Leu Val
                165                 170                 175

Gly Ala Val Thr Ser Leu Gln Gln Glu Leu Ala His Met Arg Ala Arg
            180                 185                 190

Thr His Ala Pro Tyr Gly Pro Tyr Pro Val Gly Pro Tyr His His
        195                 200                 205

Pro His Ala Asp Thr Glu Thr Pro Ala Gln Pro Pro Arg Tyr Pro Ala
    210                 215                 220

Lys Ala Val Tyr Leu Pro Pro His Ile Ala Pro Pro Gly Pro Pro
225                 230                 235                 240

Leu Ser Gly Ala Val Pro Pro Ser Tyr Pro Val Ala Val Thr
                245                 250                 255

Pro Gly Pro Ala Pro Pro Leu His Gln Pro Ser Pro Ala His Ala His
            260                 265                 270

Pro Pro Pro Pro Pro Gly Pro Thr Pro Pro Ala Ala Ser Leu
        275                 280                 285

Pro Gln Pro Glu Ala Pro Gly Ala Glu Ala Gly Ala Leu Val Asn Ala
    290                 295                 300

Ser Ser Ala Ala His Val Asn Val Asp Thr Ala Arg Ala Ala Asp Leu
305                 310                 315                 320

Phe Val Ser Gln Met Met Gly Ser Arg
                325

<210> SEQ ID NO 30
<211> LENGTH: 1240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Phe Cys Ala Ala Gly Gly Pro Ala Ser Pro Gly Gly Lys Pro Ala
1               5                   10                  15

Ala Arg Ala Ala Ser Gly Phe Phe Ala Pro His Asn Pro Arg Gly Ala
            20                  25                  30

Thr Gln Thr Ala Pro Pro Cys Arg Arg Gln Asn Phe Tyr Asn Pro
        35                  40                  45

His Leu Ala Gln Thr Gly Thr Gln Pro Lys Ala Leu Gly Pro Ala Gln
    50                  55                  60

Arg His Thr Tyr Tyr Ser Glu Cys Asp Glu Phe Arg Phe Ile Ala Pro
65                  70                  75                  80

Arg Ser Leu Asp Glu Asp Ala Pro Ala Glu Gln Arg Thr Gly Val His
                85                  90                  95

Asp Gly Arg Leu Arg Arg Ala Pro Lys Val Tyr Cys Gly Gly Asp Glu
            100                 105                 110

Arg Asp Val Leu Arg Val Gly Pro Glu Gly Phe Trp Pro Arg Arg Leu
        115                 120                 125

Arg Leu Trp Gly Gly Ala Asp His Ala Pro Glu Gly Phe Asp Pro Thr
    130                 135                 140

Val Thr Val Phe His Val Tyr Asp Ile Leu Glu His Val Glu His Ala
```

```
            145                 150                 155                 160
        Tyr Ser Met Arg Ala Ala Gln Leu His Glu Arg Phe Met Asp Ala Ile
                        165                 170                 175
        Thr Pro Ala Gly Thr Val Ile Thr Leu Leu Gly Leu Thr Pro Glu Gly
                        180                 185                 190
        His Arg Val Ala Val His Val Tyr Gly Thr Arg Gln Tyr Phe Tyr Met
                        195                 200                 205
        Asn Lys Ala Glu Val Asp Arg His Leu Gln Cys Arg Ala Pro Arg Asp
                        210                 215                 220
        Leu Cys Glu Arg Leu Ala Ala Leu Arg Glu Ser Pro Gly Ala Ser
        225                 230                 235                 240
        Phe Arg Gly Ile Ser Ala Asp His Phe Glu Ala Val Val Glu Arg
                        245                 250                 255
        Ala Asp Val Tyr Tyr Glu Thr Arg Pro Thr Leu Tyr Tyr Arg Val
                        260                 265                 270
        Phe Val Arg Ser Gly Arg Ala Leu Ala Tyr Leu Cys Asp Asn Phe Cys
                        275                 280                 285
        Pro Ala Ile Arg Lys Tyr Glu Gly Val Asp Ala Thr Thr Arg Phe
                        290                 295                 300
        Ile Leu Asp Asn Pro Gly Phe Val Thr Phe Gly Trp Tyr Arg Leu Lys
        305                 310                 315                 320
        Pro Gly Arg Gly Asn Ala Pro Ala Gln Pro Arg Pro Thr Ala Phe
                        325                 330                 335
        Gly Thr Ser Ser Asp Val Glu Phe Asn Cys Thr Ala Asp Asn Leu Ala
                        340                 345                 350
        Val Glu Gly Ala Met Cys Asp Leu Pro Ala Tyr Lys Leu Met Cys Phe
                        355                 360                 365
        Asp Ile Glu Cys Lys Ala Gly Gly Glu Asp Leu Ala Phe Pro Val
                        370                 375                 380
        Ala Glu Arg Pro Glu Asp Leu Val Ile Gln Ile Ser Cys Leu Leu Tyr
        385                 390                 395                 400
        Asp Leu Ser Thr Thr Ala Leu Glu His Ile Leu Leu Phe Ser Leu Gly
                        405                 410                 415
        Ser Cys Asp Leu Pro Glu Ser His Leu Ser Asp Leu Ala Ser Arg Gly
                        420                 425                 430
        Leu Pro Ala Pro Val Val Leu Glu Phe Asp Ser Glu Phe Glu Met Leu
                        435                 440                 445
        Leu Ala Phe Met Thr Phe Val Lys Gln Tyr Gly Pro Glu Phe Val Thr
                        450                 455                 460
        Gly Tyr Asn Ile Ile Asn Phe Asp Trp Pro Phe Val Leu Thr Lys Leu
        465                 470                 475                 480
        Thr Glu Ile Tyr Lys Val Pro Leu Asp Gly Tyr Gly Arg Met Asn Gly
                        485                 490                 495
        Arg Gly Val Phe Arg Val Trp Asp Ile Gly Gln Ser His Phe Gln Lys
                        500                 505                 510
        Arg Ser Lys Ile Lys Val Asn Gly Met Val Asn Ile Asp Met Tyr Gly
                        515                 520                 525
        Ile Ile Thr Asp Lys Val Lys Leu Ser Ser Tyr Lys Leu Asn Ala Val
                        530                 535                 540
        Ala Glu Ala Val Leu Lys Asp Lys Lys Asp Leu Ser Tyr Arg Asp
        545                 550                 555                 560
        Ile Pro Ala Tyr Tyr Ala Ser Gly Pro Ala Gln Arg Gly Val Ile Gly
                        565                 570                 575
```

```
Glu Tyr Cys Val Gln Asp Ser Leu Leu Val Gly Gln Leu Phe Phe Lys
            580                 585                 590

Phe Leu Pro His Leu Glu Leu Ser Ala Val Ala Arg Leu Ala Gly Ile
            595                 600                 605

Asn Ile Thr Arg Thr Ile Tyr Asp Gly Gln Gln Ile Arg Val Phe Thr
            610                 615                 620

Cys Leu Leu Arg Leu Ala Gly Gln Lys Gly Phe Ile Leu Pro Asp Thr
625                 630                 635                 640

Gln Gly Arg Phe Arg Gly Leu Asp Lys Glu Ala Pro Lys Arg Pro Ala
            645                 650                 655

Val Pro Arg Gly Glu Gly Arg Pro Gly Asp Gly Asn Gly Asp Glu
            660                 665                 670

Asp Lys Asp Asp Asp Glu Asp Gly Asp Glu Asp Gly Asp Glu Arg Glu
            675                 680                 685

Glu Val Ala Arg Glu Thr Gly Gly Arg His Val Gly Tyr Gln Gly Ala
            690                 695                 700

Arg Val Leu Asp Pro Thr Ser Gly Phe His Val Asp Pro Val Val Val
705                 710                 715                 720

Phe Asp Phe Ala Ser Leu Tyr Pro Ser Ile Ile Gln Ala His Asn Leu
            725                 730                 735

Cys Phe Ser Thr Leu Ser Leu Arg Pro Glu Ala Val Ala His Leu Glu
            740                 745                 750

Ala Asp Arg Asp Tyr Leu Glu Ile Glu Val Gly Gly Arg Arg Leu Phe
            755                 760                 765

Phe Val Lys Ala His Val Arg Glu Ser Leu Leu Ser Ile Leu Leu Arg
            770                 775                 780

Asp Trp Leu Ala Met Arg Lys Gln Ile Arg Ser Arg Ile Pro Gln Ser
785                 790                 795                 800

Thr Pro Glu Glu Ala Val Leu Leu Asp Lys Gln Gln Ala Ala Ile Lys
            805                 810                 815

Val Val Cys Asn Ser Val Tyr Gly Phe Thr Gly Val Gln His Gly Leu
            820                 825                 830

Leu Pro Cys Leu His Val Ala Ala Thr Val Thr Thr Ile Gly Arg Glu
            835                 840                 845

Met Leu Leu Ala Thr Arg Ala Tyr Val His Ala Arg Trp Ala Glu Phe
            850                 855                 860

Asp Gln Leu Leu Ala Asp Phe Pro Glu Ala Ala Gly Met Arg Ala Pro
865                 870                 875                 880

Gly Pro Tyr Ser Met Arg Ile Ile Tyr Gly Asp Thr Asp Ser Ile Phe
            885                 890                 895

Val Leu Cys Arg Gly Leu Thr Ala Ala Gly Leu Val Ala Met Gly Asp
            900                 905                 910

Lys Met Ala Ser His Ile Ser Arg Ala Leu Phe Leu Pro Pro Ile Lys
            915                 920                 925

Leu Glu Cys Glu Lys Thr Phe Thr Lys Leu Leu Leu Ile Ala Lys Lys
            930                 935                 940

Lys Tyr Ile Gly Val Ile Cys Gly Gly Lys Met Leu Ile Lys Gly Val
945                 950                 955                 960

Asp Leu Val Arg Lys Asn Asn Cys Ala Phe Ile Asn Arg Thr Ser Arg
            965                 970                 975

Ala Leu Val Asp Leu Leu Phe Tyr Asp Asp Thr Val Ser Gly Ala Ala
            980                 985                 990
```

```
Ala Ala Leu Ala Glu Arg Pro Ala  Glu Glu Trp Leu Ala  Arg Pro Leu
            995                 1000                 1005

Pro Glu  Gly Leu Gln Ala Phe  Gly Ala Val Leu Val  Asp Ala His
    1010                 1015                 1020

Arg Arg  Ile Thr Asp Pro Glu  Arg Asp Ile Gln Asp  Phe Val Leu
    1025                 1030                 1035

Thr Ala  Glu Leu Ser Arg His  Pro Arg Ala Tyr Thr  Asn Lys Arg
    1040                 1045                 1050

Leu Ala  His Leu Thr Val Tyr  Tyr Lys Leu Met Ala  Arg Arg Ala
    1055                 1060                 1065

Gln Val  Pro Ser Ile Lys Asp  Arg Ile Pro Tyr Val  Ile Val Ala
    1070                 1075                 1080

Gln Thr  Arg Glu Val Glu Glu  Thr Val Ala Arg Leu  Ala Ala Leu
    1085                 1090                 1095

Arg Glu  Leu Asp Ala Ala Ala  Pro Gly Asp Glu Pro  Ala Pro Pro
    1100                 1105                 1110

Ala Ala  Leu Pro Ser Pro Ala  Lys Arg Pro Arg Glu  Thr Pro Ser
    1115                 1120                 1125

His Ala  Asp Pro Pro Gly Gly  Ala Ser Lys Pro Arg  Lys Leu Leu
    1130                 1135                 1140

Val Ser  Glu Leu Ala Glu Asp  Pro Gly Tyr Ala Ile  Ala Arg Gly
    1145                 1150                 1155

Val Pro  Leu Asn Thr Asp Tyr  Tyr Phe Ser His Leu  Leu Gly Ala
    1160                 1165                 1170

Ala Cys  Val Thr Phe Lys Ala  Leu Phe Gly Asn Asn  Ala Lys Ile
    1175                 1180                 1185

Thr Glu  Ser Leu Leu Lys Arg  Phe Ile Pro Glu Thr  Trp His Pro
    1190                 1195                 1200

Pro Asp  Asp Val Ala Ala Arg  Leu Arg Ala Ala Gly  Phe Gly Pro
    1205                 1210                 1215

Ala Gly  Ala Gly Ala Thr Ala  Glu Glu Thr Arg Arg  Met Leu His
    1220                 1225                 1230

Arg Ala  Phe Asp Thr Leu Ala
    1235                 1240

<210> SEQ ID NO 31
<211> LENGTH: 881
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Ala Ala Ser Gly Gly Glu Gly Ser Arg Asp Val Arg Ala Pro Gly
1               5                   10                  15

Pro Pro Pro Gln Gln Pro Gly Ala Arg Pro Ala Val Arg Phe Arg Asp
            20                  25                  30

Glu Ala Phe Leu Asn Phe Thr Ser Met His Gly Val Gln Pro Ile Ile
        35                  40                  45

Ala Arg Ile Arg Glu Leu Ser Gln Gln Gln Leu Asp Val Thr Gln Val
    50                  55                  60

Pro Arg Leu Gln Trp Phe Arg Asp Val Ala Ala Leu Glu Val Pro Thr
65                  70                  75                  80

Gly Leu Pro Leu Arg Glu Phe Pro Phe Ala Ala Tyr Leu Ile Thr Gly
                85                  90                  95
```

```
Asn Ala Gly Ser Gly Lys Ser Thr Cys Val Gln Thr Leu Asn Glu Val
                100                 105                 110

Leu Asp Cys Val Val Thr Gly Ala Thr Arg Ile Ala Ala Gln Asn Met
            115                 120                 125

Tyr Val Lys Leu Ser Gly Ala Phe Leu Ser Arg Pro Ile Asn Thr Ile
        130                 135                 140

Phe His Glu Phe Gly Phe Arg Gly Asn His Val Gln Ala Gln Leu Gly
145                 150                 155                 160

Gln His Pro Tyr Thr Leu Ala Ser Ser Pro Ala Ser Leu Glu Asp Leu
                165                 170                 175

Gln Arg Arg Asp Leu Thr Tyr Tyr Trp Glu Val Ile Leu Asp Ile Thr
            180                 185                 190

Lys Arg Ala Leu Ala Ala His Gly Gly Glu Asp Ala Arg Asn Glu Phe
        195                 200                 205

His Ala Leu Thr Ala Leu Glu Gln Thr Leu Gly Leu Gly Gln Gly Ala
    210                 215                 220

Leu Thr Arg Leu Ala Ser Val Thr His Gly Ala Leu Pro Ala Phe Thr
225                 230                 235                 240

Arg Ser Asn Ile Ile Val Ile Asp Glu Ala Gly Leu Leu Gly Arg His
                245                 250                 255

Leu Leu Thr Thr Val Val Tyr Cys Trp Trp Met Ile Asn Ala Leu Tyr
            260                 265                 270

His Thr Pro Gln Tyr Ala Gly Arg Leu Arg Pro Val Leu Val Cys Val
        275                 280                 285

Gly Ser Pro Thr Gln Thr Ala Ser Leu Glu Ser Thr Phe Glu His Gln
290                 295                 300

Lys Leu Arg Cys Ser Val Arg Gln Ser Glu Asn Val Leu Thr Tyr Leu
305                 310                 315                 320

Ile Cys Asn Arg Thr Leu Arg Glu Tyr Thr Arg Leu Ser His Ser Trp
                325                 330                 335

Ala Ile Phe Ile Asn Asn Lys Arg Cys Val Glu His Glu Phe Gly Asn
            340                 345                 350

Leu Met Lys Val Leu Glu Tyr Gly Leu Pro Ile Thr Glu Glu His Met
        355                 360                 365

Gln Phe Val Asp Arg Phe Val Val Pro Glu Ser Tyr Ile Thr Asn Pro
    370                 375                 380

Ala Asn Leu Pro Gly Trp Thr Arg Leu Phe Ser Ser His Lys Glu Val
385                 390                 395                 400

Ser Ala Tyr Met Ala Lys Leu His Ala Tyr Leu Lys Val Thr Arg Glu
                405                 410                 415

Gly Glu Phe Val Val Phe Thr Leu Pro Val Leu Thr Phe Val Ser Val
            420                 425                 430

Lys Glu Phe Asp Glu Tyr Arg Arg Leu Thr Gln Gln Pro Thr Leu Thr
        435                 440                 445

Met Glu Lys Trp Ile Thr Ala Asn Ala Ser Arg Ile Thr Asn Tyr Ser
    450                 455                 460

Gln Ser Gln Asp Gln Asp Ala Gly His Val Arg Cys Glu Val His Ser
465                 470                 475                 480

Lys Gln Gln Leu Val Val Ala Arg Asn Asp Ile Thr Tyr Val Leu Asn
                485                 490                 495

Ser Gln Val Ala Val Thr Ala Arg Leu Arg Lys Met Val Phe Gly Phe
            500                 505                 510
```

```
Asp Gly Thr Phe Arg Thr Phe Glu Ala Val Leu Arg Asp Asp Ser Phe
            515                 520                 525

Val Lys Thr Gln Gly Glu Thr Ser Val Glu Phe Ala Tyr Arg Phe Leu
530                 535                 540

Ser Arg Leu Met Phe Gly Gly Leu Ile His Phe Tyr Asn Phe Leu Gln
545                 550                 555                 560

Arg Pro Gly Leu Asp Ala Thr Gln Arg Thr Leu Ala Tyr Gly Arg Leu
                565                 570                 575

Gly Glu Leu Thr Ala Glu Leu Leu Ser Leu Arg Arg Asp Ala Ala Gly
            580                 585                 590

Ala Ser Ala Thr Arg Ala Ala Asp Thr Ser Asp Arg Ser Pro Gly Glu
        595                 600                 605

Arg Ala Phe Asn Phe Lys His Leu Gly Pro Arg Asp Gly Gly Pro Asp
    610                 615                 620

Asp Phe Pro Asp Asp Asp Leu Asp Val Ile Phe Ala Gly Leu Asp Glu
625                 630                 635                 640

Gln Gln Leu Asp Val Phe Tyr Cys His Tyr Ala Leu Glu Glu Pro Glu
                645                 650                 655

Thr Thr Ala Ala Val His Ala Gln Phe Gly Leu Leu Lys Arg Ala Phe
            660                 665                 670

Leu Gly Arg Tyr Leu Ile Leu Arg Glu Leu Phe Gly Glu Val Phe Glu
        675                 680                 685

Ser Ala Pro Phe Ser Thr Tyr Val Asp Asn Val Ile Phe Arg Gly Cys
    690                 695                 700

Glu Leu Leu Thr Gly Ser Pro Arg Gly Gly Leu Met Ser Val Ala Leu
705                 710                 715                 720

Gln Thr Asp Asn Tyr Thr Leu Met Gly Tyr Thr Tyr Thr Arg Val Phe
                725                 730                 735

Ala Phe Ala Glu Glu Leu Arg Arg Arg His Ala Thr Ala Gly Val Ala
            740                 745                 750

Glu Phe Leu Glu Glu Ser Pro Leu Pro Tyr Ile Val Leu Arg Asp Gln
        755                 760                 765

His Gly Phe Met Ser Val Val Asn Thr Asn Ile Ser Glu Phe Val Glu
    770                 775                 780

Ser Ile Asp Ser Thr Glu Leu Ala Met Ala Ile Asn Ala Asp Tyr Gly
785                 790                 795                 800

Ile Ser Ser Lys Leu Ala Met Thr Ile Thr Arg Ser Gln Gly Leu Ser
                805                 810                 815

Leu Asp Lys Val Ala Ile Cys Phe Thr Pro Gly Asn Leu Arg Leu Asn
            820                 825                 830

Ser Ala Tyr Val Ala Met Ser Arg Thr Thr Ser Ser Glu Phe Leu His
        835                 840                 845

Met Asn Leu Asn Pro Leu Arg Glu Arg His Glu Arg Asp Asp Val Ile
    850                 855                 860

Ser Glu His Ile Leu Ser Ala Leu Arg Asp Pro Asn Val Val Ile Val
865                 870                 875                 880

Tyr

<210> SEQ ID NO 32
<211> LENGTH: 752
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 32

```
Met Glu Ala Pro Gly Ile Val Trp Val Glu Ser Val Ser Ala Ile
1               5                  10                  15

Thr Leu Tyr Ala Val Trp Leu Pro Pro Arg Thr Arg Asp Cys Leu His
            20                  25                  30

Ala Leu Leu Tyr Leu Val Cys Arg Asp Ala Ala Gly Glu Ala Arg Ala
        35                  40                  45

Arg Phe Ala Glu Val Ser Val Gly Ser Ser Asp Leu Gln Asp Phe Tyr
    50                  55                  60

Gly Ser Pro Asp Val Ser Ala Pro Gly Ala Val Ala Ala Arg Ala
65                  70                  75                  80

Ala Thr Ala Pro Ala Ala Ser Pro Leu Glu Pro Leu Gly Asp Pro Thr
                85                  90                  95

Leu Trp Arg Ala Leu Tyr Ala Cys Val Leu Ala Ala Leu Glu Arg Gln
                100                 105                 110

Thr Gly Arg Trp Ala Leu Phe Val Pro Leu Arg Leu Gly Trp Asp Pro
            115                 120                 125

Gln Thr Gly Leu Val Val Arg Val Glu Arg Ala Ser Trp Gly Pro Pro
130                 135                 140

Ala Ala Pro Arg Ala Ala Leu Leu Asp Val Glu Ala Lys Val Asp Val
145                 150                 155                 160

Asp Pro Leu Ala Leu Ser Ala Arg Val Ala Glu His Pro Gly Ala Arg
                165                 170                 175

Leu Ala Trp Ala Arg Leu Ala Ala Ile Arg Asp Ser Pro Gln Cys Ala
            180                 185                 190

Ser Ser Ala Ser Leu Ala Val Thr Ile Thr Thr Arg Thr Ala Arg Phe
        195                 200                 205

Ala Arg Glu Tyr Thr Thr Leu Ala Phe Pro Pro Thr Arg Lys Glu Gly
    210                 215                 220

Ala Phe Ala Asp Leu Val Glu Val Cys Glu Val Gly Leu Arg Pro Arg
225                 230                 235                 240

Gly His Pro Gln Arg Val Thr Ala Arg Val Leu Leu Pro Arg Gly Tyr
                245                 250                 255

Asp Tyr Phe Val Ser Ala Gly Asp Gly Phe Ser Ala Pro Ala Leu Val
            260                 265                 270

Ala Leu Phe Arg Gln Trp His Thr Val His Ala Ala Pro Gly Ala
        275                 280                 285

Leu Ala Pro Val Phe Ala Phe Leu Gly Pro Gly Phe Glu Val Arg Gly
    290                 295                 300

Gly Pro Val Gln Tyr Phe Ala Val Leu Gly Phe Pro Gly Trp Pro Thr
305                 310                 315                 320

Phe Thr Val Pro Ala Ala Ala Ala Glu Ser Ala Arg Asp Leu Val
                325                 330                 335

Arg Gly Ala Ala Ala Thr His Ala Ala Cys Leu Gly Ala Trp Pro Ala
            340                 345                 350

Val Gly Ala Arg Val Val Leu Pro Pro Arg Ala Trp Pro Ala Val Ala
        355                 360                 365

Ser Glu Ala Ala Gly Arg Leu Leu Pro Ala Phe Arg Glu Ala Val Ala
    370                 375                 380

Arg Trp His Pro Thr Ala Thr Thr Ile Gln Leu Leu Asp Pro Pro Ala
385                 390                 395                 400

Ala Val Gly Pro Val Trp Thr Ala Arg Phe Cys Phe Ser Gly Leu Gln
```

```
            405                 410                 415
Ala Gln Leu Leu Ala Ala Leu Ala Gly Leu Gly Glu Ala Gly Leu Pro
        420                 425                 430

Glu Ala Arg Gly Arg Ala Gly Leu Glu Arg Leu Asp Ala Leu Val Ala
        435                 440                 445

Ala Ala Pro Ser Glu Pro Trp Ala Arg Ala Val Leu Glu Arg Leu Val
    450                 455                 460

Pro Asp Ala Cys Asp Ala Cys Pro Ala Leu Arg Gln Leu Leu Gly Gly
465                 470                 475                 480

Val Met Ala Ala Val Cys Leu Gln Ile Glu Gln Thr Ala Ser Ser Val
                485                 490                 495

Lys Phe Ala Val Cys Gly Gly Thr Gly Ala Ala Phe Trp Gly Leu Phe
            500                 505                 510

Asn Val Asp Pro Gly Asp Ala Asp Ala Ala His Gly Ala Ile Gln Asp
            515                 520                 525

Ala Arg Arg Ala Leu Glu Ala Ser Val Arg Ala Val Leu Ser Ala Asn
        530                 535                 540

Gly Ile Arg Pro Arg Leu Ala Pro Ser Leu Ala Pro Glu Gly Val Tyr
545                 550                 555                 560

Thr His Val Val Thr Trp Ser Gln Thr Gly Ala Trp Phe Trp Asn Ser
                565                 570                 575

Arg Asp Asp Thr Asp Phe Leu Gln Gly Phe Pro Leu Arg Gly Ala Ala
            580                 585                 590

Tyr Ala Ala Ala Glu Val Met Arg Asp Ala Leu Arg Arg Ile Leu
            595                 600                 605

Arg Arg Pro Ala Ala Gly Pro Pro Glu Glu Ala Val Cys Ala Ala Arg
610                 615                 620

Gly Val Met Glu Asp Ala Cys Asp Arg Phe Val Leu Asp Ala Phe Gly
625                 630                 635                 640

Arg Arg Leu Asp Ala Glu Tyr Trp Ser Val Leu Thr Pro Pro Gly Glu
            645                 650                 655

Ala Asp Asp Pro Leu Pro Gln Thr Ala Phe Arg Gly Gly Ala Leu Leu
            660                 665                 670

Asp Ala Glu Gln Tyr Trp Arg Arg Val Val Arg Val Cys Pro Gly Gly
            675                 680                 685

Gly Glu Ser Val Gly Val Pro Val Asp Leu Tyr Pro Arg Pro Leu Val
        690                 695                 700

Leu Pro Pro Val Asp Cys Ala His His Leu Arg Glu Ile Leu Arg Glu
705                 710                 715                 720

Ile Gln Leu Val Phe Thr Gly Val Leu Glu Gly Val Trp Gly Glu Gly
            725                 730                 735

Gly Ser Phe Val Tyr Pro Phe Asp Glu Lys Ile Arg Phe Leu Phe Pro
            740                 745                 750

<210> SEQ ID NO 33
<211> LENGTH: 292
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Asp Gly Ala Val Arg Arg Thr Ala Asp Leu Phe Leu Pro Asp Ser
1               5                   10                  15
```

```
Phe Met Gln Glu Ile Ile Gly Gly Gln Ala Arg Glu Thr Gly Asp Asp
            20                  25                  30

Arg Pro Val Leu Thr Lys Ser Ala Gly Glu Arg Phe Leu Leu Tyr Arg
        35                  40                  45

Pro Ser Thr Thr Thr Asn Ser Gly Leu Met Ala Pro Glu Leu Tyr Val
    50                  55                  60

Tyr Val Asp Pro Ala Phe Thr Ala Asn Thr Arg Ala Ser Gly Thr Gly
65                  70                  75                  80

Ile Ala Val Val Gly Arg Tyr Arg Asp Asp Phe Ile Ile Phe Ala Leu
                85                  90                  95

Glu His Phe Phe Leu Arg Ala Leu Thr Gly Ser Ala Pro Ala Asp Ile
            100                 105                 110

Ala Arg Cys Val Val His Ser Leu Ala Gln Val Leu Ala Leu His Pro
        115                 120                 125

Gly Ala Phe Arg Ser Val Arg Val Ala Val Glu Gly Asn Ser Ser Gln
    130                 135                 140

Asp Ser Ala Val Ala Ile Ala Thr His Val His Thr Glu Met His Arg
145                 150                 155                 160

Ile Leu Ala Ser Ala Gly Ala Asn Gly Pro Gly Pro Glu Leu Leu Phe
                165                 170                 175

Tyr His Cys Glu Pro Pro Gly Gly Ala Val Leu Tyr Pro Phe Phe Leu
            180                 185                 190

Leu Asn Lys Gln Lys Thr Pro Ala Phe Glu Tyr Phe Ile Lys Lys Phe
        195                 200                 205

Asn Ser Gly Gly Val Met Ala Ser Gln Glu Leu Val Ser Val Thr Val
    210                 215                 220

Arg Leu Gln Thr Asp Pro Val Glu Tyr Leu Ser Glu Gln Leu Asn Asn
225                 230                 235                 240

Leu Ile Glu Thr Val Ser Pro Asn Thr Asp Val Arg Met Tyr Ser Gly
                245                 250                 255

Lys Arg Asn Gly Ala Ala Asp Asp Leu Met Val Ala Val Ile Met Ala
            260                 265                 270

Ile Tyr Leu Ala Ala Pro Thr Gly Ile Pro Pro Ala Phe Phe Pro Ile
        275                 280                 285

Thr Arg Thr Ser
    290

<210> SEQ ID NO 34
<211> LENGTH: 598
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Ala Thr Ser Ala Pro Gly Val Pro Ser Ser Ala Ala Val Arg Glu
1               5                   10                  15

Glu Ser Pro Gly Ser Ser Trp Lys Glu Gly Ala Phe Glu Arg Pro Tyr
            20                  25                  30

Val Ala Phe Asp Pro Asp Leu Leu Ala Leu Asn Glu Ala Leu Cys Ala
        35                  40                  45

Glu Leu Leu Ala Ala Cys His Val Val Gly Val Pro Pro Ala Ser Ala
    50                  55                  60

Leu Asp Glu Asp Val Glu Ser Asp Val Ala Pro Ala Pro Pro Arg Pro
65                  70                  75                  80
```

```
Arg Gly Ala Ala Arg Glu Ala Ser Gly Gly Arg Gly Pro Gly Ser Ala
                85                  90                  95

Arg Gly Pro Pro Ala Asp Pro Thr Ala Glu Gly Leu Leu Asp Thr Gly
            100                 105                 110

Pro Phe Ala Ala Ala Ser Val Asp Thr Phe Ala Leu Asp Arg Pro Cys
            115                 120                 125

Leu Val Cys Arg Thr Ile Glu Leu Tyr Lys Gln Ala Tyr Arg Leu Ser
130                 135                 140

Pro Gln Trp Val Ala Asp Tyr Ala Phe Leu Cys Ala Lys Cys Leu Gly
145                 150                 155                 160

Ala Pro His Cys Ala Ala Ser Ile Phe Val Ala Ala Phe Glu Phe Val
                165                 170                 175

Tyr Val Met Asp His His Phe Leu Arg Thr Lys Lys Ala Thr Leu Val
            180                 185                 190

Gly Ser Phe Ala Arg Phe Ala Leu Thr Ile Asn Asp Ile His Arg His
            195                 200                 205

Phe Phe Leu His Cys Cys Phe Arg Thr Asp Gly Val Pro Gly Arg
210                 215                 220

His Ala Gln Lys Gln Pro Arg Pro Thr Pro Ser Pro Gly Ala Ala Lys
225                 230                 235                 240

Val Gln Tyr Ser Asn Tyr Ser Phe Leu Ala Gln Ser Ala Thr Arg Ala
                245                 250                 255

Leu Ile Gly Thr Leu Ala Ser Gly Gly Asp Asp Gly Ala Gly Ala Gly
                260                 265                 270

Ala Gly Gly Gly Ser Gly Thr Gln Pro Ser Leu Thr Thr Ala Leu Met
            275                 280                 285

Asn Trp Lys Asp Cys Ala Arg Leu Leu Asp Cys Thr Glu Gly Lys Arg
            290                 295                 300

Gly Gly Gly Asp Ser Cys Cys Thr Arg Ala Ala Ala Arg Asn Gly Glu
305                 310                 315                 320

Phe Glu Ala Ala Ala Gly Ala Leu Ala Gln Gly Gly Glu Pro Glu Thr
                325                 330                 335

Trp Ala Tyr Ala Asp Leu Ile Leu Leu Leu Ala Gly Thr Pro Ala
            340                 345                 350

Val Trp Glu Ser Gly Pro Arg Leu Arg Ala Ala Asp Ala Arg Arg
            355                 360                 365

Ala Ala Val Ser Glu Ser Trp Glu Ala His Arg Gly Ala Arg Met Arg
            370                 375                 380

Asp Ala Ala Pro Arg Phe Ala Gln Phe Ala Glu Pro Gln Pro Gln Pro
385                 390                 395                 400

Asp Leu Asp Leu Gly Pro Leu Met Ala Thr Val Leu Lys His Gly Arg
                405                 410                 415

Gly Arg Gly Arg Thr Gly Gly Glu Cys Leu Leu Cys Asn Leu Leu Leu
            420                 425                 430

Val Arg Ala Tyr Trp Leu Ala Met Arg Arg Leu Arg Ala Ser Val Val
            435                 440                 445

Arg Tyr Ser Glu Asn Asn Thr Ser Leu Phe Asp Cys Ile Val Pro Val
450                 455                 460

Val Asp Gln Leu Glu Ala Asp Pro Glu Ala Gln Pro Gly Asp Gly Gly
465                 470                 475                 480

Arg Phe Val Ser Leu Leu Arg Ala Ala Gly Pro Glu Ala Ile Phe Lys
            485                 490                 495
```

```
His Met Phe Cys Asp Pro Met Cys Ala Ile Thr Glu Met Glu Val Asp
            500                 505                 510

Pro Trp Val Leu Phe Gly His Pro Arg Ala Asp His Arg Asp Glu Leu
        515                 520                 525

Gln Leu His Lys Ala Lys Leu Ala Cys Gly Asn Glu Phe Glu Gly Arg
    530                 535                 540

Val Cys Ile Ala Leu Arg Ala Leu Ile Tyr Thr Phe Lys Thr Tyr Gln
545                 550                 555                 560

Val Phe Val Pro Lys Pro Thr Ala Leu Ala Thr Phe Val Arg Glu Ala
                565                 570                 575

Gly Ala Leu Leu Arg Arg His Ser Ile Ser Leu Leu Ser Leu Glu His
            580                 585                 590

Thr Leu Cys Thr Tyr Val
            595

<210> SEQ ID NO 35
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Glu Tyr Asp Ser Phe Asp Ala Leu Leu Ala Ala Arg Leu Glu Ser
1               5                   10                  15

Gly Gln Thr Leu Gly Pro Ala Gly Gly Arg Glu Ala Ser Leu Pro Glu
            20                  25                  30

Ala Pro His Ala Leu Tyr Arg Pro Thr Gly Gln His Val Ala Val Leu
        35                  40                  45

Ala Ala Ala Thr His Arg Thr Pro Ala Ala Arg Val Thr Ala Met Asp
    50                  55                  60

Leu Val Leu Ala Ala Val Leu Leu Gly Ala Pro Val Val Val Ala Leu
65                  70                  75                  80

Arg Asn Thr Thr Ala Phe Ser Arg Glu Ser Glu Leu Glu Leu Cys Leu
                85                  90                  95

Thr Leu Phe Asp Ser Arg Pro Gly Gly Pro Asp Ala Ala Leu Arg Asp
            100                 105                 110

Val Val Ser Ser Asp Ile Glu Thr Trp Ala Val Gly Leu Leu His Thr
        115                 120                 125

Asp Leu Asn Pro Ile Glu Asn Ala Cys Leu Ala Ala Gln Leu Pro Arg
    130                 135                 140

Leu Ser Ala Leu Ile Ala Glu Arg Pro Leu Ala Asp Gly Pro Pro Cys
145                 150                 155                 160

Leu Val Leu Val Asp Ile Ser Met Thr Pro Val Ala Val Leu Trp Glu
                165                 170                 175

Ala Pro Glu Pro Pro Gly Pro Pro Asp Val Arg Phe Val Gly Ser Glu
            180                 185                 190

Ala Thr Glu Glu Leu Pro Phe Val Ala Thr Ala Gly Asp Val Leu Ala
        195                 200                 205

Ala Ser Ala Ala Asp Ala Asp Pro Phe Ala Arg Ala Ile Leu Gly
    210                 215                 220

Arg Pro Phe Asp Ala Ser Leu Leu Thr Gly Glu Leu Phe Pro Gly His
225                 230                 235                 240

Pro Val Tyr Gln Arg Pro Leu Ala Asp Glu Ala Gly Pro Ser Ala Pro
                245                 250                 255
```

```
Thr Ala Ala Arg Asp Pro Arg Asp Leu Ala Gly Gly Asp Gly Gly Ser
            260                 265                 270

Gly Pro Glu Asp Pro Ala Ala Pro Ala Arg Gln Ala Asp Pro Gly
            275                 280                 285

Val Leu Ala Pro Thr Leu Leu Thr Asp Ala Thr Thr Gly Glu Pro Val
    290                 295                 300

Pro Pro Arg Met Trp Ala Trp Ile His Gly Leu Glu Glu Leu Ala Ser
305                 310                 315                 320

Asp Asp Ala Gly Gly Pro Thr
                325

<210> SEQ ID NO 36
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Ala Thr Asp Ile Asp Met Leu Ile Asp Leu Gly Leu Asp Leu Ser
1               5                   10                  15

Asp Ser Glu Leu Glu Glu Asp Ala Leu Glu Arg Asp Glu Glu Gly Arg
            20                  25                  30

Arg Asp Asp Pro Glu Ser Asp Ser Ser Gly Glu Cys Ser Ser Ser Asp
        35                  40                  45

Glu Asp Met Glu Asp Pro Cys Gly Asp Gly Ala Glu Ala Ile Asp
50                  55                  60

Ala Ala Ile Pro Lys Gly Pro Pro Ala Arg Pro Glu Asp Ala Gly Thr
65                  70                  75                  80

Pro Glu Ala Ser Thr Pro Arg Pro Ala Ala Arg Gly Ala Asp Asp
                85                  90                  95

Pro Pro Pro Ala Thr Thr Gly Val Trp Ser Arg Leu Gly Thr Arg Arg
            100                 105                 110

Ser Ala Ser Pro Arg Glu Pro His Gly Gly Lys Val Ala Arg Ile Gln
        115                 120                 125

Pro Pro Ser Thr Lys Ala Pro His Pro Arg Gly Gly Arg Gly Arg
130                 135                 140

Arg Arg Gly Arg Gly Arg Tyr Gly Pro Gly Gly Ala Asp Ser Thr Pro
145                 150                 155                 160

Lys Pro Arg Arg Arg Val Ser Arg Asn Ala His Asn Gln Gly Gly Arg
                165                 170                 175

His Pro Ala Ser Ala Arg Thr Asp Gly Pro Gly Ala Thr His Gly Glu
            180                 185                 190

Ala Arg Arg Gly Gly Glu Gln Leu Asp Val Ser Gly Gly Pro Arg Pro
        195                 200                 205

Arg Gly Thr Arg Gln Ala Pro Pro Leu Met Ala Leu Ser Leu Thr
210                 215                 220

Pro Pro His Ala Asp Gly Arg Ala Pro Val Pro Glu Arg Lys Ala Pro
225                 230                 235                 240

Ser Ala Asp Thr Ile Asp Pro Ala Val Arg Ala Val Leu Arg Ser Ile
                245                 250                 255

Ser Glu Arg Ala Ala Val Glu Arg Ile Ser Glu Ser Phe Gly Arg Ser
            260                 265                 270

Ala Leu Val Met Gln Asp Pro Phe Gly Gly Met Pro Phe Pro Ala Ala
```

```
                275                 280                 285
Asn Ser Pro Trp Ala Pro Val Leu Ala Thr Gln Ala Gly Gly Phe Asp
    290                 295                 300
Ala Glu Thr Arg Arg Val Ser Trp Glu Thr Leu Val Ala His Gly Pro
305                 310                 315                 320
Ser Leu Tyr Arg Thr Phe Ala Ala Asn Pro Arg Ala Ala Ser Thr Ala
                325                 330                 335
Lys Ala Met Arg Asp Cys Val Leu Arg Gln Glu Asn Leu Ile Glu Ala
                340                 345                 350
Leu Ala Ser Ala Asp Glu Thr Leu Ala Trp Cys Lys Met Cys Ile His
                355                 360                 365
His Asn Leu Pro Leu Arg Pro Gln Asp Pro Ile Ile Gly Thr Ala Ala
                370                 375                 380
Ala Val Leu Glu Asn Leu Ala Thr Arg Leu Arg Pro Phe Leu Gln Cys
385                 390                 395                 400
Tyr Leu Lys Ala Arg Gly Leu Cys Gly Leu Asp Asp Leu Cys Ser Arg
                405                 410                 415
Arg Arg Leu Ser Asp Ile Lys Asp Ile Ala Ser Phe Val Leu Val Ile
                420                 425                 430
Leu Ala Arg Leu Ala Asn Arg Val Glu Arg Gly Val Ser Glu Ile Asp
                435                 440                 445
Tyr Thr Thr Val Gly Val Gly Ala Gly Glu Thr Met His Phe Tyr Ile
                450                 455                 460
Pro Gly Ala Cys Met Ala Gly Leu Ile Glu Ile Leu Asp Thr His Arg
465                 470                 475                 480
Gln Glu Cys Ser Ser Arg Val Cys Glu Leu Thr Ala Ser His Thr Ile
                485                 490                 495
Ala Pro Leu Tyr Val His Gly Lys Tyr Phe Tyr Cys Asn Ser Leu Phe
                500                 505                 510

<210> SEQ ID NO 37
<211> LENGTH: 87
<212> TYPE: PRT
<213> ORGANISM: Human herpesvirus 2

<400> SEQUENCE: 37

Met Thr Gly Lys Pro Ala Arg Leu Gly Arg Trp Val Val Leu Leu Phe
1               5                   10                  15
Val Ala Leu Val Ala Gly Val Pro Gly Glu Pro Pro Asn Ala Ala Gly
                20                  25                  30
Ala Arg Gly Val Ile Gly Asp Ala Gln Cys Arg Gly Asp Ser Ala Gly
            35                  40                  45
Val Val Ser Val Pro Gly Val Leu Val Pro Phe Tyr Leu Gly Met Thr
        50                  55                  60
Ser Met Gly Val Cys Met Ile Ala His Val Tyr Gln Ile Cys Gln Arg
65                  70                  75                  80
Ala Leu Ala Ala Gly Ser Ala
                85

<210> SEQ ID NO 38
<211> LENGTH: 302
<212> TYPE: PRT
<213> ORGANISM: Human herpesvirus 2

<400> SEQUENCE: 38

Asn Arg Trp Gly Ser Gly Val Pro Gly Pro Ile Asn Pro Pro Asn Ser
```

```
 1               5                  10                 15
Asp Val Val Phe Pro Gly Gly Ser Pro Val Ala Gln Tyr Cys Tyr Ala
                20                  25                 30

Tyr Pro Arg Leu Asp Asp Pro Gly Pro Leu Gly Ser Ala Asp Ala Gly
                35                  40                 45

Arg Gln Asp Leu Pro Arg Arg Val Val Arg His Glu Pro Leu Gly Arg
            50                  55                 60

Ser Phe Leu Thr Gly Gly Leu Val Leu Leu Ala Pro Pro Val Arg Gly
 65                 70                  75                 80

Phe Gly Ala Pro Asn Ala Thr Tyr Ala Ala Arg Val Thr Tyr Tyr Arg
                85                  90                 95

Leu Thr Arg Ala Cys Arg Gln Pro Ile Leu Leu Arg Gln Tyr Gly Gly
                100                 105                110

Cys Arg Gly Gly Glu Pro Pro Ser Pro Lys Thr Cys Gly Ser Tyr Thr
                115                 120                125

Tyr Thr Tyr Gln Gly Gly Gly Pro Pro Thr Arg Tyr Ala Leu Val Asn
                130                 135                140

Ala Ser Leu Leu Val Pro Ile Trp Asp Arg Ala Ala Glu Thr Phe Glu
145                 150                 155                160

Tyr Gln Ile Glu Leu Gly Gly Glu Leu His Val Gly Leu Leu Trp Val
                165                 170                175

Glu Val Gly Gly Glu Gly Pro Gly Pro Thr Ala Pro Pro Gln Ala Ala
                180                 185                190

Arg Ala Glu Gly Gly Pro Cys Val Pro Pro Val Pro Ala Gly Arg Pro
                195                 200                205

Trp Arg Ser Val Pro Pro Val Trp Tyr Ser Ala Pro Asn Pro Gly Phe
                210                 215                220

Arg Gly Leu Arg Phe Arg Glu Arg Cys Leu Pro Pro Gln Thr Pro Ala
225                 230                 235                240

Ala Pro Ser Asp Leu Pro Arg Val Ala Phe Ala Pro Gln Ser Leu Leu
                245                 250                255

Val Gly Ile Thr Gly Arg Thr Phe Ile Arg Met Ala Arg Pro Thr Glu
                260                 265                270

Asp Val Gly Val Leu Pro Pro His Trp Ala Pro Gly Ala Leu Asp Asp
                275                 280                285

Gly Pro Tyr Ala Pro Phe Pro Pro Arg Pro Arg Phe Arg Arg
                290                 295                300

<210> SEQ ID NO 39
<211> LENGTH: 3987
<212> TYPE: DNA
<213> ORGANISM: Human herpesvirus 2

<400> SEQUENCE: 39
atgtcgtact accatcacca tcaccatcac agtgccgaac agcgtaaaaa gaaaaaaacc     60
accaccacga cccaaggacg tggagctgaa gttgctatgg cggatgagga tggaggccgc    120
ttgagagctg ctgctgagac tactggagga cctggatcac cggaccctgc cgatggaccc    180
ccccctacac caaacccega tcgtagaccg gctgctagac ctggattcgg atggcatgga    240
ggacccgagg aaaacgagga cgaggcggac gacgccgctg ccgacgccga cgccgatgag    300 gctgccctg cttctggaga ggcggtagac gaacctgctg ccgatggagt tgttagccct    360
aggcaattgg ctttgttggc gagcatggta gacgaggctg tgagaacaat ccccttccct    420
ccccctgaac gtgatggagc acaagaggag gcggctagga gtccctcacc acccgtaca    480
```

```
ccttctatga gagcggatta cggcgaggaa aacgacgacg acgacgatga tgatgacgac    540
gatgatcgtg atgccggacg ctgggttagg ggacctgaaa ccacttctgc tgtccgtgga    600
gcataccccg atcctatggc gagtttgagc cctagaccac ctgccccgag gagacaccac    660
caccaccacc atcataggcg tagacgtgct cctagacgtc gttctgccgc tagtgactct    720
tccaaatctg gctcttcttc atctgcctct tccgcttcat cttcggcctc atcgtcctct    780
tcggcatccg cttcgagtag tgatgatgat gatgacgacg acgctgctag agccccgct    840
tctgctgccg accacgctgc tggcggaact ttgggagccg acgacgagga ggcgggagtt    900
cctgctcgtg ccccgggagc tgctcccgagg ccttctccac cccgtgctga acctgctccg    960
gctagaacac cggccgctac tgctggtaga ctggagcgta gacgtgcccg tgctgctgtg   1020
gctggtagag atgctactgg ccgcttcact gctggccgtc ctagacgtgt tgaactggac   1080
gccgatgctg cttctggtgc tttctacgcc cgttaccgtg atggttacgt gtctggtgaa   1140
ccttggcctg gcgctggtcc acctccgccc ggacgtgtac tctacggtgg attgggcgat   1200
tctcgccctg gtctgtgggg cgctccggag gctgaggagg ctagagcccg tttcgaggct   1260
tctggtgccc ctgctcctgt ttgggctcct gaattgggcg acgctgctca acaatacgcc   1320
ctcatcacac gcttgctgta cactcccgac gccgaggcta tgggatggct ccaaaaccct   1380
agagttgccc ctggtgatgt tgctctggat caggcttgtt tccgtatctc cggcgctgct   1440
cgtaactctt cttcgttcat ctccggttct gtggctagag ctgtgcctca cttgggatac   1500
gccatgccg ctggacgttt cggctgggga ctggctcatg ttgctgccgc tgtagcaatg   1560
tctagacgct acgaccgtgc tcaaaaagga ttcttgctca cgtcactgag gcgtgcttac   1620
gccccttttgt tggcccgtga aaacgctgcc ctcactggcg cccgtacccc cgatgacggt   1680
ggcgacgcca accgccacga tggtgatgat gctagaggca aacccgctgc cgctgctgct   1740
cctttgccct ctgccgccgc ttcccctgcc gatgaacgtg ctgttcctgc cggttacggt   1800
gccgctggtg tgttggctgc tttgggacgc ttgagtgctg ccccggctag tgcccccgct   1860
ggtgccgatg acgatgacga tgacgatggt gctggcggag gcggtggcgg tagacgtgct   1920
gaggctggac gtgttgctgt tgaatgcctg gctgcctgta aggaatcttt ggaggctctg   1980
gccgagggat tcgacggaga cttggcggct gtaccgggac tggcgggagc gaggcctgcc   2040
gctccacctc gccccggtcc tgctggtgct gccgctcctc ctcatgccga cgctcctaga   2100
ctccgtgctt ggctccgtga actccgtttc gttcgtgacg ctttggttct gatgagactg   2160
agaggcgact tgagagtggc tggaggatcc gaggctgctg ttgctgctgt ccgtgctgtt   2220
tctttggttg ctggtgcttt gggccctgct ttgccgagat ctccccgttt gttgtcgagt   2280
gccgccgctg ctgccgccga tttgttgttc caaaaccaat ccctccgccc tctgctcgcc   2340
gacactgttg ccgctgccga ttctctggct gctccggctt ctgccccacg tgaagctcgt   2400
aaacgtaaat cacccgctcc ggctcgtgct ccccctggtg gcgcccctag acccctaaa   2460
aaatcccgtg ccgatgcccc tagacctgct gctgctcccc ccgctggtgc tgctcccccc   2520
gctccccta ctccccccccc acgcccacct cgtcccgctg ccctcacacg ccgtcctgct   2580
gagggacccg atccacaagg cggctggcgt agacaacctc ctggcccatc ccatacaccg   2640
gcaccatctg ccgctgcttt ggaggcttac tgtgctcctc gtgctgtggc tgaactcacc   2700
gatcatccgc tgttccctgc tccctggcgt ccgcccctca tgttcgatcc tagagctttg   2760
gcttccttgg ccgctcgttg tgctgccccct ccccctggcg gtgctccggc tgctttcggt   2820
```

```
cctctccgtg cctctggtcc actccgccgt gccgctgcct ggatgagaca agttcccgac    2880
cctgaggatg ttagagttgt gatcttgtac tcgcccttgc ctggcgagga tttggccgct    2940
ggtagagctg gcggtggccc ccctcctgaa tggtctgctg aacgtggtgg tttgtcttgc    3000
ttgttggccg ccctgggaaa ccgtctgtgt ggtcctgcta ctgctgcttg ggctggaaac    3060
tggactggcg ctcccgatgt ttctgctctc ggtgctcaag gagttttgct gctctctact    3120
cgtgacttgg cattcgctgg agctgttgaa ttcctgggac tcttggctgg cgcttgtgat    3180
aggagactca tcgtcgtaaa cgctgtgaga gctgccgatt ggcctgccga tggtcctgtt    3240
gtgtctcgtc aacacgctta cttggcttgt gaagtgttgc ccgctgtcca atgtgctgtt    3300
cgctggcctg ctgctcgtga tctgaggcgt actgttctgg ctagtggtcg tgttttcgga    3360
cctggtgttt tcgctcgtgt cgaagctgct cacgctagac tgtacccga tgccccaccc    3420 ctccgtttgt gtcgtggagc aaacgttcgc taccgtgtcc gtactcgttt cggacccgat    3480
actctggttc caatgtcccc tcgtgaatac cgtcgtgctg ttctgcctgc cctcgatgga    3540
cgtgctgccg cttctggcgc tggtgacgct atggctcctg cgctccgga cttctgtgag    3600 gatgaggctc actcacatcg tgcctgtgcc cgctggggac tgggcgctcc attgaggcct    3660
gtatacgtgg cactgggccg tgatgctgtt agaggcggac ccgctgaatt gagaggccct    3720
cgtcgtgaat tctgtgctag ggctctgctc gaacccgatg agatgctccc tcctttggta    3780
ctccgtgacg acgccgatgc tggtcctccc ccacaaattc gctgggctag tgctgctgga    3840
cgtgctggta ctgtattggc tgctgctggc ggtggcgttg aagttgttgg tactgccgct    3900
ggactcgcta cacctccccg ccgtgaacct gtagacatgg atgctgaact cgaggatgat    3960
gacgacggat tgttcggaga gtaatag                                       3987
```

<210> SEQ ID NO 40  
<211> LENGTH: 1128  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 40

```
atgaagttcc tcgtgaacgt ggccctggtg ttcatggtgg tgtacatcag ctacatctac      60
gccaaccgtt ggaagtacgc tctggctgac ccatccctga gatggctga ccccaaccgt     120 ttccgtggca agaacctgcc cgtgctggac cagctgaccg acccccctgg cgtgaagcgt     180
gtgtaccaca tccagccatc cctcgaagac ccctccagc ccccctccat ccccatcacc     240
gtgtactacg ctgtgctgga acgcgcttgc cgttccgtgc tgctgcacgc tccttccgag     300
gctccccaga tcgtgcgtgg tgcttccgac gaggctcgca agcacaccta caacctgact     360
atcgcttggt acaggatggg tgacaactgc gctatcccta tcaccgtcat ggaatacacc     420
gagtgcccct acaacaagtc cctgggcgtg tgccctatcc gtaccagcc ccgttggtcc     480 tactacgact ccttcagcgc tgtgtccgag acaacctgg gtttcctgat gcacgctccc     540
gctttcgaga ctgctggcac ctacctgcgt ctggtcaaga tcaacgactg gaccgagatc     600
acccagttca tcctggaaca ccgtgctcgt gcttcgtgca agtacgccct gcccctgcgt     660
atccctcctg ctgcttgcct gacctccaag gcttaccagc agggcgtgac cgtggactcc     720
atcggcatgc tgccccgttt catccccgag aaccagcgta ccgtggctct gtactctctg     780
aagatcgctg gctggcacgg tcctaagccc cctacacct ccactctgct gccccctgag     840
```

| | |
|---|---|
| ctgtccgaca ccaccaacgc tactcagccc gagttggtgc ctgaggaccc cgaggactcc | 900 |
| gctctgttgg aggaccccgc tggaaccgtg tcctcccaga tcccccccaa ctggcacatc | 960 |
| ccttccatcc aggacgtggc ccctcaccac gctccagctg ctccctccaa ccccgtcgt | 1020 |
| cgtgctcaga tggctcccaa gcgtctgcgt ctgcccaca tccgtgacga cgacgctcct | 1080 |
| ccatcccacc agcccctgtt ctaccaccac caccatcacc actaataa | 1128 |

<210> SEQ ID NO 41
<211> LENGTH: 783
<212> TYPE: DNA
<213> ORGANISM: Human herpesvirus 2

<400> SEQUENCE: 41

| | |
|---|---|
| atgtctcgtc gtcgtggtcc tcgtcgtcgt ggtcctcgtc gtcgtccgcg tccgggtgcg | 60 |
| ccggcggtac cacgcccggg tgcgccggca gtgccgcgtc caggcgcact gcctaccgcg | 120 |
| gactctcaaa tggtgccggc gtatgattct ggtactgccg tcgaatctgc tccggcagcg | 180 |
| agctccctgc tgcgtcgttg gctgctggtc cctcaggcgg acgattccga tgacgcagac | 240 |
| tacgcgggca acgacgacgc ggagtgggct aacagcccgc caagcgaggg tggtggcaaa | 300 |
| gcgccggagg ctccgcacgc agcgcctgcc gcagcgtgcc cgcctccgcc tcctcgtaaa | 360 |
| gaacgtggcc ctcaacgtcc tctgccgccg cacctggctc tgcgtctgcg tactaccact | 420 |
| gagtacctgg cgcgtctgtc tctgcgtcgt cgccgtccgc cggctagccc gccggccgat | 480 |
| gcaccgcgtg gcaaagtgtg cttctctcca cgtgttcaag ttcgtcacct ggtggcttgg | 540 |
| gaaacggctg cccgtctggc tcgccgtggc agctgggcac gtgagcgcgc agaccgtgac | 600 |
| cgcttccgtc gccgtgtggc ggctgctgaa gccgttatcg gcccgtgcct ggaacctgag | 660 |
| gctcgcgctc gcgcgcgtgc gcgcgctcgt gcccacgaag atggcggtcc agcagaggaa | 720 |
| gaagaggcag ctgcagcagc gcgcggtagc tccgcggctg cgggtccagg tcgtcgtgcc | 780 |
| gta | 783 |

<210> SEQ ID NO 42
<211> LENGTH: 2523
<212> TYPE: DNA
<213> ORGANISM: Human herpesvirus 2

<400> SEQUENCE: 42

| | |
|---|---|
| atgtcgtact accatcacca tcaccatcac atggagccac gtcctggtac ttcttctcgc | 60 |
| gctgatcctg gtcctgaacg tccgccacgc cagactccgg gcacccagcc ggccgcccct | 120 |
| cacgcttggg gcatgctgaa cgatatgcag tggctggcgt cctctgattc cgaagaggag | 180 |
| actgaggttg gtatcagcga tgatgatctg caccgcgact ctaccagcga agcaggttcc | 240 |
| actgacaccg aaatgtttga agcgggcctg atggatgccg cgaccccgcc ggctcgtccg | 300 |
| ccggctgaac gtcagggtag ccctacgcct gcggatgcgc aaggctcttg tggtggtggt | 360 |
| ccagtaggcg aagaggaggc tgaggccggt ggcggcggtg atgtgtgtgc ggtttgtacc | 420 |
| gatgaaatcg caccgccgct gcgttgtcag tctttcccgt gcctgcaccc gttttgcatt | 480 |
| ccgtgcatga aacctggat cccgctgcgc aacacttgcc cgctgtgcaa cactccggtt | 540 |
| gcttatctga tcgttggtgt aaccgcatct ggttcctttt ctaccatccc gattgtcaac | 600 |
| gacccacgta cgcgtgttga ggcggaggcg gctgtacgtg cggcaccgc ggtggacttt | 660 |
| atctggaccg gtaacccgcg caccgcgcca cgctccctgt ctctgggtgg ccataccgtt | 720 |
| cgtgctctga gcccgacccc accttggcca ggcaccgatg acgaagacga cgatctggct | 780 |

```
gacgttgact atgttccgcc ggcaccgcgt cgcgcaccac gccgtggtgg cggtggcgcc      840
ggtgcgacgc gcggtacctc ccagccggca gcaactcgcc cagcaccgcc gggtgccccg      900
cgttctagca gctccggtgg cgcaccgctg cgtgctggcg tgggttctgg ttccggtggt      960
ggtccggccg tggcggctgt cgtcccgcgt gtggcttctc tgccaccggc agctggtggc     1020
ggtcgtgctc aagctcgtcg tgtcggcgag gacgcagcgg ctgctgaggg ccgtactcca     1080
ccggcccgtc aaccgcgcgc agcacaggaa ccgccgatcg tgatctccga ttccccgcca     1140
ccgagcccgc gtcgcccggc gggtccgggt ccgctgtctt ttgtatcctc cagctctgct     1200
caggtaagca gcggtcctgg cggtggcggc ctgccacagt cctctggtcg tgctgctcgt     1260
cctcgtgcgg cggttgctcc tcgtgtacgt tctccgccac gcgctgctgc cgcgccggtc     1320
gtttctgcct ctgctgacgc ggcaggtccg gctccgcctg cagttccggt tgatgcacac     1380
cgtgcaccgc gctctcgtat gacccaggcg cagactgata cccaggcaca atccctgggt     1440
cgcgcgggtg cgactgacgc tcgtggtagc ggtggtccgg gcgctgaagg tggcccgggt     1500
gttccacgcg gtactaacac tccgggcgct gcgccacacg cggctgaagg tgcggctgca     1560
cgtccgcgta acgtcgtggg ttccgacagc ggtccggctg caagcagcag cgcgagctct     1620
tccgctgcgc ctcgcagccc gctggcgccg cagggtgttg gcgccaagcg tgctgctccg     1680
cgtcgtgcac cggactccga ttctggcgac gcggtcacg gccgctggc ccctgctagc      1740 gcaggcgctg cgccgccatc cgccagcccg tcttctcagg cagctgtggc tgcggcgtcc     1800
tcttcttccg ctagcagctc ttccgcctct tctagcagcg cgtcctctag cagcgcatct     1860
tcctcttctg cttcttcttc tagcgcttct agctcttccg cgtcctcttc cgctggcggt     1920
gcaggcggct ctgttgcttc cgccagcggc gcaggtgagc gtcgtgaaac gagcctgggc     1980
ccacgtgctg ctgcaccgcg tggcccgcgt aagtgtgcgc gcaagacccg ccacgctgaa     2040
ggcggtccgg agccgggtgc gcgtgatccg gctccgggtc tgacccgtta cctgccgatt     2100
gcgggtgtgt cctccgttgt ggcactggcg ccgtatgtga acaaaactgt cacgggcgat     2160
tgcctgcctg ttctggacat ggaaaccggt catatcggcg cttacgtcgt tctggttgac     2220
caaaccggca acgtggcgga tctgctgcgt gcggccgctc cggcttggtc ccgtcgtacc     2280
ctgctgccgg aacatgctcg caactgtgta cgcccaccgg attacccaac cccgccggcc     2340
tccgagtgga actccctgtg gatgaccccg gttggtaaca tgctgttcga ccagggcacg     2400
ctggttggtg ctctggactt tcacggcctg cgctcccgtc acccgtggtc ccgtgagcaa     2460
ggcgctccgg cccctgcggg cgatgccccg gctggccacg gcgagagtac tagaggatca     2520
taa                                                                  2523
```

<210> SEQ ID NO 43
<211> LENGTH: 2928
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

```
atgtcgtact accatcacca tcaccatcac gccgctcaac gtgctagggg atcctctgaa       60
cgctgggctg ctggtgtcga ggctgctttg gatagagtgg agaaccgtgc cgaattcgat      120
gttgtcgagc tgaggagact ccaagctttg gctggtactc acggctacaa ccctcgtgat      180
ttccgtaaac gtgccgaaca ggctttggcg gcaaacgctg aggccgtaac attggctctg      240
```

```
gacactgcct tcgctttcaa cccatacacg cccgaaaacc aacgtcatcc tatgctccca    300
cctctcgctg ctattcaccg cctgggatgg agcgctgctt tccatgctgc tgctgaaact    360
tacgccgaca tgttccgtgt cgatgccgaa ccactggcta gactgctccg tatcgctgag    420
ggactgctgg agatggctca agctggcgac ggattcatcg attaccatga ggctgtcggt    480
agactggccg atgatatgac ttctgtgccc ggattgaggc gctacgttcc tttcttccaa    540
catggctacg ccgattacgt ggaactgaga gatcgcctgg atgctattag gccgacgtc     600 catagagcac tcggtggtgt tccgctggat ttggcggctg ctgccgaaca aatttccgct    660
gctcgtaacg atcctgaggc tactgctgaa ttggtccgta ctggtgtaac attgccttgc    720
cctagtgagg acgctctcgt ggcttgtgct gctgccctgg agagagtcga tcaatctccc    780
gtgaaaaaca cggcttacgc cgaatacgtt gccttcgtga cccgtcaaga cactgctgag    840
actaaagacg ctgtggtccg tgctaaacaa caacgtgctg aggccactga acgtgttatg    900
gctggcctga gagaggctct ggctgctaga aacgtcgtg ctcaaattga ggctgaggga     960
ttggcaaacc tgaaaaccat gctcaaagtc gtggctgtac ccgctactgt tgctaaaact    1020
ctcgaccagc tcgtagtgt tgccgaaatt gccgatcaag tcgaagtgtt gctggatcaa    1080
accgaaaaaa ctcgtgaact ggatgtgcct gctgtgatct ggctcgaaca cgcccaaaga    1140
acattcgaga cacacccttt gtctgccgct cgtggtgatg gtcctggacc cttggctcgt    1200
catgctggcc gcctcggtgc cctcttcgat actcgtcgta gagtagacgc cttgaggaga    1260
tccctggagg aggctgaggc tgaatgggac gaagtttggg gacgcttcgg tagagtgagg    1320
ggcggagcgt ggaaatctcc ggagggattc cgtgcaatgc atgagcaact gagggccctc    1380
caagacacaa caaacaccgt gtctggcctg agggctcaac ctgcttacga acgcttgtct    1440
gctcgctacc aaggagtact cggagcgaaa ggcgctgaga gagctgaggc tgttgaggaa    1500
ctcggtgctc gtgtcactaa acacaccgct ctgtgtgcta ggctgagaga tgaggtcgtc    1560
cgtagagtgc cttgggaaat gaacttcgat gctctgggag gattgttggc tgagttcgat    1620
gccgctgctg ccgatttggc accttgggct gtagaggaat ccgtggtgc tagagaactc     1680 attcaatacc gtatgggcct gtactctgcc tacgctagag ctggaggaca aactggtgct    1740
ggagctgaat ctgctcctgc tccttttgctc gtggatctga gggctttgga tgctcgtgct    1800
cgtgcttctt cttcccctga gggacatgaa gtggacccac aactgctgag gaggcgtgga    1860
gaggcttact tgagagctgg cggcgaccct ggacctctcg tgctccgtga agctgtttct    1920
gctttggacc tgccattcgc cacatctttc ttggcccccg atggaactcc cctccaatac    1980
gctttgtgct tccctgccgt aacggacaaa ctcggagctt tgctcatgag gcccgaggcc    2040
gcttgtgtta gacctccttt gcctaccgat gtgctggaat ctgccccaac tgtgactgcc    2100
atgtacgtac tcactgtggt caaccgcctc caactggcat tgagtgatgc tcaagcggca    2160
aacttccaac tgttcggtcg tttcgttcgt cataggcagg caacctgggg agcgtcaatg    2220
gatgccgccg ctgaattgta cgttgccctg gtggctacaa ctctcacacg tgaattcggt    2280
tgtcgctggg cacaattggg atgggctagt ggagctgctg ctcctagacc cccacctgga    2340
ccccgtggct cacaacgtca ctgtgtggca ttcaacgaga acgatgtcct cgtcgctttg    2400
gttgccggtg ttcccgaaca catctacaac ttctggcgcc tggacttggt ccgtcaacac    2460
gagtacatgc acctcacact ggagcgtgcc ttcgaggatg ctgccgagtc tatgctcttc    2520
gttcaacgcc tcactccaca tcccgacgct cgtattagag ttctgccgac cttcttggat    2580
```

```
ggtggtcctc ctacacgtgg tctgttgttc ggaacccgct tggcggactg gcgtcgtggt    2640
aaactgtctg aaaccgaccc attggcccca tggagatctg cttttggaact cggaacccaa   2700 cgtcgtgacg tgcctgcttt gggaaaactg tcccctgctc aagctttggc cgctgtgtcg   2760
gtactgggcc gtatgtgctt gccctcggct gccttggctg ctttgtggac ctgtatgttc   2820
cccgacgact acactgaata cgactcattc gacgccctct ggcggctcg cctggaatcg   2880 ggacaaacat tgggacctgc tggcggtaga gaggcttcat tgtaatag              2928
```

<210> SEQ ID NO 44  
<211> LENGTH: 2646  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 44

```
atgtcgtact accatcacca tcaccatcac gaatacgact ccttcgacgc tttgttggct     60
gctagactgg aatctggtca aaccttggga cccgctggcg gtagagaggc ttcttttgccc   120 gaggctcctc atgctttgta ccgtccaacc ggacaacatg ttgctgtgtt ggcggctgct   180
actcatagaa cccctgctgc tcgtgttact gctatggacc tggtcttggc ggccgttttg   240
ctgggcgctc ctgtggtggt cgctctgaga aacactactg ccttctcccg tgaatccgaa   300
ttggaactgt gcctcaccct gttcgattct cgtcccggcg gaccggatgc tgccctgaga   360
gatgtggtat cctccgacat tgaaaccctgg gctgtgggct tgctccacac cgatttgaac   420
cctattgaga acgcttgctt ggcggctcaa ctgccacgct tgtctgccct cattgctgaa   480
cgtcctttgg ccgatggacc cccttgtttg gtgttggtgg acatttcgat gacacctgtc   540
gctgttttgt gggaggcccc tgaaccacct ggccctcccg atgttcgttt cgtcggtagc   600
gaggccactg aggaattgcc tttcgtggct actgctggtg atgttttggc ggcgagtgct   660
gccgatgccg atcctttctt cgctcgtgct atcctgggcc gtccttttcga tgcttctctg   720 ctcactggtg aactgttccc tggtcacccc gtttaccaac gtcccctggc ggatgaggct   780
ggtccttctg ctcctactgc cgctcgtgat cctagagatc tggctggagg cgacggtgga   840
tccggacctg aggatcccgc tgctccacct gctagacagg ccgatcctgg tgttttggct   900
cctactctgc tcaccgatgc tactactggc gaacctgtgc caccccgtat gtgggcttgg   960
attcatggac tggaggaact ggcttccgat gatgccggcg gtcctacccc aaaccctgcc  1020
ccggctttgc tgcccctcc tgctacggat caatctgtcc ccacttccca atacgcccct  1080
agaccaattg gcccggctgc cactgctaga gaaaactcgtc cttccgttcc ccctcaacaa  1140
aacactggtc gtgtccctgt ggctccacgt gatgaccta gaccttcccc cctactcct  1200 tcccccctg ccgatgctgc tttgccacct cctgccttct ctggttctgc tgctgctttc  1260
tccgctgctg ttccacgtgt tcgtcgttct aggcgtactc gtgccaaatc ccgtgcccct  1320
cgtgcttctg ccccacccga gggatggcgt cccccgcgct tgcctgcccc tgttgctcct  1380
gtggcggctt ctgctcgtcc ccccgatcaa cctcctactc ccgaatctgc tccccggct  1440 tgggtttccg ctctgccatt gccacccgga cctgctagtc tcgtggtgc tttccctgct  1500 ccaaccttgg ccctattcc cccaccccc gctgagggag ctgttgttcc cgtggtgat  1560 cgtagacgtg gtcgccgtca aacaactgct ggaccatccc ctacaccgcc acgtggcccg  1620
gctgctggtc ctcctcgtcg cctcactagg cctgctgttg ctagtctgtc cgcttctttg  1680
```

```
aactctctgc cttcccccg tgatcctgcc gatcatgctg ctgccgtttc tgctgccgcc    1740
gctgccgtac caccttcacc tggactggct cccccaactt ctgctgtcca aacctctcct    1800
cctcccttgg cgcctggtcc tgttgcccca tctgaaccct tgtgtggctg ggttgtgcct    1860
ggaggccctg ttgctagacg tcccccaccc caatctccgg ctactaaacc ggctgctcgt    1920
acccgtatta gggctcgttc tgtgccccaa ccacccttgc cccaacctcc actgcctcaa    1980 cccccttgc ctcaacccc tctccccaa ccacctctgc ctcaacctcc gctgccccaa    2040
cctcctttgc cccaacctcc tttgccccaa cctcctttgc cccaacctcc gctgccccaa    2100
cctccgctgc cacctgttac tcgtacactc actccccaat tcgtgactc tgtgcctaca    2160 cctgagtctc caactcacac aaacacccac ttgcccgtta gtgctgtgac ttcttgggct    2220
tcgtccctgg ctctccatgt ggattctgcc cctcccctg cttcattgct ccaaactctc    2280
cacatttcct ccgatgatga acactccgac gccgactcac tccgcttctc cgattccgat    2340
gacactgagg ctctcgatcc tttgcctcct gaacctcact tgccacctgc cgatgaaccc    2400
cccggacctc tggctgccga ccatctccaa tcacctcact cacaattcgg tcctttgccc    2460
gttcaagcga acgctgttct gtctcgtcgt tacgtgagat caactggccg ttctgccttg    2520
gctgtgctca ttagagcttg tcgccgtatc caacaacaac tccagcgtac taggagagca    2580
ctcttccaac gctcaaacgc cgtgctcaca tcactccacc atgtccgtat gctcttggga    2640
taatag                                                               2646

<210> SEQ ID NO 45
<211> LENGTH: 261
<212> TYPE: DNA
<213> ORGANISM: Human herpesvirus 2

<400> SEQUENCE: 45
atgtcttggg ctctgaaaac caccgacatg ttcctggact cttctcgttg cacccaccgt      60
acctacggtg acgtttgcgc tgaaatccac aaacgtgaac gtgaagaccg tgaagctgct     120
cgtaccgctg ttaccgaccc ggaactgccg ctgctgtgcc cgccggacgt tcgttctgac     180
ccggcttctc gtaaccccgac ccagcagacc cgtggttgcg ctcgttctaa cgaacgtcag    240
gaccgtgttc tggctccgtg a                                               261

<210> SEQ ID NO 46
<211> LENGTH: 993
<212> TYPE: DNA
<213> ORGANISM: Human herpesvirus 2

<400> SEQUENCE: 46
atgaagttcc tcgtgaacgt ggccctggtg ttcatggtgg tgtacatcag ctacatctac      60
gctaaccgtt ggggttccgg cgtgcccggt cccatcaacc cccccaactc cgacgtggtg     120
ttccccggtg gttccccggt ggctcagtac tgctacgctt accccgtct ggacgaccct     180 ggtcccctgg gttctgctga cgctggtcgt caggacctgc ccgtcgtgt cgtgcgtcac     240 gagcccctgg gtcgtagctt cctgaccggt ggcctggtgc tgttggctcc cctgtgcgc     300 ggtttcggtg ctcccaacgc tacctacgct gtcgtgtga cctactaccg tctgacccgt     360
gcttgccgtc agcccatcct gctgcgtcag tacggtggtt gccgtggtgg agagccccca     420
tcccccaaga cctgcggttc ttacacctac acctaccagg gtggtggtcc cctacccgt     480 tacgctctgg tcaacgcttc cctgctggtg cccatctggg accgtgctgc tgagacttc     540 gagtaccaga tcgagctggg tggcgagctg cacgtgggtc tgctgtgggt ggaagtgggt    600
```

```
ggagagggtc ccggtcctac cgctcctcct caggctgctc gtgctgaggg tggtccttgc    660
gtgccacccg tgcctgctgg tcgtccttgg cgttccgtgc ccccgtgtg gtactccgct     720 cccaaccccg gtttccgcgg tctgcgtttc cgtgagcgtt gcctgcctcc ccagacccct    780
gctgctcctt ccgacctgcc tcgtgtggct ttcgctcccc agtccctgct cgtgggtatc    840
accggtcgta ccttcatccg tatggctcgt cccaccgagg acgtgggtgt cctgcctcct    900
cactgggctc caggtgctct ggacgacggt ccctacgctc ccttcccccc tcgtcccgt     960 ttccgtcgtc accaccacca tcaccactaa taa                                 993
```

```
<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Leu Ala His Val Ala Ala Ala Val
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Phe Ile Ser Gly Ser Val Ala Arg Ala
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Tyr Ala Leu Ile Thr Arg Leu Leu
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Tyr Asp Arg Ala Gln Lys Gly Phe
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 51

Gly Tyr Ala Met Ala Ala Gly Arg Phe
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Pro His Ala Asp Ala Pro Arg Leu
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Pro Ala Ala Ala Ala Ala Pro Leu
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Glu Ala Ala Val Ala Ala Val
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Phe Gly Trp Gly Leu Ala His Val
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Tyr Ala Leu Ile Thr Arg Leu Leu Tyr
1               5

<210> SEQ ID NO 57
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Leu Pro Arg Ser Pro Arg Leu Leu
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Leu Leu Phe Gln Asn Gln Ser Leu
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Asp Leu Leu Phe Gln Asn Gln Ser
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Arg Asn Ser Ser Ser Phe Ile Ser
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Ala Cys Phe Arg Ile Ser Gly Ala
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Phe Val Arg Asp Ala Leu Val Leu Met
```

```
1               5
```

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Phe Asp Gly Asp Leu Ala Ala Val Pro
1               5
```

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Gly Leu Gly Asp Ser Arg Pro Gly Leu
1               5
```

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Trp Ala Pro Glu Leu Gly Asp Ala Ala
1               5
```

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Glu Cys Leu Ala Ala Cys Arg Gly Ile
1               5
```

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

```
Arg Ala Trp Leu Arg Glu Leu Arg Phe
1               5
```

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic

```
                             peptide

<400> SEQUENCE: 68

Ala Leu Ala Gly Ser Thr Leu Ala Val
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Leu Leu Glu Asp Pro Ala Gly Thr Val
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Val Ile Gly Gly Ile Ala Phe Trp Val
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Val Tyr Tyr Ala Val Leu Glu Arg
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Lys Tyr Ala Leu Ala Asp Pro Ser Leu
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Phe Glu Thr Ala Gly Thr Tyr Leu
1               5

<210> SEQ ID NO 74
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Pro Ser Asn Pro Gly Leu Ile Ile
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ile Pro Ile Thr Val Tyr Tyr Ala Val
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Pro Pro Ser His Gln Pro Leu Phe
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Phe Leu Met His Ala Pro Ala Phe Glu
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Phe Ser Ala Val Ser Glu Asp Asn Leu
1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79
```

```
Val Tyr Tyr Ala Val Leu Glu Arg
1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ile Gly Met Leu Pro Arg Phe Ile
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Tyr Thr Glu Cys Pro Tyr Asn Lys Ser
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Phe Leu Met His Ala Pro Ala Phe Glu
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asn Leu Gly Phe Leu Met His Ala Pro
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Val Ile Gly Gly Ile Ala Phe Trp Val
1               5

<210> SEQ ID NO 85
<211> LENGTH: 9
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 85

Gly Ile Ala Phe Trp Val Arg Arg Arg
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Glu Asp Asn Leu Gly Phe Leu Met
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Thr Gln Pro Arg Trp Ser Tyr Tyr
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ile Ala Phe Trp Val Arg Arg Arg Ala
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Leu Val Ile Gly Gly Ile Ala Phe Trp
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Phe Trp Val Arg Arg Arg Ala Gln Met
1               5

```
<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Pro Tyr Thr Ser Thr Leu Leu Pro Pro
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Val Gly Thr Ala Ala Leu Leu Val Val
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr Ala Ala Leu Leu Val Val Ala Val
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Thr Ser Thr Leu Leu Pro Pro Glu Leu
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Thr Val Ser Ser Gln Ile Pro Pro
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96
```

```
Thr Ala Gly Thr Tyr Leu Arg Leu Val
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Val Thr Val Asp Ser Ile Gly Met
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Phe Trp Val Arg Arg Arg Ala Gln
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Val Tyr His Ile Gln Pro Ser Leu
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Tyr Leu Val Asn Pro Phe Leu Phe
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Pro Phe Leu Phe Ala Ala Gly Phe Leu
1               5

<210> SEQ ID NO 102
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 102

Thr Glu Tyr Val Leu Arg Ser Val Ile
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Ser Gln Ala Thr Glu Tyr Val Leu
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Ile Asp Gly Ile Phe Leu Arg Tyr
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Phe Leu Glu Asp Leu Ser His Ser Val
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Tyr Val Leu Arg Ser Val Ile Ala Lys
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Tyr Val Leu Arg Ser Val Ile Ala Lys
1               5
```

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ala Tyr Leu Val Asn Pro Phe Leu Phe
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Glu Thr Thr Thr Arg Arg Ala Leu Tyr
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Ile Asp Gly Ile Phe Leu Arg Tyr
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Tyr Leu Val Asn Pro Phe Leu Phe Ala
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Phe Val Cys Leu Phe Gly Leu Val Val
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 113

Leu Tyr Lys Glu Ile Arg Asp Ala Leu
1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Leu Asp Thr Phe Leu Trp Asp Arg
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Arg Val Ser Pro Thr Arg Gly Arg Arg
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Leu Asp Thr Phe Leu Trp Asp Arg
1               5

<210> SEQ ID NO 117
<211> LENGTH: 1221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
atgtcgtact accatcacca tcaccatcac atggtgctgt acggcgggct gggcgacagc      60
cgccccggcc tctgggggc gcccgaggcg gaggaggcgc gggccccggtt cgaggcctcg     120 ggcgccccgg cgcccgtgtg ggcgcccgag ctgggcgacg cggcgcagca gtacgccctg     180
atcacgcggc tgctgtacac gccggacgcg gaggcgatgg ggtggctcca gaacccgcgc     240
gtggcgcccg gggacgtggc gctggaccag gcctgcttcc ggatctcggg cgcggcgcgc     300
aacagcagct ccttcatctc cggcagcgtg gcgcgggccg tgccccacct ggggtacgcc     360
atggcggcgg gccgcttcgg ctggggcctg gcgcacgtgg cggccgccgt ggccatgagc     420
cgccgctacg accgcgcgca aagggcttc ctgctgacca gcctgcgccg cgcctacgcg     480 ccctgctgg cgcgcgagaa cgcggcgctg accggggcgc ggaccccga cgacggcggc     540 gacgccaacc gccgcgacgg cgacgacgcc cgcgggaagc ccgccgccgc cgccgccccg     600
ttgccgtcgg cggcggcgtc gccggccgac gagcgcgcgg tgcccgccgg ctacggcgcc     660
```

```
gcggggtgc tcgccgccct ggggcgcctg agcgccgcgc cgcctccgc gccggccggg      720
gccgacgacg acgacgacga cgacgacggc cggcggtg gtggcggtgg tggcggtggt      780
ggcggcggcc ggcgcgcgga ggcgggccgc gtggccgtgg agtgcctggc cgcctgccgc    840
gggatcctgg aggcgctggc ggagggcttc gacggcgacc tggcggccgt gccggggctg    900
gccggagccc ggcccgccgc gccccgcgc ccggggcccg cgggcgcggc cgccccgccg     960
cacgccgacg cgccccgcct gcgcgcctgg ctgcgcgagc tgcggttcgt gcgcgacgcg   1020
ctggtgctga tgcgcctgcg cggggacctg cgcgtggccg cggcagcga ggccgccgtg   1080
gccgccgtgc gcgccgtgag cctggtcgcc ggggccctgg gccggcgct gccgcggagc    1140
ccgcgcctgc tgagctccgc cgccgccgcc gccgcggacc tgctcttcca gaaccagagc   1200
ctgagtacta gaggatcata a                                             1221

<210> SEQ ID NO 118
<211> LENGTH: 705
<212> TYPE: DNA
<213> ORGANISM: Human herpesvirus 2

<400> SEQUENCE: 118
atgtcgtact accatcacca tcaccatcac atggggttcg tctgtctgtt tgggcttgtc     60
gttatgggag cctgggggc gtggggtggg tcacaggcaa ccgaatatgt tcttcgtagt    120
gttattgcca aagaggtggg ggacatacta agagtgcctt gcatgcggac ccccgcggac   180
gatgtttctt ggcgctacga ggccccgtcc gttattgact atgccgcat agacggaata    240
tttcttcgct atcactgccc ggggttggac acgttttgt gggataggca cgcccagagg    300
gcgtatcttg ttaacccctt tctctttgcg gcgggatttt tggaggactt gagtcactct   360
gtgtttccgg ccgacaccca ggaaacaacg acgcgccggg cccttataaa agagatacgc   420
gatgcgttgg gcagtcgaaa acaggccgtc agccacgcac ccgtcagggc cgggtgtgta   480
aactttgact actcacgcac tcgccgctgc gtcgggcgac gcgatttacg gcctgccaac   540
accacgtcaa cgtgggaacc gcctgtgtcg tcggacgatg aagcgagctc gcagtcgaag   600
ccctcgcca cccagccgcc cgtcctcgcc ctttcgaacg ccccccacg gcgggtctcc     660
ccgacgcgag gtcggcgccg gcatactcgc ctccgacgca actga                   705

<210> SEQ ID NO 119
<211> LENGTH: 762
<212> TYPE: DNA
<213> ORGANISM: Human herpesvirus 2

<400> SEQUENCE: 119
atgaagttcc tcgtgaacgt ggccctggtg ttcatggtgg tgtacatcag ctacatctac    60
gccaaccgtt gggggttcgt ctgtctgttt gggcttgtcg ttatgggagc ctgggggcg   120
tggggtgggt cacaggcaac cgaatatgtt cttcgtagtg ttattgccaa agaggtgggg   180
gacatactaa gagtgccttg catgcggacc cccgcggacg atgtttcttg gcgctacgag   240
gccccgtccg ttattgacta tgccgcata gacggaatat tcttcgcta tcactgcccg    300
gggttggaca cgttttgtg ggataggcac gcccagaggg cgtatcttgt taacccctt    360
ctctttgcgg cgggattttt ggaggacttg agtcactctg tgtttccggc cgacacccag   420
gaaacaacga cgcgccgggc cctttataaa gagatacgcg atgcgttggg cagtcgaaaa   480
caggccgtca gccacgcacc cgtcagggcc gggtgtgtaa actttgacta ctcacgcact   540
```

-continued

| | | |
|---|---|---|
| cgccgctgcg tcgggcgacg cgatttacgg cctgccaaca ccacgtcaac gtgggaaccg | 600 | |
| cctgtgtcgt cggacgatga agcgagctcg cagtcgaagc ccctcgccac ccagccgccc | 660 | |
| gtcctcgccc tttcgaacgc cccccacgg cgggtctccc cgacgcgagg tcggcgccgg | 720 | |
| catactcgcc tccgacgcaa ccatcaccat caccatcact ga | 762 | |

<210> SEQ ID NO 120
<211> LENGTH: 4155
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 120

| | | |
|---|---|---|
| atgtcgtact accatcacca tcaccatcac atggccgctc ctgcccgcga ccccccgggt | 60 | |
| taccggtacg ccgcggccat ggtgcccacc ggctccatcc tgagtacgat cgaggtggcg | 120 | |
| tcccaccgca gactctttga ttttttcgcc cgcgtgcgct ccgacgaaaa cagcctgtat | 180 | |
| gacgtagagt ttgacgccct gctggggtcc tactgcaaca ccctgtcgct cgtgcgcttt | 240 | |
| ctggagctcg gcctgtccgt ggcgtgcgtg tgcaccaagt tcccggagct ggcttacatg | 300 | |
| aacgaagggc gtgtgcagtt cgaggtccac cagcccctca tcgcccgcga cggcccgcac | 360 | |
| cccgtcgagc agcccgtgca taattacatg acgaaggtca tcgaccgccg ggccctgaac | 420 | |
| gccgccttca gcctggccac cgaggccatt gccctgctca cggggaggc cctggacggg | 480 | |
| acgggcatta gcctgcatcg ccagctgcgc gccatccagc agctcgcgcg caacgtccag | 540 | |
| gccgtcctgg gggcgtttga gcgcggcacg gccgaccaga tgctgcacgt gctgttggag | 600 | |
| aaggcgcctc ccctggccct gctgttgccc atgcaacgat atctcgacaa cgggcgcctg | 660 | |
| gcgaccaggg ttgcccgggc gaccctggtc gccgagctga agcggagctt tgcgacacg | 720 | |
| agcttcttcc tgggcaaggc gggccatcgc cgcgaggcca tcgaggcctg gctcgtggac | 780 | |
| ctgaccacgg cgacgcagcc gtccgtggcc gtgccccgcc tgacgcacgc cgacacgcgc | 840 | |
| gggcggccgg tcgacggggt gctggtcacc accgccgcca tcaaacagcg cctcctgcag | 900 | |
| tccttcctga aggtggagga caccgaggcc gacgtgccgg tgacctacgg cgagatggtc | 960 | |
| ttgaacgggg ccaacctcgt cacggcgctg gtgatgggca aggccgtgcg gagcctggac | 1020 | |
| gacgtgggcc gccacctgct ggagatgcag gaggagcaac tcgaggcgaa ccgggagacg | 1080 | |
| ctggatgaac tcgaaagcgc cccccagaca acgcgcgtgc gcgcggatct ggtggccata | 1140 | |
| ggcgacaggc tggtcttcct ggaggccctg agaagcgca tctacgccgc caccaacgtg | 1200 | |
| ccctaccccc tggtgggcgc catggacctg acgttcgtcc tgcccctggg gctgttcaac | 1260 | |
| ccggccatgg agcgcttcgc cgcgcacgcc ggggacctgg tgcccgcccc cggccacccg | 1320 | |
| gagccccgcg cgttccctcc ccggcagctg ttttttttggg gaaaggacca ccaggttctg | 1380 | |
| cggctgtcca tggagaacgc ggtcgggacc gtgtgtcatc cttcgctcat gaacatcgac | 1440 | |
| gcggccgtcg ggggcgtgaa ccacgacccc gtcgaggccg cgaatccgta cggggcgtac | 1500 | |
| gtcgcggccc cggccggccc cggcgcggac atgcagcagc gttttctgaa cgcctggcgg | 1560 | |
| cagcgcctcg cccacggccg ggtccggtgg gtcgccgagt gccagatgac cgcggagcag | 1620 | |
| ttcatgcagc ccgacaacgc caacctggct ctggagctgc accccgcgtt cgacttcttc | 1680 | |
| gcgggcgtgg ccgacgtcga gcttcccggc ggcgaagtcc ccccgccgg tccggggcg | 1740 | |
| atccaggcca cctggcgcgt ggtcaacggc aacctgcccc tggcgctgtg tccggtggcg | 1800 | |

```
tttcgtgacg cccgggcct ggagctcggc gttggccgcc acgccatggc gccggctacc    1860
atagccgccg tccgcgggc gttcgaggac cgcagctacc cggcggtgtt ctacctgctg    1920
caagccgcga ttcacggcag cgagcacgtg ttctgcgccc tggcgcggct cgtgactcag    1980
tgcatcacca gctactggaa caacacgcga tgccgcggcgt tcgtgaacga ctactcgctg    2040
gtctcgtaca tcgtgaccta cctcggggc gacctccccg aggagtgcat ggccgtgtat    2100
cgggacctgg tgcccacgt cgaggccctg gcccagctgg tggacgactt taccctgccg    2160
ggcccggagc tgggcgggca ggctcaggcc gagctgaatc acctgatgcg cgacccggcg    2220
ctgctgccgc ccctcgtgtg ggactgcgac ggccttatgc gacacgcggc cctggaccgc    2280
caccgagact gccggattga cgcggggag cacgagcccg tctacgcggc ggcgtgcaac    2340
gtggcgacgg ccgactttaa ccgcaacgac ggccggctgc tgcacaacac ccaggcccgc    2400
gcggccgacg ccgccgacga ccggccgcac cggccggccg actggaccgt ccaccacaaa    2460
atctactatt acgtgctggt gccggccttc tcgcggggc gctgctgcac cgcggggtc    2520
cgcttcgacc gcgtgtacgc cacgctgcag aacatggtgg tcccggagat cgcccccggc    2580
gaggagtgcc cgagcgatcc cgtgaccgac cccgcccacc cgctgcatcc cgccaatctg    2640
gtggccaaca cggtcaacgc catgttccac aacgggcgcg tcgtcgtcga cgggcccgcc    2700
atgctcacgc tgcaggtgct ggcgcacaac atggccgagc gcacgacggc gctgctgtgc    2760
tccgcgcgcg ccgacgcggg cgccaacacc gcgtcgacgg ccaacatgcg catcttcgac    2820
ggggcgctgc acgccggcgt gctgctcatg gccccccagc acctggacca caccatccaa    2880
aatggcgaat acttctacgt cctgcccgtc cacgcgctgt tgcgggcgc cgaccacgtg    2940
gccaacgcgc ccaacttccc cccggccctg cgcgacctgg cgcgccacgt ccccctggtc    3000
cccccggcc tggggccaa ctacttctcc tccatccgcc agcccgtggt gcagcacgcc    3060
cgcgagagcg cggcggggga aacgcgctg acctacgcgc tcatggcggg gtacttcaag    3120
atgagccccg tggccctgta tcaccagctc aagacgggcc tccacccgg gttcgggttc    3180
accgtcgtgc ggcaggaccg cttcgtgacc gagaacgtgc tgttttccga gcgcgcgtcg    3240
gaggcgtact ttctgggcca gctccaggtg gcccgccacg aaacgggcgg ggggtcagc    3300
ttcacgctca cccagccgcg cggaaacgtg gacctgggtg tgggctacac cgccgtcgcg    3360
gccacggcca ccgtccgcaa ccccgttacg gacatgggca acctccccca aaacttttac    3420
ctcggccgcg gggcccccc gctgctagac aacgcggccg ccgtgtacct gcgcaacgcg    3480
gtcgtggcg gaaaccggct ggggccggcc cagccctcc cggtctttgg ctgcgcccag    3540
gtgccgcggc gcgccggcat ggaccacggg caggatgccg tgtgtgagtt catcgccacc    3600
cccgtggcca cggacatcaa ctactttcgc cggccctgca acccgcgggg acgcgcggcc    3660
ggcggcgtgt acgcggggga caaggagggg gacgtcatag ccctcatgta cgaccacggc    3720
cagagcgacc cggcgcggcc cttcgcggcc acgccaacc cgtgggcgtc gcagcggttc    3780
tcgtacgggg acctgctgta caacgggccc tatcacctca cggggccctc gcccgtcctc    3840
agcccctgct tcaagttctt caccgcggcc gacatcacgg ccaaacatcg ctgcctggag    3900
cgtcttatcg tggaaacggg atcgcggta tccacggcca ccgctgccag cgacgtgcag    3960
tttaagcgcc cgccggggtg ccgcgagctc gtggaagacc cgtgcggcct gtttcaggaa    4020
gcctacccga tcacctgcgc cagcgacccc gccctgctac gcagcgcccg cgatggggag    4080
gcccacgcgc gagagaccca ctttacgcag tatctcatct acgacgcctc cccgctaaag    4140
ggcctgtctc tgtaa                                                    4155
```

<210> SEQ ID NO 121
<211> LENGTH: 1200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121

```
atgagtgccg aacagcgtaa aaagaaaaaa accaccacca cgacccaagg acgtggagct     60
gaagttgcta tggcggatga ggatggaggc cgcttgagag ctgctgctga gactactgga    120
ggacctggat caccggaccc tgccgatgga ccccccccta caccaaaccc cgatcgtaga    180
ccggctgcta gacctggatt cggatggcat ggaggacccg aggaaaacga ggacgaggcg    240
gacgacgccg ctgccgacgc cgacgccgat gaggctgccc ctgcttctgg agaggcggta    300
gacgaacctg ctgccgatgg agttgttagc cctaggcaat ggctttgtt ggcgagcatg     360
gtagacgagg ctgtgagaac aatcccttcc cctcccctg aacgtgatgg agcacaagag     420
gaggcggcta ggagtccctc accccccgt acaccttcta tgagagcgga ttacggcgag    480
gaaaacgacg acgacgacga tgatgatgac gacgatgatc gtgatgccgg acgctgggtt    540
aggggacctg aaaccacttc tgctgtccgt ggagcatacc ccgatcctat ggcgagtttg    600
agccctagac cacctgcccc gaggagacac caccaccacc accatcatag cgtagacgt     660
gctcctagac gtcgttctgc cgctagtgac tcttccaaat ctggctcttc ttcatctgcc    720
tcttccgctt catcttcggc ctcatcgtcc tcttcggcat ccgcttcgag tagtgatgat    780
gatgatgacg acgacgctgc tagagccccc gcttctgctg ccgaccacgc tgctggcgga    840
actttgggag ccgacgacga ggaggcggga gttcctgctc gtgccccggg agctgctccg    900
aggccttctc caccccgtgc tgaacctgct ccggctagaa caccggccgc tactgctggt    960
agactggagc gtagacgtgc ccgtgctgct gtggctggta gagatgctac tggccgcttc   1020
actgctggcc gtcctagacg tgttgaactg gacgccgatg ctgcttctgg tgctttctac   1080
gcccgttacc gtgatggtta cgtgtctggt gaaccttggc ctggcgctgg tccacctccg   1140
cccggacgtg tactctacgg tggattgggc gattctcgcc ctggtctgtg gggcgctccg   1200
```

<210> SEQ ID NO 122
<211> LENGTH: 825
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122

```
tcgagtgccg ccgctgctgc cgccgatttg ttgttccaaa accaatccct ccgccctctg     60
ctcgccgaca ctgttgccgc tgccgattct ctggctgctc cggcttctgc cccacgtgaa    120
gctcgtaaac gtaaatcacc cgctccggct cgtgctcccc ctggtggcgc ccctagaccc    180
cctaaaaaat cccgtgccga tgcccctaga cctgctgctg ctccccccgc tggtgctgct    240
cccccgctc cccctactcc cccccacgc ccacctcgtc ccgctgccct cacacgccgt     300
cctgctgagg gacccgatcc acaaggcggc tggcgtagac aacctcctgg cccatcccat    360
acaccggcac catctgccgc tgctttggag gcttactgtg ctcctcgtgc tgtggctgaa    420
ctcaccgatc atccgctgtt ccctgctccc tggcgtcccg ccctcatgtt cgatcctaga    480
```

| | |
|---|---|
| gctttggctt ccttggccgc tcgttgtgct gccctcccc ctggcggtgc tccggctgct | 540 |
| ttcggtcctc tccgtgcctc tggtccactc cgccgtgccg ctgcctggat gagacaagtt | 600 |
| cccgaccctg aggatgttag agttgtgatc ttgtactcgc ccttgcctgg cgaggatttg | 660 |
| gccgctggta gagctggcgg tggcccccct cctgaatggt ctgctgaacg tggtggtttg | 720 |
| tcttgcttgt tggccgccct gggaaaccgt ctgtgtggtc ctgctactgc tgcttgggct | 780 |
| ggaaactgga ctggcgctcc cgatgtttct gctctcggtg ctcaa | 825 |

<210> SEQ ID NO 123
<211> LENGTH: 933
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 123

| | |
|---|---|
| tgggctggaa actggactgg cgctcccgat gtttctgctc tcggtgctca aggagttttg | 60 |
| ctgctctcta ctcgtgactt ggcattcgct ggagctgttg aattcctggg actcttggct | 120 |
| ggcgcttgtg ataggagact catcgtcgta aacgctgtga gagctgccga ttggcctgcc | 180 |
| gatggtcctg ttgtgtctcg tcaacacgct tacttggctt gtgaagtgtt gcccgctgtc | 240 |
| caatgtgctg ttcgctggcc tgctgctcgt gatctgaggc gtactgttct ggctagtggt | 300 |
| cgtgttttcg gacctggtgt tttcgctcgt gtcgaagctg ctcacgctag actgtacccc | 360 |
| gatgccccac ccctccgttt gtgtcgtgga gcaaacgttc gctaccgtgt ccgtactcgt | 420 |
| ttcggacccg atactctggt tccaatgtcc cctcgtgaat accgtcgtgc tgttctgcct | 480 |
| gccctcgatg gacgtgctgc cgcttctggc gctggtgacg ctatggctcc tggcgctccg | 540 |
| gacttctgtg aggatgaggc tcactcacat cgtgcctgtg cccgctgggg actgggcgct | 600 |
| ccattgaggc ctgtatacgt ggcactgggc cgtgatgctg ttagaggcgg acccgctgaa | 660 |
| ttgagaggcc ctcgtcgtga attctgtgct agggctctgc tcgaacccga tggagatgct | 720 |
| cctcctttgg tactccgtga cgacgccgat gctggtcctc ccccacaaat tcgctgggct | 780 |
| agtgctgctg gacgtgctgg tactgtattg gctgctgctg gcggtggcgt tgaagttgtt | 840 |
| ggtactgccg ctggactcgc tacacctccc cgccgtgaac ctgtagacat ggatgctgaa | 900 |
| ctcgaggatg atgacgacgg attgttcgga gag | 933 |

<210> SEQ ID NO 124
<211> LENGTH: 1707
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 124

| | |
|---|---|
| tcgagtgccg ccgctgctgc cgccgatttg ttgttccaaa accaatccct ccgccctctg | 60 |
| ctcgccgaca ctgttgccgc tgccgattct ctggctgctc cggcttctgc cccacgtgaa | 120 |
| gctcgtaaac gtaaatcacc cgctccggct cgtgctcccc ctggtggcgc cctagaccc | 180 |
| cctaaaaaat cccgtgccga tgcccctaga cctgctgctg ctccccccgc tggtgctgct | 240 |
| cccccgctc ccctactcc cccccacgc ccactcgtc ccgctgccct cacacgccgt | 300 |
| cctgctgagg gacccgatcc acaaggcggc tggcgtagac aacctcctgg cccatcccat | 360 |
| acaccggcac catctgccgc tgctttggag gcttactgtg ctcctcgtgc tgtggctgaa | 420 |

```
ctcaccgatc atccgctgtt ccctgctccc tggcgtcccg ccctcatgtt cgatcctaga    480
gctttggctt ccttggccgc tcgttgtgct gcccctcccc ctggcggtgc tccggctgct    540
ttcggtcctc tccgtgcctc tggtccactc cgccgtgccg ctgcctggat gagacaagtt    600
cccgaccctg aggatgttag agttgtgatc ttgtactcgc ccttgcctgg cgaggatttg    660
gccgctggta gagctggcgg tggcccccct cctgaatggt ctgctgaacg tggtggtttg    720
tcttgcttgt tggccgccct gggaaaccgt ctgtgtggtc ctgctactgc tgcttgggct    780
ggaaactgga ctggcgctcc cgatgtttct gctctcggtg ctcaaggagt tttgctgctc    840
tctactcgtg acttggcatt cgctggagct gttgaattcc tgggactctt ggctggcgct    900
tgtgatagga gactcatcgt cgtaaacgct gtgagagctg ccgattggcc tgccgatggt    960
cctgttgtgt ctcgtcaaca cgcttacttg gcttgtgaag tgttgcccgc tgtccaatgt   1020
gctgttcgct ggcctgctgc tcgtgatctg aggcgtactg ttctggctag tggtcgtgtt   1080
ttcggacctg gtgttttcgc tcgtgtcgaa gctgctcacg ctagactgta ccccgatgcc   1140
ccacccctcc gtttgtgtcg tggagcaaac gttcgctacc gtgtccgtac tcgtttcgga   1200
cccgatactc tggttccaat gtcccctcgt gaataccgtc gtgctgttct gcctgccctc   1260
gatggacgtg ctgccgcttc tggcgctggt gacgctatgg ctcctggcgc tccggacttc   1320
tgtgaggatg aggctcactc acatcgtgcc tgtgcccgct ggggactggg cgctccattg   1380
aggcctgtat acgtggcact gggccgtgat gctgttagag gcggacccgc tgaattgaga   1440
ggccctcgtc gtgaattctg tgctagggct ctgctcgaac ccgatggaga tgctcctcct   1500
ttggtactcc gtgacgacgc cgatgctggt cctcccccac aaattcgctg ggctagtgct   1560
gctggacgtg ctggtactgt attggctgct gctggcggtg gcgttgaagt tgttggtact   1620
gccgctggac tcgctacacc tccccgccgt gaacctgtag acatggatgc tgaactcgag   1680
gatgatgacg acggattgtt cggagag                                        1707
```

<210> SEQ ID NO 125
<211> LENGTH: 1629
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 125

```
actgctggcc gtcctagacg tgttgaactg gacgccgatg ctgcttctgg tgctttctac     60
gcccgttacc gtgatggtta cgtgtctggt gaaccttggc ctggcgctgg tccacctccg    120
cccggacgtg tactctacgg tggattgggc gattctcgcc ctggtctgtg gggcgctccg    180
gaggctgagg aggctagagc ccgtttcgag gcttctggtg cccctgctcc tgtttgggct    240
cctgaattgg gcgacgctgc tcaacaatac gccctcatca cacgcttgct gtacactccc    300
gacgccgagg ctatgggatg gctccaaaac cctagagttg cccctggtga tgttgctctg    360
gatcaggctt gtttccgtat ctccggcgct gctcgtaact cttcttcgtt catctccggt    420
tctgtggcta gagctgtgcc tcacttggga tacgccatgg ccgctggacg tttcggctgg    480
ggactggctc atgttgctgc cgctgtagca atgtctagac gctacgaccg tgctcaaaaa    540
ggattcttgc tcacgtcact gaggcgtgct tacgcccctt tgttggcccg tgaaaacgct    600
gccctcactg gcgcccgtac ccccgatgac ggtggcgacg ccaaccgcca cgatggtgat    660
gatgctagag gcaaacccgc tgccgctgct gctcctttgc cctctgccgc cgcttcccct    720
```

```
gccgatgaac gtgctgttcc tgccggttac ggtgccgctg gtgtgttggc tgctttggga        780
cgcttgagtg ctgccccggc tagtgccccc gctggtgccg atgacgatga cgatgacgat        840
ggtgctggcg gaggcggtgg cggtagacgt gctgaggctg gacgtgttgc tgttgaatgc        900
ctggctgcct gtagaggaat cttggaggct ctggccgagg gattcgacgg agacttggcg        960
gctgtaccgg gactggcggg agcgaggcct gccgctccac ctcgccccgg tcctgctggt       1020
gctgccgctc ctcctcatgc cgacgctcct agactccgtg cttggctccg tgaactccgt       1080
ttcgttcgtg acgctttggt tctgatgaga ctgagaggcg acttgagagt ggctggagga       1140
tccgaggctg ctgttgctgc tgtccgtgct gtttctttgg ttgctggtgc tttgggccct       1200
gctttgccga gatctccccg tttgttgtcg agtgccgccg ctgctgccgc cgatttgttg       1260
ttccaaaacc aatccctccg ccctctgctc gccgacactg ttgccgctgc cgattctctg       1320
gctgctccgg cttctgcccc acgtgaagct cgtaaacgta aatcaccgc tccggctcgt       1380 gctccccctg gtggcgcccc tagaccccct aaaaaatccc gtgccgatgc ccctagacct       1440
gctgctgctc ccccgctgg tgctgctccc cccgctcccc ctactccccc cccacgccca       1500
cctcgtcccg ctgccctcac acgccgtcct gctgagggac ccgatccaca aggcggctgg       1560
cgtagacaac ctcctggccc atcccataca ccggcaccat ctgccgctgc tttggaggct       1620
tactgtgct                                                               1629

<210> SEQ ID NO 126
<211> LENGTH: 1632
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
gccgctgccg attctctggc tgctccggct tctgccccac gtgaagctcg taaacgtaaa         60 tcaccgctc cggctcgtgc tccccctggt ggcgcccta gaccccctaa aaatcccgt          120 gccgatgccc ctagacctgc tgctgctccc ccgctggtg ctgctccccc cgctcccct         180 actccccccc cacgcccacc tcgtcccgct gccctcacac gccgtcctgc tgagggaccc        240
gatccacaag gcggctggcg tagacaacct cctggcccat cccataacc ggcaccatct        300 gccgctgctt tggaggctta ctgtgctcct cgtgctgtgg ctgaactcac cgatcatccg        360
ctgttccctg ctccctggcg tcccgccctc atgttcgatc ctagagcttt ggcttccttg        420
gccgctcgtt gtgctgcccc tccccctggc ggtgctccgg ctgctttcgg tcctctccgt        480
gcctctggtc cactccgccg tgccgctgcc tggatgagac aagttcccga ccctgaggat        540
gttagagttg tgatcttgta ctcgcccttg cctggcgagg atttggccgc tggtagagct        600
ggcggtggcc cccctcctga atggtctgct gaacgtggtg gtttgtcttg cttgttggcc        660
gccctgggaa accgtctgtg tggtcctgct actgctgctt gggctggaaa ctggactggc        720
gctcccgatg tttctgctct cggtgctcaa ggagttttgc tgctctctac tcgtgacttg        780
gcattcgctg gagctgttga attcctggga ctcttggctg gcgcttgtga taggagactc        840
atcgtcgtaa acgctgtgag agctgccgat tggcctgccg atggtcctgt tgtgtctcgt        900
caacacgctt acttggcttg tgaagtgttg cccgctgtcc aatgtgctgt tcgctggcct        960
gctgctcgta atctgaggcg tactgttctg gctagtggtc gtgttttcgg acctggtgtt       1020
ttcgctcgtg tcgaagctgc tcacgctaga ctgtacccccg atgccccacc cctccgtttg       1080
```

```
tgtcgtggag caaacgttcg ctaccgtgtc cgtactcgtt tcggacccga tactctggtt    1140
ccaatgtccc ctcgtgaata ccgtcgtgct gttctgcctg ccctcgatgg acgtgctgcc    1200
gcttctggcg ctggtgacgc tatggctcct ggcgctccgg acttctgtga ggatgaggct    1260
cactcacatc gtgcctgtgc ccgctgggga ctgggcgctc cattgaggcc tgtatacgtg    1320
gcactgggcc gtgatgctgt tagaggcgga cccgctgaat tgagaggccc tcgtcgtgaa    1380
ttctgtgcta gggctctgct cgaacccgat ggagatgctc ctcctttggt actccgtgac    1440
gacgccgatg ctggtcctcc cccacaaatt cgctgggcta gtgctgctgg acgtgctggt    1500
actgtattgg ctgctgctgg cggtggcgtt gaagttgttg gtactgccgc tggactcgct    1560
acacctcccc gccgtgaacc tgtagacatg gatgctgaac tcgaggatga tgacgacgga    1620
ttgttcggag ag                                                        1632

<210> SEQ ID NO 127
<211> LENGTH: 3330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127
caccaccacc accaccatca taggcgtaga cgtgctccta gacgtcgttc tgccgctagt      60
gactcttcca aatctggctc ttcttcatct gcctcttccg cttcatcttc ggcctcatcg     120
tcctcttcgg catccgcttc gagtagtgat gatgatgatg acgacgacgc tgctagagcc     180
cccgcttctg ctgccgacca cgctgctggc ggaactttgg gagccgacga cgaggaggcg     240
ggagttcctg ctcgtgcccc gggagctgct ccgaggcctt ctccacccccg tgctgaacct    300 gctccggcta gaacaccggc cgctactgct ggtagactgg agcgtagacg tgcccgtgct    360
gctgtggctg gtagagatgc tactggccgc ttcactgctg gccgtcctag acgtgttgaa    420
ctggacgccg atgctgcttc tggtgctttc tacgcccgtt accgtgatgg ttacgtgtct    480
ggtgaacctt ggcctggcgc tggtccacct ccgcccggac gtgtactcta cggtggattg    540
ggcgattctc gccctggtct gtggggcgct ccggaggctg aggaggctag agcccgtttc    600
gaggcttctg gtgcccctgc tcctgtttgg gctcctgaat tgggcgacgc tgctcaacaa    660
tacgccctca tcacacgctt gctgtacact cccgacgccg aggctatggg atggctccaa    720
aaccctagag ttgcccctgg tgatgttgct ctggatcagg cttgtttccg tatctccggc    780
gctgctcgta actcttcttc gttcatctcc ggttctgtgg ctagagctgt gcctcacttg    840
ggatacgcca tggccgctgg acgtttcggc tggggactgg ctcatgttgc tgccgctgta    900
gcaatgtcta gacgctacga ccgtgctcaa aaaggattct tgctcacgtc actgaggcgt    960
gcttacgccc ctttgttggc ccgtgaaaac gctgccctca ctggcgcccg taccccccgat   1020 gacggtggcg acgccaaccg ccacgatggt gatgatgcta gaggcaaacc cgctgccgct   1080
gctgctcctt tgccctctgc cgccgcttcc cctgccgatg aacgtgctgt tcctgccggt   1140
tacggtgccg ctggtgtgtt ggctgctttg ggacgcttga gtgctgcccc ggctagtgcc   1200
cccgctggtg ccgatgacga tgacgatgac gatggtgctg gcggaggcgg tggcggtaga   1260
cgtgctgagg ctggacgtgt tgctgttgaa tgcctggctg cctgtagagg aatcttggag   1320
gctctgccca aggattcga cggagacttg gcggctgtac cgggactggc gggagcgagg    1380
cctgccgctc cacctcgccc cggtcctgct ggtgctgccg ctcctcctca tgccgacgct   1440
```

```
cctagactcc gtgcttggct ccgtgaactc cgtttcgttc gtgacgcttt ggttctgatg     1500
agactgagag gcgacttgag agtggctgga ggatccgagg ctgctgttgc tgctgtccgt     1560
gctgtttctt tggttgctgg tgctttgggc cctgctttgc cgagatctcc ccgtttgttg     1620
tcgagtgccg ccgctgctgc cgccgatttg ttgttccaaa accaatccct ccgccctctg     1680
ctcgccgaca ctgttgccgc tgccgattct ctggctgctc cggcttctgc cccacgtgaa     1740
gctcgtaaac gtaaatcacc cgctccggct cgtgctcccc ctggtggcgc ccctagaccc     1800
cctaaaaaat cccgtgccga tgcccctaga cctgctgctg ctcccccccgc tggtgctgct     1860 cccccccgctc ccctactcc cccccacgc ccacctcgtc ccgctgccct cacacgccgt     1920
cctgctgagg gacccgatcc acaaggcggc tggcgtagac aacctcctgg cccatcccat     1980
acaccggcac catctgccgc tgctttggag gcttactgtg ctcctcgtgc cgtggctgaa     2040
ctcaccgatc atccgctgtt ccctgctccc tggcgtcccg ccctcatgtt cgatcctaga     2100
gctttggctt cctggccgc tcgttgtgct gcccctcccc ctggcggtgc tccggctgct     2160
ttcggtcctc tccgtgcctc tggtccactc cgccgtgccg ctgcctggat gagacaagtt     2220
cccgaccctg aggatgttag agttgtgatc ttgtactcgc ccttgcctgg cgaggatttg     2280
gccgctggta gagctggcgg tggcccccct cctgaatggt ctgctgaacg tggtggtttg     2340
tcttgcttgt tggccgccct gggaaaccgt ctgtgtggtc ctgctactgc tgcttgggct     2400
ggaaactgga ctggcgctcc cgatgtttct gctctcggtg ctcaaggagt tttgctgctc     2460
tctactcgtg acttggcatt cgctggagct gttgaattcc tgggactctt ggctggcgct     2520
tgtgatagga gactcatcgt cgtaaacgct gtgagagctg ccgattggcc tgccgatggt     2580
cctgttgtgt ctcgtcaaca cgcttacttg gcttgtgaag tgttgcccgc tgtccaatgt     2640
gctgttcgct ggcctgctgc tcgtgatctg aggcgtactg ttctggctag tggtcgtgtt     2700
ttcggacctg gtgttttcgc tcgtgtcgaa gctgctcacg ctagactgta ccccgatgcc     2760 ccaccccctcc gtttgtgtcg tggagcaaac gttcgctacc gtgtccgtac tcgtttcgga     2820
cccgatactc tggttccaat gtcccctcgt gaataccgtc gtgctgttct gcctgccctc     2880
gatggacgtg ctgccgcttc tggcgctggt gacgctatgg ctcctggcgc tccggacttc     2940
tgtgaggatg aggctcactc acatcgtgcc tgtgcccgct ggggactggg cgctccattg     3000
aggcctgtat acgtggcact gggccgtgat gctgttagag gcggacccgc tgaattgaga     3060
ggccctcgtc gtgaattctg tgctagggct ctgctcgaac ccgatggaga tgctcctcct     3120
ttggtactcc gtgacgacgc cgatgctggt cctcccccac aaaattcgctg ggctagtgct     3180 gctggacgtg ctggtactgt attggctgct gctggcggtg gcgttgaagt tgttggtact     3240
gccgctggac tcgctacacc tccccgccgt gaacctgtag acatggatgc tgaactcgag     3300
gatgatgacg acggattgtt cggagagtaa                                      3330
```

<210> SEQ ID NO 128  
<211> LENGTH: 3492  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 128

```
atgagtgccg aacagcgtaa aaagaaaaaa accaccacca cgacccaagg acgtggagct      60
gaagttgcta tggcggatga ggatggaggc cgcttgagag ctgctgctga gactactgga     120
```

```
ggacctggat caccggaccc tgccgatgga cccccccta caccaaaccc cgatcgtaga    180
ccggctgcta gacctggatt cggatggcat ggaggacccg aggaaaacga ggacgaggcg    240
gacgacgccg ctgccgacgc cgacgccgat gaggctgccc ctgcttctgg agaggcggta    300
gacgaacctg ctgccgatgg agttgttagc cctaggcaat tggctttgtt ggcgagcatg    360
gtagacgagg ctgtgagaac aatcccttcc cctcccctg aacgtgatgg agcacaagag    420
gaggcggcta ggagtccctc accacccgt acaccttcta tgagagcgga ttacggcgag    480
gaaaacgacg acgacgacga tgatgatgac gacgatgatc gtgatgccgg acgctgggtt    540
aggggacctg aaaccacttc tgctgtccgt ggagcatacc ccgatcctat ggcgagtttg    600
agccctagac cacctgcccc gaggagacac caccaccacc accatcatag gcgtagacgt    660
gctcctagac gtcgttctgc cgctagtgac tcttccaaat ctggctcttc ttcatctgcc    720
tcttccgctt catcttcggc ctcatcgtcc tcttcggcat ccgcttcgag tagtgatgat    780
gatgatgacg acgacgctgc tagagccccc gcttctgctg ccgaccacgc tgctggcgga    840
actttgggag ccgacgacga ggaggcggga gttcctgctc gtgccccggg agctgctccg    900
aggccttctc caccccgtgc tgaacctgct ccggctagaa caccggccgc tactgctggt    960
agactggagc gtagacgtgc ccgtgctgct gtggctggta gagatgctac tggccgcttc   1020
actgctggcc gtcctagacg tgttgaactg gacgccgatg ctgcttctgg tgctttctac   1080
gcccgttacc gtgatggtta cgtgtctggt gaaccttggc ctggcgctgg tccacctccg   1140 cccgacgtg tactctacgg tggattgggc gccgtaccc ccgatgacgg tggcgacgcc   1200
aaccgccacg atggtgatga tgctagaggc aaacccgctg ccgctgctgc tccttttgccc   1260 tctgccgccg cttcccctgc cgatgaacgt gctgttcctg ccggttacgg tgccgctggt   1320
gtgttggctg ctttgggacg cttgagtgct gccccggcta gtgccccgc tggtgccgat   1380 gacgatgacg atgacgatgg tgctggcgga ggcggtggcg gtagacgtgc tgaggctgga   1440
cgtgttgctg ttgaatgcct ggctgcctgt agaggaatct tggaggctct ggccgaggga   1500
ttcgacggag acttggcggc tgtaccggga ctggcgggag cgaggcctgc cgctccacct   1560
cgccccggtc ctgctggtgc tgccgctcct cctcatgccg acgctcctag actccgtgct   1620
tggctccgtg aactccgttt cgttcgtgac gctttggttc tgatgagact gagaggcgac   1680
ttgagagtgg ctggaggatc cgaggctgct gttgctgctg tccgtgctgt ttctttggtt   1740
gctggtgctt tgggccctgc tttgccgaga tctccccgtt tgttgtcgag tgccgccgct   1800
gctgccgcca atttgttgtt ccaaaaccaa tccctccgcc ctctgctcgc cgacactgtt   1860
gccgctgccg attctctggc tgctccggct tctgcccac gtgaagctcg taaacgtaaa   1920
tcacccgctc cggctcgtgc tccccctggt ggcgcccta gacccctaa aaaatcccgt   1980 gccgatgccc ctagacctgc tgctgctccc ccgctggtg ctgctccccc cgctcccct   2040 actccccccc cacgcccacc tcgtcccgct gccctcacac gccgtcctgc tgagggaccc   2100
gatccacaag gcggctggcg tagacaacct cctggcccat cccatacacc ggcaccatct   2160
gccgctgctt tggaggctta ctgtgctcct cgtgctgtgg ctgaactcac cgatcatccg   2220
ctgttccctg ctccctggcg tcccgccctc atgttcgatc ctagagctttt ggcttccttg   2280 gccgctcgtt gtgctgcccc tccccctggc ggtgctccgg ctgctttcgg tcctctccgt   2340
gcctctggtc cactccgccg tgccgctgcc tggatgagac aagttcccga ccctgaggat   2400
gttagagttg tgatcttgta ctcgcccttg cctggcgagg atttggccgc tggtagagct   2460
```

| | |
|---|---|
| ggcggtggcc cccctcctga atggtctgct gaacgtggtg gtttgtcttg cttgttggcc | 2520 |
| gccctgggaa accgtctgtg tggtcctgct actgctgctt gggctggaaa ctggactggc | 2580 |
| gctcccgatg tttctgctct cggtgctcaa ggagttttgc tgctctctac tcgtgacttg | 2640 |
| gcattcgctg gagctgttga attcctggga ctcttggctg gcgcttgtga taggagactc | 2700 |
| atcgtcgtaa acgctgtgag agctgccgat tggcctgccg atggtcctgt tgtgtctcgt | 2760 |
| caacacgctt acttggcttg tgaagtgttg cccgctgtcc aatgtgctgt tcgctggcct | 2820 |
| gctgctcgtg atctgaggcg tactgttctg gctagtggtc gtgttttcgg acctggtgtt | 2880 |
| ttcgctcgtg tcgaagctgc tcacgctaga ctgtaccccg atgccccacc cctccgtttg | 2940 |
| tgtcgtggag caaacgttcg ctaccgtgtc cgtactcgtt tcggacccga tactctggtt | 3000 |
| ccaatgtccc ctcgtgaata ccgtcgtgct gttctgcctg ccctcgatgg acgtgctgcc | 3060 |
| gcttctggcg ctggtgacgc tatggctcct ggcgctccgg acttctgtga ggatgaggct | 3120 |
| cactcacatc gtgcctgtgc ccgctgggga ctgggcgctc cattgaggcc tgtatacgtg | 3180 |
| gcactgggcc gtgatgctgt tagaggcgga cccgctgaat tgagaggccc tcgtcgtgaa | 3240 |
| ttctgtgcta gggctctgct cgaacccgat ggagatgctc ctcctttggt actccgtgac | 3300 |
| gacgccgatg ctggtcctcc cccacaaatt cgctgggcta gtgctgctgg acgtgctggt | 3360 |
| actgtattgg ctgctgctgg cggtggcgtt gaagttgttg gtactgccgc tggactcgct | 3420 |
| acacctcccc gccgtgaacc tgtagacatg gatgctgaac tcgaggatga tgacgacgga | 3480 |
| ttgttcggag ag | 3492 |

<210> SEQ ID NO 129
<211> LENGTH: 3702
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 129

| | |
|---|---|
| atgagtgccg aacagcgtaa aaagaaaaaa accaccacca cgacccaagg acgtggagct | 60 |
| gaagttgcta tggcggatga ggatggaggc cgcttgagag ctgctgctga gactactgga | 120 |
| ggacctggat caccggaccc tgccgatgga cccccccta caccaaaccc cgatcgtaga | 180 |
| ccggctgcta gacctggatt cggatggcat ggaggacccg aggaaaacga ggacgaggcg | 240 |
| gacgacgccg ctgccgacgc cgacgccgat gaggctgccc tgcttctgg agaggcggta | 300 |
| gacgaacctg ctgccgatgg agttgttagc cctaggcaat tggctttgtt ggcgagcatg | 360 |
| gtagacgagg ctgtgagaac aatcccttcc cctcccctg aacgtgatgg agcacaagag | 420 |
| gaggcggcta ggagtccctc accaccccgt acaccttcta tgagagcgga ttacggcgag | 480 |
| gaaaacgacg acgacgacga tgatgatgac gacgatgatc gtgatgccgg acgctgggtt | 540 |
| aggggacctg aaaccacttc tgctgtccgt ggagcatacc ccgatcctat ggcgagtttg | 600 |
| agccctagac cacctgcccc gaggagacac caccaccacc accatcatag gcgtagacgt | 660 |
| gctcctagac gtcgttctgc cgctagtgac tcttccaaat ctggctcttc ttcatctgcc | 720 |
| tcttccgctt catcttcggc ctcatcgtcc tcttcggcat ccgcttcgag tagtgatgat | 780 |
| gatgatgacg acgacgctgc tagagccccc gcttctgctg ccgaccacgc tgctggcgga | 840 |
| actttgggag ccgacgacga ggaggcggga gttcctgctc gtgcccgggg agctgctccg | 900 |
| aggccttctc caccccgtgc tgaacctgct ccggctagaa caccggccgc tactgctggt | 960 |

```
agactggagc gtagacgtgc ccgtgctgct gtggctggta gagatgctac tggccgcttc    1020
actgctggcc gtcctagacg tgttgaactg gacgccgatg ctgcttctgg tgctttctac    1080
gcccgttacc gtgatggtta cgtgtctggt gaaccttggc ctggcgctgg tccacctccg    1140
cccggacgtg tactctacgg tggattgggc gattctcgcc ctggtctgtg gggcgctccg    1200
gaggctgagg aggctagagc ccgtttcgag gcttctggtg cccctgctcc tgtttgggct    1260
cctgaattgg gcgacgctgc tcaacaatac gccctcatca cacgcttgct gtacactccc    1320
gacgccgagg ctatgggatg ctccaaaac cctagagttg cccctggtga tgttgctctg     1380
gatcaggctt gtttccgtat ctccggcgct gctcgtaact cttcttcgtt catctccggt    1440
tctgtggcta gagctgtgcc tcacttggga tacgccatgg ccgctggacg tttcggctgg    1500
ggactggctc atgttgctgc cgctgtagca atgtctagac gctacgaccg tgctcaaaaa    1560
ggattcttgc tcacgtcact gaggcgtgct tacgccccctt tgttggcccg tgaaaacgct   1620
gccctcactg gcgcccgtac ccccgatgac ggtggcgacg ccaaccgcca cgatggtgat    1680
gatgctagag gcaaacccgc tgccgctgct gctcctttgc cctctgccgc cgcttcccct    1740
gccgatgaac gtgctgttcc tgccggttac ggtgccgctg gtgtgttggc tgctttggga    1800
cgcttgagtg ctgccccggc tagtgccccc gctggtgccg atgacgatga cgatgacgat    1860
ggtgctggcg gaggcggtgg cggtagacgt gctgaggctg gacgtgttgc tgttgaatgc    1920
ctggctgcct gtagaggaat cttggaggct ctggccgagg gattcgacgg agacttggcg    1980
gctgtaccgg gactggcggg agcgaggcct gccgctccac ctcgccccgg tcctgctggt    2040
gctgccgctc ctcctcatgc cgacgctcct agactccgtg cttggctccg tgaactccgt    2100
ttcgttcgtg acgctttggt tctgatgaga ctgagaggcg acttgagagt ggctggagga    2160
tccgaggctg ctgttgctgc tgtccgtgct gtttctttgg ttgctggtgc tttgggccct    2220
gctttgccga gatctccccg tttgttgtcg agtgccgccg ctgctgccgc cgatttgttg    2280
ttccaaaacc aatccctccg ccctctgctc gccgacactg ttgccgctgc cgattctctg    2340
gctgctccgg cttctacacc ggcaccatct gccgctgctt tggaggctta ctgtgctcct    2400
cgtgctgtgg ctgaactcac cgatcatccg ctgttccctg ctcccggcg tcccgccctc     2460
atgttcgatc ctagagcttt ggcttccttg gccgctcgtt gtgctgcccc tccccctggc    2520
ggtgctccgg ctgctttcgg tcctctccgt gcctctggtc cactccgccg tgccgctgcc    2580
tggatgagac aagttcccga ccctgaggat gttagagttg tgatcttgta ctcgcccttg    2640
cctggcgagg atttggccgc tggtagagct ggcggtggcc cccctcctga atggtctgct    2700
gaacgtggtg gtttgtcttg cttgttggcc gccctgggaa accgtctgtg tggtcctgct    2760
actgctgctt gggctggaaa ctggactggc gctcccgatg tttctgctct cggtgctcaa    2820
ggagttttgc tgctctctac tcgtgacttg gcattcgctg gagctgttga attcctggga    2880
ctcttggctg gcgcttgtga taggagactc atcgtcgtaa acgctgtgag agctgccgat    2940
tggcctgccg atggtcctgt tgtgtctcgt caacacgctt acttggcttg tgaagtgttg    3000
cccgctgtcc aatgtgctgt tcgctggcct gctgctcgtg atctgaggcg tactgttctg    3060
gctagtggtc gtgttttcgg acctggtgtt ttcgctcgtg tcgaagctgc tcacgctaga    3120
ctgtaccccg atgccccacc cctccgtttg tgtcgtggag caaacgttcg ctaccgtgtc    3180
cgtactcgtt tcggacccga tactctggtt ccaatgtccc ctcgtgaata ccgtcgtgct    3240
gttctgcctg ccctcgatgg acgtgctgcc gcttctggcg ctggtgacgc tatggctcct    3300
ggcgctccgg acttctgtga ggatgaggct cactcacatc gtgcctgtgc ccgctgggga    3360
```

```
ctgggcgctc cattgaggcc tgtatacgtg gcactgggcc gtgatgctgt tagaggcgga    3420
cccgctgaat tgagaggccc tcgtcgtgaa ttctgtgcta gggctctgct cgaacccgat    3480
ggagatgctc ctcctttggt actccgtgac gacgccgatg ctggtcctcc cccacaaatt    3540
cgctgggcta gtgctgctgg acgtgctggt actgtattgg ctgctgctgg cggtggcgtt    3600
gaagttgttg gtactgccgc tggactcgct cacctccccc gccgtgaacc tgtagacatg    3660
gatgctgaac tcgaggatga tgacgacgga ttgttcggag ag                       3702
```

<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 130

His His His His His His
1               5

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Met Ser Tyr Tyr His His His His His His
1               5                   10

<210> SEQ ID NO 132
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Met Lys Phe Leu Val Asn Val Ala Leu Val Phe Met Val Val Tyr Ile
1               5                   10                  15

Ser Tyr Ile Tyr Ala
            20

<210> SEQ ID NO 133
<211> LENGTH: 294
<212> TYPE: DNA
<213> ORGANISM: Human herpesvirus 2

<400> SEQUENCE: 133

```
atgtcgtact accatcacca tcaccatcac atgacgggga aacccgcaag actgggccgc    60
tgggtggtgc tgttgttcgt cgcgctcgtc gcgggcgtgc ccggggagcc gccgaacgcg    120
gcaggcgcac gcggcgttat cggggacgcg caatgccggg cgacagcgc cggtgtggtg     180 tccgtcccgg gggtcctggt gccctttat ctaggcatga cctcgatggg cgtatgtatg     240
atcgcgcacg tgtatcagat atgccagcgg gcactggccg ccgggtcagc ctga          294
```

<210> SEQ ID NO 134
<211> LENGTH: 1404

```
<212> TYPE: DNA
<213> ORGANISM: Human herpesvirus 2

<400> SEQUENCE: 134
atgggacgcc gggcccccag gggatccccc gaggccgcgc cgggcgccga cgtcgcgccc      60
ggggcgcggg cggcgtggtg ggtctggtgt gtgcaggtgg cgacgttcat cgtctcggcc     120
atctgcgtcg tggggctcct ggtgctggcc tctgtgttcc gggacaggtt ccctgccttt     180
tacgccccg cgacctctta tgcgaaggcg aacgccacgg tcgaggtgcg cggggggtgta     240
gccgtccccc tccggttgga cacgcagagc ctgctggcca cgtacgcaat tacgtctacg     300
ctgttgctgg cggcggccgt gtacgccgcg gtgggcgcgg tgacctcgcg ctacgagcgc     360
gcgctggatg cggcccgtcg cctggcggcg gcccgtatgg cgatgccaca cgccacgcta     420
atcgccggaa acgtctgcgc gtggctgttg cagatcacag tcctgctgct ggcccaccgc     480
atcagccagc tggcccacct tatctacgtc ctgcactttg cgtgcctcgt gtatctcgcg     540
gcccattttt gcaccagggg ggtcctgagc gggacgtacc tgcgtcaggt tcacggcctg     600
attgacccgg cgccgacgca ccatcgtatc gtcggtccgg tgcgggcagt aatgacaaac     660
gccttattac tgggcaccct cctgtgcacg gccgccgccg cggtctcgtt gaacacgatc     720
gccgccctga acttcaactt ttccgccccg agcatgctca tctgcctgac gacgctgttc     780
gccctgcttg tcgtgtcgct gttgttggtg gtcgagggg tgctgtgtca ctacgtgcgc     840
gtgttggtgg gcccccacct cggggccatc gccgccaccg gcatcgtcgg cctggcctgc     900
gagcactacc acaccggtgg ttactacgtg gtggagcagc agtggccggg ggcccagacg     960
ggagtccgcg tcgccctggc gctcgtcgcc gcctttgccc tcgccatggc cgtgcttcgg    1020
tgcacgcgcg cctacctgta tcaccggcga caccacacta aatttttcgt gcgcatgcgc    1080
gacacccggc accgcgccca ttcggcgctt cgacgcgtac gcagctccat gcgcggttct    1140
aggcgtggcg ggccgcccgg agacccgggc tacgcgaaaa ccccctacgc gagcgtgtcc    1200
caccacgccg agatcgaccg gtatggggat tccgacgggg acccgatcta cgacgaagtg    1260
gcccccgacc acgaggccga gctctacgcc cgagtgcaac gccccgggcc tgtgcccgac    1320
gccgagccca tttacgacac cgtggagggg tatgcgccaa ggtccgcggg ggagccggtg    1380
tacagcaccg ttcggcgatg gtag                                           1404

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Tyr Val Leu Arg Ser Val Ile Ala Lys
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asp Ile Leu Arg Val Pro Cys Met Arg
```

```
<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Asp Arg His Ala Gln Arg Ala Tyr Leu
1               5
```

VACCINES AGAINST HERPES SIMPLEX VIRUS TYPE 2: COMPOSITIONS AND METHODS FOR ELICITING AN IMMUNE RESPONSE

RELATED APPLICATIONS

This application is a continuation of U.S. application Ser. No. 12/786,425, filed May 24, 2010, now U.S. Pat. No. 8,617,564, which claims the benefit of U.S. Provisional Application No. 61/180,784, filed on May 22, 2009, U.S. Provisional Application No. 61/235,628, filed on Aug. 20, 2009, U.S. Provisional Application No. 61/240,587, filed on Sep. 8, 2009, U.S. Provisional Application No. 61/240,626, filed on Sep. 8, 2009, and U.S. Provisional Application No. 61/305,918 filed on Feb. 18, 2010, the entire contents of each of which are incorporated herein by reference.

I. BACKGROUND

Herpes simplex virus type 2 (HSV-2) is the leading cause of genital herpes. HSV-2 is most often transmitted by sexual contact, and infection with the virus typically leads to recurring outbreaks of lesions on the genitals and perianal regions, combined with shedding of virus particles into the genital tract. Viral shedding can also occur in the absence of lesions or other symptoms. HSV-2 also establishes latency in sensory ganglia. HSV-2 infection causes physical discomfort and psychosexual morbidity in affected patients, and introduces additional health risks. In particular, patients infected with HSV-2 are at increased risk for contracting HIV, and pregnant mothers infected with HSV-2 can vertically transmit HSV-2 to their fetuses. In immunocompromised individuals or in neonates, HSV-2 infections can be fatal. Currently, there is no cure for HSV-2 infection.

HSV-2 infection is widespread, with one study estimating that nearly 20% of the population worldwide is infected (Looker et al., 2008, Bulletin of the World Health Organization, October 2008, 86(10)). More women than men are infected, and the prevalence of the disease increases with age. High numbers of adolescents diagnosed with HSV-2 indicate that the prevalence across the population will continue to rise, as HSV-2 infection is lifelong.

Treatment options for HSV-2 symptoms are limited. Antiviral therapy, using compounds such as famciclovir, valaciclovir, or aciclovir, limits the duration of symptoms and, in some cases, speeds healing of lesions and reduces incidence of viral shedding. Antiviral drugs are not curative, however, and do not prevent recurrence of outbreaks or clear the virus completely. In addition, use of antiviral drugs requires patients to recognize symptoms of HSV-2 infection, then obtain a confirmative diagnosis, and ultimately, comply with the antiviral regimen. These requirements may be untenable in regions of the world where antiviral drugs are not readily available. In addition, patients are often unaware that they are infected, either because they do not present symptoms, or because the symptoms of the initial infection subside, suggesting recovery from the disease.

To address the medical and social problems associated with HSV-2, it is highly desirable to develop pharmaceutical compositions to inhibit or counteract infection by HSV-2. An effective composition may be used to elicit an enhanced immune response against HSV-2, thereby preventing initial infection, blocking the ability of the virus to establish latency in sensory ganglia, eliminating recurrence of outbreaks, and/or preventing viral shedding. The immune system is known to mount a defense against HSV-2, as evidenced by recurrent infections which manifest with fewer, less intense symptoms and decreased frequency over time.

While the ultimate goal of an HSV vaccine would be long-lasting protection from viral infection, the suppression of disease symptoms would also provide significant health benefits. One of the current goals for either a prophylactic or therapeutic vaccine is to reduce clinical episodes and viral shedding from primary and latent infections. Three categories of prophylactic vaccines have been tested in clinical trials with disappointing results i) whole virus, ii) protein subunit and iii) gene-based subunit vaccines (Stanberry et al., Clinical Infect. Dis., 30(3):549-566, 2000). In the 1970s a number of killed virus vaccines were explored, none of which were efficacious. More recently an attenuated HSV was found to be poorly immunogenic. Subunit vaccines based on two recombinant glycoproteins have been clinically evaluated in combination with different adjuvant formulations. One developed by Chiron contains truncated forms of both glycoprotein D (gD2) and glycoprotein B (gB2) of HSV-2, purified from transfected Chinese Hamster Ovary (CHO) cells and formulated in the adjuvant MF59. Another developed by Glaxo-Smithkline (GSK) contains a truncated gD2 formulated with adjuvants alum and 3-O-deacylated monophosphoryl lipid A (MPL). Both vaccines were immunogenic and well tolerated in phase I/II trials. However in phase III analyses, the Chiron vaccine showed no overall efficacy against HSV-2 seroconversion and work was discontinued. The GSK vaccine showed significant efficacy (73-74%) in HSV-1, HSV-2 seranegative women volunteers but no efficacy in men.

While even limited vaccine efficacy would beneficially impact HSV sufferers, these trials are testing only a small number of vaccine possibilities. This is because the vaccine discovery has not been systematic. Pursuance of a whole-virus vaccine assumes that presentation of the pathogen itself to the immune system will generate optimal immunity. Indeed the breadth and duration of immune responses to whole pathogen vaccines historically have been better than subunit vaccines. However, pathogenicity of the vaccine strain must be considered. Subunit vaccines, to date, have been selected for vaccine testing based on their assumed importance in disease pathogenesis and immunogenicity during infection. These approaches have identified one candidate against HSV with limited efficacy in some but no efficacy in other formulations. Thus, new and improved methodologies for herpesvirus vaccine discovery are needed to protect against herpes diseases.

II. SUMMARY OF THE INVENTION

Infection and transmission of HSV-2 is a major health concern. The present disclosure provides, inter alia, certain highly effective vaccines against HSV-2. Such vaccines can be used either therapeutically or prophylactically. The present disclosure also provides specific antigens and methods for using the antigens to elicit an immune response against HSV-2.

In one aspect, the present disclosure describes a vaccine formulation comprising a pharmaceutical-acceptable carrier and at least one polypeptide consisting of SEQ ID NOS: 2, 3, 4 and 5 or an immunogenic fragment thereof, and optionally further comprising SEQ ID NO:1 or an immunogenic fragment thereof. The vaccine formulation may comprise a first polypeptide consisting of one of the above SEQ ID NOS, and a second polypeptide consisting of another one of the above SEQ ID NOS.

Another aspect of the present invention provides a vaccine formulation comprising a pharmaceutically acceptable carrier, an adjuvant comprising one or more purified fractions of *quillaja* saponins, and at least one polypeptide comprising any of SEQ ID NOS: 2, 3, 4 and 5 or an immunogenic fragment thereof, and optionally further comprising SEQ ID NO:1 or an immunogenic fragment thereof.

A further aspect of the present invention provides a vaccine formulation comprising a pharmaceutically-acceptable carrier and a polypeptide consisting of SEQ ID NO: 2 or an immunogenic fragment thereof. Residues may be truncated from SEQ ID NO:2. The polypeptide may be glycosylated, or may be unglycosylated.

In still a further aspect, the present invention provides a vaccine formulation comprising a pharmaceutically-acceptable carrier and a polypeptide comprising SEQ ID NO:5, wherein the polypeptide lacks all or at least an 8 contiguous amino acid residue portion of the transmembrane domain spanning residues 340-363. Accordingly, one aspect of the present invention provides a vaccine formulation comprising a pharmaceutically-acceptable carrier and a polypeptide comprising SEQ ID NO:4. The polypeptide may be glycosylated, or may be unglycosylated.

Still another aspect of the present invention provides a vaccine formulation comprising a pharmaceutically-acceptable carrier, a polypeptide comprising SEQ ID NO:5. The polypeptide may be glycosylated, or may be unglycosylated.

Yet another aspect of the present invention provides a vaccine formulation comprising a pharmaceutically-acceptable carrier, a polypeptide comprising SEQ ID NO:3. The polypeptide may be glycosylated, or may be unglycosylated.

In some embodiments, polypeptides in the vaccine formulations that may be conjugated to an immunogenic carrier, for example keyhole limpet hemocyanin. In other embodiments, the vaccine formulations further comprise an adjuvant. The adjuvant may be one or more purified fractions of *quillaja* saponins.

The invention provides methods or treating a subject suffering from or susceptible to HSV-2 infection by administering an effective amount of a vaccine formulation disclosed herein. In some embodiments, the method inhibits HSV-2 symptoms, for example by reducing the number of herpetic lesions, reducing the number of days a subject experiences herpetic lesions, reducing infection by HSV-2 in an uninfected subject, increasing the IgG titer and/or T cell response to one or more HSV-2 antigens, and/or reducing the number of herpetic lesions at the onset of HSV-2 infection.

In another aspect, the present disclosure describes the results of a high-throughput system for in vitro screening of libraries of efficacious T cells to identify their specific target antigens from the complete proteome of HSV-2. This technology allowed the identification of individual antigens, likely to be effective in vivo, as either a prophylactic or therapeutic composition. In one aspect, herein are provided several critical protective T cell antigens that can be incorporated into protein-based compositions that elicit an immune response.

One aspect of the present invention provides pharmaceutical compositions comprising two or more isolated polypeptides selected from polypeptides having an amino acid sequence of at least one of SEQ ID NOS: 1-38, or an immunogenic fragment thereof.

In another aspect, the invention provides vaccine formulations that include a pharmaceutically-acceptable carrier and a polypeptide comprising at least one of SEQ ID NOS: 1-38, or an immunogenic fragment thereof. In certain embodiments, the polypeptide consists of at least one of SEQ ID NOS: 1-38.

Another aspect of the present invention provides a method of inducing an immune response in a subject, comprising administering to said subject an effective amount of a vaccine formulation or a pharmaceutical composition comprising an effective amount of two or more isolated polypeptides selected from polypeptides having an amino acid sequence of at least one of SEQ ID NOS: 1-38, or an immunogenic fragment thereof.

Yet another aspect of the present invention provides a method of reducing one or more symptoms of HSV-2 infection in a subject, comprising administering to said subject an effective amount of a vaccine formulation or a pharmaceutical composition comprising two or more isolated polypeptides selected from polypeptides having an amino acid sequence of at least one of SEQ ID NOS: 1-38, or an immunogenic fragment thereof. In some embodiments, the symptoms of HSV-2 infection comprise one or more of lesion formation, pain, irritation, itching, fever, malaise, headache, viral shedding, and prodrome.

A further aspect of the present invention provides a method of inhibiting the onset of HSV-2 infection, comprising administering an effective amount of a vaccine formulation or a composition comprising two or more isolated HSV polypeptides selected from polypeptides having an amino acid sequence of at least one of SEQ ID NOS: 1-38, or an immunogenic fragment thereof.

Applicants disclose another aspect of the present invention, which provides a method of inhibiting development of a latent HSV-2 infection in a subject exposed to HSV-2, comprising administering an effective amount of a vaccine formulation or a composition comprising two or more isolated HSV-2 polypeptides selected from polypeptides having an amino acid sequence of at least one of SEQ ID NOS: 1-38, or an immunogenic fragment thereof.

In a related aspect, the present invention provides a method of reducing viral shedding in a subject infected with HSV-2, comprising administering an effective amount of a vaccine formulation or a composition comprising two or more isolated HSV-2 polypeptides selected from polypeptides having an amino acid sequence of at least one of SEQ ID NOS: 1-38, or an immunogenic fragment thereof.

Further, an aspect of the present invention provides a method of reducing recurrence of outbreaks in a subject infected with HSV-2, comprising administering an effective amount of a vaccine formulation or a composition comprising two or more isolated HSV-2 polypeptides selected from polypeptides having an amino acid sequence of at least one of SEQ ID NOS: 1-38, or an immunogenic fragment thereof.

An additional aspect of the present invention provides a method of producing any of the pharmaceutical compositions described above, comprising expressing said two or more polypeptides; and isolating said two or more polypeptides.

Applicants further disclose an aspect of the present invention which provides a method for diagnosing severity of symptoms in a subjected infected with HSV-2, comprising (i) measuring activation of T cells in response to autologous antigen presenting cells (APC) pulsed with one or more isolated HSV-2 polypeptides selected from polypeptides set forth in SEQ ID NOS: 1-38, or an immunogenic fragment thereof, and (ii) comparing said levels to reference levels obtained from infected subjects experiencing frequent outbreaks; whereby a significant increase in said responses relative to reference levels indicates that said subject has less severe symptoms (e.g., the subject is asymptomatic). A significant increase in response can, for example, comprise a 1.5-fold or greater, 2-fold or greater, 3-fold or greater, 5-fold or greater, 10-fold or greater or even 20-fold or greater increase.

Another aspect of the present invention provides a method for diagnosing severity of symptoms in a subjected infected with HSV-2, comprising (i) measuring activation of T cells from naturally infected or virus-exposed subjects in response to APC presenting one or more isolated HSV-2 polypeptides selected from polypeptides set forth in SEQ ID NOS: 1-38, or an immunogenic fragment thereof, and (ii) comparing said levels to reference levels obtained from infected subjects experiencing frequent outbreaks; whereby a significant decrease in said activation relative to reference levels indicates that said subject has more severe symptoms (e.g., frequent outbreaks).

Another aspect of the present invention provides pharmaceutical compositions comprising an antibody that binds to one or more isolated HSV polypeptides selected from the list consisting of SEQ ID NOS: 1-38, or an immunogenic fragment thereof.

Moreover, a different aspect of the present invention provides a method of identifying immunogenic compositions for HSV-2 by testing two or more polypeptides selected from polypeptides having an amino acid sequence of any one of SEQ ID NOs. 1-38, or an immunogenic fragment thereof, for ability to promote cytokine production in a mammalian T cell, wherein an immunogenic composition is one that elevates levels of a cytokine significantly above the levels of that cytokine produced by a naïve mammalian T cell. A significant increase in cytokine levels is typically one that is at least 1.5-fold, 2-fold, 3-fold, 5-fold, 10-fold or even 20-fold the level produced by a naïve cell.

Still another aspect of the present invention provides a method of detecting HSV-2 in a sample from a subject, said method comprising (i) contacting said sample with one or more antibodies raised against one or more polypeptides having an amino acid sequence of SEQ ID NOS: 1-38 or an immunogenic fragment thereof, and (ii) detecting said one or more antibodies bound to said one or more HSV-2 polypeptide from the sample.

Finally, one aspect of the present invention provides pharmaceutical compositions comprising two or more isolated polynucleotides, selected from nucleotide SEQ ID NOS: 1-38, or fragments encoding immunogenic peptides thereof.

III. BRIEF DESCRIPTION OF THE DRAWINGS

FIG. 1A and FIG. 1B are graphs showing, respectively, CD4$^+$ and CD8' T cell responses following immunization with gD2 full-length protein, gD2ΔTMR, or gD2 truncated immediately upstream of the transmembrane domain (denoted 306t).

FIG. 2A and FIG. 2B are graphs showing, respectively, CD4$^+$ and CD8$^+$ T cell responses following immunization with pooled, overlapping peptides spanning gL2 or ICP4 fragments encoded by RS1.1, RS1.3.1 and RS1.3.2.

FIG. 3A and FIG. 3B are graphs showing, respectively, CD4$^+$ and CD8$^+$ T cell responses following immunization with gD2ΔTMR, or gD2ΔTMR and ICP4.2.

IV. DETAILED DESCRIPTION

Figure 3B:
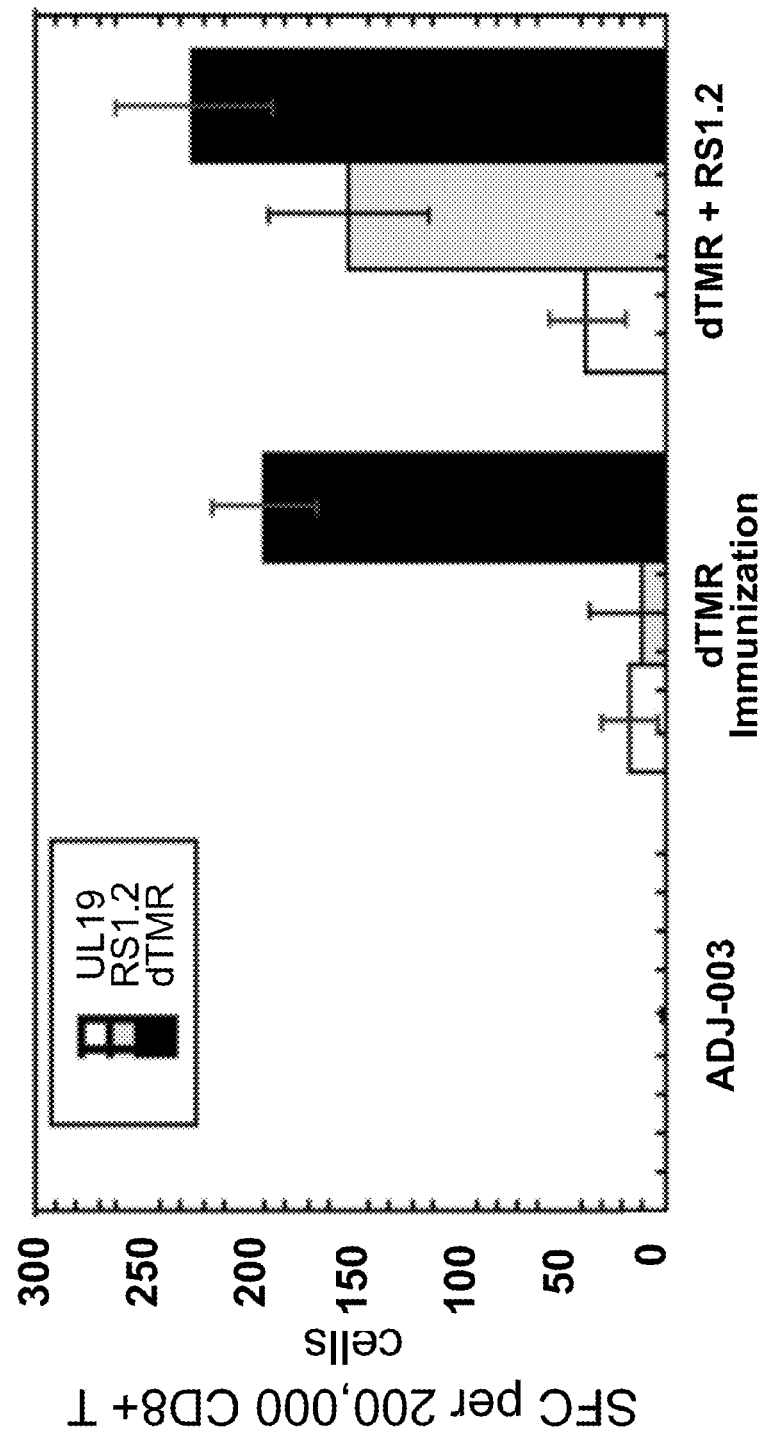

This application describes vaccines and immunogenic compositions against HSV-2. Vaccine formulations may include a polypeptide comprising a sequence from Table 1 or an immunogenic fragment thereof, or a combination of at least two polypeptides comprising sequences from Table 1 or immunogenic fragments thereof. In certain embodiments, the polypeptide(s) of the vaccines comprise the entire sequence of at least one of SEQ ID NOS: 1-26 or consist of the entire sequence of any one of SEQ ID NOS: 1-26 Immunogenic compositions may include a polypeptide comprising a sequence from Table 1 or Table 2 or an immunogenic fragment thereof or a combination of at least two polypeptides comprising sequences from Table 1 or Table 2, or immunogenic fragments thereof. In certain embodiments, the polypeptide(s) of the immunogenic compositions comprise the entire sequence of any one of SEQ ID NOS: 1-38 or consist of the entire sequence of SEQ ID NO: 1-38. The polypeptides in Tables 1 or 2 may be encoded by SEQ ID NOS: 39-46 and 117-134 as indicated and/or by cDNA sequences publically available on http://www.ncbi.nlm.nih-.gov/sites/entrez. cDNA and protein sequences may also be obtained from any known strains of HSV-2, including HG52, 333, and Strain G. Accordingly, cDNA sequences may be accessed by gene or protein name from genomic sequence at NC_001798.1, and may be approximately 97% conserved with sequences disclosed at NC_001798.1). As described herein, the polypeptides may be referred to by protein name, by SEQ ID NO, and/or by the name of the gene encoding the protein.

The polypeptides can be prepared in a variety of expression systems. Suitable expression systems include E. coli and Baculovirus-based expression systems (e.g., in insect cells). Polypeptides prepared using E. coli are typically full-length and unglycosylated, although truncated variants can be prepared. In certain embodiments, these truncated variants retain all or part of the signal domain. Polypeptides prepared using a Baculovirus system typically lack the N-terminal signal sequence, but are fully or partially glycosylated.

TABLE 1

HSV-2 antigens for vaccines or immunogenic compositions

| Protein SEQ ID No. | DNA SEQ ID No. | Gene Name Protein Name | Gene ID No. | GenBank Accession Nos. |
|---|---|---|---|---|
| 1 | 39 | RS1 ICP4 | 1869897 | NP_044530.1 |
| 2 | 117 | RS1.2 ICP4 internal fragment (ICP4.2) | | RS1.2 corresponds to amino acid residues 383-766 or nucleotides 1150-2398 of the RS1 sequence |
| 3 | 118 | UL1 gL2 cytoplasmic | 1487292 | NP_044470.1 |

TABLE 1-continued

HSV-2 antigens for vaccines or immunogenic compositions

| Protein SEQ ID No. | DNA SEQ ID No. | Gene Name Protein Name | Gene ID No. | GenBank Accession Nos. |
|---|---|---|---|---|
| 4 | 40 | US6ΔTMR gD2 internal deletion (gDΔTMR) | 9629336 | NP_044536.1 US6ΔTMR corresponds to gD2 will a deletion of amino acids 341-363 |
| 5 |  | US6 gD2 |  |  |
| 6 | 41 | RL1 ICP34.5 | 9629329 | NP_044529.1 |
| 7 | 42 | RL2 ICP0 | 109676722 | NP_044528.2 |
| 8 | 121 | RS1.1 ICP4 internal fragments | 1869897 | NP_044530.1 RS1.1 corresponds to residues 1-400 of RS1 |
| 9 | 122 | RS1.3.1 ICP4 internal fragments | 1869897 | NP_044530.1 RS1.3.1 corresponds to residues 750-1024 of RS1 |
| 10 | 123 | RS1.3.2 ICP4 internal fragments | 1869897 | NP_044530.1 RS1.3.2 corresponds to residues 1008-1319 of RS1 |
| 11 | 124 | RS1.3 ICP4 internal fragments | 1869897 | NP_044530.1 RS1.3 corresponds to residues 750-1319_of RS1 |
| 12 | 125 | RS1.4 ICP4 internal fragments | 1869897 | NP_044530.1 RS1.4 corresponds to residues 340-883 of RS1 |
| 13 | 126 | RS1.5 ICP4 internal fragments | 1869897 | NP_044530.1 RS1.5 corresponds to residues 775-1318 of RS1 |
| 14 | 127 | RS1.6 ICP4 internal fragments | 1869897 | NP_044530.1 RS1.6 corresponds to residues 209-1318 of RS1 |
| 15 | 128 | RS1.7 ICP4 internal fragments | 1869897 | NP_044530.1 RS1.7 has a deletion of residues 391-544 of RS1 |
| 16 | 129 | RS1.8 ICP4 internal fragments | 1869897 | NP_044530.1 RS1.8 has a deletion of residues 786-864 of RS1 |
| 17 |  | UL2 uracil DNA glycosylase |  |  |
| 18 |  | UL11 myristylated tegument protein |  |  |
| 19 | 119 | UL1 gL2 secreted | 1487292 | NP_044470.1 |
| 20 |  | UL19 VP5 |  |  |
| 21 | 120 | UL19ΔTEV VP5 | 9629288 | NP_044488.1 UL19ΔTEV is lacking the last 5 amino acids from the C-terminal end of UL19 |
| 22 |  | UL36 ICP1/2 |  |  |
| 23 | 43 | UL36.3.4.1 ICP1/2 internal fragments | 1487322 | NP_044506.1 UL 36.3.4.1 corresponds to residues 1318-2280 of UL36 |
| 24 | 44 | UL36.4.2.5 ICP1/2 internal fragments | 1487322 | NP_044506.1 UL 36.4.2.5 corresponds to residues 2253-3122 of UL36 |
| 25 |  | UL40 ribonucleoside reductase |  |  |
| 26 | 45 | US12 ICP47 | 9629343 | NP_044543.1 |

TABLE 2

Additional HSV-2 antigens for immunogenic compositions

| Protein SEQ ID No. | DNA SEQ ID No. | Gene Name Protein Name | Gene ID No. | GenBank Accession Nos. |
|---|---|---|---|---|
| 27 | 134 | UL10 gM2 | 9629279 | NP_044479.1 |
| 28 | | UL15 DNA cleavage/packaging protein | | |
| 29 | | UL26.5 ICP35 | | |
| 30 | | UL30 DNA-directed polymerase | | |
| 31 | | UL5 DNA helicase/primase complex | | |
| 32 | | UL8 DNA helicase/primase complex | | |
| 33 | | UL15.5 unknown | | |
| 34 | | UL32 cleavage and packaging protein | | |
| 35 | | UL36.4.2 ICP1/2 fragment | | |
| 36 | | UL54 ICP27 | | |
| 37 | 133 | UL49.5 Membrane associated virion protein | 1487337 | NP_044520.1 |
| 38 | 46 | US4 gG2 | 9629334 | NP_044534.1 |

A. Immunogenic HSV-2 Polypeptides

Immunogenic polypeptides or polynucleotides as indicated in Table 1 and/or Table 2 may be used in pharmaceutical compositions. The invention provides pharmaceutical compositions containing immunogenic polypeptides or polynucleotides encoding these immunogenic polypeptides together with a pharmaceutical carrier. Antigens from HSV-2 may be identified by screening immune cells from patients infected with HSV-2. Briefly, a library of HSV-2 antigens was expressed by bacteria and mixed with antigen presenting cells (APCs). The APCs, in turn, processed and presented HSV-2-derived polypeptides to lymphocytes that had been isolated from human patients infected with HSV-2. The patients belonged to several populations: (1) exposed to HSV-2 but seronegative for infection, (2) infected with HSV-2 but asymptomatic, (3) infected with HSV-2 and experiencing infrequent outbreaks, (4) infected with HSV-2 and experiencing frequent outbreaks, (5) naïve and (6) seronegative for HSV-2 (HSV-2⁻) but seropositive for HSV-1 (HSV-1⁺). Lymphocyte responses from each population were compared for reactivity to HSV-2-derived polypeptides, and the screen detected antigens that induced reactive lymphocytes with greater frequency in one patient population as compared to the others. Infected but asymptomatic, and exposed but seronegative patients may activate protective immune responses that patients who experience frequent outbreaks do not; in particular, exposed but seronegative patients are presumed to have mounted sterilizing immunity to HSV-2 infection. It is believed that a unique set of polypeptides will activate lymphocytes from these patient populations. Thus, the present invention contemplates compositions of the specific HSV-2 polypeptides that activate the lymphocytes of infected but asymptomatic, or exposed but seronegative patients or a combination of these polypeptides for inhibiting or counteracting infection by HSV-2.

Antigens identified on the basis of their immunogenicity in infected but asymptomatic, or exposed but seronegative patients are similarly expected to be immunogenic in any subject.

In some embodiments, a polypeptide may induce an innate immune response, a humoral immune response, or a cell-mediated immune response. The cell-mediated immune response may involve $T_H1$ cells, and in certain embodiments, the immune response involving $T_H1$ cells is an immune response in which $T_H1$ cells are activated. In some embodiments, an immunogenic polypeptide avoids induction of $T_H2$ cytokines. In some embodiments, the cell-mediated immune response may involve $T_H17$ cells, and in certain embodiments, the immune response involving $T_H17$ cells is an immune response in which $T_H17$ cells are activated.

Polypeptides (or immunogenic fragments thereof) in compositions of the invention may induce T cell responses in multiple individuals, regardless of the HLA haplotype of the individuals. Specifically, epitopes on the polypeptides may induce T cell responses in individuals with one or more of the following HLA supertypes: HLA-A2, -A3, -A24, -A1, -B7, -B8, -B27, -B44, -B58, and B62, and HLA-DQB01, -DQB02, -DQB03, -DQB-04, and -DQB05.

In some embodiments, one or more, e.g. two, three, four, or more polypeptides from Table 1 and/or Table 2 (or immunogenic fragments thereof) are provided in a composition of the invention. In some embodiments, two polypeptides from Table 1 and/or Table 2 are provided in a composition of the invention. In other embodiments, three polypeptides from Table 1 and/or Table 2 are provided in a composition of the invention.

In some embodiments, two, three, four, or more polypeptides from Table 1 and/or Table 2 (or immunogenic fragments thereof) are provided together as a conjugate. In some embodiments, two polypeptides from Table 1 and/or Table 2, or three polypeptides from Table 1 and/or Table 2, are provided as a conjugate. In some embodiments, two, three, four, or more polypeptides from Table 1 and/or Table 2 are covalently bound to each other, e.g., as a fusion protein. In some embodiments, two, three, four, or more polypeptides from Table 1 and/or Table 2 are covalently bound to each other, e.g., as a fusion protein. In some embodiments, two polypeptides from Table 1 and/or Table 2, or three polypeptides from Table 1 and/or Table 2, are covalently bound to each other, e.g. as a fusion protein.

In some embodiments, the compositions comprise two or more polypeptides selected from the group consisting of SEQ ID Nos. 1-38, and may contain or may not contain any other HSV-2 polypeptides.

In certain embodiments, Applicants provide polypeptides that are at least 70%, 80%, 90%, 95%, 96%, 97%, 98%, 99%, or 100% identical to a polypeptide encoded by a gene in Table 1 and/or Table 2, or a portion of said polypeptide. In certain embodiments, the homologous polypeptide is at least 8, 10, 15, 20, 30, 40, 50, 60, 80, 100, 120, 140, 160, 180, 200, 220, 240, 260, 280, 300, 350, 400, 450, or 500 amino acids in length. In some embodiments, such as those described immediately above, the polypeptide is no more than 300, 350, 400, 450, or 500 amino acids in length.

An immunogenic composition may also comprise portions of said polypeptides and genes, for example deletion mutants, truncation mutants, oligonucleotides, and peptide fragments. In some embodiments, the portions of said proteins are immunogenic.

The immunogenicity of a portion of a protein or a homolog thereof can be readily determined using the same assays that are used to determine the immunogenicity of the full-length protein. In some embodiments, the portion of the protein has substantially the same immunogenicity as the full-length proteins. In some embodiments, the immunogenicity is no more than 10%, 20%, 30%, 40%, or 50% less than that of the full-length protein. The protein fragments may be, for example, linear, circular, or branched. In some embodiments, a protein or protein fragment comprises one or more non-natural amino acids (e.g. an amino acid other than the 20 typically found in natural proteins). A non-natural amino acid may have an atypical side chain. In addition, peptidomimetics may be used; these may incorporate alterations to the peptide backbone.

Some embodiments of the polypeptide composition described herein include an immunogenic polypeptide that contains a membrane translocating sequence (MTS), to facilitate introduction of the polypeptide into the mammalian cell and subsequent stimulation of the cell-mediated immune response. Exemplary membrane translocating sequences include hydrophobic region in the signal sequence of Kaposi fibroblast growth factor, the MTS of α-synuclein, β-synuclein, or γ-synuclein, the third helix of the Antennapedia homeodomain, SN50, integrin β3 h-region, HIV Tat, pAntp, PR-39, abaecin, apidaecin, Bac5, Bac7, *P. berghei* CS protein, and those MTSs described in U.S. Pat. Nos. 6,248,558, 6,432,680 and 6,248,558.

In certain embodiments, the immunogenic polypeptide is conjugated (i.e. covalently bound) to another molecule. This may, for example, increase the half-life, solubility, bioavailability, or immunogenicity of the antigen. Molecules that may be conjugated to an immunogenic polypeptide include a carbohydrate, biotin, poly(ethylene glycol) (PEG), polysialic acid, N-propionylated polysialic acid, nucleic acids, polysaccharides, and PLGA. There are many different types of PEG, ranging from molecular weights of below 300 g/mol to over 10,000,000 g/mol. PEG chains can be linear, branched, or with comb or star geometries.

B. Immunogenic HSV-2 Polypeptides and Nucleic Acids for Use in Vaccines

In certain embodiments, one or more, e.g. two, three, four, or more immunogenic fragments or variants thereof are provided in a mixture. For example, a vaccine formulation may comprise any one or more of SEQ ID NOS: 1-26.

In certain embodiments, a vaccine formulation may comprise any one, two, or three of ICP4, ICP4.2, gL2, gD2ΔTMR and gD2 (SEQ ID NOS: 1-5), or immunogenic fragment(s) thereof. In certain embodiments, combinations contain polypeptides or immunogenic fragments from only one of ICP4 (SEQ ID NO 1) and ICP4.2 (SEQ ID NO 2). In other embodiments, combinations contain polypeptides or immunogenic fragments from only one of gD2ΔTMR (SEQ ID NO:4) and gD2 (SEQ ID NO:5).

Exemplary combinations of ICP4, ICP4.2, gL2, gD2ΔTMR and gD2 include:

| Two antigen combinations | |
|---|---|
| ICP4<br>SEQ ID NO: 1 | gL2<br>SEQ ID NO: 3 |
| ICP4<br>SEQ ID NO: 1 | gD2ΔTMR<br>SEQ ID NO: 4 |
| ICP4<br>SEQ ID NO: 1 | gD2<br>SEQ ID NO: 5 |
| ICP4.2<br>SEQ ID NO: 2 | gL2<br>SEQ ID NO: 3 |
| ICP4.2<br>SEQ ID NO: 2 | gD2ΔTMR<br>SEQ ID NO: 4 |
| ICP4.2<br>SEQ ID NO: 2 | gD2<br>SEQ ID NO: 5 |
| gL2<br>SEQ ID NO: 3 | gD2ΔTMR<br>SEQ ID NO: 4 |
| gL2<br>SEQ ID NO: 3 | gD2<br>SEQ ID NO: 5 |

| Three antigen combinations | | |
|---|---|---|
| ICP4<br>SEQ ID NO: 1 | gL2<br>SEQ ID NO: 3 | gD2ΔTMR<br>SEQ ID NO: 4 |
| ICP4.2<br>SEQ ID NO: 2 | gL2<br>SEQ ID NO: 3 | gD2ΔTMR<br>SEQ ID NO: 4 |
| ICP4<br>SEQ ID NO: 1 | gL2<br>SEQ ID NO: 3 | gD2<br>SEQ ID NO: 5 |
| ICP4.2<br>SEQ ID NO: 2 | gL2<br>SEQ ID NO: 3 | gD2<br>SEQ ID NO: 5 |

The individual antigens and combinations described above can also include additional peptides from or derived from HSV-2, such as polypeptides comprising sequences selected from SEQ ID NO:6-26 or immunogenic fragments thereof.

1. ICP4 (SEQ ID NO: 1) Encoded by RS1

RS1 encodes ICP4, a transcriptional transactivator that may interact with and recruit specific components of the general transcription machinery to viral promoters and stabilize their formation for transcription initiation. ICP4 contains distinct domains for transactivation/phosphorylation (approximately spanning acid residues 150-200 of SEQ ID NO:1), DNA binding (approximately spanning residues 380-540 of SEQ ID NO:1), nuclear localization (approximately spanning residues 630-730 of SEQ ID NO:1), and late regulatory transactivation (approximately spanning residues 1220-1319 of SEQ ID NO:1). The DNA and protein sequence of RS1 may be found by searching for RS1 in the publicly available database, Entrez Gene (on the NCBI NIH web site on the World Wide Web, at www.ncbi.nlm.nih.gov/sites/entrez?db=gene), in the Human herpesvirus 2 complete genome.

In some embodiments, vaccines against HSV-2 include a polypeptide containing at least 20 consecutive amino acid residues selected from residues 383-766 of ICP4 (SEQ ID NO: 1), but no more than 1000 amino acids of ICP4 (SEQ ID NO: 1). The polypeptide may also be a variant of the at least 20 residue fragment.

In certain embodiments, the polypeptide includes no more than 950, 900, 850, 800, 750, 700, 650, 600, 550, 500, 450 or even 400 consecutive amino acids from ICP4. Exemplary polypeptides correspond approximately to amino acids residues of full-length ICP4 as follows: 383-766; 1-400 (RS1.1); 750-1024 (RS1.3.1); 1008-1319 (RS1.3.2); 750-1319 (RS1.3); 280-785 (RS1.4 comprising the full DNA binding region); 680-1319 (RS1.5 comprising the glycosylase/C-terminal region); 208-1319 (RS1.6 which may also comprise a Met residue at the N-term end); 1-380 plus 545-1319 (RS1.7, in which a region spanning approximately residues 381-544 is deleted, removing the DNA binding regions); 1-785 plus 870-1319 (RS1.8, in which a region spanning approximately residues 786-869 is deleted, removing the nuclear localization domain), or 1-766, 383-1318, 100-750, 400-1300, 250-766, 383-900 of ICP4 (SEQ ID NO. 1) and the like.

2. ICP4 Internal Fragment ICP4.2 (SEQ ID NO: 2) Encoded by RS1.2

RS1.2 encodes a 391 amino acid fragment of ICP4 denoted ICP4.2.

In specific embodiments, vaccines against HSV-2 include a polypeptide containing from 50 to all 391 amino acids residues of ICP4.2 (SEQ ID NO: 2), such as from 100 to 391, 200 to 391 or 250 to 350 residues. In particular embodiments, the polypeptide includes all of ICP4.2 (SEQ ID NO: 2) or is ICP4.2 (SEQ ID NO: 2) itself. These polypeptides may, for example, include the full length or fragments of ICP4.2 (SEQ ID NO:2) described herein with amino acids residues 1-382 or 767-1318 of ICP4 (SEQ ID NO. 1) or fragments thereof, which, in certain embodiments, are consecutive with the amino acid residues of ICP4.2 being used. Exemplary fragments that combine the residues of SEQ ID NO:2 with select residues from 1-382 or 767-1318 of SEQ ID NO:1 are described above.

An immunogenic fragment of ICP4.2 comprises at least one immunogenic portion, as measured experimentally or identified by algorithm. Peptides identified by such methods include the following:

GLAHVAAAV (SEQ ID NO: 47)

FISGSVARA (SEQ ID NO: 48)

QYALITRLL (SEQ ID NO: 49)

RYDRAQKGF (SEQ ID NO: 50)

GYAMAAGRF (SEQ ID NO: 51)

PPHADAPRL (SEQ ID NO: 52)

KPAAAAAPL (SEQ ID NO: 53)

SEAAVAAV (SEQ ID NO: 54)

FGWGLAHV (SEQ ID NO: 55)

YALITRLLY (SEQ ID NO: 56)

ALPRSPRLL (SEQ ID NO: 57)

DLLFQNQSL (SEQ ID NO: 58)

ADLLFQNQS (SEQ ID NO: 59)

ARNSSSFIS (SEQ ID NO: 60)

QACFRISGA (SEQ ID NO: 61)

FVRDALVLM (SEQ ID NO: 62)

FDGDLAAVP (SEQ ID NO: 63)

GLGDSRPGL (SEQ ID NO: 64)

WAPELGDAA (SEQ ID NO: 65)

ECLAACRGI (SEQ ID NO: 66)

RAWLRELRF. (SEQ ID NO: 67)

Thus, in some aspects, this application provides an immunogenic fragment of ICP4.2. The fragments, in some instances, are close in size to the full-length polypeptide. For example, they may lack at most one, two, three, four, five, ten, or twenty amino acids from one or both termini. In other embodiments, the fragment is 100-391 amino acids in length, or 150-391, or 200-391, or 250-391 amino acids in length. Other exemplary fragments are amino acid residues 1-350, 1-300, 1-250, 1-200, 1-150, 1-100, 1-50, 50-391, 50-350, 50-300, 50-250, 50-200, 50-150, 50-100, 100-391, 100-350, 100-300, 100-250, 100-200, 100-150, 150-391, 150-350, 150-300, 150-250, 150-200, 200-391, 200-350, 200-300, 200-250, 250-391, 250-350, 250-300, 300-391 and 350-391. The fragments described above or sub-fragments thereof (e.g., fragments of 8-50, 8-30, or 8-20 amino acid residues) preferably have one of the biological activities described below, such as increasing the T cell response by at least 1.5 fold or 2 fold. A fragment may be used as the polypeptide in the vaccines described herein or may be fused to another protein, protein fragment or a polypeptide.

In certain aspects, this application provides immunogenic polypeptides with at least 90%, 95%, 97%, 98%, 99%, or 99.5% identity to ICP4.2 or an immunogenic fragment thereof.

3. Glycoprotein L-2 (SEQ ID NO: 3) Encoded by UL1

UL1 encodes Glycoprotein L-2 (gL2), a heterodimer glycoprotein that is required for the fusion of viral and cellular membranes and enables the virus to enter the host cell. The DNA and protein sequence of UL1 may be found by searching in the publicly available database, Entrez Gene (on the NCBI NIH web site on the World Wide Web, at ww.ncbi.nlm.nih.gov/sites/entrez?db=gene), in the Human herpesvirus 2 complete genome.

In some embodiments, vaccines against HSV-2 include a polypeptide containing at least 20 consecutive amino acid residues selected from residues 1-224 of gL2 (SEQ ID NO: 3), but no more than 224 amino acids of gL2 (SEQ ID NO: 3). The polypeptide may also be a variant of the at least 20 residue fragment.

In some embodiments, the polypeptide is at least 85% identical to a fragment of 200-250 amino acids of SEQ ID NO: 3.

In certain embodiments, the polypeptide includes no more than 200 or 100 consecutive amino acids from gL2. Exemplary polypeptides are amino acids residues 1-20, 21-40, 41-60, of 61-80, 81-100, 101-120, 121-140, 141-160, 161-180, 181-200, 201-221 of gL2 (SEQ ID NO: 3) and the like.

In other aspects, this application provides an immunogenic fragment of gL2. An immunogenic fragment of gL2 comprises at least one immunogenic portion, as measured experimentally or identified by algorithm. Peptides identified by such methods include the following:

| | |
|---|---|
| AYLVNPFLF | (SEQ ID NO: 100) |
| PFLFAAGFL | (SEQ ID NO: 101) |
| TEYVLRSVI | (SEQ ID NO: 102) |
| GSQATEYVL | (SEQ ID NO: 103) |
| RIDGIFLRY | (SEQ ID NO: 104) |
| FLEDLSHSV | (SEQ ID NO: 105) |
| YVLRSVIAK | (SEQ ID NO: 106) |
| YVLRSVIAK | (SEQ ID NO: 107) |
| AYLVNPFLF | (SEQ ID NO: 108) |
| ETTTRRALY | (SEQ ID NO: 109) |
| RIDGIFLRY | (SEQ ID NO: 110) |
| YLVNPFLFA | (SEQ ID NO: 111) |
| FVCLFGLVV | (SEQ ID NO: 112) |
| LYKEIRDAL | (SEQ ID NO: 113) |
| GLDTFLWDR | (SEQ ID NO: 114) |
| RVSPTRGRR | (SEQ ID NO: 115) |
| YVLRSVIAK | (SEQ ID NO: 115) |
| GLDTFLWDR | (SEQ ID NO: 116) |
| DILRVPCMR | (SEQ ID NO: 117) |
| DRHAQRAYL | (SEQ ID NO: 118) |

4. Glycoprotein D-2 (SEQ ID NO:5) Encoded by US6 and Internally-Deleted Glycoprotein D-2 (SEQ ID NO:4) Encoded by US6ΔTMR US6 encodes envelope glycoprotein D-2 (gD2), an envelope glycoprotein that binds to host cell entry receptors and may trigger fusion of the virus with the host membrane. The gD2 protein has several distinct domains, including a signal domain (amino acid residues 1-25) which is cleaved from the mature protein, and a transmembrane domain (spanning approximately amino acids residues 340-363). The DNA and protein sequence of US6 may be found by searching in the publicly available database, Entrez Gene (on the NCBI NIH web site on the World Wide Web, at www.ncbi.nlm-.nih.gov/sites/entrez?db=gene), in the Human herpesvirus 2 complete genome.

In some embodiments, vaccines against HSV-2 include a polypeptide comprising gD2 that is missing all or part of the transmembrane domain (which spans approximately amino acids residues 340-363 inclusive) as well as the signal sequence. In other embodiments, the deleted region may additionally include 5-10 amino acids of the sequence flanking the transmembrane domain. The deleted region may also comprise a portion of the transmembrane domain, for example at least 3 amino acids between residues 340-363. In some embodiments, at least one residue in the transmembrane domain has been modified, deleted or substituted, such that the transmembrane domain is no longer functional. For example, a variant may have its internal deletion begin at amino acid residue 336, 337, 338, 339, 340, 341, 342, 343, 344, 345 or 346 and end at amino acid residue 358, 359, 360, 361, 362, 363, 364, 365, 366, 367 or 368.

A construct encoding gD2 which is missing amino acid residues 340-363 (the transmembrane domain) is called US6ΔTMR (SEQ ID NO: 40). The corresponding protein is denoted gD2ΔTMR (SEQ ID NO:4). In other embodiments, an immunogenic fragment of gD2 or gD2ΔTMR may comprise a deletion in a portion of the transmembrane domain, and/or may comprise a deletion in the flanking sequence outside of the transmembrane domain.

In other aspects, this application provides an immunogenic fragment of gD2 or gD2ΔTMR. An immunogenic fragment of gD2 or gDΔTMR comprises at least one immunogenic portion, as measured experimentally or identified by algorithm. Peptides identified by such methods include the following:

| | |
|---|---|
| ALAGSTLAV | (SEQ ID NO. 68) |
| LLEDPAGTV | (SEQ ID NO. 69) |
| VIGGIAFWV | (SEQ ID NO. 70) |
| TVYYAVLER | (SEQ ID NO. 71) |
| KYALADPSL | (SEQ ID NO. 72) |
| AFETAGTYL | (SEQ ID NO. 73) |
| APSNPGLII | (SEQ ID NO. 74) |
| IPITVYYAV | (SEQ ID NO. 75) |
| APPSHQPLF | (SEQ ID NO. 76) |
| FLMHAPAFE | (SEQ ID NO. 77) |
| FSAVSEDNL | (SEQ ID NO. 78) |
| VYYAVLER | (SEQ ID NO. 79) |
| IGMLPRFI | (SEQ ID NO. 80) |
| YTECPYNKS | (SEQ ID NO. 81) |

-continued

FLMHAPAFE (SEQ ID NO. 82)

NLGFLMHAP (SEQ ID NO. 83)

VIGGIAFWV (SEQ ID NO. 84)

GIAFWVRRR (SEQ ID NO. 85)

SEDNLGFLM (SEQ ID NO. 86)

RTQPRWSYY (SEQ ID NO. 87)

IAFWVRRRA (SEQ ID NO. 88)

LVIGGIAFW (SEQ ID NO. 89)

FWVRRRAQM (SEQ ID NO. 90)

PYTSTLLPP (SEQ ID NO. 91)

VGTAALLVV (SEQ ID NO. 92)

TAALLVVAV (SEQ ID NO. 93)

TSTLLPPEL (SEQ ID NO. 94)

GTVSSQIPP (SEQ ID NO. 95)

TAGTYLRLV (SEQ ID NO. 96)

GVTVDSIGM (SEQ ID NO. 97)

AFWVRRRAQ (SEQ ID NO. 98)

RVYHIQPSL (SEQ ID NO. 99)

Thus, in some aspects, this application provides an immunogenic fragment of gD2 (SEQ ID NO:5) or gDΔTMR (SEQ ID NO: 4). The fragments, in some instances, are close in size to the full-length polypeptide. For example, they may lack at most one, two, three, four, five, ten, or twenty amino acids from one or both termini. In other embodiments, the fragment is 100-393 amino acids in length, or 150-393, or 200-393, or 250-393 amino acids in length. Other exemplary fragments are amino acid residues 1-350, 1-300, 1-250, 1-200, 1-150, 1-100, 1-50, 50-393, 50-350, 50-300, 50-250, 50-200, 50-150, 50-100, 100-393, 100-350, 100-300, 100-250, 100-200, 100-150, 150-393, 150-350, 150-300, 150-250, 150-200, 200-393, 200-350, 200-300, 200-250, 250-393, 250-350, 250-300, 300-393 and 350-393. The fragments described above or sub-fragments thereof (e.g., fragments of 8-50, 8-30, or 8-20 amino acid residues) preferably have one of the biological activities described below, such as increasing the T cell response by at least 1.5 fold or 2 fold. A fragment may be used as the polypeptide in the vaccines described herein or may be fused to another protein, protein fragment or a polypeptide.

In other embodiments, the polypeptide comprises the entire sequence of SEQ ID NO: 4 or SEQ ID NO:5, or consists of the entire sequence of SEQ ID NO: 4 or SEQ ID NO:5. In certain embodiments, an immunogenic fragment of gD2 retains all or part of the signal domain (amino acid residues 1-25) and/or the transmembrane domain (amino acids residues 340-363).

In certain embodiments, polypeptides have less than 20%, 30%, 40%, 50%, 60% or 70% homology with human autoantigens. Examples of such autoantigens include UL6 from HSV-1 and gK or UL53 from HSV-2.

In certain aspects, this application provides immunogenic polypeptides with at least 90%, 95%, 97%, 98%, 99%, or 99.5% identity to gDΔTMR, or an immunogenic fragment thereof.

C. Additional Features of HSV-2 Polypeptides

Typically, the polypeptides present in the vaccine formulations or pharmaceutical compositions described herein are immunogenic, either alone or as a variant, which includes polypeptides fused to another polypeptide or mixed with or complexed to an adjuvant. Variants also include sequences with less than 100% sequence identity, as described herein. In addition, one may use fragments, precursors and analogs that have an appropriate immunogenicity.

These polypeptides may be immunogenic in mammals, for example, mice, guinea pigs, or humans. An immunogenic polypeptide is typically one capable of raising a significant immune response in an assay or in a subject. Alternatively, an immunogenic polypeptide may (i) induce production of antibodies, e.g., neutralizing antibodies, that bind to the polypeptide (ii) induce $T_H1$ immunity, (iii) activate the CD8+ CTL response, for example by increasing CD8+ T cells and/or increasing localization of CD8+ T cells to the site of infection or reinfection, (iv) induce $T_H17$ immunity, and/or (v) activate innate immunity. In some embodiments, an immunogenic polypeptide causes the production of a detectable amount of antibody specific to that antigen.

In certain embodiments, polypeptides have less than 20%, 30%, 40%, 50%, 60% or 70% homology with human autoantigens.

A polypeptide may comprise one or more immunogenic portions and one or more non-immunogenic portions. The immunogenic portions may be identified by various methods, including protein microarrays, ELISPOT/ELISA techniques, and/or specific assays on different deletion mutants (e.g., fragments) of the polypeptide in question. Immunogenic portions may also be identified by computer algorithms. Some such algorithms, like EpiMatrix (produced by EpiVax), use a computational matrix approach. Other computational tools for identifying antigenic epitopes include PEPVAC (Promiscuous EPitope-based VACcine, hosted by Dana Farber Cancer Institute on the world wide web at immunax.dfci.harvard.edu/PEPVAC), MHCPred (which uses a partial least squares approach and is hosted by The Jenner Institute on the world wide web at www.jenner.ac.uk/MHCPred), and Syfpeithi, hosted on the world wide web at www.syfpeithi.de/.

In some embodiments, the vaccine or pharmaceutical composition may comprise fusion proteins and/or fusion DNA constructs. The underlying DNA sequences above may be modified in ways that do not affect the sequence of the protein product. For instance, the DNA sequence may be codon-optimized to improve expression in a host such as *E. coli* or an insect cell line (e.g. using the baculovirus expression system) or mammalian (e.g. Chinese Hamster Ovary) cell line. In particular embodiments, such as when smaller related polypeptides, including those having a molecular weight less than about 5000 daltons, e.g., 1500 to 5000 daltons, are used, modification may be useful in eliciting the desired immune response. For example, the smaller polypeptides can be conjugated to an appropriate immunogenic carrier such as proteins from other pathogenic organisms or viruses (e.g., tetanus toxoid), large proteins (e.g., keyhole limpet hemocyanin) or the like. Conjugation may be direct or indirect (e.g., via a linker). In other particular embodiments, a fusion protein may comprise a polypeptide disclosed above or an immunogenic fragment or variant thereof and a tag. A tag may be N-terminal or C-terminal. For instance, tags may be added to the nucleic acid or polypeptide to facilitate purification, detection, solubility, or confer other desirable characteristics on the protein or nucleic acid. For instance, a purification tag may be a peptide, oligopeptide, or polypeptide that may be used in affinity purification. Examples include His, GST, TAP, FLAG, myc, HA, MBP, VSV-G, thioredoxin, V5, avidin, streptavidin, BCCP, Calmodulin, Nus, S tags, lipoprotein D, and 13 galactosidase. In some embodiments, the fused portion is short. Thus, in some instances, the fusion protein comprises no more than 1, 2, 3, 4, 5, 10, 20, or 50 additional amino acids on one or both termini of a polypeptide described above, such as consecutive amino acids from any of the polypeptides in Table 1.

In some embodiments, tags, secretion signals, or other signal sequences may be added to the C-terminal end and/or to the N-terminal end of the polypeptide. Tags may be used to aid in purification of expressed polypeptides. Exemplary tags include HHHHHH (SEQ ID NO: 130) and MSYYH-HHHHH (SEQ ID NO: 131). Secretion signals may be optimized for use with non-mammalian cells, such as insect cells. An exemplary secretion signal is (SEQ ID NO: 132)
MKFLVNVALVFMVVYISYIYA.

A detection tag may be used to detect the tag and, consequently, any amino acid sequence fused to it. Detection tags include fluorescent proteins, proteins that bind a fluorescent label, and proteins that bind an electron-dense moeity. Examples of fluorescent proteins include dsRed, mRFP, YFP, GFP, CFP, BFP, and Venus. An example of a protein that binds a fluorescent or electron-dense label is FlAsH.

Another aspect disclosed herein is an antibody preparation generated against a composition of the invention (e.g., a composition comprising one or more or two or more of the polypeptides listed in Table 1). Any of a variety of antibodies are included. Such antibodies include, e.g., polyclonal, monoclonal, recombinant, humanized or partially humanized, single chain, Fab, and fragments thereof, etc. The antibodies can be of any isotype, e.g., IgA, IgG, various IgG isotypes such as $IgG_1$, $IgG_2$, $IgG_{2a}$, $IgG_{2b}$, $IgG_3$, $IgG_4$, etc.; and they can be from any animal species that produces antibodies, including goat, rabbit, mouse, chicken or the like. In some embodiments, Fab molecules are expressed and assembled in a genetically transformed host like *E. coli*. A lambda vector system is available thus to express a population of Fab's with a potential diversity equal to or exceeding that of subject generating the predecessor antibody. See Huse et al. (1989), Science 246, 1275-81.

D. Components of Vaccines and Pharmaceutical Compositions

In certain embodiments, the vaccines and pharmaceutical compositions comprise one or more of the polypeptides and nucleic acids described above and one or more of the following: an adjuvant, stabilizer, buffer, surfactant, controlled release component, salt, preservative, and an antibody specific to said antigen.

1. Adjuvants

The vaccine formulations and pharmaceutical compositions described herein may each include an adjuvant. Adjuvants can be broadly separated into two classes, based on their principal mechanisms of action: vaccine delivery systems and immunostimulatory adjuvants (see, e.g., Singh et al., Curr. HIV Res. 1:309-20, 2003). Vaccine delivery systems are often particulate formulations, e.g., emulsions, microparticles, immune-stimulating complexes (ISCOMs), which may be, for example, particles and/or matrices, and liposomes. In contrast, immunostimulatory adjuvants are sometimes derived from pathogens and can represent pathogen associated molecular patterns (PAMP), e.g., lipopolysaccharides (LPS), monophosphoryl lipid (MPL), or CpG-containing DNA, which activate cells of the innate immune system.

Alternatively, adjuvants may be classified as organic and inorganic. Inorganic adjuvants include alum salts such as aluminum phosphate, amorphous aluminum hydroxyphosphate sulfate, and aluminum hydroxide, which are commonly used in human vaccines. Organic adjuvants comprise organic molecules including macromolecules. An example of an organic adjuvant is cholera toxin.

Adjuvants may also be classified by the response they induce, and adjuvants can activate more than one type of response. In some embodiments, the adjuvant induces the activation of CD4+ T cells. The adjuvant may induce activation of $T_H1$ cells and/or activation of $T_H17$ cells and/or activation of $T_H2$ cells. Alternately, the adjuvant may induce activation of $T_H1$ cells and/or $T_H17$ cells but not activation of $T_H2$ cells, or vice versa. In some embodiments, the adjuvant induces activation of CD8+ T cells. In further embodiments, the adjuvant may induce activation of Natural Killer T (NKT) cells. In some embodiments, the adjuvant induces the activation of $T_H1$ cells or $T_H17$ cells or $T_H2$ cells. In other embodiments, the adjuvant induces the activation of B cells. In yet other embodiments, the adjuvant induces the activation of antigen-presenting cells. These categories are not mutually exclusive; in some cases, an adjuvant activates more than one type of cell.

In certain embodiments, an adjuvant is a substance that increases the numbers or activity of antigen presenting cells such as dendritic cells. In certain embodiments, an adjuvant promotes the maturation of antigen presenting cells such as dendritic cells. In some embodiments, the adjuvant is or comprises a saponin. Typically, the saponin is a triterpene glycoside, such as those isolated from the bark of the *Quillaja saponaria* tree. A saponin extract from a biological source can be further fractionated (e.g., by chromatography) to isolate the portions of the extract with the best adjuvant activity and with acceptable toxicity. Typical fractions of extract from *Quillaja saponaria* tree used as adjuvants are known as fractions A and C. An exemplary saponin adjuvant is QS-21, which is available from Antigenics. QS-21 is an oligosaccharide-conjugated small molecule. Optionally, QS-21 may be admixed with a lipid such as 3D-MPL or cholesterol.

A particular form of saponins that may be used in vaccine formulations described herein is immuno stimulating complexes (ISCOMs). ISCOMs are an art-recognized class of adjuvants, that generally comprise *Quillaja* saponin fractions and lipids (e.g., cholesterol and phospholipids such as phosphatidyl choline). In certain embodiments, an ISCOM is assembled together with a polypeptide or nucleic acid of interest. However, different saponin fractions may be used in different ratios. In addition, the different saponin fractions may either exist together in the same particles or have substantially only one fraction per particle (such that the indicated ratio of fractions A and C are generated by mixing together particles with the different fractions). In this context, "substantially" refers to less than 20%, 15%, 10%, 5%, 4%, 3%, 2% or even 1%. Such adjuvants may comprise fraction A and fraction C mixed into a ratio of 70-95 A:30-5 C, such as 70 A:30 C to 75 A:25 C, 75 A:25 C to 80 A:20 C, 80 A:20 C to 85 A:15 C, 85 A:15 C to 90 A:10 C, 90 A:10 C to 95 A:5 C, or 95 A:5 C to 99 A:1 C. ISCOMatrix, produced by CSL, and AbISCO 100 and 300, produced by Isconova, are ISCOM matrices comprising saponin, cholesterol and phospholipid (lipids from cell membranes), which form cage-like structures typically 40-50 nm in diameter. Posintro, produced by Nordic Vaccines, is an ISCOM matrix where the immunogen is bound to the particle by a multitude of different mechanisms, e.g. electrostatic interaction by charge modification, incorporation of chelating groups or direct binding.

In some embodiments, the adjuvant is a TLR ligand. TLRs are proteins that may be found on leukocyte membranes, and recognize foreign antigens (including microbial antigens). An exemplary TLR ligand is IC-31, which is available from Intercell. IC31 comprises an antimicrobial peptide, KLK, and an immunostimulatory oligodeoxynucleotide, ODN1a. IC31 has TLR9 agonist activity. Another example is CpG-containing DNA, and different varieties of CpG-containing DNA are available from Prizer (Coley): VaxImmune is CpG 7909 (a (CpG)-containing oligodeoxynucleotide), and Actilon is TLR9 agonist, CpG 10101 (a (CpG)-containing oligodeoxy-nucleotide).

In some embodiments, the adjuvant is a nanoemulsion. One exemplary nanoemulsion adjuvant is Nanostat Vaccine, produced by Nanobio. This nanoemulsion is a high-energy, oil-in-water emulsion. This nanoemulsion typically has a size of 150-400 nanometers, and includes surfactants to provide stability. More information about Nanostat can be found in U.S. Pat. Nos. 6,015,832, 6,506,803, 6,559,189, 6,635,676, and 7,314,624.

Adjuvants may be covalently bound to antigens (e.g., the polypeptides described above). In some embodiments, the adjuvant may be a protein which induces inflammatory responses through activation of antigen-presenting cells (APCs). In some embodiments, one or more of these proteins can be recombinantly fused with an antigen of choice, such that the resultant fusion molecule promotes dendritic cell maturation, activates dendritic cells to produce cytokines and chemokines, and ultimately, enhances presentation of the antigen to T cells and initiation of T cell responses (see Wu et al., Cancer Res 2005; 65(11), pp 4947-4954). Other exemplary adjuvants that may be covalently bound to antigens comprise polysaccharides, synthetic peptides, lipopeptides, and nucleic acids.

The adjuvant can be used alone or in combination of two or more kinds. Adjuvants may be directly conjugated to antigens. Adjuvants may also be combined to increase the magnitude of the immune response to the antigen. Typically, the same adjuvant or mixture of adjuvants is present in each dose of a vaccine. Optionally, however, an adjuvant may be administered with the first dose of vaccine and not with subsequent doses (i.e. booster shots). Alternatively, a strong adjuvant may be administered with the first dose of vaccine and a weaker adjuvant or lower dose of the strong adjuvant may be administered with subsequent doses. The adjuvant can be administered before the administration of the antigen, concurrent with the administration of the antigen or after the administration of the antigen to a subject (sometimes within 1, 2, 6, or 12 hours, and sometimes within 1, 2, or 5 days). Certain adjuvants are appropriate for human patients, non-human animals, or both.

2. Additional Components of Vaccines and Pharmaceutical Compositions

In addition to the antigens and the adjuvants described above, a vaccine formulation or pharmaceutical composition may include one or more additional components.

In certain embodiments, the vaccine formulation or pharmaceutical composition may include one or more stabilizers such as sugars (such as sucrose, glucose, or fructose), phosphate (such as sodium phosphate dibasic, potassium phosphate monobasic, dibasic potassium phosphate, or monosodium phosphate), glutamate (such as monosodium L-glutamate), gelatin (such as processed gelatin, hydrolyzed gelatin, or porcine gelatin), amino acids (such as arginine, asparagine, histidine, L-histidine, alanine, valine, leucine, isoleucine, serine, threonine, lysine, phenylalanine, tyrosine, and the alkyl esters thereof), inosine, or sodium borate.

In certain embodiments, the vaccine formulation or pharmaceutical composition includes one or more buffers such as a mixture of sodium bicarbonate and ascorbic acid. In some embodiments, the vaccine formulation may be administered in saline, such as phosphate buffered saline (PBS), or distilled water.

In certain embodiments, the vaccine formulation or pharmaceutical composition includes one or more surfactants such as polysorbate 80 (Tween 80), Triton X-100, Polyethylene glycol tert-octylphenyl ether t-Octylphenoxypolyethoxyethanol 4-(1,1,3,3-Tetramethylbutyl)phenyl-polyethylene glycol (TRITON X-100); Polyoxyethylenesorbitan monolaurate Polyethylene glycol sorbitan monolaurate (TWEEN 20); and 4-(1,1,3,3-Tetramethylbutyl)phenol polymer with formaldehyde and oxirane (TYLOXAPOL). A surfactant can be ionic or nonionic.

In certain embodiments, the vaccine formulation or pharmaceutical composition includes one or more salts such as sodium chloride, ammonium chloride, calcium chloride, or potassium chloride.

In certain embodiments, a preservative is included in the vaccine. In other embodiments, no preservative is used. A preservative is most often used in multi-dose vaccine vials, and is less often needed in single-dose vaccine vials. In certain embodiments, the preservative is 2-phenoxyethanol, methyl and propyl parabens, benzyl alcohol, and/or sorbic acid.

In certain embodiments, the vaccine formulation or pharmaceutical composition is a controlled release formulation.

E. DNA Vaccines

In certain aspects, the vaccine comprises one of the nucleic acids disclosed herein. When a nucleic acid vaccine is administered to a patient, the corresponding gene product (such as a desired antigen) is produced in the patient's body. In some embodiments, nucleic acid vaccine vectors that include optimized recombinant polynucleotides can be delivered to a mammal (including humans) to induce a therapeutic or prophylactic immune response. The nucleic acid may be, for example, DNA, RNA, or a synthetic nucleic acid. The nucleic acid may be single stranded or double stranded.

Nucleic acid vaccine vectors (e.g., adenoviruses, liposomes, papillomaviruses, retroviruses, etc.) can be administered directly to the mammal for transduction of cells in vivo. The nucleic acid vaccines can be formulated as pharmaceutical compositions for administration in any suitable manner, including parenteral administration.

In determining the effective amount of the vector to be administered in the treatment or prophylaxis of an infection or other condition, the physician evaluates vector toxicities, progression of the disease, and the production of anti-vector antibodies, if any. Often, the dose equivalent of a naked nucleic acid from a vector is from about 1 μg to 1 mg for a typical 70 kilogram patient, and doses of vectors used to deliver the nucleic acid are calculated to yield an equivalent amount of therapeutic nucleic acid. Administration can be accomplished via single or divided doses. The toxicity and therapeutic efficacy of the nucleic acid vaccine vectors can be determined using standard pharmaceutical procedures in cell cultures or experimental animals.

A nucleic acid vaccine can contain DNA, RNA, a modified nucleic acid, or a combination thereof. In some embodiments, the vaccine comprises one or more cloning or expression vectors; for instance, the vaccine may comprise a plurality of expression vectors each capable of autonomous expression of a nucleotide coding region in a mammalian cell to produce at least one immunogenic polypeptide. An expression vector often includes a eukaryotic promoter sequence, such as the nucleotide sequence of a strong eukaryotic promoter, operably linked to one or more coding regions. The compositions and methods herein may involve the use of any particular eukaryotic promoter, and a wide variety are known; such as a CMV or RSV promoter. The promoter can be, but need not be, heterologous with respect to the host cell. The promoter used may be a constitutive promoter.

A vector useful in the present compositions and methods can be circular or linear, single-stranded or double stranded and can be a plasmid, cosmid, or episome. In a suitable embodiment, each nucleotide coding region is on a separate vector; however, it is to be understood that one or more coding regions can be present on a single vector, and these coding regions can be under the control of a single or multiple promoters.

Numerous plasmids may be used for the production of nucleic acid vaccines. Suitable embodiments of the nucleic acid vaccine employ constructs using the plasmids VR1012 (Vical Inc., San Diego Calif.), pCMVI.UBF3/2 (S. Johnston, University of Texas) or pcDNA3.1 (InVitrogen Corporation, Carlsbad, Calif.) as the vector. In addition, the vector construct can contain immunostimulatory sequences (ISS), such as unmethylated dCpG motifs, that stimulate the animal's immune system. The nucleic acid vaccine can also encode a fusion product containing the immunogenic polypeptide. Plasmid DNA can also be delivered using attenuated bacteria as delivery system, a method that is suitable for DNA vaccines that are administered orally. Bacteria are transformed with an independently replicating plasmid, which becomes released into the host cell cytoplasm following the death of the attenuated bacterium in the host cell.

An alternative approach to delivering the nucleic acid to an animal involves the use of a viral or bacterial vector. Examples of suitable viral vectors include adenovirus, polio virus, pox viruses such as alphaviruses, vaccinia, canary pox, and fowl pox, herpes viruses, including catfish herpes virus, adenovirus-associated vector, and retroviruses. Virus-like vectors include virosomes and virus-like particles. Exemplary bacterial vectors include attenuated forms of *Salmonella, Shigella, Edwardsiella ictaluri, Yersinia ruckerii*, and *Listeria monocytogenes*. In some embodiments, the nucleic acid is a vector, such as a plasmid, that is capable of autologous expression of the nucleotide sequence encoding the immunogenic polypeptide.

F. Use of Vaccines

The vaccines described herein may be used for prophylactic and/or therapeutic treatment of herpes, including HSV-1 and particularly HSV-2. The subject receiving the vaccination may be a male or a female, and may be a child or adult. In some embodiments, the subject being treated is a human. In other embodiments, the subject is a non-human animal.

1. Prophylactic Use

In prophylactic embodiments, the HSV-2 vaccine is administered to a subject to induce an immune response that can help protect against the establishment of HSV-2.

In some embodiments, the vaccine compositions of the invention confer protective immunity, allowing a vaccinated individual to exhibit delayed onset of symptoms or reduced severity of symptoms (e.g., reduced number of lesions at the onset of infection), as the result of his/her exposure to the vaccine (e.g., a memory response). In certain embodiments, the reduction in severity of symptoms is at least 25%, 40%, 50%, 60%, 70%, 80% or even 90%. Some vaccinated individuals may display no symptoms upon contact with HSV-2 or even no infection by HSV-2. Protective immunity is typically achieved by one or more of the following mechanisms: mucosal, humoral, or cellular immunity. Mucosal immunity is primarily the result of secretory IgA (sIGA) antibodies on mucosal surfaces of the respiratory, gastrointestinal, and genitourinary tracts. The sIGA antibodies are generated after a series of events mediated by antigen-processing cells, B and T lymphocytes, that result in sIGA production by B lymphocytes on mucosa-lined tissues of the body. Humoral immunity is typically the result of IgG antibodies and IgM antibodies in serum. For example, the IgG titer can be raised by 1.5-fold, 2-fold, 3-fold, 4-fold, 5-fold, 10-fold, 20-fold, 50-fold, or even 100-fold or more following administration of a vaccine formulation described herein. Cellular immunity can be achieved through cytotoxic T lymphocytes or through delayed-type hypersensitivity that involves macrophages and T lymphocytes, as well as other mechanisms involving T cells without a requirement for antibodies. In particular, cellular immunity may be mediated by $T_H1$ cells or $T_H17$ cells. Activation of $T_H1$ cells can be measured by secretion of IFN-γ, relative to the level of IFN-γ released in response to a polypeptide that does not generate an immunologic response. In certain embodiments, the amount of IFN-γ released in 1.5-fold, 2-fold, 3-fold, 4-fold, 5-fold, 10-fold, 20-fold, 50-fold or even 100-fold greater. The primary result of protective immunity is the destruction of HSV-2 viral particles or inhibition of HSV-2's ability to replicate. In some embodiments, the protective immunity conferred by presentation of antigen before exposure to HSV-2 will reduce the likelihood of seroconversion to an HSV-2-positive status.

The duration of protective immunity is preferably as long as possible. In certain embodiments, vaccine formulations produce protective immunity lasting six months, one year, two years, five years, ten years, twenty years or even a lifetime.

2. Therapeutic Use

In therapeutic applications, the vaccine comprising a polypeptide or nucleic acid of the invention may be administered to a patient suffering from HSV-2, in an amount sufficient to treat the patient. Treating the patient, in this case, may refer to delaying or reducing symptoms of HSV-2 in an infected individual. In some embodiments, treating the patient refers to reducing the duration of lesions, reducing the number of lesions, reducing the duration of symptoms per episode, and/or otherwise reducing the intensity of symptoms per episode. In certain embodiments, the vaccine reduces the duration or severity of mild symptoms; in some embodiments, the vaccine reduces the duration or severity of serious symptoms. In some embodiments, the vaccine reduces viral shedding and therefore the transmissibility of HSV-2 from the vaccinated patient. In certain embodiments, the reductions described above are at least 25%, 30%, 40%, 50%, 60%, 70%, 80% or even 90%. In certain embodiments, the reductions described above include the complete cessation of symptoms, viral shedding and/or future outbreaks (e.g., by blocking the ability of the virus to establish latency in sensory ganglia).

In therapeutic embodiments, the HSV-2 vaccine is administered to an individual post-infection. The HSV-2 vaccine may be administered shortly after infection, e.g. before symptoms manifest, or may be administered during or after manifestation of symptoms. In some embodiments, the HSV-2 may prevent endogenous reactivation of earlier infection. In some embodiments, a postinfection vaccine could be administered to patients in high-risk groups.

The duration of therapeutic effects of a vaccine formulation disclosed herein is preferably as long as possible. In certain embodiments, vaccine formulations produce therapeutic effects lasting one month, two months, three months, six months, one year, two years, five years, ten years, twenty years or even a lifetime.

3. Assaying Vaccination Efficacy

The efficacy of vaccination with the vaccines disclosed herein may be determined in a number of ways.

Vaccine efficacy may be assayed in various model systems. Suitable model systems used to study HSV-2 include a guinea pig model and a mouse model, as described in the examples below. Briefly, the animals are vaccinated and then challenged with HSV-2 or the vaccine is administered to already-infected animals. The response of the animals to the HSV-2 challenge or the vaccine is then compared with control animals, using one of the measures described above. A similar assay could be used for clinical testing of humans. The treatment and prophylactic effects described above represent additional ways of determining efficacy of a vaccine.

In addition, efficacy may be evaluated by in vitro immunization of naïve human peripheral blood mononuclear cells (PBMC), where APCs are exposed to the vaccine and then the APCs are co-cultured with naïve T cells from the same donor to evaluate the primary response to immunization in a test tube. An activation of the T-cells by 1.5 fold, 2-fold, 5-fold, 10-fold, 20-fold, 50-fold or 100-fold or more relative to activation of T-cells using APCs not exposed to a vaccine, in certain embodiments, is considered an adequate response.

Vaccine efficacy may further be determined by viral neutralization assays. Briefly, animals are immunized and serum is collected on various days post-immunization. Serial dilutions of serum are pre-incubated with virus during which time antibodies in the serum that are specific for the virus will bind to it. The virus/serum mixture is then added to permissive cells to determine infectivity by a plaque assay. If antibodies in the serum neutralize the virus, there are fewer plaques compared to the control group.

G. Uses of Pharmaceutical Compositions

1. Defense Against HSV Infection

The pharmaceutical compositions of the present disclosure are designed to elicit an immune response against HSV-2. Compositions described herein may stimulate an innate immune response, an antibody response or a cell-mediated immune response, or a combination of these responses, in the subject to which it is administered. In some embodiments, the composition stimulates immune cells at the peripheral site of infection or sensory ganglia, such as neutrophils, macrophages, and NK cells. The composition may stimulate infiltration by macrophages; production of antiviral compounds, such including nitric oxide, TNF-α, interferons (IFN), and interleukin 12 (IL-12) by neutrophils; and/or stimulation of NK cells to produce IFN-γ. IL-2, IFN-α and IFN-β production may also be triggered by the polypeptides of the present composition, and are believed to aid in controlling infection.

In some embodiments, the composition comprises antigens that stimulate production of neutralizing antibodies. Neutralizing antibodies may target the glycoproteins of the viral envelope, which mediate the interaction of virions with host cell and are responsible for attachment, binding, and entry of HSV-2 into cells. Accordingly, an exemplary composition comprises one or more glycoproteins described above or encoded by nucleic acids described above Immunogenic antigens and/or epitopes as described herein may be administered separately, in series, or in combination with one another.

In some embodiments, the composition elicits a cell-mediated response, which may involve CD4+ T cells, CD8+ T cells and/or production of antiviral cytokines. The composition may trigger IFN-γ secretion, for example through the activation of the innate immune response, and mediate CD8+ T cell clearing of the virus. IFN-γ is also secreted by $T_H1$ cells, ($T_H17$ cells?) $T_C$ cells, dendritic cells, and NK cells, and the composition may trigger IFN-γ secretion by any of these cell types. Such activity of CD8+ T cells may be cytolytic, or, alternately, may be regulated by inhibitor molecules on the surface of the neurons which prevent neuronal killing CD4+ and/or CD8+ T cells may play a role in maintaining latency of the virus, thus preventing reactivation. In some embodiments, the composition boosts a CD4+ T cell response and/or a CD8+ T cell response that prevents reactivation of the virus from its latent state.

In some embodiments, the composition blocks the ability of HSV to evade the host immune response, or, alternately, boosts immune responses normally evaded by HSV. In some embodiments, the composition inhibits HSV-2 from shifting the immunological balance towards tolerance of HSV antigens. HSV-2 may mediate tolerance through $T_H2$ cells. First, HSV-2 may induce suppressor T cells, such as CD4+ CD25+ cells and Tr1 cells that secrete IL-10, a $T_H2$ cytokine. $T_H2$ cytokines downregulate costimulatory molecules and inhibit the maturation and function of antigen-presenting dendritic cells. In addition, infection with HSV-2 inhibits the maturation and migration of dendritic cells, which are essential for efficient CTL priming Notably, $T_H2$ cytokines are produced during recurrence of HSV-2 infection, in contrast to $T_H1$ cytokines, which are produced during recurrence-free episodes. Thus, in certain embodiments, the compositions of the invention repress suppressor T cells and/or induce maturation or migration or both of dendritic cells.

In some embodiments, methods of inducing an immune response against HSV-2 in a mammal comprise administering the compositions described above. The composition may be used to induce an immune response at different time points, such as before exposure to HSV-2, after initial infection with HSV-2, before or after HSV-2 has established latency, before or after HSV-2 shedding occurs, and/or before or after recurrent outbreaks occur. In some embodiments, an immune response against HSV-2 may be induced at one or more of the timepoints above. The composition may induce a $T_H1$ response and/or a $T_H17$ response but not a $T_H2$ response, or may activate the responses at the same time or at different times.

In some embodiments, administration of the composition reduces symptoms associated with initial infection, latency, or recurrent infection with HSV. Such a composition may reduce incidence and/or severity of lesions, sores, pain, irritation, itching, fever, malaise, headache, viral shedding, or prodromes associated with HSV infection or outbreak.

In some embodiments, one or more antibodies to antigens of HSV-2 may be administered to individuals in order to produce passive immunity. Passive immunity results from the transfer of active humoral immunity in the form of ready-made antibodies, from one individual to another. Passive immunization may be used when there is a high risk of infection and insufficient time for the body to develop its own immune response, or to reduce the symptoms of ongoing or immunosuppressive diseases. Adoptive transfer of T cells may provide another method of eliciting an immune response to HSV-2 antigens in patients. In one embodiment, autologous T cells may be expanded on APCs presenting the antigens derived from the polypeptides described above. Subsequently, the expanded HSV-2-specific T cells are transferred back into the patient from which the T cells were derived.

2. Diagnostic Uses

This application provides, inter alia, a rapid, inexpensive, sensitive, and specific method for detection of HSV-2 in patients. In this respect it should be useful to hospitals and physicians examining and treating patients with or at risk for HSV-2 infection. As used herein, "patient" refers to an individual (such as a human) that either has an HSV-2 infection or has the potential to contract an HSV-2 infection.

In some embodiments, one may use an antibody against one of the polypeptides described herein, such as those of Table 1 and/or Table 2, to detect HSV-2 in an individual. The instant disclosure also provides a method of phenotyping biological samples from patients suspected of having a HSV-2 infection that involves: (a) rendering a biological sample amenable to immunoassay, if necessary; (b) contacting the sample with an appropriate HSV-2-specific antibody or antigen-binding portion thereof under conditions that allow for binding of the antibody or antigen-binding portion to an epitope of HSV-2; and (c) determining if the sample shows the presence of HSV-2 as compared to a control tissue; where if the test tissue shows the presence of HSV-2, the patient is identified as likely having a HSV-2 infection.

Alternatively, one may use the polypeptides described above to detect anti-HSV-2 antibodies in an individual. The instant disclosure also provides a method of phenotyping biological samples from patients suspected of having a HSV-2 infection: (a) rendering a biological sample amenable to an affinity assay such as ELISA, if necessary; (b) contacting the sample with a HSV-2-specific antigen or portion thereof under conditions that allow for binding of the antigen to any host antibodies present in the sample; and (c) determining if the sample shows the presence of HSV-2 as compared to a control tissue; wherein if the test tissue shows the presence of HSV-2, the patient is identified as likely having a HSV-2 infection. The aforementioned test may be appropriately adjusted to detect other viral infections, for instance by using a homolog (from another viral species) of the proteins described above, such as in Table 1 and/or Table 2.

A number of methods for measuring antibody-antigen binding are known in the art, including ELISA (enzyme-linked immunosorbent assay), Western blotting, competition assay, and spot-blot. The detection step may be, for instance, chemiluminescent, fluorescent, or colorimetric. One suitable method for measuring antibody-protein binding is the Luminex xMAP system, where peptides are conjugated to a dye-containing microsphere. Certain systems, including the xMAP system, are amenable to measuring several different markers in multiplex, and could be used to measure levels of antibodies at once. In some embodiments, other systems are used to assay a plurality of markers in multiplex. For example, profiling may be performed using any of the following systems: antigen microarrays, bead microarrays, nanobarcodes particle technology, arrayed proteins from cDNA expression libraries, protein in situ array, protein arrays of living transformants, universal protein array, lab-on-a-chip microfluidics, and peptides on pins. Another type of clinical assay is a chemiluminescent assay to detect antibody binding. In some such assays, including the VITROS Eci anti-HCV assay, antibodies are bound to a solid-phase support made up of microparticles in liquid suspension, and a surface fluorometer is used to quantify the enzymatic generation of a fluorescent product.

In other embodiments, one may use the polypeptides described above, such as those of Table 1 and/or Table 2, to detect T cells that are specific to HSV-2. The instant disclosure provides a method of phentoyping biological samples from patients suspected of having a HSV-2 infection, involving (a) rendering a biological sample amenable to an assay for activation of T cells, if necessary, (b) contacting the sample with a HSV-2-specific polypeptide or portion thereof under conditions that allow APCs to process the polypeptide, and (c) determining activation of the T cells in response to the HSV-2-specific polypeptide, where an elevated T cell activation relative to an uninfected patient indicates HSV-2 infection. This diagnostic assay is intended to detect the presence of HSV-2-specific T cells in any patients, including those patients who have been exposed to HSV-2 but have not seroconverted to produce detectable levels of anti-HSV-2 antibodies.

T cell activation may be measured using many proliferation assays, including cytokine-specific ELISA, cell proliferation measured by tritiated thymidine incorporation or membrane intercolating (PKH-67) or cytoplasmic (CFSE) dyes, ELISPOT, flow cytometry, and bead arrays. In addition, one may measure the T cell response in T cell lines or in T cell hybridomas from mice or humans that are specific for the antigens. Readouts for activated T cells include proliferation, cytokine production, or readout of a surrogate enzyme expressed by the hybridoma that is induced when the T cell or T cell hybridoma is activated in response to an antigen. For example, activation of a T cell response may be detected by T cell hybridoma that is engineered to produce β-galactosidase. β-galactosidase may be detected through the use of colorimetric β-galactosidase substrates such as chlorophenyl red β-D galactopyranoside (CPRG).

Infection with HSV-2 may be acute or latent. In some embodiments, if the biological sample shows the presence of HSV-2, one may administer a therapeutically effective amount of the compositions and therapies described herein to the patient. The biological sample may comprise, for example, blood, semen, urine, vaginal fluid, mucus, saliva, feces, urine, cerebrospinal fluid, or a tissue sample. In some embodiments, the biological sample is an organ intended for transplantation. In certain embodiments, before the detection step, the biological sample is subject to culture conditions that promote the growth of HSV-2.

The diagnostic tests herein may be used to detect HSV-2 in a variety of samples, including samples taken from patients and samples obtained from other sources. For example, the diagnostic tests may be used to detect HSV-2 on objects such as medical instruments. In some embodiments, the tests herein may be performed on samples taken from animals such as agricultural animals (cows, pigs, chickens, goats, horses and the like), companion animals (dogs, cats, birds, and the like), or wild animals. In certain embodiments, the tests herein may be performed on samples taken from cell cultures such as cultures of human cells that produce a therapeutic protein, cultures of bacteria intended to produce a useful biological molecule, or cultures of cells grown for research purposes.

The invention also includes a method of determining the location of a HSV-2 infection in a patient comprising: (a) administering a pharmaceutical composition comprising a labeled HSV-2 antibody or antigen-binding portion thereof to the patient, (b) detecting the label, and (c) determining if the patient has HSV-2 compared to a control. In certain embodiments, the method further comprises, if the patient has an HSV-2 infection, administering a therapeutically effective amount of a composition described herein to the patient. The method may further comprise determining the infected cell types and/or volume of the HSV-2 in the patient. This method may be used to evaluate the spread of HSV-2 in the patient and determine whether a localized therapy is appropriate.

In some embodiments, the polypeptides described herein may be used to make a prognosis of the course of infection. In some embodiments, T cell or antibody responses specific for the polypeptides herein may be detected in a sample taken from a patient. If antibodies or T cells are present at normal levels, it would indicate that the patient has raised an effective immune response against the pathogen. If antibodies or T cells are absent, or present at reduced levels, it would indicate that the patient is failing to raise a sufficient response against the pathogen, and a more aggressive treatment would be recommended. In some embodiments, antibody or T cells present at reduced levels refers to responses that are present at less than 50%, 20%, 10%, 5%, 2%, or 1% the typical level in a patient with a protective immune response. T cell responses may be detected by methods known in the art such as T cell proliferation, ELISPOT or ELISA, and antibodies may be detected by affinity for any of the antigens described herein, using methods known in the art such as ELISA.

In some embodiments, detection of T cells specific for HSV-2 antigens may be used to predict the progress and symptoms of HSV-2 infection in a patient. After infection with HSV-2, some patients remain asymptomatic, although the virus may establish latency. Other patients exhibit symptoms of HSV-2 infection, and may experience recurrent outbreaks. The HSV-2 antigens found in asymptomatic patients may differ from those antigens found in patients who present symptoms and/or recurrent outbreaks. Accordingly, the detection methods of the present invention may be used to distinguish between subgroups within the population of patients infected with HSV-2. Subgroups may be further divided into patients who experience frequent outbreaks and those who infrequently or never experience outbreaks, or patients who shed high levels of virus and those who shed low levels or do not shed. The categorization of patients, based on the presence and levels of T cell responses to certain HSV-2 antigens but not others, may help health care practitioners to determine appropriate treatment regimens. Similarly, differences in the magnitude of T cell responses and/or differences in the combination and levels of cytokines produced by T cells may also be used to predict the progress and symptoms of HSV-2 infection in a patient. Thus, an infected patient whose complement of HSV-2 antigens to which T cells respond predicts severe symptoms, frequent outbreaks, and/or high levels of viral shedding may require more intensive antiviral therapy and/or a longer course of therapeutic treatment than a patient whose complement of HSV-2 antigens predicts an asymptomatic infection.

It will be understood by one of skill in the art that the methods herein are not limited to detection of HSV-2. Other embodiments include the detection of related viruses including viruses with proteins homologous to the proteins described above, such as those in Table 1 and/or Table 2. Such related viruses include, for example, other members of the Herpesviridae family. Depending on the homology, these related viruses may also include viruses that are not members of the Herpesviridae family.

3. Use in Groups with Increased Risk for Infection by HSV-2

Essentially any individual has a certain risk of infection with HSV-2. However, certain sub-populations have an increased risk of infection. In some embodiments, patients receiving the composition for HSV-2 are immunocompromised.

An immunocompromising condition arising from a medical treatment is likely to expose the individual in question to a higher risk of infection. It is possible to treat an infection prophylactically in an individual having the immunocompromised condition before or during treatments known to generate such a condition. By prophylactically treating with the antigen before or during a treatment known to generate such a condition it is possible to prevent a subsequent infection or to reduce the risk of the individual contracting an infection due to the immunocompromised condition. Should the individual contract an infection, e.g., following a treatment leading to an immunocompromised condition, it is also possible to treat the infection by administering to the individual an antigen composition.

In certain embodiments, the compositions are administered to children or adult patients. In other embodiments, compositions are appropriate for pregnant women who were infected before becoming pregnant, or who became infected during pregnancy, such as to inhibit infection of a fetus or baby. The compositions may also be administered to neonates and infants who became infected in utero or during delivery.

H. Doses and Routes of Administration

1. Dosage Amounts and Timing

The amount of antigen in each vaccine dose is selected as an effective amount, which induces an prophylactic or therapeutic response, as described above, in either a single dose or over multiple doses. Preferably, the dose is without significant adverse side effects in typical vaccines. Such amount will vary depending upon which specific antigen is employed. Generally, it is expected that a dose will comprise 1-1000 µg of protein, in some instances 2-100 µg, for instance 4-40 µg. An optimal amount for a particular vaccine can be ascertained by standard studies involving observation of antibody titers, T cell activation levels, and other responses in subjects. In some embodiments, the appropriate amount of antigen to be delivered will depend on the age, weight, and health (e.g.; immunocompromised status) of a subject. When present, typically an adjuvant will be present in amounts from 1 µg-250 µg per dose, for example 50-150 µg, 75-125 µg or 100 µg.

In some embodiments, only one dose of the vaccine is administered to achieve the results described above. In other embodiments, following an initial vaccination, subjects receive one or more boost vaccinations, for a total of two, three, four or five vaccinations. Advantageously, the number is three or fewer. A boost vaccination may be administered, for example, about 1 month, 2 months, 4 months, 6 months, or 12 months after the initial vaccination, such that one vaccination regimen involves administration at 0, 0.5-2 and 4-8 months. It may be advantageous to administer split doses of vaccines which may be administered by the same or different routes.

The pharmaceutical compositions described herein may take on a variety of dosage forms. In certain embodiments, the composition is provided in solid or powdered (e.g., lyophilized) form; it also may be provided in solution form. In certain embodiments, a dosage form is provided as a dose of lyophilized composition and at least one separate sterile container of diluent.

In some embodiments, the antigen is delivered to a patient at an amount of 1 μmmol per dose. In some embodiments, the antigen is delivered at a dose ranging from 10 nmol to 100 nmol per dose. The appropriate amount of antigen to be delivered may be determined by one of skill in the art. In some embodiments, the appropriate amount of antigen to be delivered will depend on the age, weight, and health (e.g., immunocompromised status) of a subject.

Pharmaceutical compositions disclosed herein are (in some embodiments) administered in amounts sufficient to elicit production of antibodies as part of an immunogenic response. In some embodiments, the composition may be formulated to contain 5 mcg/0.5 mL or an amount ranging from 10 mcg/1 mL to 200 mcg/1 mL of an antigen. In other embodiments, the composition may comprise a combination of antigens. The plurality of antigens may each be the same concentration, or may be different concentrations.

In some embodiments, the composition will be administered in a dose escalation manner, such that successive administrations of the composition contain a higher concentration of composition than previous administrations. In some embodiments, the composition will be administered in a manner such that successive administrations of the composition contain a lower concentration of composition than previous administrations.

In therapeutic applications, compositions are administered to a patient suffering from a disease in an amount sufficient to cure or at least partially arrest the disease and its complications.

Therapeutic applications of a composition described herein include reducing transmissibility, slowing disease progression, reducing viral shedding, or eliminating recurrent infections in patients that have been infected with HSV-2, such as by 90%, 80%, 70%, 60%, 50%, 40%, 30%, 20% or 10% of the levels at which they would occur in individuals who are not treated with the composition. The composition may also reduce the quantity of HSV-2 shed by infected individuals, inhibit the expression of proteins required for reactivation of HSV-2 from the latent stage in infected patients, and/or inhibit replication of HSV-2 in neurons of infected patients, such as by 90%, 80%, 70%, 60%, 50%, 40%, 30%, 20%, or 10% of the levels at which they would occur in individuals not treated with the composition.

In prophylactic embodiments, compositions are administered to a human or other mammal to induce an immune response that can inhibit the establishment of an infectious disease or other condition. In some embodiments, a composition may partially block the virus from establishing latency or reduce the efficiency with which latency is established.

In some embodiments, only one dose (administration) of the composition is given. In other embodiments, the composition is administered in multiple doses. In various embodiments, the composition is administered once, twice, three times, or more than three times. The number of doses administered to a subject is dependent upon the antigen, the extent of the disease or the expected exposure to the disease, and the response of a subject to the composition.

In some embodiments, the compositions are administered in combination with antimicrobial molecules. Antimicrobial molecules may include antiviral molecules. Many antiviral molecules are currently known in the art, and target one or more stage of the viral life cycle, including viral attachment to host cells, release of viral genes and/or enzymes into the host cell, replication of viral components using host-cell machinery, assembly of viral components into complete viral particles, and release of viral particles to infect new hosts.

2. Routes of Administration

The vaccine formulations and pharmaceutical compositions herein can be delivered by administration to an individual, typically by systemic administration (e.g., intravenous, intraperitoneal, intramuscular, intradermal, subcutaneous, transdermal, subdermal, intracranial, intranasal, mucosal, anal, vaginal, oral, sublingual, buccal route or they can be inhaled) or they can be administered by topical application.

In some embodiments, the composition may be administered directly to the likely sites of infection. In female patients, the composition may be applied topically to mucosal membranes, or delivery vaginally or rectally using devices and methods known in the art. The vaginal and rectal routes of delivery permits extended, continuous or pulsed delivery and administration of composition dosages, and may be administered either before or after exposure to HSV, depending on the use of a prophylactic or therapeutic composition. In male patients, the composition may be applied topically to the skin or mucosal membranes, or delivered rectally. In both patient populations, the composition may also be targeted to the sensory ganglia.

An HSV-2 vaccine or pharmaceutical composition is often administered via the intramuscular route. Typically, in this route, the vaccine is injected into an accessible area of muscle tissue. Intramuscular injections are, in some embodiments, given in the deltoid, vastus lateralis, ventrogluteal or dorsogluteal muscles. The injection is typically given at an approximately 90° angle to the surface of the skin, so the vaccine penetrates the muscle.

An HSV-2 vaccine may also be administered subcutaneously. The injection is typically given at a 45° angle to the surface of the skin, so the vaccine is administered to the subcutis and not the muscle.

In some embodiments, the HSV-2 vaccine is administered intradermally. Intradermal administration is similar to subcutaneous administration, but the injection is not as deep and the target skin layer is the dermis. The injection is typically given at a 10-15° angle to the surface of the skin, so the vaccine is delivered just beneath the epidermis.

3. Formulations

The vaccine formulation may be suitable for administration to a human patient, and vaccine preparation may conform to USFDA guidelines. In some embodiments, the vaccine formulation is suitable for administration to a non-human animal. In some embodiments, the vaccine is substantially free of either endotoxins or exotoxins. Endotoxins include pyrogens, such as lipopolysaccharide (LPS) molecules. The vaccine may also be substantially free of inactive protein fragments. In some embodiments, the vaccine has lower levels of pyrogens than industrial water, tap water, or distilled water. Other vaccine components may be purified using methods known in the art, such as ion-exchange chromatography, ultrafiltration, or distillation. In other embodiments, the pyrogens may be inactivated or destroyed prior to administration to a patient. Raw materials for vaccines, such as water, buffers, salts and other chemicals may also be screened and depyrogenated. All materials in the vaccine may be sterile, and each lot of the vaccine may be tested for sterility. Thus, in certain embodiments the endotoxin levels in the vaccine fall below the levels set by the USFDA, for example 0.2 endotoxin (EU)/kg of product for an intrathecal injectable composition; 5 EU/kg of product for a non-intrathecal injectable composition, and 0.25-0.5 EU/mL for sterile water.

In some embodiments, the vaccine comprising a polypeptide contains less than 5%, 2%, 1%, 0.5%, 0.2%, 0.1% of other, undesired unpolypeptides, relative to the amount of desired polypeptides. In some embodiments, the vaccine contains less than 5%, less than 2%, less than 1%, less than 0.5%, less than 0.2%, or less than 0.1% DNA and/or RNA.

It is preferred that the vaccine has low or no toxicity, within a reasonable risk-benefit ratio.

The formulations suitable for introduction of the pharmaceutical composition vary according to route of administration. Formulations suitable for parenteral administration, such as, for example, by intraarticular (in the joints), intravenous, intramuscular, intradermal, intraperitoneal, intranasal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampoules and vials.

Injection solutions and suspensions can be prepared from sterile powders, granules, and tablets of the kind previously described. Cells transduced by the packaged nucleic acid can also be administered intravenously or parenterally.

Formulations suitable for oral administration can consist of (a) liquid solutions, such as an effective amount of the polypeptides or packaged nucleic acids suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. The pharmaceutical compositions can be encapsulated, e.g., in liposomes, or in a formulation that provides for slow release of the active ingredient.

The antigens, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Suitable formulations for vaginal or rectal administration include, for example, suppositories, which consist of the polypeptides or packaged nucleic acids with a suppository base. Suitable suppository bases include natural or synthetic triglycerides or paraffin hydrocarbons. In addition, it is also possible to use gelatin rectal capsules which consist of a combination of the polypeptides or packaged nucleic acids with a base, including, for example, liquid triglycerides, polyethylene glycols, and paraffin hydrocarbons. The formulation may be suitable for administration to a human patient, and the preparation may conform to US FDA guidelines. In some embodiments, the formulation is suitable for administration to a non-human animal. In some embodiments, the composition is substantially free of either endotoxins or exotoxins. Endotoxins may include pyrogens, such as lipopolysaccharide (LPS) molecules. The composition may also be substantially free of inactive protein fragments which may cause a fever or other side effects. In some embodiments, the composition contains less than 1%, less than 0.1%, less than 0.01%, less than 0.001%, or less than 0.0001% of endotoxins, exotoxins, and/or inactive protein fragments. In some embodiments, the composition has lower levels of pyrogens than industrial water, tap water, or distilled water. Other components may be purified using methods known in the art, such as ion-exchange chromatography, ultrafiltration, or distillation. In other embodiments, the pyrogens may be inactivated or destroyed prior to administration to a patient. Raw materials for compositions, such as water, buffers, salts and other chemicals may also be screened and depyrogenated. All materials in the composition may be sterile, and each lot of the composition may be tested for sterility. Thus, in certain embodiments the endotoxin levels in the composition fall below the levels set by the USFDA: 0.2 endotoxin (EU)/kg of product for an intrathecal injectable composition; 5 EU/kg of product for a non-intrathecal injectable composition, and 0.25-0.5 EU/mL for sterile water.

In certain embodiments, the preparation comprises less than 50%, 20%, 10%, or 5% (by dry weight) contaminating protein. In certain embodiments, the desired molecule is present in the substantial absence of other biological macromolecules, such as other proteins (particularly other proteins which may substantially mask, diminish, confuse or alter the characteristics of the component proteins either as purified preparations or in their function in the subject reconstituted mixture). In certain embodiments, at least 80%, 90%, 95%, 99%, or 99.8% (by dry weight) of biological macromolecules of the same type present (but water, buffers, and other small molecules, especially molecules having a molecular weight of less than 5000, can be present).

It is preferred that the composition has low or no toxicity, within a reasonable risk-benefit ratio. In certain embodiments, the composition comprises ingredients at concentrations that are less than $LD_{50}$ measurements for the animal being treated with the composition. $LD_{50}$ measurements may be obtained in mice or other experimental model systems, and extrapolated to humans and other animals. Methods for estimating the $LD_{50}$ of compounds in humans and other animals are well-known in the art. A composition, and any component within it, might have an $LD_{50}$ value in rats of greater than 100 g/kg, greater than 50 g/kg, greater than 20 g/kg, greater than 10 g/kg, greater than 5 g/kg, greater than 2 g/kg, greater than 1 g/kg, greater than 500 mg/kg, greater than 200 mg/kg, greater than 100 mg/kg, greater than 50 mg/kg, greater than 20 mg/kg, or greater than 10 mg/kg. In some embodiments, the therapeutic index of the composition (measured as the toxic dose for 50% of the population ($TD_{50}$) divided by the minimum effective dose for 50% of the population ($ED_{50}$)), is greater than 1, greater than 10, or greater than 100.

I. Preparation and Storage of Vaccines Formulations and Immunogenic Compositions The HSV-2 vaccines described herein may be produced using a variety of techniques. For example, a polypeptide may be produced using recombinant DNA technology in a suitable host cell. A suitable host cell may be bacterial, yeast, mammalian, or other type of cell. The host cell may be modified to express an exogenous copy of one of the relevant polypeptide genes. Typically, the gene is operably linked to appropriate regulatory sequences such as a strong promoter and a polyadenylation sequence. In some embodiments, the promoter is inducible or repressible. Other regulatory sequences may provide for secretion or excretion of the polypeptide of interest or retention of the polypeptide of interest in the cytoplasm or in the membrane, depending on how one wishes to purify the polypeptide. The gene may be present on an extrachromosomal plasmid, or may be integrated into the host genome. One of skill in the art will recognize that it is not necessary to use a nucleic acid 100% identical to the naturally-occurring sequence. Rather, some alterations to these sequences are tolerated and may be desirable. For instance, the nucleic acid may be altered to take advantage of the degeneracy of the genetic code such that the encoded polypeptide remains the same. In some embodiments, the gene is codon-optimized to improve expression in a particular host. The nucleic acid may be produced, for example, by PCR or by chemical synthesis.

Once a recombinant cell line has been produced, a polypeptide may be isolated from it. The isolation may be accomplished, for example, by affinity purification techniques or by physical separation techniques (e.g., a size column).

In a further aspect of the present disclosure, there is provided a method of manufacture comprising mixing one or more polypeptides or an immunogenic fragment or variant thereof with a carrier and/or an adjuvant. In some embodiments, the adjuvant is one that stimulates a $T_H1$ cell response.

In some embodiments, antigens for inclusion in compositions of the invention may be produced in cell culture. One method comprises providing one or more mammalian expression vectors and cloning nucleotides encoding two or more polypeptides selected from polypeptides having an amino acid sequence of any one of SEQ ID NOS: 1-38, then expressing and isolating the polypeptides.

The immunogenic polypeptides described herein, and nucleic acid compositions that express the polypeptides, can be packaged in packs, dispenser devices, and kits for administering nucleic acid compositions to a mammal. For example, packs or dispenser devices that contain one or more unit dosage forms are provided. Typically, instructions for administration of the compounds will be provided with the packaging, along with a suitable indication on the label that the compound is suitable for treatment of an indicated condition, such as those disclosed herein.

V. EXAMPLES

Example 1. Identification of HSV-2 Antigens

A library of HSV-2 antigens (from HSV-2 Strain G, Lot #7C0013, from Advanced Biotechnologies Inc, Maryland) was prepared and screened with peripheral blood mononuclear cells (PBMC) from human donors. Briefly, a library of HSV antigens was expressed by bacteria and mixed with antigen presenting cells (APCs). The APCs, in turn, presented HSV-derived peptides to lymphocytes that had been isolated from human patients infected with HSV-2. The patients belonged to several populations, as described below. Lymphocyte responses from each population were compared for reactivity to each expressed protein, and the screen detected antigens that induced reactive lymphocytes with greater frequency in one patient population as compared to the others. Infected but asymptomatic, and exposed but seronegative patients may activate protective immune responses that patients who experience frequent outbreaks do not; in particular, exposed but seronegative patients are presumed to have mounted sterilizing immunity to HSV-2 infection. It is believed that a unique set of polypeptides will activate lymphocytes from these patient populations.

The release of IFN-γ from $CD4^+$ T cells and $CD8^+$ T cells from each population was measured by ELISA following exposure to candidate antigens. Antigens were selected on the basis of the fold increase of IFN-γ released, relative to the level of IFN-γ released by frequent recurrers who experience more than four outbreaks per year.

A. Identification of Antigens Encoded by UL10, UL19, UL40, US4, US6, RS1 (RS1.1, RS1.2, RS1.3), UL 36 (UL36.3, UL36.4, UL36.5), UL32, and RL2

Lymphocytes were isolated from patients belonging to several populations: asymptomatic (n=40), exposed (n=40), frequent recurrers who experience 4 or more outbreaks per year (n=43), less-frequent recurrers who experience less than 4 outbreaks per year (n=19), naïve (n=10), and $HSV\text{-}2^-/HSV\text{-}1^+$ (n=10). Table 3 shows the frequency analysis for thirteen HSV-2 antigens encoded by UL10, UL19, UL40, US4, US6, RS1 (RS1.1, RS1.2, RS1.3), UL36 (UL36.3, UL36.4, UL36.5), UL32, and RL2 in the exposed patient cohort compared to recurrers with 2 or more outbreaks per year.

TABLE 3

Frequency analysis for antigens encoded by UL10, UL19, UL40, US4, US6, RS1 (RS1.1, RS1.2, RS1.3), UL36 (UL36.3, UL36.4, UL36.5), UL32 and RL2

| | | Frequency Analysis (HSV-1/HSV-2 seronegative) | |
|---|---|---|---|
| HSV-2 Gene | Protein Name | % response from exposed donors | fold increase over recurrer response |
| UL10 | gM | 23% | 1.4 |
| UL19 | VP5 | — | — |
| UL40 | ribonucleotide reductase | 36% | 3.0 |
| Us4 | gG | 24% | 1.6 |
| Us6 | gD | 27% | 1.9 |
| RS1 | ICP4 | | |
| RS1.1 | | 54% | 3.0 |
| RS1.2 | | 46% | 2.3 |
| RS1.3 | | 23% | 1.2 |
| UL36 | Major tegument protein | | |
| UL36.3 | | 46% | 2.3 |
| UL36.4 | | 46% | 4.2 |
| UL36.5 | | 31% | 1.9 |

TABLE 3-continued Frequency analysis for antigens encoded by UL10, UL19,
UL40, US4, US6, RS1 (RS1.1, RS1.2, RS1.3), UL36
(UL36.3, UL36.4, UL36.5), UL32 and RL2

| HSV-2 Gene | Protein Name | Frequency Analysis (HSV-1/HSV-2 seronegative) | |
|---|---|---|---|
| | | % response from exposed donors | fold increase over recurrer response |
| UL32 | DNA cleavage & packaging proteiin | — | — |
| RL2 | ICP0 | 45% | 1.6 |

B. Identification of Antigens Encoded by UL1, UL49.5, and UL54

Lymphocytes were isolated from patients belonging to several populations: asymptomatic (n=40), exposed (n=40), frequent recurrers who experience 4 or more outbreaks per year (n=43), less-frequent recurrers who experience less than 4 outbreaks per year (n=19), naïve (n=10), and HSV-2$^-$/HSV-1$^+$ (n=10).

Table 4 shows the frequency analysis for three HSV-2 antigens encoded by UL1, UL49.5 and UL54, in the exposed patient cohort compared to recurrers with 2 or more outbreaks per year.

TABLE 4

Frequency analysis for antigens encoded by UL1, UL49.5, and UL54

| HSV-2 Gene | Protein Name | Frequency Analysis (HSV-1/HSV-2 seronegative) | |
|---|---|---|---|
| | | % response from exposed donors | fold increase over recurrer response |
| UL1 | gL2 | 64% | 2.7 |
| UL49.5 | (virion p) | 37% | 2.1 |
| UL54 | ICP27 | 22% | 5.8 |

C. Identification of Antigens Encoded by RL1, UL2, and UL11

Lymphocytes were isolated from patients belonging to several populations: asymptomatic (n=40), exposed (n=40), frequent recurrers who experience 4 or more outbreaks per year (n=43), less-frequent recurrers who experience less than 4 outbreaks per year (n=19), naïve (n=10), and HSV-2$^-$/HSV-1$^+$ (n=10).

Table 5 shows the frequency analysis for three HSV-2 antigens encoded by RL1, UL2, and UL11 in the exposed patient cohort compared to recurrers with 2 or more outbreaks per year.

TABLE 5

Frequency analysis for HSV-2 antigens encoded by RL1, Ul1, and UL11

| HSV-2 Gene | Protein Name | Frequency Analysis (HSV-1/HSV-2 seronegative) | |
|---|---|---|---|
| | | % response from exposed donors | fold increase over recurrer response |
| RL1 | ICP34.5 | 45% | 1.3 |
| UL2 | DNA glycosylase | 23% | 1.4 |
| UL11 | tegument protein | 21% | <1.0 |

Example 2. In Vivo Data

A. [Protocol A] Guinea Pig Therapeutic Vaccination Protocol

Female Hartley guinea pigs were challenged intravaginally with HSV-2 strain MS at $5 \times 10^5$ pfu to establish a genital tract infection. Animals were monitored for infection by vaginal swab on day 1 post-infection, and acute disease between days 3 and 14 post-infection. On day 14, after resolution of primary disease, the animals were randomized into groups of 12 and immunized subcutaneously with antigen (HSV-2 polypeptide at 15 µg dose) plus adjuvant (50 µg dose of an ISCOM matrix with a 91:9 mixture of *Quillaja* saponin fractions A and C). Each group received a total of 3 vaccinations, on days 14, 21, and 34 post-infection. Genital swabs were collected during the vaccination period to monitor viral shedding, and daily observations were recorded. Symptoms were scored on a scale from 0 to 4 based upon severity, 0=no symptoms; 1=redness or swelling; 2=a few small vesicles; 3=several large vesicles; 4=several large vesicles with maceration. In addition, animals with lesions intermediate in severity between the above scores were given a score of 0.5, 1.5, 2.5, or 3.5.

1. Results of Therapeutic Vaccination Studies with ICP4.2, gD2ΔTMR, and gD2

The results of the studies are presented below in Tables 6-10. The IgG titer was determined at day 41 post-infection and 7 days after third immunization using an average of 4 out of the 12 animals in each group. The mean recurrent lesion scores and mean lesion days were each determined from day 15 to day 63 post-infection. The lesion scores represent total lesions for each group from day 15 to 60 and then a mean was calculated. Mean lesion days represent the mean number of days post-infection that immunized or non-immunized animals had herpetic lesions present. Vaginal-swab samples were collected from all animals for 12 days between days 20-59 post-infection and stored at −80° C. until assayed for virus shedding titers by quantitative real-time PCR.

TABLE 6

Results of therapeutic vaccination studies with ICP4.2 (SEQ ID NO: 2): lesions

| Groups N = 12 | Dose | gD2 IgG Titer | Mean Recurrent Lesion Score | % Reduction | Mean Lesion Days | % Reduction |
|---|---|---|---|---|---|---|
| Phosphate-Buffered Saline | — | 1:263 | 8.1 | — | 9.0 | — |
| adjuvant only | 50 µg × 3 | 1:331 | 7.1 | 14 | 8.5 | 6 |
| ICP4.2 + adjuvant | 15 µg × 3 | 1:1079 | 4.3 | 47 | 5.1 | 44 |

TABLE 7

Results of therapeutic vaccination studies with ICP4.2
(SEQ ID NO: 2): viral shedding

| Groups | No. of animals/total with no detectable viral shedding | Mean number of days viral shedding detected ± SEM | % Reduction | P value* |
|---|---|---|---|---|
| Phosphate-Buffered Saline | 0/11 | 4.5 ± 0.8 | — | — |
| Adjuvant only | 0/12 | 4.4 ± 0.7 | 2 | 0.971 |
| ICP4.2 + adjuvant | 5/11 | 1.5 ± 0.5 | 67 | 0.004 |

TABLE 8

Results of therapeutic vaccination studies with
gD2ΔTMR (SEQ ID NO: 4): lesions

| Groups | Mean Recurrent Lesion Score | % Reduction | Mean Lesion Days | % Reduction |
|---|---|---|---|---|
| Adjuvant only | 8.7 | — | 11.7 | — |
| gD2ΔTMR | 5.7 | 34 | 8.6 | 26 |

TABLE 9

Results of therapeutic vaccination studies with
gD2 (SEQ ID NO: 5): lesions

| Groups N = 12 | Dose | gD2 IgG Titer | Mean Recurrent Lesion Score | % Reduction | Mean Lesion Days | % Reduction |
|---|---|---|---|---|---|---|
| Phosphate-Buffered Saline | — | 1:263 | 8.1 | — | 9.0 | — |
| Adjuvant only | 50 µg × 3 | 1:331 | 7.1 | 14 | 8.5 | 6 |
| gD2 + adjuvant | 15 µg × 3 | >1:6400 | 4.0 | 51 (p = 0.04) | 5.0 | 45 |

TABLE 10

Results of therapeutic vaccination studies with
gD2 (SEQ ID NO: 5): viral shedding

| Groups | No. of animals/total with no detectable viral shedding | Mean number of days viral shedding detected ± SEM | % Reduction | P value* |
|---|---|---|---|---|
| Phosphate-Buffered Saline | 0/11 | 4.5 ± 0.8 | — | — |
| Adjuvant only | 0/12 | 4.4 ± 0.7 | 2 | 0.971 |
| gD2 + adjuvant | 4/12 | 2.4 ± 0.6 | 47 | 0.047 |

B. [Protocol B] Murine Prophylactic Vaccination Protocol

Female C57BL/6 mice from 6 to 8 weeks of age were immunized subcutaneously with antigen (HSV-2 polypeptide) plus adjuvant (12 µg dose of an ISCOM matrix with a 82:18 mixture of Quillaja saponin fractions A and C) on day 0 and day 9. On day 11, estrous cycles were synchronized with depo provera and then the mice were challenged on day 16 via intravaginal deposition of 10 times the $LD_{50}$ of HSV-2 strain 333 while under anaesthesia. All animals were monitored for morbidity (clinical score) and mortality, and body weights and vaginal swabs were collected between days 17 and 28 post-infection. Clinical scores were recorded using the following scale: 0=no symptoms, 1=vaginal erythema, 2=vaginal erythema and edema, 3=vaginal herpetic lesions, 4=unilateral paralysis or severe genital ulceration, and 5=bilateral paralysis or death.

1. Results of Murine Prophylactic Vaccination Studies with ICP4.2, VP5, gD2ΔTMR and gD2ΔTMR and ICP4.2

In the experimental group, mice were immunized subcutaneously with either 5 μg or 10 μg of antigen plus adjuvant (12 μg dose of an ISCOM matrix with a 82:18 mixture of *Quillaja* saponin fractions A and C) on day 0 and day 9. Control animals received phosphate buffered saline (PBS) only, or adjuvant only.

Mice receiving PBS only or adjuvant only all died by day 9 post-challenge (no survivors). In contrast, mice receiving antigen largely survived to day 9, and 20-75% survived to day 12 post-challenge. The severity of disease symptoms (genital and neurological disease) were also scored at either day 9 or 10 post-challenge. Mice immunized with ICP4.2, VP5, gD2ΔTMR, or gD2ΔTMR and ICP4.2 with ISCOM adjuvant showed a significant decrease in disease symptoms compared to the PBS only or adjuvant only groups.

TABLE 11

Results of murine prophylactic vaccination studies

| Groups | Mean Disease Score Day 10 | % Reduction | P value* | % Survival Day 12 |
|---|---|---|---|---|
| PBS only/adjuvant only | 5.00/4.81 | — | — | 0% |
| ICP4.2 | 3.6 | 28 | X- | 22.0% |
| VP5 + adjuvant | 3.13 | 35 | 0.146 | 33.8% |
| gD2ΔTMR + adjuvant | 1.44 | 70 | 0.023 | 77.5% |
| gD2ΔTMR + ICP4.2 + adjuvant | 0.75 | 84 | 0.020 | 88.8% |

*Student's t test

C. [Protocol C] Guinea Pig Prophylactic Vaccination Protocol

Female Hartley guinea pigs from 250-350 grams (weight) were immunized subcutaneously with 15 μg of antigen plus adjuvant (50 μg dose of an ISCOM matrix with a 91:9 mixture of *Quillaja* saponin fractions A and C) on day 0 and day 14-21. Sera were collected by toenail clip 2-3 weeks after the boost and then the guinea pigs were challenged via intravaginal deposition of $5\times10^5$ PFU of HSV-2 strain MS. Vaginal-swab samples were collected from all animals on days 30 and 32 and stored at −80° C. until assayed for virus titers by quantitative real-time PCR. Guinea pigs were evaluated daily (day 1-14), and primary genital skin disease was quantified using a lesion severity score scale from 1-4. Numerical scores were assigned to specific disease signs as follows: 0, no disease; 1, redness or swelling; 2, a few small vesicles; 3, several large vesicles; 4, several large vesicles with maceration. At the end of the study, the guinea pigs were euthanized, and the dorsal root ganglia (DRG) were harvested, stored at −80° C. until they were processed for quantitative real-time PCR analysis.

TABLE 12

Results of guinea pig prophylactic vaccination studies with gD2ΔTMR and VP5

| Groups | Viral titer, PFU/ml Day 2 | Total mean acute lesion score | % Reduction | Copies HSV-2 DNA/ 1 µg DRG DNA | % Reduction |
|---|---|---|---|---|---|
| Adjuvant only | 2.3 × 10$^6$ | 22.6 | — | 959 | — |
| gD2ΔTMR + Adjuvant | 1.7 × 10$^6$ | 7.7 | 66% | 274 | 71% |
| VP5 + adjuvant | 5.9 × 10$^5$ | 18.2 | 17% | 283 | 70% |

D. [Protocol D] Immunogenicity Assay I (Standard)

Mice were immunized subcutaneously in the scruff of the neck with a 100 µl injection of 5 µg antigen plus adjuvant (12 µg dose of an ISCOM matrix with a 82:18 mixture of *Quillaja* saponin fractions A and C) in saline. The mice received one or two injections, 7 days apart. Analysis of the immunogenicity of the injection occurred 7 days after the final injection.

The immunogenicity assay was an ex vivo IFN-γ ELISPOT. CD4$^+$ and CD8$^+$ T cells were enriched from the spleen and analyzed separately. For the ELISPOT assay, membrane plates were prepared by coating them overnight with capture antibody and subsequently blocked by supplemented medium for a minimum of 2 hours at 37° C. The mice were euthanized and their spleens harvested. The T cells were then prepared by sorting the splenocytes for CD4$^+$ and CD8$^+$ T cells using magnetic beads. The blocking solution was washed out from ELISPOT plates and the T cells were plated out onto the blocked plates. The plates were returned to the incubator to allow the T cells to settle. APCs were prepared by pulsing naïve T-depleted splenocytes with antigen for 2 hours at 37° C. For CD4$^+$ ELISPOTs, APCs were pulsed with whole protein. For CD8$^+$ ELISPOTs, APCs were pulsed with *E. coli* expressing protein plus cLLO. A medium control was APCs incubated for 2 hours at 37° C. with no additional antigen. The pulsed APCs were irradiated, washed and adjusted to 2×10$^6$ cells/ml. The APCs were added to appropriate wells of plates containing T cells. Then phorbol myristate acetate (PMA) and ionomycin were added to control wells as a positive control. The plates were allowed to incubate for 18 hours at 37° C. under 5% CO$_2$. The plates were then developed using a secondary biotinylated antibody, horseradish peroxidase (HRP) and 3-amino-9-ethylcarbazole (AEC) substrate.

1. Results of Immunogenicity Assay I with ICP4.2

The immunogenicity assay I showed a robust immunogenic response for both the one and two injection regimens with ICP4.2. For the one injection regimen, the number of IFN-γ spots per 200,000 T cells were 8 and 101 for CD4$^+$ and CD8$^+$ cells, respectively. For the two injection regimen, there were 50 and 70 spots, respectively. In contrast, less than 15 spots were observed for media or adjuvant alone in either CD4$^+$ or CD8$^+$ cells.

2. Results of Immunogenicity Assay I with gD2ΔTMR and gD2

Results of immunogenicity assay I are shown in FIGS. 1A and B. Robust CD4$^+$ and CD8$^+$ T cell responses were obtained for both full-length gD2 and for gD2ΔTMR. In contrast, gD2 antigen truncated immediately upstream of the transmembrane domain (denoted 306t in FIG. 1) showed significantly reduced responses.

E. [Protocol E] Immunogenicity Assay II (Rapid)

Recombinant *E. coli* from Genocea's proprietary library of HSV-2 orfeome were induced to express gL2 or fragments of ICP4 protein (ICP4.2, and polypeptides encoded by RS1.1, RS1.3.1 and RS1.3.2). The protein was retained within bacterial cells. The bacteria were then fixed with PFA, washed extensively with PBS and stored at −80 C until used for immunization.

Three mice per group were immunized with 1×10$^8$ bacteria in PBS per mouse by intraperitoneal injection. Mice received 1-2 additional boosters at 1 week intervals. Seven days after last boost, sera were collected and analyzed in an HSV-2 neutralization assay. Five-fold serial dilutions were prepared for plasma or serum samples in a 96-well round-bottom plate, followed by the addition of 50 PFUs HSV-2 (strain 333) to each well. The plates were covered and incubated at 37° C. for 1 hour. 200 µl of virus-serum dilution was transferred in duplicate to Vero cells grown in a 48-well tissue culture plate and incubated for 1 hour at 37° C. 300 µl of DMEM containing 2% FBS was then added to each well and the plates were incubated for 48 hours at 37° C. To visualize virus plaques the plates were stained with crystal violet.

TABLE 13

Results of HSV-2 neutralization assay with gL2, ICP4.2, and polypeptides encoded by RS1.1, RS1.3.1 and RS1.3.2

| Immunogen | HSV-2 Neutralization IgG Titer* |
|---|---|
| *E coli*//gL2 | 1:50 |
| *E coli*//RS1.1 | <1:20 |
| *E coli*//ICP4.2 | <1:20 |
| *E. coli*//RS1.3.1 | 1:100 |
| *E. coli*//RS1.3.2 | <1:20 |
| Positive control (DL11 Mab) | 1:2500 |
| Negative control (Naïve mouse serum) | <1:20 |

*Serum dilution that inhibits 50% of virus control

F. [Protocol F] Immunogenicity Assay III (Overlapping Peptide Pools)

Mice were immunized with 2 µg/mouse of pooled, overlapping peptides (OLP) spanning the entire sequence of gL2, ICP4, and ICP4 fragments encoded by RS1.3.1 and RS1.3.2. OLPs were formulated in TiterMax adjuvant (Alexis Biochemical) in a total volume of 100 µl per mouse where adjuvant represented ⅓ of the subcutaneous dose. Mice were immunized on day 0, boosted on day 6 and spleens and blood were collected on day 11. Single cell suspensions were prepared from spleens and erythrocytes were lysed. The splenocyte suspensions were then divided into halves. The first half was separated into antigen presenting cells, CD4$^+$ and CD8$^+$ T cells; 200,000 T cells were seeded per well of IFN-gamma ELISPOT plate and stimulated with 100,000 APCs and OLP pool corresponding to immunization, irrelevant peptide, positive and negative control. Cells were incubated in plates overnight after which the plates were developed and spots per well were counted. The second half of each splenocyte suspension was run as unseparated splenocytes (400,000/well), pulsed with peptides, and assayed as described above. Results are shown in FIGS. 2A and B as magnitude of response per immunization group.

G. [Protocol G] Vaccination with at Least Two Antigens

Example 1. Immunogenicity of gD2ΔTMR and ICP4 or ICP4.2 in C57BL/6 Mice

Purified protein was mixed with adjuvant and immunized into naïve mice to evaluate the ability to make CD4$^+$ and CD8+ T cell responses to the protein antigens. Briefly, antigen alone (gD2ΔTMR (5 μg)) or combinations of antigens (gD2ΔTMR and ICP4.2 (10 μg)) were mixed with adjuvant (12 μg dose of an ISCOM matrix with a 82:18 mixture of *Quillaja* saponin fractions A and C) and administered subcutaneously to mice, twice, 9 days apart. Seven days after the second immunization, mice were euthanized and spleens were harvested for ex vivo IFNγ ELISPOT assays. CD4+ and CD8+ T cells were sorted out of the splenocyte population using antibody-coated magnetic beads and then co-cultured on IFNγ-specific antibody-coated membranes in 96-well plates with naïve splenocytes that were pulsed with specific or non-specific antigens (as described) and irradiated with an x-ray irradiator. After 18 hours of incubation, captured IFNγ was detected with a biotinylated secondary IFNγ-specific antibody and visualized with horseradish peroxidase and 3-amino-9-ethylcarbazole substrate. Data are reported as the number of IFN-γ spot forming units per $2\times10^5$ T cells±standard deviation of three mice per group. FIG. 3 shows the number of IFN-γ spot forming units per $2\times10^5$ CD4+ or CD8+ T cells±standard deviation of three mice per group. As seen in FIGS. 3A and B, the number of IFN-γ spot forming units per CD4+ T cells or CD8+ T cells is increased in mice immunized with gD2ΔTMR antigen combined with ICP4.2 compared to gD2ΔTMR antigen alone.

Example 2. Combinations of gD2 and ICP4.2 Plus Adjuvant Immunization Reduced Disease Symptoms and Mortality in Mice The ability to trigger protective immunity after immunization with the ICP4.2 protein in combination with gD2 plus adjuvant was evaluated in a lethal HSV-2 challenge mouse model. Briefly, eight C57BL/6 mice per group were immunized with either gD2 (2 μg) or ICP4.2 (10 μg) plus adjuvant individually or with both antigens mixed together plus adjuvant. Formulations were administered subcutaneously in the scruff of the neck twice, 9 days apart. Estrus cycles were synchronized with depo provera 5 days prior to virus infection, and animals were challenged intravaginally 7 days after the second immunization with 20 times the $LD_{50}$ of HSV-2 strain 333. Disease symptoms were scored post-infection, and survival monitored. Disease severity scores were as follows: 0=no symptoms, 1=redness, 2=redness and swelling, 3=herpetic lesions, 4=severe ulceration or unilateral paralysis, and 5=bilateral paralysis or death.

Example 3. Combinations of gD2ΔTMR and ICP4.2 Plus Adjuvant Immunization Reduced Disease Symptoms and Mortality in Mice Mice immunized with a combination of gD2ΔTMR and ICP4.2 antigens showed a lower mean disease score at ten days after virus challenge compared to animals receiving the individual antigen with adjuvant.

TABLE 15

Effect of HSV-2 proteins gD2ΔTMR and ICP4.2 on disease symptoms and survival rate in mice

| Groups | Mean Disease Score Day 10 | % Reduction | P value* | % Survival Day 12 |
|---|---|---|---|---|
| Adjuvant only | 4.81 | — | — | 00% |
| gD2ΔTMR + adjuvant | 1.44 | 70 | 0.023 | 75% |
| gD2ΔTMR + ICP4.2 + adjuvant | 0.75 | 84 | 0.020 | 88% |

Example 4. Combination of gD2 and ICP4.2 Plus Adjuvant Immunization Reduces Severity of Recurrent Lesions when Administered Therapeutically to HSV-2 Infected Guinea Pigs The ability to affect HSV-2 reactivation in infected guinea pigs after therapeutic immunization with antigens plus adjuvant was evaluated. Briefly, guinea pigs were infected intravaginally with $5\times10^5$ pfu of HSV-2 strain MS, monitored for primary disease for 14 days, and then randomized into immunization groups (N=15). Animals were immunized three times subcutaneously on day 14, 21, and 35 post-infection with antigen (15 μg) plus adjuvant (50 μg) or adjuvant alone, or vehicle control and scored daily for local disease severity. The scoring system was as follows: 0=no symptoms, 1=redness, 2=single lesions, 3=large or fused lesions, 4=severe ulceration or unilateral paralysis, and 5=bilateral paralysis or death. Table 16 shows the data as the mean recurrent lesion score for each week after the guinea pigs recovered from their acute disease. The guinea pigs treated with a combination of gD2 and ICP4.2 antigens showed a reduction in the mean lesion score at 7 (day 42) and 14 (day 49) days after their last immunization compared to animals receiving the individual antigens with adjuvant.

TABLE 14

Effect of HSV-2 proteins gD2 and ICP4.2 on disease symptoms, viral replication and mortality

| Antigen (+adjuvant) N = 8 | Mean disease score Day 7 | Reduction in disease score | P value** | Reduction in virus titer | % Survival Day 11 |
|---|---|---|---|---|---|
| PBS | 3.5 ± 0.3 | — | — | — | 0% |
| gD2* (2 ug) | 2.5 ± 0.2 | 29% | 0.016 | 0% | 25% |
| ICP4.2 (10 ug) | 1.7 ± 0.4 | 51% | 0.005 | 0% | 13% |
| gD2 (2 ug) + ICP4.2 (10 ug) | 1.3 ± 0.3 | 63% | 0.0004 | 20% | 50% |

*EC;
**Student's t-test

TABLE 16

Effect of HSV-2 proteins gD2 and ICP4.2 vaccine on recurrent genital skin disease
Mean Recurrent Lesion Score Post HSV-2 Infection

| Antigen + Adjuvant | Day 15-21 | Day 22-28 | Day 29-35 | Day 36-42 | Day 43-49 |
| --- | --- | --- | --- | --- | --- |
| PBS | 2.00 ± 0.45 | 1.17 ± 0.35 | 1.50 ± 0.50 | 0.87 ± 0.28 | 1.33 ± 0.33 |
| gD2 | 1.00 ± 0.30 | 0.67 ± 0.24 | 0.80 ± 0.19 | 0.83 ± 0.26 | 0.77 ± 0.28 |
| ICP4.2 | 1.97 ± 0.38 | 1.07 ± 0.29 | 1.03 ± 0.33 | 0.53 ± 0.16 | 0.83 ± 0.29 |
| gD2 & ICP4.2 | 1.43 ± 0.32 | 0.80 ± 0.27 | 1.07 ± 0.33 | 0.43 ± 0.19 | 0.70 ± 0.27 |

Sequences

SEQ ID NO: 1 = ICP4, full-length
SAEQRKKKKTTTTQGRGAEVAMADEDGGRLRAAAETTGGPGSPDPADGPPPTPNPDRRPAARPGFGWHGGPEENE
DEADDAAADADADEAAPASGEAVDEPAADGVVSPRQLALLASMVDEAVRTIPSPPPERDGAQEEAARSPSPPRTPS
MRADYGEENDDDDDDDDDDRDAGRWVRGPETTSAVRGAYPDPMASLSPRPPAPRRHHHHHHRRRRAPRRRSAAS
DSSKSGSSSSASSASSSASSSSSASASSSDDDDDDAARAPASAADHAAGGTLGADDEEAGVPARAPGAAPRPSPP
RAEPAPARTPAATAGRLERRRARAAVAGRDATGRFTAGRPRRVELDADAASGAFYARYRDGYVSGEPWPGAGPPPP
GRVLYGGLGDSRPGLWGAPEAEEARARFEASGAPAPVWAPELGDAAQQYALITRLLYTPDAEAMGWLQNPRVAPGD
VALDQACFRISGAARNSSSFISGSVARAVPHLGYAMAAGRFGWGLAHVAAAVAMSRRYDRAQKGFLLTSLRRAYAP
LLARENAALTGARTPDDGGDANRHDGDDARGKPAAAAAPLPSAAASPADERAVPAGYGAAGVLAALGRLSAAPASA
PAGADDDDDDDGAGGGGGGRRAEAGRVAVECLAACRGILEALAEGFDGDLAAVPGLAGARPAAPPRPGPAGAAAPP
HADAPRLRAWLRELRFVRDALVLMRLRGDLRVAGGSEAAVAAVRAVSLVAGALGPALPRSPRLLSSAAAAAADLLF
QNQSLRPLLADTVAAADSLAAPASAPREARKRKSPAPARAPPGGAPRPPKKSRADAPRPAAAPPAGAAPPAPPTPP
PRPPRPAALTRRPAEGPDPQGGWRRQPPGPSHTPAPSAAALEAYCAPRAVAELTDHPLFPAPWRPALMFDPRALAS
LAARCAAPPPGGAPAAFGPLRASGPLRRAAAWMRQVPDPEDVRVVILYSPLPGEDLAAGRAGGGPPPEWSAERGGL
SCLLAALGNRLCGPATAAWAGNWTGAPDVSALGAQGVLLLSTRDLAFAGAVEFLGLLAGACDRRLIVVNAVRAADW
PADGPVVSRQHAYLACEVLPAVQCAVRWPAARDLRRTVLASGRVFGPGVFARVEAAHARLYPDAPPLRLCRGANVR
YRVRTRFGPDTLVPMSPREYRRAVLPALDGRAAASGAGDAMAPGAPDFCEDEAHSHRACARWGLGAPLRPVYVALG
RDAVRGGPAELRGPRREFCARALLEPDGDAPPLVLRDDADAGPPPQIRWASAAGRAGTVLAAAGGGVEVVGTAAGL
ATPPRREPVDMDAELEDDDDGLFGE SEQ ID NO: 2 = ICP4 internal fragment
MVLYGGLGDSRPGLWGAPEAEEARARFEASGAPAPVWAPELGDAAQQYALITRLLYTPDAEAMGWLQNPRVAPGDV
ALDQACFRISGAARNSSSFISGSVARAVPHLGYAMAAGRFGWGLAHVAAAVAMSRRYDRAQKGFLLTSLRRAYAPL
LARENAALTGARTPDDGGDANRRDGDDARGKPAAAAAPLPSAAASPADERAVPAGYGAAGVLAALGRLSAAPASAP
AGADDDDDDDGAGGGGGGGGGGGRRAEAGRVAVECLAACRGILEALAEGFDGDLAAVPGLAGARPAAPPRPGPA
GAAAPPHADAPRLRAWLRELRFVRDALVLMRLRGDLRVAGGSEAAVAAVRAVSLVAGALGPALPRSPRLLSSAAAA
AADLLFQNQSL SEQ ID NO: 3 = gL2 cytoplasmic
MGFVCLFGLVVMGAWGAWGGSQATEYVLRSVIAKEVGDILRVPCMRTPADDVSWRYEAPSVIDYARIDGIFLRYHC
PGLDTFLWDRHAQRAYLVNPFLFAAGFLEDLSHSVFPADTQETTTRRALYKEIRDALGSRKQAVSHAPVRAGCVNF
DYSRTRRCVGRRDLRPANTTSTWEPPVSSDDEASSQSKPLATQPPVLALSNAPPRRVSPTRGRRRHTRLRRN SEQ ID NO: 4 = gD2 internal deletion
NRWKYALADPSLKMADPNRFRGKNLPVLDQLTDPPGVKRVYHIQPSLEDPFQPPSIPITVYYAVLERACRSVLLHA
PSEAPQIVRGASDEARKHTYNLTIAWYRMGDNCAIPITVMEYTECPYNKSLGVCPIRTQPRWSYYDSFSAVSEDNL
GFLMHAPAFETAGTYLRLVKINDWTEITQFILEHRARASCKYALPLRIPPAACLTSKAYQQGVTVDSIGMLPRFIP
ENQRTVALYSLKIAGWHGPKPPYTSTLLPPELSDTTNATQPELVPEDPEDSALLEDPAGTVSSQIPPNWHIPSIQD
VAPHHAPAAPSNPRRRAQMAPKRLRLPHIRDDDAPPSHQPLFY SEQ ID NO: 5 = predicted gD2 sequence
MGRLTSGVGTAALLVVAVGLRVVCAKYALADPSLKMADPNRFRGKNLPVLDQLTDPPGVKRVYHIQPSLEDPFQPP
SIPITVYYAVLERACRSVLLHAPSEAPQIVRGASDEARKHTYNLTIAWYRMGDNCAIPITVMEYTECPYNKSLGVC
PIRTQPRWSYYDSFSAVSEDNLGFLMHAPAFETAGTYLRLVKINDWTEITQFILEHRARASCKYALPLRIPPAACL
TSKAYQQGVTVDSIGMLPRFIPENQRTVALYSLKIAGWHGPKPPYTSTLLPPELSDTTNATQPELVPEDPEDSALL
EDPAGTVSSQIPPNWHIPSIQDVAPHHAPAAPSNPGLIIGALAGSTLAVLVIGGIAFWVRRRAQMAPKRLRLPHIR
DDDAPPSHQPLFY SEQ ID NO: 6 = ICP34.5
MSRRRGPRRRGPRRRPRPGAPAVPRPGAPAVPRPGALPTADSQMVPAYDSGTAVESAPAASSLLRRWLLVPQADDS
DDADYAGNDDAEWANSPPSEGGGKAPEAPHAAPAAACPPPPPRKERGPQRPLPPHLALRLRTTTEYLARLSLRRRR
PPASPPADAPRGKVCFSPRVQVRHLVAWETAARLARRGSWARERADRDRFRRRVAAAEAVIGPCLEPEARARARAR
ARAHEDGGPAEEEEAAAAARGSSAAAGPGRRAV SEQ ID NO: 7 = ICP0
MEPRPGTSSRADPGPERPPRQTPGTQPAAPHAWGMLNDMQWLASSDSEEETEVGISDDDLHRDSTSEAGSTDTEMF
EAGLMDAATPPARPPAERQGSPTPADAQGSCGGGPVGEEEAEAGGGGDVCAVCTDEIAPPLRCQSFPCLHPFCIPC
MKTWIPLRNTCPLCNTPVAYLIVGVTASGSFSTIPIVNDPRTRVEAEAAVRAGTAVDFIWTGNPRTAPRSLSLGGH
TVRALSPTPPWPGTDDEDDDLADVDYVPPAPRRAPRRGGGGAGATRGTSQPAATRPAPPGAPRSSSSGGAPLRAGV
GSGSGGGPAVAAVVPRVASLPPAAGGGRAQARRVGEDAAAAEGRTPPARQPRAAQEPPIVISDSPPPSPRRPAGPG
PLSFVSSSSAQVSSGPGGGGLPQSSGRAARPRAAVAPRVRSPPRAAAAPVVSASADAAGPAPPAVPVDAHRAPRSR
MTQAQTDTQAQSLGRAGATDARGSGGPGAEGGPGVPRGTNTPGAAPHAAEGAAARPRKRRGSDSGPAASSSASSSA
APRSPLAPQGVGAKRAAPRRAPDSDSGDRGHGPLAPASAGAAPPSASPSSQAAVAAASSSSASSSSASSSSASSSS
ASSSSASSSSASSSSASSSAGGAGGSVASASGAGERRETSLGPRAAAPRGPRKCARKTRHAEGGPEPGARDPAPGL

| Sequences |
| --- |
| TRYLPIAGVSSVVALAPYVNKTVTGDCLPVLDMETGHIGAYVVLVDQTGNVADLLRAAAPAWSRRTLLPEHARNCV<br>RPPDYPTPPASEWNSLWMTPVGNMLFDQGTLVGALDFHGLRSRHPWSREQGAPAPAGDAPAGHGE<br><br>SEQ ID NO: 8 = ICP4 internal fragments(RS1.1, #1-400)<br>msaeqrkkkkttttttqgrgaevamadedggrlraaaettggpgspdpadgpppptpnpdrrpaarpgfgwhggpeen<br>edeaddaaadadadeaapasgeavdepaadgvvsprqlallasmvdeavrtipspppperdgageeaarspspprtp<br>smradygeenddddddddddrdagrwvrgpettsavrgaypdpmaslsprppaprrhhhhhhrrrraprrrsaa<br>sdssksgssssassasssassssssasasssdddddddaarapasaadhaaggtlgaddeeagvparapgaaprpsp<br>praepapartpaatagrlerrraraavagrdatgrftagrprrveldadaasgafyaryrdgyvsgepwpgagppp<br>pgrvlygglgdsrpglwgap<br><br>SEQ ID NO: 9 = ICP4 internal fragments(RS1.3.1, #750-1024)<br>ssaaaaaadllfqnqslrplladtvaaadslaapasaprearkrkspaparappggaprppkksradaprpaaapp<br>agaapppapptppprpprpaaltrrpaegpdpqggwrrqppgpshtpapsaaaleaycapravaeltdhplfpapwr<br>palmfdpralaslaarcaapppggapaafgplrasgplrraaawmrqvpdpedvrvvllysplpgedlaagraggg<br>pppewsaergglscllaalgnrlcgpataawagnwtgapdvsalgaq<br><br>SEQ ID NO: 10 = ICP4 internal fragments(RS1.3.2, #1008-1319)<br>wagnwtgapdvsalgaggvlllstrdlafagaveflgllagacdrrlivvnavraadwpadgpvvsrqhaylacev<br>lpavqcavrwpaardlrrtvlasgrvfgpgvfarveaaharlypdapplrlcrganvryrvrtrfgpdtlvpmspr<br>eyrravlpaldgraaasgagdamapgapdfcedeahshracarwglgaplrpvyvalgrdavrggpaelrgprref<br>carallepdgdapplvlrddadagpppqirwasaagragtvlaaagggvevvgtaaglatpprrepvdmdaeledd<br>ddglfge<br><br>SEQ ID NO: 11 = ICP4 internal fragments(RS1.3, #750-1319)<br>Ssaaaaaadllfqnqslrplladtvaaadslaapasaprearkrkspaparappggaprppkksradaprpaaapp<br>agaapppapptppprpprpaaltrrpaegpdpqggwrrqppgpshtpapsaaaleaycapravaeltdhplfpapwr<br>palmfdpralaslaarcaapppggapaafgplrasgplrraaawmrqvpdpedvrvvllysplpgedlaagraggg<br>pppewsaergglscllaalgnrlcgpataawagnwtgapdvsalgaggvlllstrdlafagaveflgllagacdrr<br>livvnavraadwpadgpvvsrqhaylacevlpavqcavrwpaardlrrtvlasgrvfgpgvfarveaaharlypda<br>pplrlcrganvryrvrtrfgpdtlvpmspreyrravlpaldgraaasgagdamapgapdfcedeahshracarwgl<br>gaplrpvyvalgrdavrggpaelrgprrefcarallepdgdapplvlrddadagpppqirwasaagragtvlaaag<br>ggvevvgtaaglatpprrepvdmdaeleddddglfge<br><br>SEQ ID NO: 12 = ICP4 internal fragments(RS1.4, #340-883)<br>tagrprrveldadaasgafyaryrdgyvsgepwpgagppppgrvlygglgdsrpglwgapeaeeararfeasgapa<br>pvwapelgdaaqqyalitrllytpdaeamgwlqnprvapgdvaldqacfrlsgaarnsssfisgsvaravphlgya<br>maagrfgwglahvaaavamsrrydraqkgflltslrrayapllarenaaltgartpddggdanrhdgddargkpaa<br>aaaaplpsaaaspaderavpagygaagvlaalgrlsaapasapagaddddddgagggggrraeagrvaveclaac<br>rgilealaegfdgdlaavpglagarpaapprpgpagaaapphadaprlrawlrelrfvrdalvlmrlrgdlrvagg<br>seaavaavrayslvagalgpalprsprllssaaaaaadllfqngslrplladtvaaadslaapasaprearkrksp<br>aparappggaprppkksradaprpaaappagaappapptppprpprpaaltrrpaegpdpqggwrrqppgpshtpa<br>psaaaleayca<br><br>SEQ ID NO: 13 = ICP4 internal fragments(RS1.5, #775-1318)<br>aaadslaapasaprearkrkspaparappggaprppkksradaprpaaappagaappapptppprpprpaaltrrp<br>aegpdpqggwrrqppgpshtpapsaaaleaycapravaeltdhplfpapwrpalmfdpralaslaarcaapppgga<br>paafgplrasgplrraaawmrqvpdpedvrvvllysplpgedlaagragggpppewsaergglscllaalgnrlcg<br>pataawagnwtgapdvsalgaggvlllstrdlafagaveflgllagacdrrlivvnavraadwpadgpvvsrghay<br>lacevlpavqcavrwpaardlrrtvlasgrvfgpgvfarveaaharlypdapplrlcrganvryrvrtrfgpdtlv<br>pmspreyrravlpaldgraaasgagdamapgapdfcedeahshracarwglgaplrpvyvalgrdavrggpaelrg<br>prrefcarallepdgdapplvlrddadagpppqirwasaagragtvlaaagggvevvgtaaglatpprrepvdmda<br>eleddddglfge<br><br>SEQ ID NO: 14 = ICP4 internal fragments(RS1.6, #209-1318)<br>hrrrraprrrsaasdssksgsssssassasssasssssasasssdddddddaarapasaadhaaggtlgaddeeagv<br>parapgaaprpspppraepapartpaatagrlerrraraavagrdatgrftagrprrveldadaasgafyaryrdgy<br>vsgepwpgagppppgrvlygglgdsrpglwgapeaeeararfeasgapapvwapelgdaaqqyalitrllytpdae<br>amgwlqnprvapgdvaldqacfrisgaarnsssfisgsvaravphlgyamaagrfgwglahvaaavamsrrydraq<br>kgflltslrrayapllarenaaltgartpddggdanrhdgddargkpaaaaaplpsaaaspaderavpagygaagv<br>laalgrlsaapasapagaddddddgagggggrraeagrvaveclaacrgilealaegfdgdlaavpglagarpa<br>apprpgpagaaapphadaprlrawlrelrfvrdalvlmrlrgdlrvaggseaavaavravslvagalgpalprspr<br>llssaaaaaadllfqnqslrplladtvaaadslaapasaprearkrkspaparappggaprppkksradaprpaaa<br>ppagaappapptppprpprpaaltrrpaegpdpqggwrrqppgpshtpapsaaaleaycapravaeltdhplfpap<br>wrpalmfdpralaslaarcaapppggapaafgplrasgplrraaawmrqvpdpedvrvvilysplpgedlaagrag<br>ggpppewsaergglscllaalgnrlcgpataawagnwtgapdvsalgaqgvlllstrdlafagaveflgllagacd<br>rrlivvnavraadwpadgpvvsrqhaylacevlpavqcavrwpaardlrrtvlasgrvfgpgvfarveaaharlyp<br>dapplrlcrganvryrvrtrfgpdtlvpmspreyrravlpaldgraaasgagdamapgapdfcedeahshracarw<br>glgaplrpvyvalgrdavrggpaelrgprrefcarallepdgdapplvlrddadagpppqirwasaagragtvlaa<br>agggvevvgtaaglatpprrepvdmdaeleddddglfge<br><br>SEQ ID NO: 15 = ICP4 internal fragments(RS1.7, deletion of 391-544)<br>msaeqrkkkkttttttqgrgaevamadedggrlraaaettggpgspdpadgpppptpnpdrrpaarpgfgwhggpeen<br>edeaddaaadadadeaapasgeavdepaadgvvsprqlallasmvdeavrtipspppperdgageeaarspspprtp<br>smradygeenddddddddddrdagrwvrgpettsavrgaypdpmaslsprppaprrhhhhhhrrrraprrrsaa<br>sdssksgsssssassasssassssssasasssdddddddaarapasaadhaaggtlgaddeeagvparapgaaprpsp<br>praepapartpaatagrlerrraraavagrdatgrftagrprrveldadaasgafyaryrdgyvsgepwpgagppp | pgrylygglgartpddggdanrhdgddargkpaaaaaplpsaaaspaderavpagygaagvlaalgrlsaapasap
agaddddddgagggggrraeagrvaveclaacrgilealaegfdgdlaavpglagarpaapprpgpagaaapph
adaprlrawlrelrfvrdalvlmrlrgdlrvaggseaavaavravslvagalgpalprsprllssaaaaaadllfq
nqslrplladtvaaadslaapasapreararkrkspaparappggaprppkksradaprpaaappagaappapptppp
rpprpaaltrrpaegpdpqggwrrqppgpshtpapsaaaleaycapravaeltdhplfpapwrpalmfdpralasl
aarcaapppggapaafgplrasgplrraaawmrqvpdpedvrvvilysplpgedlaagragggpppewsaerggls
cllaalgnrlogpataawagnwtgapdvsalgaqgvllllstrdlafagaveflgllagacdrrlivvnavraadwp
adgpvvsrqhaylacevlpavqcavrwpaardlrrtvlasgrvfgpgvfarveaaharlypdappllrcrganvry
rvrtrfgpdtlvpmspreyrravlpaldgraaasgagdamapgapdfcedeahshracarwglgaplrpvyvalgr
davrggpaelrgprrefcarallepdgdapplvlrddadagpppqirwasaagragtvlaaagggvevvgtaagla
tpprrepvdmdaeledddddglfge SEQ ID NO: 16 = ICP4 internal fragments(RS1.8, deletion of 786-864)
msaeqrkkkktttttqgrgaevamadedggrlraaaettggpgspdpadgppptpnpdrrpaarpgfgwhggpeen
edeaddaaadadadeaapasgeavdepaadgvvsprqllallasmvdeavrtipsppperdgaqeeaarspspprtp
smradygeendddddddddddrdagrwvrgpettsavrgaypdpmaslsprppaprrhhhhhhrrrraprrrsaa
sdsskgsssssassasssasssssasasssdddddddaarapasaadhaaggtlgaddeeagvparapgaaprpsp
praepapartpaatagrlerrraraavagrdatgrftagrprrveldadaasgafyaryrdgyvsgepwpgagppp
pgrvlygglgdsrpglwgapeaeeararfeasgapapvwapelgdaaqqyalitrllytpdaeamgwlqnprvapg
dvaldqacfrisgaarnsssfisgsvaravphlgyamaagrfgwglahvaaavamsrrydraqkgflltslrraya
pllarenaaltgartpddggdanrhdgddargkpaaaaaplpsaaaspaderavpagygaagvlaalgrlsaapas
apagaddddddgagggggrraeagrvaveclaacrgilealaegfdgdlaavpglagarpaapprpgpagaaap
phadaprlrawlrelrfvrdalvlmrlrgdlrvaggseaavaavravslvagalgpalprsprllssaaaaaadll
fqnqslrplladtvaaadslaapastpapsaaaleaycapravaeltdhplfpapwrpalmfdpralaslaarcaa
ppppggapaafgplrasgplrraaawmrqvpdpedvrvvilysplpgedlaagragggpppewsaerggllscllaal
gnrlcgpataawagnwtgapdvsalgaqgvllllstrdlafagaveflgllagacdrrlivvnavraadwpadgpvv
srqhaylacevlpavqcavrwpaardlrrtvlasgrvfgpgvfarveaaharlypdappllrcrganyryrvrtrf
gpdtlvpmspreyrravlpaldgraaasgagdamapgapdfcedeahshracarwglgaplrpvyvalgrdavrgg
paelrgprrefcarallepdgdapplvlrddadagpppqirwasaagragtvlaaagggvevvgtaaglatpprre
pvdmdaeledddddglfge SEQ ID NO: 17 = predicted sequence for uracil DNA glycosylase(encoded by UL2)
MFSASTTPEQPLGLSGDATPPLPTSVPLDWAAFRRAFLIDDAWRPLLEPELANPLTARLLAEYDRRCQTEEVLPPR
EDVFSWTRYCTPDDVRVVIIGQDPYHHPGQAHGLAFSVRADVPVPPSLRNVLAAVKNCYPDARMSGRGCLEKWARD
GVLLLNTTLTVKRGAAASHSKLGWDRFVGGVVQRLAARRPGLVFMLWGAHAQNAIRPDPRQHYVLKFSHPSPLSKV
PFGTCQHFLAANRYLETRDIMPIDWSV SEQ ID NO: 18 = predicted sequence for tegument protein encoded by UL11
MGLAFSGARPCCCRHNVITTDGGEVVSLTAHEFDVVDIESEEEGNFYVPPDVRVVTRAPGPQYRRASDPPSRHTRR
RDPDVARPPATLTPPLSDSE SEQ ID NO: 19 = gL2 secreted
NRWGFVCLFGLVVMGAWGAWGGSQATEYVLRSVIAKEVGDILRVPCMRTPADDVSWRYEAPSVIDYARIDGIFLRY
HCPGLDTFLWDRHAQRAYLVNPFLFAAGFLEDLSHSVFPADTQETTTRRALYKEIRDALGSRKQAVSHAPVRAGCV
NFDYSRTRRCVGRRDLRPANTTSTWEPPVSSDDEASSQSKPLATQPPVLALSNAPPRRVSPTRGRRRHTRLRRN SEQ ID NO: 20 = predicted sequence for VP5 encoded by UL19
DYDIPTTENLYFQGMAAPARDPPGYRYAAAMVPTGSILSTIEVASHRRLFDFFARVRSDENSLYDVEFDALLGSYC
NTLSLVRFLELGLSVACVCTKFPELAYMNEGRVQFEVHQPLIARDGPHPVEQPVHNYMTKVIDRRALNAAFSLATE
AIALLTGEALDGTGISLHRQLRAIQQLARNVQAVLGAFERGTADQMLHVLLEKAPPLALLLPMQRYLDNGRLATRV
ARATLVAELKRSFCDTSFFLGKAGHRREAIEAWLVDLTTATQPSVAVPRLTHADTRGRPVDGVLVTTAAIKQRLLQ
SFLKVEDTEADVPVTYGEMVLNGANLVTALVMGKAVRSLDDVGRHLLEMQEEQLEANRETLDELESAPQTTRVRAD
LVAIGDRLVFLEALEKRIYAATNVPYPLVGAMDLTFVLPLGLFNPAMERFAAHAGDLVPAPGHPEPRAFPPRQLFF
WGKDHQVLRLSMENAVGTVCHPSLMNIDAAVGGVNHDPVEAANPYGAYVAAPAGPGADMQQRFLNAWRQRLAHGRV
RWVAECQMTAEQFMQPDNANLALELHPAFDFFAGVADVELPGGEVPPAGPGAIQATWRVVNGNLPLALCPVAFRDA
RGLELGVGRHAMAPATIAAVRGAFEDRSYPAVFYLLQAAIHGSEHVFCALARLVTQCITSYWNNTRCAAFVNDYSL
VSYIVTYLGGDLPEECMAVYRDLVAHVEALAQLVDDFTLPGPELGGQAQAELNHLMRDPALLPPLVWDCDGLMRHA
ALDRHRDCRIDAGEHEPVYAAACNVATADFNRNDGRLLHNTQARAADAADDRPHRPADWTVHHKIYYYVLVPAFSR
GRCCTAGVRFDRVYATLQNMVVPEIAPGEECPSDPVTDPAHPLHPANLVANTVNAMFHNGRVVVDGPAMLTLQVLA
HNMAERTTALLCSAAPDAGANTASTANMRIFDGALHAGVLLMAPQHLDHTIQNGEYFYVLPVHALFAGADHVANAP
NFPPALRDLARHVPLVPPALGANYFSSIRQPVVQHARESAAGENALTYALMGPFYKMSPVALYHQLKTGLHPGFGF
TVVRQDRFVTENVLFSERASEAYFLGQLQVARHETGGGVSFTLTQPRGNVDLGVGYTAVAATATVRNPVTDMGNLP
QNFYLGRGAPPLLDNAAAVYLRNAVVAGNRLGPAQPLPVFGCAQVPRRAGMDHGQDAVCEFIATPVATDINYFRRP
CNPRGRAAGGVYAGDKEGDVIALMYDHGQSDPARPFAATANPWASQRFSYGDLLYNGAYHLNGASPVLSPCFKFFT
AADITAKHRCLERLIVETGSAVSTATAASDVQFKRPPGCRELVEDPCGLFQEAYPITCASDPALLRSARDGEAHAR
ETHETQYLIYDASPLKGLSL SEQ ID NO: 21 = VP5 encoded by UL19ΔTEV
MAAPARDPPGYRYAAAMVPTGSILSTIEVASHRRLFDFFARVRSDENSLYDVEFDALLGSYCNTLSLVRFLELGLS
VACVCTKEPELAYMNEGRVQFEVHQPLIARDGPHPVEQPVHNYMTKVIDRRALNAAFSLATEAIALLTGEALDGTG
ISLHRQLRAIQQLARNVQAVLGAFERGTADQMLHVLLEKAPPLALLLPMQRYLDNGRLATRVARATLVAELKRSFC
DTSEELGKAGHRREAIEAWLVDLTTATQPSVAVPRLTHADTRGRPVDGVLVTTAAIKQRLLQSFLKVEDTEADVPV
TYGEMVLNGANLVTALVMGKAVRSLDDVGRHLLEMQEEQLEANRETLDELESAPQTTRVRADLVAIGDRLVFLEAL
EKRIYAATNVPYPLVGAMDLTFVLPLGLENPAMERFAAHAGDLVPAPGHPEPRAFPPRQLFFWGKDHQVLRLSMEN
AVGTVCHPSLMNIDAAVGGVNHDPVEAANPYGAYVAAPAGPGADMQQRFLNAWRQRLAHGRVRWVAECQMTAEQFM
QPDNANLALELHPAFDFFAGVADVELPGGEVPPAGPGAIQATWRVVNGNLPLALCPVAFRDARGLELGVGRHAMAP
ATIAAVRGAFEDRSYPAVFYLLQAAIHGSEHVFCALARLVTQCITSYWNNTRCAAFVNDYSLVSYIVTYLGGDLPE

| Sequences |
|---|
| ECMAVYRDLVAHVEALAQLVDDFTLPGPELGGQAQAELNHLMRDPALLPPLVWDCDGLMRHAALDRHRDCRIDAGE<br>HEPVYAAACNVATADFNRNDGRLLHNTQARAADAADDRPHRPADWTVHHKIYYYVLVPAFSRGRCCTAGVRFDRVY<br>ATLQNMVVPEIAPGEECPSDPVTDPAHPLHPANLVANTVNAMFHNGRVVVDGPAMLTLQVLAHNMAERTTALLCSA<br>APDAGANTASTANMRIFDGALHAGVLLMAPQHLDHTIQNGEYFYVLPVHALFAGADHVANAPNEPPALRDLARHVP<br>LVPPALGANYFSSIRQPVVQHARESAAGENALTYALMAGYFKMSPVALYHQLKTGLHPGEGFTVVRQDREVTENVL<br>FSERASEAYFLGQLQVARHETGGGVSFTLTQPRGNVDLGVGYTAVAATATVRNPVTDMGNLPQNFYLGRGAPPLLD<br>NAAAVYLRNAVVAGNRLGPAQPLPVFGCAQVPRRAGMDHGQDAVCEFIATPVATDINYFRRPCNPRGRAAGGVYAG<br>DKEGDVIALMYDHGQSDPARPFAATANPWASQRFSYGDLLYNGAYHLNGASPVLSPCFKFFTAADITAKHRCLERL<br>IVETGSAVSTATAASDVQFKRPPGCRELVEDPCGLFQEAYPITCASDPALLRSARDGEAHARETHETQYLIYDASP<br>LKGLSL<br><br>SEQ ID NO: 22 = predicted sequence for ICP1/2 encoded by UL36<br>MIPAALPHPTMKRQGDRDIVVTGVRNQFATDLEPGGSVSCMRSSLSFLSLLEDVGPRDVLSAEAIEGCLVEGGEWTR<br>AAAGSGPPRMCSIIELPNFLEYPAARGGLRCVFSRVYGEVGFFGEPTAGLLETQCPAHTFFAGPWAMRPLSYTLLTI<br>GPLGMGLYRDGDTAYLFDPHGLPAGTPAFIAKVRAGDVYPYLTYYAHDRPKVRWAGAMVFFVPSGPGAVAPADLTAA<br>ALHLYGASETYLQDEPFVERRVAITHPLRGEIGGLGALFVGVVPRGDGEGSGPVVPALPAPTHVQTPGADRPPEAPR<br>GASGPPDTPQAGHPNRPPDDVWAAALEGTPPAKPSAPDAAASGPPHAAPPPQTPAGDAAEEAEDLRVLEVGAVPVGR<br>HRARYSTGLPKRRRPTWTPPSSVEDLTSGERPAPKAPPAKAKKKSAPKKKAPVAAEVPASSPTPIAATVPPAPDTPP<br>QSGQGGGDDGPASPSSPSVLETLGARRPPEPPGADLAQLFEVHPNVAATAVRLAARDAALAREVAACSQLTINALRS<br>PYPAHPGLLELCVIFFFERVLAFLIENGARTHTQAGVAGPAAALLDFTLRMLPRKTAVGDFLASTRMSLADVAAHRP<br>LIQHVLDENSQIGRLALAKLVLVARDVIRETDAFYGDLADLDLQLRAAPPANLYARLGEWLLERSRAHPNTLFAPAT<br>PTHPEPLLHRIQALAQPARGEEMRVEAEAREMREALDALARGVDSVSQRAGPLTVMPVPAAPGAGGRAPCPPALGPE<br>AIQARLEDVRIQARRAIESAVKEYFHRGAVYSAKALQASDSHDCRFHVASAAVVPMVQLLESLPAFDQHTRDVAQRA<br>ALPPPPPLATSPQAILLRDLLQRGQPLDAPEDLAAWLSVLTDAATQGLIERKPLEELARSIHGINDQQARRSSGLAE<br>LQRFDALDAALAQQLDSDAAFVPATGPAPYVDGGGLSPEATRMAEDALRQARAMEAAKMTAELAPEARSRLRERAHA<br>LEAMLNDAREREAKVAHDAREKFLHKLQGVLRPLPDFVGLKACPAVLATLRASLPAGWTDLADAVRGPPPEVTAALRA<br>DLWGLLGQYREALEHPTPDTATALAGLHPAFVVVLKTLFADAPETPVLVQFFSDHAPTIAKAVSNAINAGSAAVATA<br>SPAATVDAAVRAHGALADAVSALGAAARDPASPLSFLAVLADSAAGYVKATRLALEARGAIDELTTLGSAAADLVVQ<br>ARRACAQPEGDHAALIDAAARATTAARESLAGHEAGFGGLLHAEGTAGDHSPSGRALQELGKVIGATRRRADELEAA<br>VADLTAKMAAQRARGSSERWAAGVEAALDRVENRAEFDVVELRRLQALAGTHGYNPRDFRKRAEQALAANAEAVTLA<br>LDTAFAFNPYTPENQRHPMLPPLAAIHRLGWSAAFHAAAETYADMFRVDAEPLARLLRIAEGLLEMAQAGDGFIDYH<br>EAVGRLADDMTSVPGLRRYVPFFQHGYADYVELRDRLDAIRADVHRALGGVPLDLAAAAEQISAARNDPEATAELVR<br>TGVTLPCPSEDALVACAAALERVDQSPVKNTAYAEYVAFVTRQDTAETKDAVVRAKQQRAEATERVMAGLREALAAR<br>ERRAQIEAEGLANLKTMLKVVAVPATVAKTLDQARSVAEIADQVEVLLDQTEKTRELDVPAVIWLEHAQRTFETHPL<br>SAARGDGPGPLARHAGRLGALEDTRRRVDALRRSLEEAEAEWDEVWGRFGRVRGGAWKSPEGFRAMHEQLRALQDTT<br>NTVSGLRAQPAYERLSARYQGVLGAKGAERAEAVEELGARVTKHTALCARLRDEVVRRVPWEMNFDALGGLLAEFDA<br>AAADLAPWAVEEFRGARELIQYRMGLYSAYARAGGQTGAGAESAPAPLLVDLRALDARARASSSPEGHEVDPQLLRR<br>RGEAYLRAGGDPGPLVLREAVSALDLPFATSFLAPDGTPLQYALCFPAVTDKLGALLMRPEAACVRPPLPTDVLESA<br>PTVTAMYVLTVVNRLQLALSDAQAANFQLFGRFVRHRQATWGASMDAAAELYVALVATTLTREFGCRWAQLGWASGA<br>AAPRPPPGPRGSQRHCVAFNENDVLVALVAGVPEHIYNFWRLDLVRQHEYMHLTLERAFEDAAESMLFVQRLTPHPD<br>ARIRVLPTELDGGPPTRGLLEGTRLADWRRGKLSETDPLAPWRSALELGTQRRDVPALGKLSPAQALAAVSVLGRMC<br>LPSAALAALWTCMFPDDYTEYDSFDALLAARLESGQTLGPAGGREASLPEAPHALYRPTGQHVAVLAAATHRTPAAR<br>VTAMDLVLAAVLLGAPVVVALRNTTAFSRESELELCLTLFDSRPGGPDAALRDVVSSDIETWAVGLLHTDLNPIENA<br>CLAAQLPRLSALIAERPLADGPPCLVLVDISMTPVAVLWEAPEPPGPPDVRFVGSEATEELPFVATAGDVLAASAAD<br>ADPFFARAILGRPFDASLLTGELFPGHPVYQRPLADEAGPSAPTAARDPRDLAGGDGGSGPEDPAAPPARQADPGVL<br>APTLLTDATTGEPVPPRMWAWIHGLEELASDDAGGPTPNPAPALLPPPATDQSVPTSQYAPRPIGPAATARETRPSV<br>PPQQNTGRVPVAPRDDPRPSPPTPSPPADAALPPPAFSGSAAAFSAAVPRVRRSRRTRAKSRAPRASAPPEGWRPPA<br>LPAPVAPVAASARPPDQPPTPESAPPAWVSALPLPPGPASARGAFPAPTLAPIPPPPAEGAVVPGGDRRRGRRQTTA<br>GPSPTPPRGPAAGPPRRLTRPAVASLSASLNSLPSPRDPADHAAAVSAAAAVPPPSPGLAPPTSAVQTSPPPLAPGP<br>VAPSEPLCGWVVPGGPVARRPPPQSPATKPAARTRIRARSVPQPPLPQPPLPQPPLPQPPLPQPPLPQPPLPQPPLP<br>QPPLPQPPLPQPPLPQPPLPPVTRTLTPQSRDSVPTPESPTHTNTHLPVSAVTSWASSLALHVDSAPPPASLLQTLH<br>ISSDDEHSDADSLRFSDSDDTEALDPLPPEPHLPPADEPPGPLAADHLQSPHSQFGPLPVQANAVLSRRYVRSTGRS<br>ALAVLIRACRRIQQQLQRTRRALFQRSNAVLTSLHHVRMLLG<br><br>SEQ ID NO: 23 = ICP1/2 internal fragments encoded by UL36.3.4.1<br>AAQRARGSSERWAAGVEAALDRVENRAEFDVVELRRLQALAGTHGYNPRDFRKRAEQALAANAEAVTLALDTAFAFN<br>PYTPENQRHPMLPPLAAIHRLGWSAAFHAAAETYADMFRVDAEPLARLLRIAEGLLEMAQAGDGFIDYHEAVGRLAD<br>DMTSVPGLRRYVPFFQHGYADYVELRDRLDAIRADVHRALGGVPLDLAAAAEQISAARNDPEATAELVRTGVTLPCP<br>SEDALVACAAALERVDQSPVKNTAYAEYVAFVTRQDTAETKDAVVRAKQQRAEATERVMAGLREALAARERRAQIEA<br>EGLANLKTMLKVVAVPATVAKTLDQARSVAEIADQVEVLLDQTEKTRELDVPAVIWLEHAQRTFETHPLSAARGDGP<br>GPLARHAGRLGALFDTRRRVDALRRSLEEAEAEWDEVWGRFGRVRGGAWKSPEGFRAMHEQLRALQDTTNTVSGLRA<br>QPAYERLSARYQGVLGAKGAERAEAVEELGARVTKHTALCARLRDEVVRRVPWEMNFDALGGLLAEFDAAAADLAPW<br>AVEEFRGARELIQYRMGLYSAYARAGGQTGAGAESAPAPLLVDLRALDARARASSSPEGHEVDPQLLRRRGEAYLRA<br>GGDPGPLVLREAVSALDLPFATSFLAPDGTPLQYALCFPAVTDKLGALLMRPEAACVRPPLPTDVLESAPTVTAMYV<br>LTVVNRLQLALSDAQAANFQLFGRFVRHRQATWGASMDAAAELYVALVATTLTREFGCRWAQLGWASGAAAPRPPPG<br>PRGSQRHCVAFNENDVLVALVAGVPEHIYNFWRLDLVRQHEYMHLTLERAFEDAAESMLFVQRLTPHPDARIRVLPT<br>FLDGGPPTRGLLFGTRLADWRRGKLSETDPLAPWRSALELGTQRRDVPALGKLSPAQALAAVSVLGRMCLPSAALAA<br>LWTCMFPDDYTEYDSFDALLAARLESGQTLGPAGGREASL<br><br>SEQ ID NO: 24 = ICP1/2 internal fragments encoded by UL36.4.2.5<br>EYDSFDALLAARLESGQTLGPAGGREASLPEAPHALYRPTGQHVAVLAAATHRTPAARVTAMDLVLAAVLLGAPVVV<br>ALRNTTAFSRESELELCLTLFDSRPGGPDAALRDVVSSDIETWAVGLLHTDLNPIENACLAAQLPRLSALIAERPLA<br>DGPPCLVLVDISMTPVAVLWEAPEPPGPPDVRFVGSEATEELPFVATAGDVLAASAADADPFFARAILGRPFDASLL<br>TGELFPGHPVYQRPLADEAGPSAPTAARDPRDLAGGDGGSGPEDPAAPPARQADPGVLAPTLLTDATTGEPVPPRMW<br>AWIHGLEELASDDAGGPTPNPAPALLPPPATDQSVPTSQYAPRPIGPAATARETRPSVPPQQNTGRVPVAPRDDPRP<br>SPPTPSPPADAALPPPAFSGSAAAFSAAVPRVRRSRRTRAKSRAPRASAPPEGWRPPALPAPVAPVAASARPPDQPP<br>TPESAPPAWVSALPLPPGPASARGAFPAPTLAPIPPPPAEGAVVPGGDRRRGRRQTTAGPSPTPPRGPAAGPPRRLT |

| Sequences |
|---|
| RPAVASLSASLNSLPSPRDPADHAAAVSAAAAAVPPSPGLAPPTSAVQTSPPPLAPGPVAPSEPLCGWVVPGGPVAR RPPPQSPATKPAARTRIRARSVPQPPLPQPPLPQPPLPQPPLPQPPLPQPPLPQPPLPQPPLPQPPLPQPPLPQPPL PPVTRTLTPQSRDSVPTPESPTHTNTHLPVSAVTSWASSLAHVDSAPPPASLLQTLHISSDDEHSDADSLRFSDSD DTEALDPLPPEPHLPPADEPPGPLAADHLQSPHSQFGPLPVQANAVLSRRYVRSTGRSALAVLIRACRRIQQQLQRT RRALFQRSNAVLTSLHHVRMLLG<br><br>SEQ ID NO: 25 = predicted sequence for reductase encoded by UL40<br>MDPAVSPASTDPLDTHASGAGAAPIPVCPTPERYFYTSQCPDINHLRSLSILNRWLETELVFVGDEEDVSKLSEGEL GFYRFLFAFLSAADDLVTENLGGLSGLFEQKDILHYYVEQECIEVVHSRVYNIIQLVLFHNNDQARRAYVARTINHP AIRVKVDWLEARVRECDSIPEKFILMILIEGVFFAASFAAIAYLRTNNLLRVTCQSNDLISRDEAVHTTASCYIYNN YLGGHAKPEAARVYRLFREAVDIEIGFIRSQAPTDSSILSPGALAAIENYVRFSADRLLGLIHMQPLYSAPAPDASF PLSLMSTDKHTNFFECRSTSYAGAVVNDL<br><br>SEQ ID NO: 26 = ICP47 encoded by US12<br>MSWALKTTDMFLDSSRCTHRTYGDVCAEIHKREREDREAARTAVTDPELPLLCPPDVRSDPASRNPTQQTRGCARSN ERQDRVLAP<br><br>SEQ ID NO: 27 = gM2 encoded by UL10<br>MGRRAPRGSPEAAPGADVAPGARAAWWVWCVQVATFIVSAICVVGLLVLASVFRDRFPCLYAPATSYAKANATVEVR GGVAVPLRLDTQSLLATYAITSTLLLAAAVYAAVGAVTSRYERALDAARRLAAARMAMPHATLIAGNVCAWLLQITV LLLAHRISQLAHLIYVLHFACLVYLAAHFCTRGVLSGTYLRQVHGLIDPAPTHHRIVGPVRAVMTNALLLGTLLCTA AAAVSLNTIAALNFNFSAPSMLICLTTLFALLVVSLLLVVEGVLCHYVRVLVGPHLGAIAATGIVGLACEHYHTGGY YVVEQQWPGAQTGVRVALALVAAFALAMAVLRCTRAYLYHRRHHTKFFVRMRDTRHRAHSALRRVRSSMRGSRRGGP PGDPGYAETPYASVSHHAEIDRYGDSDGDPIYDEVAPDHEAELYARVQRPGPVPDAEPIYDTVEGYAPRSAGEPVYS TVRRW<br><br>SEQ ID NO: 28 = predicted sequence for cleavage/package protein encoded by UL15<br>MFGQQLASDVQQYLERLEKQRQQKVGVDEASAGLTLGGDALRVPFLDFATATPKRHQTVVPGVGTLHDCCEHSPLFS AVARRLLFNSLVPAQLRGRDFGGDHTAKLEFLAPELVRAVARLRFRECAPEDAVPQRNAYYSVLNTFQALHRSEAFR QLVHFVRDFAQLLKTSFRASSLAETTGPPKKRAKVDVATHGQTYGTLELFQKMILMHATYFLAAVLLGDHAEQVNTF LRLVFEIPLFSDTAVRHFRQRATVFLVPRRHGKTWFLVPLIALSLASFRGIKIGYTAHIRKATEPVFDEIDACLRGW FGSSRVDHVKGETISFSFPDGSRSTIVFASSHNTNGIRGQDFNLLFVDEANFIRPDAVQTIMGFLNQANCKIIFVSS TNTGKASTSFLYNLRGAADELLNVVTYICDDHMPRVVTHTNATACSCYILNKPVFITMDGAVRRTADLFLPDSFMQE IIGGQARETGDDRPVLTKSAGERFLLYRPSTTTNSGLMAPELYVYVDPAFTANTRASGTGIAVVGRYRDDFIIFALE HFFLRALTGSAPADIARCVVHSLAQVLALHPGAFRSVRVAVEGNSSQDSAVAIATHVHTEMHRILASAGANGPGPEL LFYHCEPPGGAVLYPFFLLNKQKTPAFEYFIKKFNSGGVMASQELVSVTVRLQTDPVEYLSEQLNNLIETVSPNTDV RMYSGKRNGAADDLMVAVIMAIYLAAPTGIPPAFFPITRTS<br><br>SEQ ID NO: 29 = predicted sequence for ICP35 encoded by UL26.5<br>MNPVSASGAPAPPPPGDGSYLWIPASHYNQLVTGQSAPRHPPLTACGLPAAGTVAYGHPGAGPSPHYPPPPAHPYPG MLFAGPSPLEAQIAALVGAIAADRQAGGLPAAAGDHGIRGSAKRRRHEVEQPEYDCGRDEPDRDFPYYPGEARPEPR PVDSRRAARQASGPHETITALVGAVTSLQQELAHMRARTHAPYGPYPPVGPYHHPHADTETPAQPPRYPAKAVYLPP PHIAPPGPPLSGAVPPPSYPPVAVTPGPAPPLHQPSPAHAHPPPPPPGPTPPPAASLPQPEAPGAEAGALVNASSAA HVNVDTARAADLFVSQMMGSR<br><br>SEQ ID NO: 30 = predicted sequence for polymerase encoded by UL30<br>MFCAAGGPASPGGKPAARAASGFFAPHNPRGATQTAPPPCRRQNFYNPHLAQTGTQPKALGPAQRHTYYSECDEFRF IAPRSLDEDAPAEQRTGVHDGRLRRAPKVYCGGDERDVLRVGPEGFWPRRLRLWGGADHAPEGFDPTVTVFHVYDIL EHVEHAYSMRAQLHERFMDAITPAGTVITLLGLTPEGHRVAVHVYGTRQYFYMNKAEVDRHLQCRAPRDLCERLAA ALRESPGASFRGISADHFEAEVVERADVYYYETRPTLYYRVFVRSGRALAYLCDNFCPAIRKYEGGVDATTRFILDN PGFVTFGWYRLKPGRGNAPAQPRPPTAFGTSSDVEFNCTADNLAVEGAMCDLPAYKLMCFDIECKAGGEDELAFPVA ERPEDLVIQISCLLYDLSTTALEHILLFSLGSCDLPESHLSDLASRGLPAPVVLEFDSEFEMLLAFMTFVKQYGPEF VTGYNIINFDWPFVLTKLTEIYKVPLDGYGRMNGRGVERVWDIGQSHFQKRSKIKVNGMVNIDMYGIITDKVKLSSY KLNAVAEAVLKDKKKDLSYRDIPAYYASGPAQRGVIGEYCVQDSLLVGQLFFKFLPHLELSAVARLAGINITRTIYD GQQIRVFTCLLRLAGQKGFILPDTQGRFRGLDKEAPKRPAVPRGEGERPGDGNGDEDKDDDEDGDEDGDEREEVARE TGGRHVGYQGARVLDPTSGEHVDPVVVEDFASLYPSIIQAHNLCFSTLSLRPEAVAHLEADRDYLEIEVGGRRLFFV KAHVRESLLSILLRDWLAMRKQIRSRIPQSTPEEAVLLDKQQAAIKVVCNSVYGFTGVQHGLLPCLHVAATVTTIGR EMLLATRAYVHARWAEFDQLLADFPEAAGMRAPGPYSMRIIYGDTDSIFVLCRGLTAAGLVAMGDKMASHISRALFL PPIKLECEKTFTKLLLIAKKKYIGVICGGKMLIKGVDLVRKNNCAFINRTSRALVDLLFYDDTVSGAAAALAERPAE EWLARPLPEGLQAFGAVLVDAHRRITDPERDIQDFVLTAELSRHPRAYTNKRLAHLTVYYKLMARRAQVPSIKDRIP YVIVAQTREVEETVARLAALRELDAAAPGDEPAPPAALPSPAKRPRETPSHADPPGGASKPRKLLVSELAEDPGYAI ARGVPLNTDYYFSHLLGAACVTFKALFGNNAKITESLLKRFIPETWHPPDDVAARLRAAGFGPAGAGATAEETRRML HRAFDTLA<br><br>SEQ ID NO: 31 = predicted sequence for helicase/primase complex encoded by UL5<br>MAASGGEGSRDVRAPGPPPQQPGARPAVRFRDEAFLNFTSMHGVQPIIARIRELSQQQLDVTQVPRLQWFRDVAALE VPTGLPLREFPFAAYLITGNAGSGKSTCVQTLNEVLDCVVTGATRIAAQNMYVKLSGAELSRPINTIFHEFGFRGNH VQAQLGQHPYTLASSPASLEDLQRRDLTYYWEVILDITKRALAAHGGEDARNEFHALTALEQTLGLGQGALTRLASV THGALPAFTRSNIIVIDEAGLLGRHLLTTVVYCWWMINALYHTPQYAGRLRPVLVCGSPTQTASLESTFEHQKLRC SVRQSENVLTYLICNRTLREYTRLSHSWAIFINNKRCVEHEFGNLMKVLEYGLPITEEHMQFVDRFVVPESYITNPA NLPGWTRLFSSHKEVSAYMAKLHAYLKVTREGEFVVFTLPVLTFVSVKEFDEYRRLTQQPTLTMEKWITANASRITN YSQSQDQDAGHVRCEVHSKQQLVVARNDITYVLNSQVAVTARLRKMVEGEDGTERTFEAVLRDDSFVKTQGETSVEF AYRFLSRLMFGGLIHEYNELQRPGLDATQRTLAYGRLGELTAELLSLRRDAAGASATRAADTSDRSPGERAFNFKHL GPRDGGPDDEPDDDLDVIFAGLDEQQLDVEYCHYALEEPETTAAVHAQFGLLKRAFLGRYLILRELFGEVFESAPFS TYVDNVIFRGCELLTGSPRGGLMSVALQTDNYTLMGYTYTRVFAFAEELRRRHATAGVAEFLEESPLPYIVLRDQHG FMSVVNTNISEFVESIDSTELAMAINADYGISSKLAMTITRSQGLSLDKVAICFTPGNLRLNSAYVAMSRTTSSEEL HMNLNPLRERHERDDVISEHILSALRDPNVVIVY |

| Sequences |
| --- |
| SEQ ID NO: 32 = predicted sequence for helicase/primase complex encoded by UL8
MEAPGIVWVEESVSAITLYAVWLPPRTRDCLHALLYLVCRDAAGEARARFAEVSVGSSDLQDFYGSPDVSAPGAVAA
ARAATAPAASPLEPLGDPTLWRALYACVLAALERQTGRWALFVPLRLGWDPQTGLVVRVERASWGPPAAPRAALLDV
EAKVDVDPLALSRVAEHPGARLAWARLAAIRDSPQCASSASLAVTITTRTARFAREYTTLAFPPTRKEGAFADLVE
VCEVGLRPRGHPQRVTARVLLPRGYDYFVSAGDGFSAPALVALFRQWHTTVHAAPGALAPVFAFLGPGFEVRGGPVQ
YFAVLGFPGWPTFTVPAAAAAESARDLVRGAAATHAACLGAWPAVGARVVLPPRAWPAVASEAAGRLLPAFREAVAR
WHPTATTIQLLDPPAAVGPVWTARFCFSGLQAQLLAALAGLGEAGLPEARGRAGLERLDALVAAAPSEPWARAVLER
LVPDACDACPALRQLLGGVMAAVCLQIEQTASSVKFAVCGGTGAAFWGLENVDPGDADAAHGAIQDARRALEASVRA
VLSANGIRPRLAPSLAPEGVYTHVVTWSQTGAWFWNSRDDTDFLQGFPLRGAAYAAAAEVMRDALRRILRPPAAGPP
EEAVCAARGVMEDACDRFVLDAFGRRLDAEYWSVLTPPGEADDPLPQTAFRGGALLDAEQYWRRVVRVCPGGGESVG
VPVDLYPRPLVLPPVDCAHHLREILREIQLVFTGVLEGVWGEGGSFVYPFDEKIRFLFP SEQ ID NO: 33 = predicted sequence for unknown protein encoded by UL15.5
MDGAVRRTADLFLPDSFMQEIIGGQARETGDDRPVLTKSAGERFLLYRPSTTTNSGLMAPELYVYVDPAFTANTRAS
GTGIAVVGRYRDDFIIFALEHFFLRALTGSAPADIARCVVHSLAQVLALHPGAFRSVRVAVEGNSSQDSAVAIATHV
HTEMHRILASAGANGPGPELLFYHCEPPGGAVLYPFFLLNKQKTPAFEYFIKKFNSGGVMASQELVSVTVRLQTDPV
EYLSEQLNNLIETVSPNTDVRMYSGKRNGAADDLMVAVIMAIYLAAPTGIPPAFFPITRTS SEQ ID NO: 34 = predicted sequence for cleavage and packaging protein encoded
by UL32
MATSAPGVPSSAAVREESPGSSWKEGAFERPYVAFDPDLLALNEALCAELLAACHVVGVPPASALDEDVESDVAPAP
PRPRGAAREASGGRGPGSARGPPADPTAEGLLDTGPFAAASVDTFALDRPCLVCRTIELYKQAYRLSPQWVADYAFL
CAKCLGAPHCAASIFVAAFEFVYVMDHHFLRTKKATLVGSFARFALTINDIHRHFFLHCCFRTDGGVPGRHAQKQPR
PTPSPGAAKVQYSNYSFLAQSATRALIGTLASGGDDGAGAGAGGGSGTQPSLTTALMNWKDCARLLDCTEGKRGGGD
SCCTRAAARNGEFEAAAGALAQGGEPETWAYADLILLLLAGTPAVWESGPRLRAAADARRAAVSESWEAHRGARMRD
AAPRFAQFAEPQPQPDLDLGPLMATVLKHGRGRGRTGGECLLCNLLLVRAYWLAMRRLRASVVRYSENNTSLFDCIV
PVVDQLEADPEAQPGDGGRFVSLLRAAGPEAIFKHMFCDPMCAITEMEVDPWVLFGHPRADHRDELQLHKAKLACGN
EFEGRVCIALRALIYTFKTYQVFVPKPTALATFVREAGALLRRHSISLLSLEHTLCTYV SEQ ID NO: 35 = predicted sequence for ICP1/2 fragment enoded by UL36.4.2
MEYDSFDALLAARLESGQTLGPAGGREASLPEAPHALYRPTGQHVAVLAAATHRTPAARVTAMDLVLAAVLLGAPVV
VALRNTTAFSRESELELCLTLFDSRPGGPDAALRDVVSSDIETWAVGLLHTDLNPIENACLAAQLPRLSALIAERPL
ADGPPCLVLVDISMTPVAVLWEAPEPPGPPDVRFVGSEATEELPFVATAGDVLAASAADADPFFARAILGRPFDASL
LTGELFPGHPVYQRPLADEAGPSAPTAARDPRDLAGGDGGSGPEDPAAPPARQADPGVLAPTLLTDATTGEPVPPRM
WAWIHGLEELASDDAGGPT SEQ ID NO: 36 = predicted sequence for ICP27 encoded by UL54
MATDIDMLIDLGLDLSDSELEEDALERDEEGRRDDPESDSSGECSSSDEDMEDPCGDGGAEAIDAAIPKGPPARPED
AGTPEASTPRPAARRGADDPPPATTGVWSRLGTRRSASPREPHGGKVARIQPPSTKAPHPRGGRRGRRRGRGRYGPG
GADSTPKPRRRVSRNAHNQGGRHPASARTDGPGATHGEARRGGEQLDVSGGPRPRGTRQAPPPLMALSLTPPHADGR
APVPERKAPSADTIDPAVRAVLRSISERAAVERISESFGRSALVMQDPFGGMPFPAANSPWAPVLATQAGGFDAETR
RVSWETLVAHGPSLYRTFAANPRAASTAKAMRDCVLRQENLIEALASADETLAWCKMCIHHNLPLRPQDPIIGTAAA
VLENLATRLRPFLQCYLKARGLCGLDDLCSRRRLSDIKDIASEVLVILARLANRVERGVSEIDYTTVGVGAGETMHE
YIPGACMAGLIEILDTHRQECSSRVCELTASHTIAPLYVHGKYFYCNSLF SEQ ID NO: 37 = virion protein encoded by UL49.5
MTGKPARLGRWVVLLEVALVAGVPGEPPNAAGARGVIGDAQCRGDSAGVVSVPGVLVPFYLGMTSMGVCMIAHVYQI
CQRALAAGSA SEQ ID NO: 38 = gG2 encoded by US4
NRWGSGVPGPINPPNSDVVFPGGSPVAQYCYAYPRLDDPGPLGSADAGRQDLPRRV
VRHEPLGRSFLTGGLVLLAPPVRGEGAPNATYAARVTYYRLTRACRQPILLRQYGGCRGGEPPSPKTCGSYTYTYQG
GGPPTRYALVNASLLVPIWDRAAETFEYQIELGGELHVGLLWVEVGGEGPGPTAPPQAARAEGGPCVPPVPAGRPWR
SVPPVWYSAPNPGFRGLRFRERCLPPQTPAAPSDLPRVAFAPQSLLVGITGRTFIRMARPTEDVGVLPPHWAPGALD
DGPYAPFPPRPRFRR SEQ ID NO: 39 = nucleotide sequence for RS1 (ICP4), full-length
ATGTCGTACTACCATCACCATCACCATCACAGTGCCGAACAGCGTAAAAAGAAAAAAACCACCACCACGACCCAAGG
ACGTGGAGCTGAAGTTGCTATGGCGGATGAGGATGGAGGCCGCTTGAGAGCTGCTGCTGAGACTACTGGAGGACCTG
GATCACCGGACCCTGCCGATGGACCCCCCCCTACACCAAACCCCGATCGTAGACCGGCTGCTAGACCTGGATTCGGA
TGGCATGGAGGACCCGAGGGAAAACGAGGACGAGGCGGACGACGCCGCTGCCGACGCCGACGCCGATGAGGCTGCCCC
TGCTTCTGGAGAGGCGGTAGACGAACCTGCTGCCGATGGAGTTGTTAGCCCTAGGCAATTGGCTTTGTTGGCGAGCA
TGGTAGACGAGGCTGTGAGAACAATCCCTTCCCCTCCCCCTGAACGTGATGGAGCACAAGAGGAGGCGGCTAGGAGT
CCCTCACCACCCCGTACACCTTCTATGAGAGCGGATTACGGCGAGGAAAACGACGACGACGACGATGATGATGACGA
CGATGATCGTGATGCCGGACGCTGGGTTAGGGGACCTGAAACCACTTCTGCTGTCCGTGGAGCATACCCCGATCCTA
TGGCGAGTTTGAGCCCTAGACCACCTGCCCCGAGGAGACACCACCACCACCACCATCATAGGCGTAGACGTGCTCCT
AGACGTCGTTCTGCCGCTAGTGACTCTTCCAAATCTGGCTCTTCTTCATCTGCCTCTTCCGCTTCATCTTCGGCCTC
ATCGTCCTCTTCGGCATCCGCTTGAGTAGTGATGATGATGATGACGACGACGCTGCTAGAGCCCCCGCTTCTGCTG
CCGACCACGCTGCTGGCGGAACTTTGGGAGCCGACGACGAGGAGGCGGGAGTTCCTGCTCGTGCCCCGGGAGCTGCT
CCGAGGCCTTCTCCACCCGTGCTGAACCTGCTCCGGCTAGAACACCGGCTGCTACTGCTGCTAGACTGGAGCGTAG
ACGTGCCCGTGCTGCTGTGGCTGGTAGAGATGCTACTGGCCGCTTCACTGCTGGCCGTCCTAGACGTGTTGAACTGG
ACGCCGATGCTGCTTCTGGTGCTTTCTACGCCCGTTACCGTGATGGTTACGTGTCTGGTGAPCCTTGGCCTGGCGCT
GGTCCACCTCCGCCCGGACGTGTACTCTACGGTGGATTGGGCGATTCTCGCCCTGGTCTGTGGGCGCTCCGGAGGC
TGAGGAGGCTAGAGCCCGTTTCGAGGCTTCTGGTGCCCCTGCTCCTGTTTGGGCTCCTGAATTGGGCGACGCTGCTC
AACAATACGCCCTCATCACACGCTTGCTGTACACTCCCGACGCCGAGGCTATGGGATGGCTCCAAAACCCTAGAGTT
GCCCCTGGTGATGTTGCTCTGGATCAGGCTTGTTTCCGTATCTCCGGCGCTGCTCGTAACTCTTCTTCGTTCATCTC |

| Sequences |
|---|
| CGGTTCTGTGGCTAGAGCTGTGCCTCACTTGGGATACGCCATGGCCGCTGGACGTTTCGGCTGGGGACTGGCTCATG
TTGCTGCCGCTGTAGCAATGTCTAGACGCTACGACCGTGCTCAAAAAGGATTCTTGCTCACGTCACTGAGGCGTGCT
TACGCCCCTTTGTTGGCCCGTGAAAACGCTGCCCTCACTGGCGCCCGTACCCCCGATGACGGTGGCGACGCCAACCG
CCACGATGGTGATGATGCTAGAGGCAAACCCGCTGCCGCTGCTGCTCCTTTGCCCTCTGCCGCCGCTTCCCCTGCCG
ATGAACGTGCTGTTCCTGCCGGTTACGGTGCCGCTGGTGTGTTGGCTGCTTTGGGACGCTTGAGTGCTGCCCCGGCT
AGTGCCCCGCTGGTGCCGATGACGATGACGATGACGATGGTGCTGGCGGAGGCGGTGGCGGTAGACGTGCTGAGGC
TGGACGTGTTGCTGTTGAATGCCTGGCTGCCTGTAGAGGAATCTTGGAGGCTCTGGCCGAGGGATTCGACGGAGACT
TGGCGGCTGTACCGGGACTGGCGGGAGCGAGGCCTGCCGCTCCACCTCGCCCCGGTCCTGCTGGTGCTGCCGCTCCT
CCTCATGCCGACGCTCCTAGACTCCGTGCTTGGCTCCGTGAACTCCGTTTCGTTCGTGACGCTTTGGTTCTGATGAG
ACTGAGAGGCGACTTGAGAGTGGCTGGAGGATCCGAGGCTGCTGTTGCTGCTGTCCGTGCTGTTTCTTTGGTTGCTG
GTGCTTTGGGCCCTGCTTTGCCGAGATCTCCCCGTTTGTTGTCGAGTGCCGCCGCTGCTGCCGCCGATTTGTTGTTC
CAAAACCAATCCCTCCGCCCTCTGCTCGCCGACACTGTTGCCGCTGCCGATTCTCTGGCTGCTCCGGCTTCTGCCCC
ACGTGAAGCTCGTAAACGTAAATCACCCGCTCCGGCTCGTGCTCCCCCTGGTGGCGCCCCTAGACCCCCTAAAAAAT
CCCGTGCCGATGCCCCTAGACCTGCTGCTGCTCCCCCCGCTGGTGCTGCTCCCCCCGCTCCCCCTACTCCCCCCCCA
CGCCCACCTCGTCCCGCTGCCCTCACACGCCGTCCTGCTGAGGGACCCGATCCACAAGGCGGCTGGCGTAGACAACC
TCCTGGCCCATCCCATACACCGGCACCATCTGCCGCTGCTTTGGAGGCTTACTGTGCTCCTCGTGCTGTGGGCTGAAC
TCACCGATCATCCGCTGTTCCCTGCTCCCTGGCGTCCCGCCCTCATGTTCGATCTAGAGCTTTGGCTTCCTTGGCC
GCTCGTTGTGCTGCCCCTCCCCCTGGCGGTGCTCCGGCTGCTTTCGGTCCTCTCCGTGCCTCTGGTCCACTCCGCCG
TGCCGCTGCCTGGATGAGACAAGTTCCCGACCCTGAGGATGTTAGAGTTGTGATCTTGTACTCGCCCTTGCCTGGCG
AGGATTTGGCGCTGGTAGAGCTGGCGGTGGCCCCCCTCCTGAATGGTCTGCTGAACGTGGTGGTTTGTCTTGCTTG
TTGGCCGCCCTGGGAAACCGTCTGTGTGGTCCTGCTACTGCTGCTTGGGCTGGAAACTGGACTGGCGCTCCCGATGT
TTCTGCTCTCGGTGCTCAAGGAGTTTTGCTGCTCTCTACTCGTGACTTGGCATTCGCTGGAGCTGTTGAATTCCTGG
GACTCTTGGCTGGCGCTTGTGATAGGAGACTCATCGTCGTAAACGCTGTGAGAGCTGCCGATTGGCCTGCCGATGGT
CCTGTTGTGTCTCGTCAACACGCTTACTTGGCTTGTGAAGTGTTGCCCGCTGTCCAATGTGCTGTTCGCTGGCCTGC
TGCTCGTGATCTGAGGCGTACTGTTCTGGCTAGTGGTCGTGTTTTCGGACCTGGTGTTTTCGCTCGTGTCGAAGCTG
CTCACGCTAGACTGTACCCCGATGCCCCACCCCTCCGTTTGTGTCGTGGAGCAAACGTTCGCTACCGTGTCCGTACT
CGTTTCGGACCCGATACTCTGGTTCCAATGTCCCCTCGTGAATACCGTCGTGCTGTTCTGCCTGCCCTCGATGGACG
TGCTGCCGCTTCTGGCGCTGGTGACGCTATGGCTCCTGGCGCTCCGGACTTCTGTGAGGATGAGGCTCACTCACATC
GTGCCTGTGCCCGCTGGGGACTGGGCGCTCCATTGAGGCCTGTATACGTGGCACTGGGCCGTGATGCTGTTAGAGGC
GGACCCGCTGAATTGAGAGGCCCTCGTCGTGAATTCTGTGCTAGGGCTCTGCTCGAACCCGATGGAGATGCTCCTCC
TTTGGTACTCCGTGACGACGCCGATGCTGGTCCTCCCCCACAAATTCGCTGGGCTAGTGCTGCTGGACGTGCTGGTA
CTGTATTGGCTGCTGCTGGCGGTGGCGTTGAAGTTGTTGGTACTGCCGCTGGACTCGCTACACCTCCCCGCCGTGAA
CCTGTAGACATGGATGCTGAACTCGAGGATGATGACGACGGATTGTTCGGAGAGTAATAG |

SEQ ID NO: 40 = US6ΔTMR
ATGAAGTTCCTCGTGAACGTGGCCCTGGTGTTCATGGTGGTGTACATCAGCTACATCTACGCCAACCGTTGGAAGTA
CGCTCTGGCTGACCCATCCCTGAAGATGGCTGACCCAACCGTTTCCGTGGCAAGAACCTGCCCGTGCTGGACCAGC
TGACCGACCCCCTGGCGTGAAGCGTGTGTACCACATCCAGCCATCCCTCGAAGACCCCTTCCAGCCCCCTCCATC
CCCATCACCGTGTACTACGCTGTGCTGGAACGCGCTTGCCGTTCCGTGCTGCTGCACGCTCCTTCCGAGGCTCCCCA
GATCGTGCGTGGTGCTTCCGACGAGGCTCGCAAGCACACCTACAACCTGACTATCGCTTGGTACAGGATGGGTGACA
ACTGCGCTATCCCTATCACCGTCATGGAATACACCGAGTGCCCCTACAACAAGTCCCTGGGCGTGTGCCCCTATCCGT
ACCCAGCCCGTTGGTCCTACTACGACTCCTTCAGCGCTGTGTCCGAGGACAACCTGGGTTTCCTGATGCACGCTCC
CGCTTTCGAGACTGCTGGCACCTACCTGCGTCTGGTCAAGATCAACGACTGGACCGAGATCACCCAGTTCATCCTGG
AACACCGTGCTCGTGCTTCGTGCAAGTACGCCCTGCCCCTGCGTATCCCTCCTGCTGCTTGCCTGACCTCCAAGGCT
TACCAGCAGGGCGTGACCGTGGACTCCATCGGCATGCTGCCCCGTTTCATCCCCGAGAACCAGCGTACCGTGGCTCT
GTACTCTCTGAAGATCGCTGGCTGGCACGGTCCTAAGCCCCCCTACACCTCCACTCTGCTGCCCCCTGAGCTGTCCG
ACACCACCAACGCTACTCAGCCCGAGTTGGTGCCTGAGGACCCCGAGGACTCCGCTCTGTTGGAGGACCCCGCTGGA
ACCGTGTCCTCCCAGATCCCCCCCAACTGGCACATCCCTTCCATCCAGGACGTGGCCCTCACCACGCTCCAGCTGC
TCCCTCCAACCCCGTCGTCGTGCTCAGATGGCTCCCAAGCGTCTGCGTCTGCCCCACATCCGTGACGACGACGCTC
CTCCATCCCACCAGCCCCTGTTCTACCACCACCACCATCACCACTAATAA

SEQ ID NO: 41 = nucleotide sequence for RL1 (ICP34.5)
ATGTCTCGTCGTCGTGGTCCTCGTCGTCGTGGTCCTCGTCGTCGTGGTCCTCGTCGTCGTGGTCCTCGGGTGCGCCGGCGGTACCACGCCC
GGGTGCGCCGGCAGTGCCGCGTCCAGGCGCACTGCCTACCGCGGACTCTCAAATGGTGCCGGCGTATGATTCTGGTA
CTGCCGTCGAATCTGCTCCGGCAGCGAGCTCCCTGCTGCGTCGTTGGCTGCTGGTCCTCAGGCGGACGATTCCGAT
GACGCAGACTACGCGGGCAACGACGACGCGGAGTGGGCTAACAGCCCGCCAAGCGAGGGTGGTGGCAAAGCGCCGGA
GGCTCCGCACGCAGCGCCTGCCGCAGCGTGCCGCCTCCGCCTCCTCGTAAAGAACGTGGCCCTCAACGTCCTCTGC
CGCCGCACCTGGCTCTGCGTCTGCGTACTACCACTGAGTACCTGGCGTCTGTCTCTGCGTCGTCGCCGTCCGCCG
GCTAGCCCGCCGGCCGATGCACCGCGTGGCAAAGTGTGCTTCTCTCACGTGTTCAAGTTCGTCACCTGGTGGCTTG
GGAAACGGCTGCCCGTCTGGCTCGCCGTGGCAGCTGGGCACGTGAGCGCGCAGACCGTGACCGCTTCCGTCGCCGTG
TGGCGGCTGCTGAAGCCGTTATCGGCCCGTGCCTGGAACCTGAGGCTCGCGTCGCGCGCGTGCGCGCGCTCGTGCC
CACGAAGATGGCGGTCCAGCAGAGGAAGAAGAGGCAGCTGCAGCAGCGCGCGGTAGCTCCGCGGCTGCGGGTCCAGG
TCGTCGTGCCGTA SEQ ID NO: 42 = nucleotide seqeunce for RL2 (ICP0)
ATGTCGTACTACCATCACCATCACCATCACATGGAGCTCCTGGTACTTCTTCTCGCGCTGATCCTGGTCCTGA
ACGTCCGCCACGCCAGACTCCGGGCACCCAGCCGGCCGCCCTCACGCTTGGGGCATGCTGAACGATATGCAGTGGC
TGGCGTCCTCTGATTCCGAAGAGGAGACTGAGGTTGGTATCAGCGATGATGATCTGCACCGCGACTCTACCAGCGAA
GCAGGTTCCACTGACACCGAAATGTTTGAAGCGGGCCTGATGGATGCCGCGACCCCGCCGGCTCGTCCGCCGGCTGA
ACGTCAGGGTAGCCCTACGCCTGCGGATGCGCAAGGCTCTTGTGGTGGTGGTCCAGTAGGCGAAGAGGAGGCTGAGG
CCGGTGGCGGCGGTGATGTGTGTCGGTTTGTACCGATGAAATCGCACCGCCGCTGCGTTGTCAGTCTTTCCCGTGC
CTGCACCCGTTTTGCATTCCGTGCATGAAAACCTGGATCCCGCTGCGCAACACTTGCCCGCTGTGCAACACTCCGGT
TGCTTATCTGATCGTTGGTGTAACCGCATCTGGTTCCTTTTCTACCATCCCGATTGTCAACGACCCACGTACGCGTG
TTGAGGCGGAGGCGGCTGTACGTGCGGGCACCGCGGTGGACTTTATCTGGACCGGTAACCCGCGCACCGCGCCACGC
TCCCTGTCTCTGGGTGGCCATACCGTTCGTGCTCTGAGCCCGACCCCACCTTGGCCAGGCACCGATGACGAGACGA
CGATCTGGCTGACGTTGACTATGTTCGCCGGCACCGCGTCGCGCACCACGCGTGGTGGCGGTGGCGCCGGTGCGA
CGCGCGGTACCTCCCAGCCGGCAGCAACTCGCCCAGCACCGCCGGGTGCCCCGCGTTCTAGCAGCTCCGGTGGCGCA |

```
CCGCTGCGTGCTGGCGTGGGTTCTGGTTCCGGTGGTGGTCCGGCCGTGGCGGCTGTCGTCCCGCGTGTGGCTTCTCT
GCCACCGGCAGCTGGTGGCGGTCGTGCTCAAGCTCGTCGTGTCGGCGAGGACGCAGCGGCTGCTGAGGGCCGTACTC
CACCGGCCCGTCAACCGCGCGCAGCACAGGAACCGCCGATCGTGATCTCCGATTCCCCGCCACCGAGCCCGCGTCGC
CCGGCGGGTCCGGGTCCGCTGTCTTTTGTATCCTCCAGCTCTGCTCAGGTAAGCAGCGGTCCTGGCGGTGGCGGCCT
GCCACAGTCCTCTGGTCGTGCTGCTCGTCCTCGTGCGGCGGTTGCTCCTCGTGTACGTTCTCCGCCACGCGCTGCTG
CCGCGCCGGTCGTTTCTGCCTCTGCTGACGCGGCAGGTCCGGCTCCGCCTGCAGTTCCGGTTGATGCACACCGTGCA
CCGCGCTCTCGTATGACCCAGGCGCAGACTGATACCCAGGCACAATCCCTGGGTCGCGCGGGTGCGACTGACGCTCG
TGGTAGCGGTGGTCCGGGCGCTGAAGGTGGCCCGGGTGTTCCACGCGGTACTAACACTCCGGGCGCTGCGCCACACG
CGGCTGAAGGTGCGGCTGCACGTCCGCGTAAACGTCGTGGTTCCGACAGCGGTCCGGCTGCAAGCAGCAGCGCGAGC
TCTTCCGCTGCGCCTCGCAGCCCGCTGGCGCCGCAGGGTGTTGGCGCCAAGCGTGCTGCTCCGCGTCGTGCACCGGA
CTCCGATTCTGGCGACCGCGGTCACGGCCCGCTGGCCCCTGCTAGCGCAGGCGCTGCGCCGCCATCCGCCAGCCCGT
CTTCTCAGGCAGCTGTGGCTGCGGCGTCCTCTTCTTCCGCTAGCAGCTCTTCCGCCTCTTCTAGCAGCGCGTCCTCT
AGCAGCGCATCTTCCTCTTCTGCTTCTTCTTCTAGCGCTTCTAGCTCTTCCGCGTCCTCTTCCGCTGGCGGTGCAGG
CGGCTCTGTTGCTTCCGCCAGCGGCGCAGGTGAGCGTCGTGAAACGAGCCTGGGCCCACGTGCTGCTGCACCGCGTG
GCCCGCGTAAGTGTGCGCGCAAGACCCGCCACGCTGAAGGCGGTCCGGAGCCGGGTGCGCGTGATCCGGCTCCGGGT
CTGACCCGTTACCTGCCGATTGCGGGTGTGTCCTCCGTTGTGGCACTGGCGCCGTATGTGAACAAAACTGTCACGGG
CGATTGCCTGCCTGTTCTGGACATGGAAACCGGTCATATCGGCGCTTACGTCGTTCTGGTTGACCAAACCGGCAACG
TGGCGGATCTGCTGCGTGCGGCCGCTCCGGCTTGGTCCCGTCGTACCCTGCTGCCGGAACATGCTCGCAACTGTGTA
CGCCCACCGGATTACCCAACCCCGCCGGCCTCCGAGTGGAACTCCCTGTGGATGACCCCGGTTGGTAACATGCTGTT
CGACCAGGGCACGCTGGTTGGTGCTCTGGACTTTCACGGCCTGCGCTCCCGTCACCCGTGGTCCCGTGAGCAAGGCG
CTCCGGCCCCTGCGGGCGATGCCCCGGCTGGCCACGGCGAGAGTACTAGAGGATCATAA

SEQ ID NO: 43 = nucleotide sequence for UL36.3.4.1
ATGTCGTACTACCATCACCATCACCATCACGCCGCTCAACGTGCTAGGGGATCCTCTGAACGCTGGGCTGCTGGTGT
CGAGGCTGCTTTGGATAGAGTGGAGAACCGTGCCGAATTCGATGTTGTCGAGCTGAGGAGACTCCAAGCTTTGGCTG
GTACTCACGGCTACAACCCTCGTGATTTCCGTAAACGTGCCGAACAGGCTTTGGCGGCAAACGCTGAGGCCGTAACA
TTGGCTCTGGACACTGCCTTCGCTTTCAACCCATACACGCCCGAAAACCAACGTCATCCTATGCTCCCACCTCTCGC
TGCTATTCACCGCCTGGGATGGAGCGCTGCTTTCCATGCTGCGTCTGAAACTTACGCCGACATGTTCCGTGTCGATG
CCGAACCACTGGCTAGACTGCTCCGTATCGCTGAGGGACTGCTGGAGATGGCTCAAGCTGGCGACGGATTCATCGAT
TACCATGAGGCTGTCGGTAGACTGGCCGATGATATGACTTCTGTGCCCGGATTGAGGCGCTACGTTCCTTTCTTCCA
ACATGGCTACGCCGATTACGTGGAACTGAGAGATCGCCTGGATGCTATTAGGGCCGACGTCCATAGAGCACTCGGTG
GTGTTCCGCTGGATTTGGCGGCTGCTGCCGAACAAATTTCCGCTGACTGTGAACGATCCTGAGGCTACTGCTGAATTG
GTCCGTACTGGTGTAACATTGCCTTGCCCTAGTGAGGACGCTCTCGTGGCTTGTGCTGCTGCCCTGGAGAGAGTCGA
TCAATCTCCCGTGAAAAACACGGCTTACGCCGAATACGTTGCCTTCGTGACCCGTCAAGACACTGCTGAGACTAAAG
ACGCTGTGGTCCGTGCTAAACAACAACGTGCTGAGGCCACTGAACGTGTTATGGCTGGCCTGAGAGAGGCTCTGGCT
GCTAGAGAACGTCGTGCTCAAATTGAGGCTGAGGGATTGGCAAACCTGAAAACCATGCTCAAGTCGTGGCTGTACC
CGCTACTGTTGCTAAAACTCTCGACCAGGCTCGTAGTGTTGCCGAAATTGCCGATCAAGTCGAAGTGTTGCTGGATC
AAAACCGAAAAAACTCGTGAACTGGATGTGCCTGCTGTGATCTGGCTCGAACACGCCCAAAGAACATTCGAGACACAC
CCTTTGTCTGCCGCTCGTGGTGATGGTCCTGGACCCTTGGCTCGTCATGCTGGCCGCCTCGGTGCCCTCTTCGATAC
TCGTCGTAGAGTAGACGCCTTGAGGAGATCCCTGAGGAGGCTGAGGCTGAATGGGACGAAGGTTTGGGGACGCTTCG
GTAGAGTGAGGGGCGGAGCGTGGAAATCTCCGGAGGGATTCCGTGCAATGCATGAGGCAACTGAGGGCCCTCCAAGAC
ACAACAAACACCGTGTCTGGCCTGAGGGCTCAACCTGCTTACGAACGCTTGTCTGCTCGCTACCAAGGAGTACTCGG
AGCGAAAGGCGCTGAGAGAGCTGAGGCTGTTGAGGAACTCGGTGCTCGTGTCACTAAACACACCGCTCTGTGTGCTA
GGCTGAGAGATGAGGTCGTCCGTAGAGTGCCTTGGGAAATGAACTTCGATGCTCGGGAGGATTGTTGGCTGAGTTC
GATGCCGCTGCTGCCGATTTGGCCACCTTGGGCTGTAGAGGAATTCCGTGGTGCTAGAGAACTCATTCAATACCGTAT
GGGCCTGTACTCTGCCTACGCTAGAGCTGGAGGACAAACTGGTGCTGGAGCTGAATCTGCTCCTGCTCCTTTGCTCG
TGGATCTGAGGGCTTTGGATGCTCGTGCTCGTGCTTCTTCTTCCCTGAGGGACATGAAGTGGACCCACAACTGCTG
AGGAGGCGTGGAGAGGCTTACTTGAGAGCTGGCGGCGACCCTGGACCTCTCGTGCTCCGTGAAGCTGTTTCTGCTTT
GGACCTGCCATTCGCCACATCTTTCTTGGCCCCCGATGGAACTCCCCTCCAATACGCTTTGTGCTTTCCCTGCCGTAA
CGGACAAACTCGGAGCTTTGCTCATGAGGCCCGAGGCCGCTTGTGTTAGACCTCCTTTGCCTACCGATGTGCTGGAA
TCTGCCCCAACTGTGACTGCCATGTACGTACTCACTGTGGTCAACCGCTCCAACTGGCATTGAGTGATGCTCAAGC
GGCAAACTTCCAACTGTTCGGTCGTTTCGTTCGTCATAGGCAGGCAACCTGGGGAGCGTCAATGGATGCCGCCGCTG
AATTGTACGTTGCCCTGGTGGCTACAACTCTCACACGTGAATTCGGGTTGTCGCTGGGCACAATTGGGATGGGCTAGT
GGAGCTGCTGCTCCTAGACCCCCACCTGGACCCCGTGGCTCACAACGTCACTGTGTGGCATTCAACGAGAACGATGT
CCTCGTCGCTTTGGTTGCCGGTGTTCCCGAACACATCTACAACTTCTGGCGCCTGGACTTGGTCCGTCAACACGAGT
ACATGCACCTCACACTGGAGCGTGCCTTCGAGGATGCTGCCGAGTCTATGCTCTTCGTTCAACGCCTCACTCCACAT
CCCGACGCTCGTATTAGAGTTCTGCCGACCTTCTTGGATGGTGGTCTGCCTCCTACACGTGGTCTGTTGTTCGGAACCCG
CTTGGCGGACTGGCGTCGTGGTAAACTGTCTGAAACCGACCCATTGGCCCCATGGAGATCTGCTTTGGAACTCGGAA
CCCAACGTCGTGACGTGCCTGCTTTGGGAAAACTGTCCCCTGCTCAAGCTTTGGCCGCTGTGTCGGTACTGGGCCGT
ATGTGCTTGCCCTCGGCTGCCTTGGCTGCTTTGTGGACCTGTATGTTCCCCGACGACTACACTGAATACGACTCATT
CGACGCCCTCTTGGCGGCTCGCCTGGAATCGGGACAAACATTGGGACCTGCTGGCGGTAGAGAGGCTTCATTGTAAT
AG SEQ ID NO: 44 = nucleotide sequence for UL36.4.2.5
ATGTCGTACTACCATCACCATCACCATCACGAPTACGACTCCTTCGACGCTTTGTTGGCTGCTAGACTGGAPTCTGG
TCAAACCTTGGGACCCGCTGGCGGTAGAGAGGCTTCTTTGCCCGAGGCTCCTCATGCTTTGTACCGTCCAACCGGAC
AACATGTTGCTGTGTTGGCGGCTGCTACTCATAGAACCCCTGCTGCTCGTGTTACTGCTATGGACCTGGTCTTGGCG
GCCGTTTTGCTGGGCGCTCCTGTGGTGGTCGCTCTGAGAAACACTACTGCCTTCTCCCGTGAATCCGAATTGGAACT
GTGCCTCACCCTGTTCGATTCTCGTCCCGGCGGACCGGATGCTGCCCTGAGAGATGTGGTATCCTCCGACATTGAAA
CCTGGGCTGTGGGCTTGCTCCACACCGATTTGAACCCTATTGAGAACGCTTGCTTGGCGGCTCAACTGCCACGCTTG
TCTGCCCTCATTGCTGAACGTCCTTTGGCCGATGGACCCCTTGTTTGGTGTTGGTGGACAATTTGATGACACCTGT
CGCTGTTTTGTGGGAGGCCCCTGAACCACCTGGCCCTCCCGATGTTCGTTTCGTCGGTAGCGAGGCCACTGAGGAAT
TGCCTTTCGTGGCTACTCTGGTGATGTTTGGCGGCGAGTGCTGCCGATGCCGATCCTTTCTTCGCTCGTGCTATC
CTGGGCCGTCCTTTCGATGCTTCTCTGCTCACTGGTGAACTGTTCCCTGGTCACCCCGTTTACCAACGTCCCCTGGC
GGATGAGGCTGGTCCTTCTGCTCCTACTGCCGCTCGTGATCCTAGAGATCTGGCTGGAGGCGACGGTGGATCCGGAC
CTGAGGATCCCGCTGCTCCACCTGCTAGACAGGCCGATCCTGGTGTTTTGGCTCCTACTCTGCTCACCGATGCTACT
ACTGGCGAACCTGTGCCACCCCGTATGTGGGCTTGGATTCATGGACTGGAGGAACTGGCTTCCGATGATGCCGGCGG
```

```
TCCTACCCCAAACCCTGCCCCGGCTTTGCTGCCCCCTCCTGCTACGGATCAATCTGTCCCCACTTCCCAATACGCCC
CTAGACCAATTGGCCCGGCTGCCACTGCTAGAGAAACTCGTCCTTCCGTTCCCCCTCAACAAAACACTGGTCGTGTC
CCTGTGGCTCCACGTGATGACCCTAGACCTTCCCCCCCTACTCCTTCCCCCCCTGCCGATGCTGCTTTGCCACCTCC
TGCCTTCTCTGGTTCTGCTGCTGCTTTCTCCGCTGCTGTTCCACGTGTTCGTCGTTCTAGGCGTACTCGTGCCAAAT
CCCGTGCCCCTCGTGCTTCTGCCCCACCCGAGGGATGCCGTCCCCCGCTTTGCCTGCCCCTGTTGCTCCTGTGGCG
GCTTCTGCTCGTCCCCCCGATCAACCTCCTACTCCCGAATCTGCTCCCCCGGCTTGGGTTTCCGCTCTGCCATTGCC
ACCCGGACCTGCTAGTGCTCGTGGTGCTTTCCCTGCTCCAACCTTGGCCCCTATTCCCCCACCCCCCGCTGAGGGAG
CTGTTGTTCCCGGTGGTGATCGTAGACGTGGTCGCCGTCAAACAACTGCTGGACCATCCCCTACACCGCCACGTGGC
CCGGCTGCTGGTCCTCCTCGTCGCCTCACTAGGCCTGCTGTTGCTAGTCTGTCCGCTTCTTTGAACTCTCTGCCTTC
CCCCCGTGATCCTGCCGATCATGCTGCTGCCGTTTCTGCTGCCGCCGCTGCCGTACCACCTTCACCTGGACTGGCTC
CCCCAACTTCTGCTGTCCAAACCTCTCCTCCTCCCTTGGCGCCTGGTCCTGTTGCCCCATCTGAACCTTTGTGTGGC
TGGGTTGTGCCTGGAGGCCCTGTTGCTAGACGTCCCCCACCCCAATCTCCGGCTACTAAACCGGCTGCTCGTACCCG
TATTAGGGCTCGTTCTGTGCCCCAACCACCCTTGCCCCAACCTCCACTGCCTCAACCCCCCTTGCCTCAACCCCCTC
TCCCCCAACCACCTCTGCCTCAACCTCCGCTGCCCCAACCTCCTTTGCCCCAACCTCCTTTGCCCCAACCTCCTTTG
CCCCAACCTCCGCTGCCCCAACCTCCGCTGCCACCTGTTACTCGTACACTCACTCCCCAATCTCGTGACTCTGTGCC
TACACCTGAGTCTCCAACTCACACAAACACCCACTTGCCCGTTAGTGCTGTGACTTCTTGGGCTTCGTCCCTGGCTC
TCCATGTGGATTCTGCCCCTCCCCCTGCTTCATTGCTCCAAACTCTCCACATTTCCTCCGATGATGAACACTCCGAC
GCCGACTCACTCCGCTTCTCCGATTCCGATGACACTGAGGCTCTCGATCCTTTGCCTCCTGAACCTCACTTGCCACC
TGCCGATGAACCCCCCGGACCTCTGGCTGCCGACCATCTCCAATCACCTCACTCACAATTCGGTCCTTTGCCCGTTC
AAGCGAACGCTGTTCTGTCTCGTCGTTACGTGAGATCAACTGGCCGTTCTGCCTTGGCTGTGCTCATTAGAGCTTGT
CGCCGTATCCAACAACAACTCCAGCGTACTAGGAGAGCACTCTTCCAACGCTCAAACGCCGTGCTCACATCACTCCA
CCATGTCCGTATGCTCTTGGGATAATAG

SEQ ID NO: 45 = nucleotide sequence for US12 (ICP47)
ATGTCTTGGGCTCTGAAAACCACCGACATGTTCCTGGACTCTTCTCGTTGCACCCACCGTACCTACGGTGACGTTTG
CGCTGAAATCCACAAACGTGAACGTGAAGACCGTGAAGCTGCTCGTACCGCTGTTACCGACCCGGAACTGCCGCTGC
TGTGCCCGCCGGACGTTCGTTCTGACCCGGCTTCTCGTAACCCGACCCAGCAGACCCGTGGTTGCGCTCGTTCTAAC
GAACGTCAGGACCGTGTTCTGGCTCCGTGA SEQ ID NO: 46 = nucleotide sequence for US4
ATGAAGTTCCTCGTGAACGTGGCCCTGGTGTTCATGGTGGTGTACATCAGCTACATCTACGCTAACCGTTGGGGTTC
CGGCGTGCCCGGTCCCATCAACCCCCCCAACTCCGACGTGGTTCCCCGGTGGTTCCCCCGTGGCTGCAGTACTGCT
ACGCTTACCCCCGTCTGGACGACCCTGGTCCCCTGGGTTCTGCTGACGCTGGTCGTCAGGACGTCTGCCCCGTCGTGTC
GTGCGTCACGAGCCCCTGGGTCGTAGCTTCCTGACCGGTGGCCTGGTGCTGTTGGCTCCCCCTGTGCGCGGTTTCGG
TGCTCCCAPCGCTACCTACGCTGCTCGTGTGACCTACTACCGTCTGACCCGTGCTTGCCGTCAGCCCATCCTGCTGC
GTCAGTACGGTGGTTGCCGTGGTGGAGAGCCCCCATCCCCCAAGACCTGCGGTTCTTACACCTACACCTACCAGGGT
GGTGGTCCCCCTACCCGTTACGCTCTGGTCAACGCTTCCCTGCTGGTGCCCATCTGGGACCGTGCTGCTGAGACTTT
CGAGTACCAGATCGAGCTGGGTGGCGAGCTGCACGTGGGTCTGCTGTGGGTGGAAGTGGGTGGAGAGGGTCCCGGTC
CTACCGCTCCTCCTCAGGCTGCTCGTGCTGAGGGTGGTCCTTGCGTGCCACCCGTGCCTGCTGGTCGTCCTTGGCGT
TCCGTGCCCCCCGTGTGGTACTCCGCTCCCAACCCCGGTTCCGCGGTCTGCGTTTCCGTGAGCGTTGCCTGCCTCC
CCAGACCCCTGCTGCTCCTTCCGACCTGCCTCGTGTGGCTTTCGCTCCCCAGTCCCTGCTGGGTATCACCGGTC
GTACCTTCATCCGTATGGCTCGTCCCACCGAGGACGTGGGTGTCCTGCCTCCTCACTGGGCTCCAGGTGCTCTGGAC
GACGGTCCCTACGCTCCCTTCCCCCCTCGTCCCCGTTTCCGTCGTCACCACCACCATCACCACTAATAA SEQ ID NO: 117 = RS1.2
ATGTCGTACTACCATCACCATCACCATCACATGGTGCTGTACGCGGGCTGGGCGACAGCCGCCCCGGCCTCTGGGG
GGCGCCCGAGGCGGAGGAGGCGCGGGCCCGGTTCGAGGCCTCGGGCGCCCCGGCGCCCGTGTGGGCGCCCGAGCTGG
GCGACGCGGCGCAGCAGTACGCCCTGATCACGCGGCTGCTGTACACGCCGGACGCGGAGGCGATGGGGTGGCTCCAG
AACCCGCGCTGGCGCCCGGGGACGTGGCGCTGGACCAGGCCTGCTTCCGGATCTCGGGCGCGGCGCAACAGCAG
CTCCTTCATCTCCGGCAGCGTGGCGCGGGCCGTGCCCCACCTGGGGTACGCCATGGCGGCGGGCCGCTTCGGCTGGG
GCCTGGCGCACGTGGCGGCCGCCGTGGCCATGAGCGCCGCTACGACGCGCGCAGAAGGGCTTCCTGCTGACCAGC
CTGCGCCGCGCCTACGCGCCCCTGCTGGCGCGCGAGAACGCGGCGCTGACCGGGCGCGGACCCCCGACGACGGCGG
CGACGCCAACGCCGCGGACGGCGACGACGCCGCGGGAAGCCCGCCGCCGCCGCCCGTTGCCGTCGGCGGCGG
CGTCGCCGGCCGACGAGCGCGCGGTGCCCGCCGGCTACGGCGCGCGGGGGTGCTCGCCGCCCTGGGCGCCTGAGC
GCCGCGCCCGCCTCCGCGCCGGCCGGGCCGACGACGACGACGACGACGACGACGGCGCCGGCGGTGGTGGCGGTGG
TGGCGGTGGTGGCGGCGGCCGGCGCGCGGAGGCGGGCCGCGTGGCCGTGGAGTGCCTGGCCGCCTGCCGCGGGATCC
TGGAGGCGCTGGCGGAGGGCTTCGACGGCGACCTGGCGGCCGTGCCGGGGCTGGCCGGAGCCGGCGGCGCGCGCGCG
CCGCGCCCGGGGCCCGCGGGCGCGGCCGCCCCGCCGCACGCCGACGCGCCCCGCCTGCGCGCCTGGCTGCGCGAGCT
GCGGTTCGTGCGCGACGCGCTGGTGCTGATGCGCCTGCGCGGGGACCTGCGCGTGGCCGGCGGCAGCGAGGCCGCCG
TGGCCGCCGTGCGCGCCGTGAGCCTGGTCGCCGGGGCCCTGGGCCCGGCGCTGCCGCGGAGCCCGCGCCTGCTGAGC
TCCGCCGCCGCCGCCGCGGACCTGCTCTTCCAGAACCAGAGCCTGAGTACTAGAGGATCATAA SEQ ID NO: 118 = UL1 (cytoplasmic), gL full length
ATGTCGTACTACCATCACCATCACCATCACATGGGGTTCGTCTGTCGTTTGGGCTTGTCGTTATGGGAGCCTGGGG
GGCGTGGGTGGGTCACAGGCAACCGAATATGTTCTTCGTAGTGTTATTGCCAAAGAGGTGGGGACATACTAAGAG
TGCCTTGCATGCGGACCCCCGGACGATGTTTCTTGGCGCTGGAGGCCCCGTCCGTTATTGACTATGCCGCATA
GACGGAATATTTCTTCGCTATCACTGCCCGGGGTTGGACACGTTTTTGTGGGATAGGCACGCCCAGAGGGCGTATCT
TGTTAACCCCTTTCTCTTTGCGGCGGGATTTTTGGAGGACTTGAGTCACTCTGTGTTTCCGGCCGACACCCAGGAAA
CAACGACGCGCCGGGCCCTTTATAAAGAGATACGCGATGCGTTGGGCAGTCGAAAACAGGCCGTCAGCCACGCACCC
GTCAGGGCCGGGTGTGTAAACTTTGACTACTCACGCACTCGCCGCTGCTCGGGCGACGCGATTTACGGCCTGCCAA
CACCACGTCAACGTGGGAACGCCTGTGTCGTCGGACGATGAAGCGAGCTCGCAGTCGAAGCCCTCGCCACCCAGC
CGCCCGTCCTCGCCCTTTCGAACGCCCCCCACGGCGGGTCTCCCCGACGCGAGGTCGGCGCCGGCATACTCGCCTC
CGACGCAACTGA SEQ ID NO: 119 = UL1 (Secreted), gL full length (preferred Ag)
ATGAAGTTCCTCGTGAACGTGGCCCTGGTGTTCATGGTGGTGTACATCAGCTACATCTACGCTAACCGTTGGGGGTT
CGTCTGTCTGTTTGGGCTTGTCGTTATGGGAGCCTGGGGGGCGTGGGTGGGTCACAGGCAACCGAATATGTTCTTC
```

| Sequences |
|---|
| GTAGTGTTATTGCCAAAGAGGTGGGGGACATACTAAGAGTGCCTTGCATGCGGACCCCCGCGGACGATGTTTCTTGG<br>CGCTACGAGGCCCCGTCCGTTATTGACTATGCCCGCATAGACGGAATATTTCTTCGCTATCACTGCCCGGGGTTGGA<br>CACGTTTTTGTGGGATAGGCACGCCCAGAGGGCGTATCTTGTTAACCCCTTTCTCTTTGCGGCGGATTTTTGGAGG<br>ACTTGAGTCACTCTGTGTTTCCGGCCGACACCCAGGAAACAACGACGCGCCGGGCCCTTTATAAAGAGATACGCGAT<br>GCGTTGGGCAGTCGAAAACAGGCCGTCAGCCACGCACCCGTCAGGGCCGGGTGTGTAAACTTTGACTACTCACGCAC<br>TCGCCGCTGCGTCGGGCGACGCGATTTACGGCCTGCCAACACCACGTCAACGTGGGAACCGCCTGTGTCGTCGGACG<br>ATGAAGCGAGCTCGCAGTCGAAGCCCCTCGCCACCCAGCCGCCCGTCCTCGCCCTTTCGAACGCCCCCCACGGCGG<br>GTCTCCCCGACGCGAGGTCGGCGCCGGCATACTCGCCTCCGACGCAACCATCACCATCACCATCACTGA |

SEQ ID NO: 120 UL19 delta TEV VP5 full length
ATGTCGTACTACCATCACCATCACCATCACATGGCCGCTCCTGCCCGCGACCCCCGGGTTACCGGTACGCCGCGGC
CATGGTGCCCACCGGCTCCATCCTGAGTACGATCGAGGTGGCGTCCCACCGCAGACTCTTTGATTTTTTCGCCCGCG
TGCGCTCCGACGAAAACAGCCTGTATGACGTAGAGTTTGACGCCCTGCTGGGGTCCTACTGCAACACCCTGTCGCTC
GTGCGCTTTCTGGAGCTCGGCCTGTCCGTGGCGTGCGTGTGCACCAAGTTCCCGGAGCTGGCTTACATGAACGAAGG
GCGTGTGCAGTTCGAGGTCCACCAGCCCCTCATCGCCCGCGACGGCCCGCACCCCGTCGAGCAGCCCGTGCATAATT
ACATGACGAAGGTCATCGACCGCCGGGCCCTGAACGCCGCCTTCAGCCTGGCCACCGAGGCCATTGCCCTGCTCACG
GGGGAGGCCCTGGACGGGACGGGCATTAGCCTGCATCGCCAGCTGCGCGCCATCCAGCAGCTCGCGCGCAACGTCCA
GGCCGTCCTGGGGGCGTTTGAGCGCGGCACGGCCGACCAGATGCTGCACGTGCTGTTGGAGAAGGCGCCTCCCCTGG
CCCTGCTGTTGCCCATGCAACGATATCTCGACAACGGGCGCCTGGCGACCAGGGTTGCCCGGGCGACCCTGGTCGCC
GAGCTGAAGCGGAGCTTTTGCGACACGAGCTTCTTCCTGGCGAAGGCGGGCCATCGCCGCGAGGCCATCGAGGCCTG
GCTCGTGGACCTGACCACGGCGACGCAGCCGTCCGTGGCCGTGCCCCGCCTGACGCACGCCGACACGCGCGGGCGGC
CGGTCGACGGGGTGCTGGTCACCACCGCCGCCATCAAACAGCGCCTCCTGCAGTCCTTCCTGAAGGTGGAGGACACC
GAGGCCGACGTGCCGGTGACCTACGGCGAGATGGTCTTGAACGGGGCCAACCTCGTCACGGCGCTGGTGATGGGCAA
GGCCGTGCGGAGCCTGGACGACGTGGGCCGCCACCTGCTGGAGATGCAGGAGGGAGCAACTCGAGGCGAACCGGGAGA
CGCTGGATGAACTCGAAAGCGCCCCCCAGACAACGCGCGTGCGCGCGGATCTGGTGGCCATAGGCGACAGGCTGGTC
TTCCTGGAGGCCCTGGAGAAGCGCATCTACGCCGCCACCAACGTGCCCTACCCCCTGGTGGGCGCCATGGACCTGAC
GTTCGTCCTGCCCCTGGGGCGTGTTCAPCCCGGCCATGGAGCGCTTCGCCGCGCACGCCGGGGACCTGGTGCCCGCCC
CCGGCCACCCGGAGCCCCGCGCGTTCCCTCCCCGGCAGCTGTTTTTTTTGGGGAAAGGACCACCAGGTTCTGCGGCTG
TCCATGGAGAACGCGGTCGGGACCGTGTGTCATCCTTCGCTCATGAACATCGACGCGGCCGTCGGGGGCGTGAACCA
CGACCCCGTCGAGGCCGCGAATCCGTACGGGGCGTACGTCGCGGCCCCGGCCGGCCCCGGCGCGGACATGCAGCAGC
GTTTTCTGAACGCCTGGCGGCAGCGCCTCGCCCACGGCCGGGTCCGGTGGGTCGCCGAGTGCCAGATGACCGCGGAG
CAGTTCATGCAGCCCGACAACGCCAACCTGGCTCTGGAGCTGCACCCCGCGGTTCGACTTCTTCGCGGGCGTGGCCGA
CGTCGAGCTTCCCGGCGGCGAAGTCCCCCCGGCCGGTCCGGGGGCGATCCAGGCCACCTGGCGCGTGGTCAACGGCA
ACCTGCCCCTGGCGCTGTGTCCGGTGGCGTTTCGTGACGCCCGGGGCCTGGAGCTCGGCGTTGGCCGCCACGCCATG
GCGCCGGCTACCATAGCCGCCGTCCGCGGGGCGTTCGAGGACCGCAGCTACCCGGCGGTGTTCTACCTGCTGCAAGC
CGCGATTCACGGCAGCAGCGAGCACGTGTTCTGCGCCCTGGCGCGGCTCGTGACTCAGTGCATCACCAGCTACTGGAACA
ACACGCGATGCGCGGCGTTCGTGAACGACTACTCGCTGGTCTCGTACATCGTGACCTACCTCGGGGGCGGACCTCCCC
GAGGAGTGCATGGCCGTGTATCGGGACCTGGTGGCCCACGTCGAGGCCCTGGCCAGCTGGTGGACGACTTTACCCT
GCCGGGCCCGGAGCTGGGCGGGCAGGCTCAGGCCGAGCTGAATCACCTGATGCGCGACCCGGCGCTGCTGCCGCCCC
TCGTGTGGGACTGCGACGGCCTTATGCGACACGCGGCCCTGGACCGCCACCGAGACTGCCGGATTGACGCGGGGGAG
CACGAGCCCGTCTACGCGGCGGCGTGCAACGTGGCGACGGCCGACTTTAACCGCAACGACGGCCGGCTGCTGCACAA
CACCCAGGCCCGCGCGGCCGACGCCGCCGACGACCGGCCGCACCGGCCGGCCGACTGGACCGTCCACCACAAAATCT
ACTATTACGTGCTGGTGCCGGCCTTCTCGCGGGGGCGCTGCTGCACCGCGGGGGTCCGCTTCGACCGCGTGTACGCC
ACGCTGCAGAACATGGTGGTCCCGGAGATCGCCCCCGGCGAGGAGTGCCCGAGCGATCCCGTGACCGACCCCGCCCA
CCCGCTGCATCCCGCCAATCTGGTGGCCAACACGGTCAACGCCATGTTCCACAACGGGCGCGTGCGTCGTCGACGGGC
CCGCCATGCTCACGCTGCAGGTGCTGGCGCACAACATGGCCGAGCGCACGGCGCTGCTGTGCTCCGCGGCGCCCC
GACGCGGGCGCCAACACCGCGTCGACGGCCAACATGCGCATCTTCGACGGGGCGCTGCACGCCGGCGTGCTGCTCAT
GGCCCCCCAGCACCTGGACCACACCATCCAAAATGGCGAATACTTCTACGTCCTGCCCGTCCACGCGCTGTTTGCGG
GCGCCGACCACGTGGCCAACGCGCCCAACTTCCCCCCGGCCCTGCGCGACCCACGAACAGGGCTGGCGCGCCACGTCCCCCTGGTCCCC
CCGGCCCTGGGGGCCAACTACTTCTCCTCCATCCGCCAGCCCGTGGTGCAGCACGCCCGCGAGAGCGCGGCGGGGGA
GAACGCGCTGACCTACGCGCTCATGGCGGGGTACTTCAAGATGAGCCCCGTGGCCCTGTATCACCAGCTCAAGACGG
GCCTCCACCCCGGGTTCGGGTTCACCGTCGTGCGGCAGGACCGCTTCGTGACCGAGAACGTGCTGTTTTCCGAGCGC
GCGTCGGAGGCGTACTTTCTGGGCCAGGCTCCAGGTGGCCCGCCACGAAACGGGCGGGGGGGTCAGCTTCACGCTCAC
CCAGCCGCGCGAAACGTGGACCTGGGTGTGGGCTACACCGCCGTCGCGGCCACGGCCACCGTCCGCAACCCCGTTA
CGGACATGGCAACCTCCCCCAAAACTTTTACCTCGGCCGCGGGGCCCCCCGCTGCTAGACAACGCGGCCGCCGTG
TACCTGCGCAACGCGGTCGTGGCGGGAAACCGGCTGGGGCCGGCCCAGCCCCTCCCGGTCTTTGGCTGCGCCCAGGT
GCCGCGGCGCGGCCATGGACCACGGGCAGGATGCCGTGTGTGAGTTCATCGCCACCCCCGTGGCCACGGACATCA
ACTACTTTCGCCGGCCCTGCAACCCGCGGGGACGCGCGGCCGGCGGCGTGTACGGGGGACAAGGAGGGGGACGTC
ATAGCCCTCATGTACGACCACGGCCAGAGCGACCCGGCGCGGCCCTTCGCGGCCACGGCCAACCCGTGGGCGTCGCA
GCGGTTCTCGTACGGGGACCTGCTGTACAACGGGGCCTATCACCTCAACGGGGCCTCGCCCGTCCTCAGCCCCTGCT
TCAAGTTCTTCACCGCGGCCGACATCACGGCCAAACATCGCTGCCTGGACGCGCTTCATCGTGGAAACGGGATCGCG
GTATCCACGGCCACCGCTGCCAGCGACGTGCAGTTTAAGCGCCCGCCGGGGTGCCGCGAGCTCGTGGAAGACCCGTG
CGGCCTGTTTCAGGAAGCCTACCCGATCACCTGCGCCAGCGACCCCGCCCTGCTACGAGCGCCCGCGATGGGGAGG
CCCACGCGCGAGAGACCCACTTTACGCAGTATCTCATCTACGACGCCTCCCGCTAAAGGGCCTGTCTCTGTAA SEQ ID NO: 121 = RS1.1
Atgagtgccgaacagcgtaaaaagaaaaaaaccaccaccacgacccaaggacgtggagctgaagttgctatggcgga
tgaggatggaggccgcttgagagctgctgctgagactactggaggacctggatcaccggaccctgccgatggacccc
cccctacaccaaaccccgatcgtagaccggctgctagacctggattcggatggcatggaggacccgaggaaaacgag
gacgaggcggacgacgccgctgccgacgccgacgccgatgaggctgcccctgcttctggagaggcggtagacgaacc
tgctgccgatggagttgttagccctaggcaattggctttgttggcgagcatggtagacgaggctgtgagaacaatcc
cttcccctcccctgaacgtgatggagcacaagaggaggcggctaggagtccctcaccacccgtacaccttctatg
agagcggattacggcgaggaaaacgacgacgacgacgatgatgatgacgacgatgatcgtgatgccgacgctgggt
tagggggacctgaaaccacttctgctgtccgtggagcataccccgatcctatggcgagtttgagccctagaccacctg
ccccgaggagacaccaccaccaccaccatcataggcgtagacgtgctcctagacgtcgttctgccgctagtgactct
tccaaatctggctcttcttcatctgcctcttccgcttcatcttcggcctcatcgtcctcttcggcatccgcttcgag
tagtgatgatgatgatgacgacgacgctgctagagccccccgcttctgctgccgaccacgctgctggcggaacttttg

| Sequences |
|---|
| gagccgacgacgaggaggcgggagttcctgctcgtgccccgggagctgctccgaggccttctccaccccgtgctgaa<br>cctgctccggctagaacaccggccgctactgctggtagactggagcgtagacgtgcccgtgctgctgtggctggtag<br>agatgctactggccgcttcactgctggccgtcctagacgtgttgaactggacgccgatgctgcttctggtgctttct<br>acgcccgttaccgtgatggttacgtgtctggtgaaccttggcctggcgctggtccacctccgcccggacgtgtactc<br>tacggtggattgggcgattctcgccctggtctgtggggcgctccg<br><br>SEQ ID NO: 122 = RS1.3.1<br>tcgagtgccgccgctgctgccgccgatttgttgttccaaaaccaatccctccgccctctgctcgccgacactgttgc<br>cgctgccgattctctggctgctccggcttctgccccacgtgaagctcgtaaacgtaaatcacccgctccggctcgtg<br>ctccccctggtggcgccccctagacccctaaaaaatcccgtgccgatgcccctagacctgctgctgctcccccgct<br>ggtgctgctcccccgctcccctactcccccccacgcccacctcgtcccgctgccctcacacgccgtcctgctga<br>gggacccgatccacaaggcggctggcgtagacaacctcctggcccatcccataccggcaccatctgccgctgctt<br>tggaggcttactgtgctcctcgtgctgtggctgaactcaccgatcatccgctgttccctgctccctggcgtcccgcc<br>ctcatgttcgatcctagagctttggcttccttggccgctcgttgtgctgcccctcccctggcggtgctccggctgc<br>tttcggtcctctccgtgcctctggtccactccgccgtgccgctgcctggatgagacaagttcccgaccctgaggatg<br>ttagagttgtgatcttgtactcgcccttgcctggcgaggatttggccgctggtagagctggcggtggcccccctcct<br>gaatggtctgctgaacgtggtggtttgtcttgcttgttggccgccctgggaaacgtctgtgtggtcctgctactgc<br>tgcttgggctggaaactggactggcgctcccgatgtttctgctctcggtgctcaa<br><br>SEQ ID NO: 123 = RS1.3.2<br>Tgggctggaaactggactggcgctcccgatgtttctgctctcggtgctcaaggagttttgctgctctctactcgtga<br>cttggcattcgctggagctgttgaattcctgggactcttggctggcgcttgtgataggagactcatcgtcgtaaacg<br>ctgtgagagctgccgattggcctgccgatggtcctgttgtgtctcgtcaacacgcttacttggcttgtgaagtgttg<br>cccgctgtccaatgtgctgttcgctggcctgctgtcgtgatctgaggcgtactgttctggctagtggtcgtgttt<br>cggacctggtgttttcgctcgtgtcgaagctgctcacgctagactgtaccccgatgccccacccctccgtttgtgtc<br>gtggagcaaacgttcgctaccgtgtccgtactcgtttcggacccgatactctggttccaatgtccctcgtgaatac<br>cgtcgtgctgttctgcctgccctcgatggacgtgctgccgcttctggcgctggtgacgctatggctcctggcgctcc<br>ggacttctgtgaggatgaggctcactcacatcgtgcctgtgcccgctggggactgggcgctccattgaggcctgtat<br>acgtggcactgggccgtgatgctgttagaggcggacccgctgaattgagaggccctcgtcgtgaattctgtgctagg<br>gctctgctcgaaccgatggagatgctcctcctttggtactccgtgacgacgccgatgctggtcctcccccacaaat<br>tcgctgggctagtgctgctggacgtgctggtactgtattggctgctgctggcggtggcgttgaagttgttggtactg<br>ccgctggactcgctacacctccccgccgtgaacctgtagacatggatgctgaactcgaggatgatgacgacggattg<br>ttcggagag<br><br>SEQ ID NO: 124 = RS1.3<br>tcgagtgccgccgctgctgccgccgatttgttgttccaaaaccaatccctccgccctctgctcgccgacactgttgc<br>cgctgccgattctctggctgctccggcttctgccccacgtgaagctcgtaaacgtaaatcacccgctccggctcgtg<br>ctccccctggtggcgccccctagacccctaaaaaatcccgtgccgatgcccctagacctgctgctgctcccccgct<br>ggtgctgctcccccgctcccctactcccccccacgcccacctcgtcccgctgccctcacacgccgtcctgctga<br>gggacccgatccacaaggcggctggcgtagacaacctcctggcccatcccataccggcaccatctgccgctgctt<br>tggaggcttactgtgctcctcgtgctgtggctgaactcaccgatcatccgctgttccctgctccctggcgtcccgcc<br>ctcatgttcgatcctagagctttggcttccttggccgctcgttgtgctgcccctcccctggcggtgctccggctgc<br>tttcggtcctctccgtgcctctggtccactccgccgtgccgctgcctggatgagacaagttcccgaccctgaggatg<br>ttagagttgtgatcttgtactcgcccttgcctggcgaggatttggccgctggtagagctggcggtggcccccctcct<br>gaatggtctgctgaacgtggtggtttgtcttgcttgttggccgccctgggaaacgtctgtgtggtcctgctactgc<br>tgcttgggctggaaactggactggcgctcccgatgtttctgctctcggtgctcaaggagttttgctgctctctactc<br>gtgacttggcattcgctggagctgttgaattcctgggactcttggctggcgcttgtgataggagactcatcgtcgta<br>aacgctgtgagagctgccgattggcctgccgatggtcctgttgtgtctcgtcaacacgcttacttggcttgtgaagt<br>gttgcccgctgtccaatgtgctgttcgctggcctgctgtcgtgatctgaggcgtactgttctggctagtggtcgtg<br>ttttcggacctggtgttttcgctcgtgtcgaagctgctcacgctagactgtaccccgatgccccacccctccgtttg<br>tgtcgtggagcaaacgttcgctaccgtgtccgtactcgtttcggacccgatactctggttccaatgtccctcgtga<br>ataccgtcgtgctgttctgcctgccctcgatggacgtgctgccgcttctggcgctggtgacgctatggctcctggcg<br>ctccggacttctgtgaggatgaggctcactcacatcgtgcctgtgcccgctggggactgggcgctccattgaggcct<br>gtatacgtggcactgggccgtgatgctgttagaggcggacccgctgaattgagaggccctcgtcgtgaattctgtgc<br>tagggctctgctcgaaccgatggagatgctcctcctttggtactccgtgacgacgccgatgctggtcctcccccac<br>aaattcgctgggctagtgctgctggacgtgctggtactgtattggctgctgctggcggtggcgttgaagttgttggt<br>actgccgctggactcgctacacctccccgccgtgaacctgtagacatggatgctgaactcgaggatgatgacgacgg<br>attgttcggagag<br><br>SEQ ID NO: 125 = RS1.4<br>actgctggccgtcctagacgtgttgaactggacgccgatgctgcttctggtgctttctacgcccgttaccgtgatgg<br>ttacgtgtctggtgaaccttggcctggcgctggtccacctccgcccggacgtgtactctacggtggattgggcgatt<br>ctcgccctggtctgtggggcgctccggaggctgaggaggctagagcccgtttcgaggcttctggtgccctgctcct<br>gtttgggctcctgaattgggcgacgctgctcaacaatacgccctcatcacacgcttgctgtacactcccgacgcga<br>ggctatgggatggctccaaaacccctagagttgcccctggtgatgttgctctggatcaggcttgtttccgtatctccg<br>gcgctgctcgtaactcttcttcgttcatctccggttctgtggctagagtcgtgcctcacttgggatacgccatggcc<br>gctggacgtttcggctggggactggctcatgttgctgccgctgcaatgtctagacgctacgaccgtgctcaaaa<br>aggattcttgctcacgtcactgaggcgtgcttacgcccctttgttggcccgtgaaaacgctgccctcactggcgccc<br>gtaccccgatgacggtggcgacgccaaccgccacgatggtgatgatgctagaggcaaaccgctgccgctgctgct<br>cctttgccctctgccgccgcttcccctgccgatgaacgtgctgttcctgccggttacggtgccgctggtgtgttggc<br>tgctttgggacgcttgagtgctgccccggctagtgcccccgctggtgccgatgacgatgacgatgacgatggtgctg<br>gcggaggcggtggcggtagacgtgctgaggctgaggcgtgttgctgttgaatgctggctgcctgtagaggaatcttg<br>gaggctctggccgagggattcgacggagacttggcggctgtaccgggactggcgggagcgaggcctgccgctccacc<br>tcgcccggtcctgctggtgctgccgctcctcctcatgccgacgctcctagactccgtgcttggcctcgtgaactcc<br>gtttcgttcgtgacgctttggttctgatgagactgagaggcgacttgagagtggctggaggatccgaggctgctgtt<br>gctgctgtccgtgctgtttctttggttgctggtgctttgggccctgctttgccgagatctccccgtttgttgtcgag<br>tgccgccgctgctgccgccgatttgttgttccaaaaccaatccctccgccctctgctcgccgacactgttgccgctg |

| Sequences |
|---|
| ccgattctctggctgctccggcttctgccccacgtgaagctcgtaaacgtaaatcaccgctccggctcgtgctccc |
| cctggtggcgccccctagaccccctaaaaaatcccgtgccgatgcccctagacctgctgctgctcccccgctggtgc |
| tgctcccccgctcccctactcccccccacgcccacctcgtcccgctgccctcacacgccgtcctgctgagggac |
| ccgatccacaaggcggctggcgtagacaacctcctggcccatcccatacaccggcaccatctgccgctgctttggag |
| gcttactgtgct |

SEQ ID NO: 126 = RS1.5
gccgctgccgattctctggctgctccggcttctgccccacgtgaagctcgtaaacgtaaatcaccgctccggctcg
tgctcccccggtggcgccccctagaccccctaaaaaatcccgtgccgatgcccctagacctgctgctgctcccccg
ctggtgctgctcccccgctcccctactcccccccacgcccacctcgtcccgctgccctcacacgccgtcctgct
gagggacccgatccacaaggcggctggcgtagacaacctcctggcccatcccatacaccggcaccatctgccgctgc
tttggaggcttactgtgctcctcgtgctgtggctgaactcaccgatcatccgctgttccctgctccctggcgtcccg
ccctcatgttcgatcctagagctttggcttccttggccgctcgttgtgctgcccctcccctggcggtgctccggct
gctttcggtcctctccgtgcctctggtccactccgccgtgccgctgcctggatgagacaagttcccgaccctgagga
tgttagagttgtgatcttgtactcgcccttgcctggcgaggatttggccgctggtagagctggcggtggccccctc
ctgaatggtctgctgaacgtggtggtttgtcttgcttgttggccgccctggggaaacgtctgtgtggtcctgctact
gctgcttgggctggaaactggactggcgctcccgatgtttctgctctcggtgctcaaggagttttgctgctctctac
tcgtgacttggcattcgctggagctgttgaattcctgggactcttggctggcgcttgtgataggagactcatcgtcg
taaacgctgtgagagctgccgattggcctgccgatggtcctgttgtgtctcgtcaacacgcttacttggcttgtgaa
gtgttgcccgctgtccaatgtgctgttcgctggcctgctgctcgtgatctgaggcgtactgttctggctagtggtcg
tgtttcggacctggtgttttcgctcgtgtcgaagctgctcacgctagactgtaccccgatgccccaccctccgtt
tgtgtcgtggagcaaacgttcgctaccgtgtccgtactcgtttcggacccgatactctggttccaatgtccctcgt
gaataccgtcgtgctgttctgcctgccctcgatggacgtgctgccgcttctggcgctggtgacgctatggctcctgg
cgctccggacttctgtgaggatgaggctcactcacatcgtgcctgtgcccgctgggactgggcgctccattgagc
ctgtatacgtggcactgggccgtgatgctgttagaggcggaccccgctgaattgagaggccctcgtcgtgaattctgt
gctagggctctgctcgaacccgatggagatgctcctcctttggtactccgtgacgacgccgatgctggtcctccccc
acaaattcgctgggctagtgctgctggacgtgctggtactgtattggctgctgctggcggtggcgttgaagttgttg
gtactgccgctggactcgctacacctccccgccgtgaacctgtagacatggatgctgaactcgaggatgatgacgac
ggattgttcggagag SEQ ID NO: 127 = RS1.6
caccaccaccaccaccatcataggcgtagacgtgctcctagacgtcgttctgccgctagtgactcttccaaatctgg
ctcttcttcatctgcctcttccgcttcatcttcggcctcatcgtcctcttcggcatccgcttcgagtagtgatgatg
atgatgacgacgacgcgtgctagagccccgcttctgctgccgaccacgctgctggcggaactttgggagccgacgac
gaggaggcgggagttcctgctcgtgccccgggagctgctccgaggccttctccaccccgtgctgaacctgctccggc
tagaacaccggccgctactgctggtagactggagcgtagacgtgcccgtgctgctgtggctggtagagatgctactg
gccgcttcactgctggccgtcctagacgtgttgaactggacgccgatgctgcttctggtgctttctacgccgttac
cgtgatggttacgtgtctggtgaacctttggcctggcgctggtccacctccgcccggacgtgtactctacggtggatt
gggcgattctcgccctggtctgtggggcgctccggaggctgaggaggctagagcccgtttcgaggcttctggtgcc
ctgctcctgtttgggctcctgaattgggcgacgctgctcaacaatacgccctcatcacacgcttgctgtacactccc
gacgccgaggctatgggatggctccaaaaccctagagttgccctggtgatgttgctctggatcaggcttgtttccg
tatctccggcgctgctcgtaactcttcttcgttcatctccggttctgtggctagagctgtgcctcacttgggatacg
ccatggccgctggacgtttcggctggggactggctcatgttgctgccgctgtagcaatgtctagacgctacgaccgt
gctcaaaaggattcttgctcacgtcactgaggcgtgcttacgccccttgttggcccgtgaaaacgctgccctcac
tggccgcccgtaccccgatgacggtggcgacgccaaccgccacgatggtgatgatgctagaggcaaacccgctgccg
ctgctgctcctttgccctctgccgccgcttccctgccgatgaacgtgctgttcctgccggttacggtgccgctggt
gtgttggctgctttgggacgcttgagtgctgccccggctagtgccccgctggtgccgatgacgatgacgatgacga
tggtgctggcggaggcggtggcggtagacgtgctgaggctggacgtgttgctgttgaatgcctggctgcctgtagag
gaatcttggaggctctggccgagggattcgacggagacttggcgctgctaccgggactggcgggagcgaggcctgcc
gctccacctcgcccggtcctgctggtgctgccgctcctcctcatgccgacgctcctagactccgtgcttggctccg
tgaactccgtttcgttcgtgacgctttggttctgatgagactgagaggcgacttgagagtggctggaggatccgagg
ctgctgttgctgctgtccgtgctgtttctttggttgctggtgctttgggccctgctttgccgagatctcccgttttg
ttgtcgagtgccgccgctgctgccgccgatttgttgttccaaaaccaatccctccgccctctgctcgccgacactgt
tgccgctgccgattctctggctgctccggcttctgccccacgtgaagctcgtaaacgtaaatcaccgctccggctc
gtgctcccctggtggcgccccctagaccccctaaaaaatcccgtgccgatgcccctagacctgctgctgctcccccc
gctggtgctgctcccccgctcccctactcccccccacgcccacctcgtcccgctgccctcacacgccgtcctgc
tgagggacccgatccacaaggcggctggcgtagacaacctcctggcccatcccatacaccggcaccatctgccgctg
ctttggaggcttactgtgctcctcgtgctgtggctgaactcaccgatcatccgctgttccctgctccctggcgtccc
gccctcatgttcgatcctagagctttggcttccttggccgctcgttgtgctgcccctcccctggcggtgctccggc
tgctttcggtcctctccgtgcctctggtccactccgccgtgccgctgcctggatgagacaagttcccgacctgagg
atgttagagttgtgatcttgtactcgcccttgcctggcgaggatttggccgctggtagagctggcggtggccccct
cctgaatggtctgctgaacgtggtggtttgtcttgcttgttggccgccctggggaaacgtctgtgtggtcctgctac
tgctgcttgggctggaaactggactggcgctcccgatgtttctgctctcggtgctcaaggagttttgctgctctcta
ctcgtgacttggcattcgctggagctgttgaattcctgggactcttggctggcgcttgtgataggagactcatcgtc
gtaaacgctgtgagagctgccgattggcctgccgatggtcctgttgtctcgtcaacacgcttacttggcttgtga
agtgttgcccgctgtccaatgtgctgttcgctggcctgctgctcgtgatctgaggcgtactgttctggctagtggtc
gtgtttcggacctggtgttttcgctcgtgtcgaagctgctcacgctagactgtaccccgatgccccaccctccgt
ttgtgtcgtggagcaaacgttcgctaccgtgtccgtactcgtttcggacccgatactctggttccaatgtccctcg
tgaataccgtcgtgctgttctgcctgccctcgatggacgtgctgccgcttctggcgctggtgacgctatggctcctg
gcgctccggacttctgtgaggatgaggctcactcacatcgtgcctgtgcccgctgggactgggcgctccattgagg
cctgtatacgtggcactgggccgtgatgctgttagaggcggaccccgctgaattgagaggccctcgtcgtgaattctg
tgctagggctctgctcgaacccgatggagatgctcctcctttggtactccgtgacgacgccgatgctggtcctcccc
cacaaattcgctgggctagtgctgctggacgtgctggtactgtattggctgctgctggcggtggcgttgaagttgtt
ggtactgccgctggactcgctacacctccccgccgtgaacctgtagacatggatgctgaactcgaggatgatgacga
cggattgttcggagagtaa Sequences SEQ ID NO: 128 = RS1.7
atgagtgccgaacagcgtaaaaagaaaaaaaccaccaccacgacccaaggacgtggagctgaagttgctatggcgga
tgaggatggaggccgcttgagagctgctgctgagactactggaggacctggatcaccggaccctgccgatggacccc
ccctacaccaaacccgatcgtagaccggctgctagacctggattcggatggcatggaggacccgaggaaaacgag
gacgaggcggacgacgccgctgccgacgccgacgccgatgaggctgcccctgcttctggagaggcggtagacgaacc
tgctgccgatggagttgttagcccataggcaattggctttgttggcgagcatggtagacgaggctgtgagaacaatcc
cttcccctcccctgaacgtgatggagcacaagaggaggcggctaggagtccctcaccaccccgtacaccttctatg
agagcggattacggcgaggaaaacgacgacgacgacgatgatgatgacgacgatgatcgtgatgccggacgctgggt
taggggacctgaaaccacttctgctgtccgtggagcatacccgatcctatggcgagtttgagcctagaccacctg
ccccgaggagacaccaccaccaccaccatcataggcgtagacgtgctcctagacgtcgttctgccgctagtgactct
tccaaatctggctcttcttcatctgcctcttccgcttcatcttcggcctcatcgtcctcttcggcatccgcttcgag
tagtgatgatgatgatgacgacgacgctgctagagccccgcttctgctgccgaccacgctgctggcggaactttgg
gagccgacgacgaggaggcgggagttcctgctcgtgccccgggagctgctccgaggccttctccaccccgtgctgaa
cctgctccggctagaacaccggccgctactgctggtagactggagcgtagacgtgcccgtgctgctgtggctggtag
agatgctactggccgcttcactgctggccgtcctagacgtgttgaactggacgccgatgctgcttctggtgctttct
acgcccgttaccgtgatggttacgtgtctggtgaaccttggcctggcgctggtccacctccgcccggacgtgtactc
tacggtggattgggcgcccgtaccccgatgacggtggcgacgccaaccgccacgatggtgatgatgctagaggcaa
acccgctgccgctgctgctcctttgccctctgccgccgcttccctgccgatgaacgtgctgttcctgccggttacg
gtgccgctggtgtgttggctgcttttgggacgcttgagtgctgccccggctagtgccccgctggtgccgatgacgat
gacgatgacgatggtgctggcggaggcggtggcggtagacgtgctgaggctggacgtgttgctgttgaatgcctggc
tgcctgtagaggaatcttggaggctctggccgagggattcgacggagacttggcggctgtaccgggactggcggagag
cgaggcctgccgctccacctcgccccggtcctgctggtgctgccgctcctcctcatgccgacgctcctagactccgt
gcttggctccgtgaactccgtttcgttcgtgacgctttggttctgatgagctgagaggcgacttgagagtggctgg
aggatccgaggctgctgttgctgtgctccgtgctgtttcttggttgctggtgctttgggccctgctttgccgagat
ctccccgtttgttgtcgagtgccgccgctgctgccgccgatttgttgttccaaaaccaatccctccgccctctgctc
gccgacactgttgccgctgccgattctctggctgctccgcttctgccccacgtgaagctcgtaaacgtaaatcacc
cgctccggctcgtgctcccctggtggcgcccctagaccccctaaaaaatcccgtgccgatgcccgtgccctagacctgctg
ctgctccccgctggtgctgctccccccgctcccctactccccccacgccacctcgtcccgctgccctcaca
cgccgtcctgctgagggacccgatccacaaggcggctggcgtagacaacctcctggcccatcccatacaccggcacc
atctgccgctgcttggaggcttactgtgctcctcgtgctgtggctgaactcaccgatcatccgctgttccctgctc
cctgcgtcccgccctcatgttcgatcctagagctttggcttccttggccgctcgttgtgctgccccctcccctggc
ggtgctccggctgctttcggtcctctccgtgcctctggtccactccgcgtgccgctgcctgcctggatgagacaagttcc
cgacctgaggatgttagagttgtgatcttgtactcgcccttgcctggcgaggatttggccgctggtagagctggcg
gtggcccccctcctgaatggtctgctgaacgtggtggtttgtcttgcttgttggccgccctgggaaaccgtctgtgt
ggtcctgctactgctgcttgggctggaaactggactggcgctcccgatgtttctgctctcggtgctcaaggagtttt
gctgctctctactcgtgacttggcattcgctggagctgttgaattcctgggactcttggctggccgatactctggttcca
atgtccctcgtgaataccgtcgtgctgttctgcctgccctcgatggacgtgctgccgcttctggcgctggtgacgc
tatggctcctggcgctccggacttctgtgaggatgaggctcactcacatcgtgcctgtgcccgctggggactgggcg
ctccattgaggcctgtatacgtggcactgggccgtgatgctgttagaggcggacccgctgaattgagaggccctcgt
cgtgaattctgtgctagggctgtctcgaacccgatggagatgctctccttggtactccgtgacgacgccgatgc
tggtcctcccccacaaattcgctgggctagtgctgctggacgtgctggtactgtattggctgctgctggcggtggcg
ttgaagttgttggtactgccgctggactcgctacacctcccgccgtgaacctgtagacatggatgctgaactcgag
gatgatgacgacggattgttcggagag SEQ ID NO: 129 = RS1.8
atgagtgccgaacagcgtaaaaagaaaaaaaccaccaccacgacccaaggacgtggagctgaagttgctatggcgga
tgaggatggaggccgcttgagagctgctgctgagactactggaggacctggatcaccggaccctgccgatggacccc
ccctacaccaaacccgatcgtagaccggctgctagacctggattcggatggcatggaggacccgaggaaaacgag
gacgaggcggacgacgccgctgccgacgccgacgccgatgaggctgcccctgcttctggagaggcggtagacgaacc
tgctgccgatggagttgttagcccataggcaattggctttgttggcgagcatggtagacgaggctgtgagaacaatcc
cttcccctcccctgaacgtgatggagcacaagaggaggcggctaggagtccctcaccaccccgtacaccttctatg
agagcggattacggcgaggaaaacgacgacgacgacgatgatgatgacgacgatgatcgtgatgccggacgctgggt
taggggacctgaaaccacttctgctgtccgtggagcatacccgatcctatggcgagtttgagcctagaccacctg
ccccgaggagacaccaccaccaccaccatcataggcgtagacgtgctcctagacgtcgttctgccgctagtgactct
tccaaatctggctcttcttcatctgcctcttccgcttcatcttcggcctcatcgtcctcttcggcatccgcttcgag
tagtgatgatgatgatgacgacgacgctgctagagccccgcttctgctgccgaccacgctgctggcggaactttgg
gagccgacgacgaggaggcgggagttcctgctcgtgccccgggagctgctccgaggccttctccaccccgtgctgaa
cctgctccggctagaacaccggccgctactgctggtagactggagcgtagacgtgcccgtgctgctgtggctggtag
agatgctactggccgcttcactgctggccgtcctagacgtgttgaactggacgccgatgctgcttctggtgctttct
acgcccgttaccgtgatggttacgtgtctggtgaaccttggcctggcgctggtccacctccgcccggacgtgtactc
tacggtggattgggcgattctcgccctggtctgtggggcgctccggaggctgaggagctagagcccgtttcgaggc
ttctggtgccctgctcctgtttgggaattgggcgacgctgcaacaatacgccctcatcacacgcttgc
tgtacactcccgacgccgaggctatgggatggctccaaaaccctagagttgcccctggtgatgttgctctggatcag
gcttgtttccgtatctccggcgctgctcgtaactcttcttcgttcatctccggttctgtggctagagctgtgcctca
cttgggatacgccatggccgctggacgtttcggctggggactggctcatgttgctgccgctgtagcaatgtctagac
gctacgaccgtgctcaaaaaggattcttgctcacgtcactgaggcgtgcttacgccccttgttggcccgtgaaaac
gctgccctcactggcgccctgctcacccgcgatgacggtggcgacgccaacgcatggtgatgatgctagaggcaa
acccgctgccgctgctgctcctttgccctctgccgccgcttccctgccgatgaacgtgctgttcctgccggttacg
gtgccgctggtgtgttggctgcttttgggacgcttgagtgctgccccggctagtgccccgctggtgccgatgacgat
gacgatgacgatggtgctggcggaggcggtggcggtagacgtgctgaggctggacgtgttgctgttgaatgcctggc
tgcctgtagaggaatcttggaggctctggccgagggattcgacggagacttggcggctgtaccgggactggcggagag
cgaggcctgccgctccacctcgccccggtcctgctggtgctgccgctcctcctcatgccgacgctcctagactccgt

| Sequences |
|---|
| gcttggctccgtgaactccgtttcgttcgtgacgctttggttctgatgagactgagaggcgacttgagagtggctgg
aggatccgaggctgctgttgctgctgtccgtgctgtttctttggttgctggtgctttgggccctgctttgccgagat
ctccccgtttgttgtcgagtgccgccgctgctgccgccgatttgttgttccaaaaccaatccctccgccctctgctc
gccgacactgttgccgctgccgattctctggctgctccggcttctacaccggcaccatctgccgctgctttggaggc
ttactgtgctcctcgtgctgtggctgaactcaccgatcatccgctgttccctgctcctggcgtcccgccctcatgt
tcgatcctagagctttggcttccttggccgctcgttgtgctgcccctcccctggcggtgctccggctgctttcggt
cctctccgtgcctctggtccactccgccgtgccgctgcctggatgagacaagttcccgaccctgaggatgttagagt
tgtgatcttgtactcgcccttgcctggcgaggatttggccgctggtagagcggcggtggcccccctcctgaatggt
ctgctgaacgtggtggtttgtcttgcttgttggccgccctgggaaaccgtctgtggtcctgctactgctgcttgg
gctgaaactggactggcgctcccgatgtttctgctctcggtgctcaaggagtttttgctgctctctactcgtgactt
ggcattcgctggagctgttgaattcctgggactcttggctggcgcttgtgataggagactcatcgtcgtaaacgctg
tgagagctgccgattggcctgccgatggtcctgttgtgtctcgtcaacacgcttacttggcttgtgaagtgttgccc
gctgtccaatgtgctgttcgctggcctgctgctcgtgatctgaggcgtactgttctggctagtggtcgtgttttcgg
acctggtgttttcgctcgtgtcgaagctgctcacgctagactgtaccccgatgccccacccctccgtttgtgtcgtg
gagcaaacgttcgctaccgtgtccgtactcgtttcggacccgatactctggttcaatgtccctcgtgaataccgt
cgtgctgttctgcctgccctcgatggacgtgctgccgcttctgacgctctggtgacgctatggctcctggcgctccgga
cttctgtgaggatgaggctcactcacatcgtgcctgtgcccgctggggactgggcgctccattgaggcctgtatacg
tggcactgggccgtgatgctgttagaggcggaccccgctgaattgagaggccctcgtcgtgaattctgtgctagggct
ctgctcgaacccgatggagatgctcctcctttggtactccgtgacgacgccgatgctggtcctccccacaaattcg
ctgggctagtgctgctggacgtgctggtactgtattggctgctgctggcggtggcgttgaagttgttggtactgccg
ctggactcgctacacctccccgccgtgaacctgtagacatggatgctgaactcgaggatgatgacgacggattgttc
ggagag |

SEQ ID NO: 130 = His tag
HHHHHH

SEQ ID NO: 131 = Tag
MSYYHHHHHH

SEQ ID NO: 132 = Secretion Signal
MKFLVNVALVFMVVYISYIYA

SEQ ID NO: 133 = UL49.5
ATGTCGTACTACCATCACCATCACCATCACATGACGGGGAAACCCGCAAGACTGGGCCGCTGGGTGGTGCTGTTGTT
CGTCGCGCTCGTCGCGGGCGTGCCCGGGGAGCCGCCGAACGCGGCAGGCGCACGCGGCGTTATCGGGGACGCGCAAT
GCCGGGGCGACAGCGCCGGTGTGGTGTCCGTCCCGGGGGTCCTGGTGCCCTTTTATCTAGGCATGACCTCGATGGGC
GTATGTATGATCGCGCACGTGTATCAGATATGCCAGCGGGCACTGGCCGCCGGGTCAGCCTGA

SEQ ID NO: 134 = UL10
ATGGGACGCCGGGCCCCCAGGGGATCCCCCGAGGCCGCGCCGGGCGCCGACGTCGCGCCCGGGGCGCGGGCGGCGTG
GTGGGTCTGGTGTGTGCAGGTGGCGACGTTCATCGTCTCGGCCATCTGCGTCGTGGGGCTCCTGGTGCTGGCCTCTG
TGTTCCGGGACAGGTTTCCCTGCCTTTACGCCCCGCGACCTCTTATGCGAPGGCGAPCGCCACGGTCGAGGTGCGC
GGGGGTGTAGCCGTCCCCCTCCGGTTGGACACGCAGAGCCTGCTGGCCACGTACGCAATTACGTCTACGCTGTTGCT
GGCGGCGGCCGTGTACGCCGCGGTGGGCGCGGTGACCTCGCTACGAGCGCGCGCTGGATGGCCCGTCGCCTGG
CGGCGGCCCGTATGGCGATGCCACACGCCACGCTAATCGCCGGAAACGTCTGCGCGTGCGTGTTGCAGATCACAGTC
CTGCTGCTGGCCCACCGCATCAGCCAGCTGGCCCACCTTATCTACGTCCTGCACTTTGCGTGCCTCGTGTATCTCGC
GGCCCATTTTTGCACCAGGGGGTCCTGAGCGGGACGTACCTGCGTCAGGTTCACGGCCTGATTGACCCGGCGCCGA
CGCACCATCGTATCGTCGGTCCGGTGCGGGCAGTAATGACAAACGCCTTATTACTGGGCACCCTCCTGTGCACGGCC
GCCGCCGCGGTCTCGTTGAACACGATCGCCGCCCTGAACTTCAACTTTTCCGCCCGAGCATGCTCATCTGCCTGAC
GACGCTGTTCGCCCTGCTTGTCGTGTCGCTGTTGTTGGTGGTCGAGGGGGTGCTGTGTCACTACGTGCGCGTGTTGG
TGGGCCCCCACCTCGGGGCCATCGCCGCCACCGGCATCGTCGGCCTGGCCTGCGAGCACTACCACACCGGTGGTTAC
TACGTGGTGGAGCAGCAGTGGCCGGGGGCCCAGACGGGAGTCCGCGTCGCCCTGGCGCTCGTCGCCGCCTTTGCCCT
CGCCATGGCCGTGCTTCGGTGCACGCGCGCCTACCTGTATCACCGGCGACACCACACTAAATTTTTCGTGCGCATGC
GCGACACCCGGCACCGCGCCCATTCGGCGCTTCGACGCGTACGCAGCTCCATGCGCGGTTCTAGGCGTGGCGGGCCG
CCCGGAGACCCGGGCTACGCGAAACCCCCTACGCGAGCGTGTCCCACCACGCCGAGATCGACCGGTATGGGGATTC
CGACGGGGACCCGATCTACGACGAAGTGGCCCCCGACCACGAGGCCGAGCTCTACGCCCGAGTGCAACGCCCCGGGC
CTGTGCCCGACGCCGAGCCCATTTACGACACCGTGGAGGGGTATGCGCCAAGGTCCGCGGGGAGCCGGTGTACAGC
ACCGTTCGGCGATGGTAG

The invention claimed is:

1. An immunogenic composition comprising a pharmaceutically-acceptable carrier, an immunostimulatory amount of an adjuvant and a polypeptide comprising:
   (a) an amino acid sequence having at least 90% identity to SEQ ID NO:2 wherein the polypeptide does not comprise a full length ICP4 polypeptide;
   (b) an amino acid sequence having at least 90% identity to SEQ ID NO:2 and lacking 1-20 amino acids from the N-terminus, C-terminus, or both; or
   (c) an amino acid sequence of SEQ ID NO:2 lacking 1-20 amino acids from the N-terminus, C-terminus, or both.

2. The immunogenic composition of claim 1, further comprising an HSV gD2 polypeptide.

3. The immunogenic composition of claim 1, further comprising an HSV gD2 polypeptide lacking a transmembrane domain.

4. The immunogenic composition of claim 1, further comprising an HSV gD2 polypeptide lacking a transmembrane domain and lacking a cytoplasmic domain.

5. The immunogenic composition of claim 1, further comprising a second polypeptide consisting of the amino acid sequence of SEQ ID NO:3 or SEQ ID NO:4 or SEQ ID NO:5.

6. The immunogenic composition of claim 1, further comprising a second polypeptide consisting of the amino acid sequence of SEQ ID NO:4 or SEQ ID NO:5.

7. The immunogenic composition of claim 1, further comprising a second polypeptide consisting of the amino acid sequence of SEQ ID NO: 4.

8. The immunogenic composition of claim 1, further comprising a second polypeptide consisting of the amino acid sequence of SEQ ID NO:3, and a third polypeptide consisting of the amino acid sequence of SEQ ID NO:4.

9. The immunogenic composition of claim 1, further comprising a second polypeptide consisting of the amino acid sequence of SEQ ID NO:3, and a third polypeptide consisting of the amino acid sequence of SEQ ID NO:5.

10. An immunogenic composition comprising a pharmaceutically-acceptable carrier, an immunostimulatory amount of an adjuvant and a polypeptide comprising an amino acid sequence having at least 90% identity to SEQ ID NO:2, and wherein the polypeptide does not comprise a full length ICP4 polypeptide.

11. An immunogenic composition comprising a pharmaceutically acceptable carrier, an immunostimulatory amount of an adjuvant and a polypeptide comprising an amino acid sequence having at least 90% identity to SEQ ID NO:2 conjugated to an immunogenic carrier, a signal sequence, or a peptide of no more than 20 amino acids at the N-terminus or C-terminus of the polypeptide, and wherein the polypeptide does not comprise a full length ICP4 polypeptide.

12. The immunogenic composition of claim 1, wherein the polypeptide of (b) or (c) comprises the amino acid sequence of SEQ ID NO:2 lacking 1-10 amino acid residues from the N-terminus, C-terminus, or both.

13. The immunogenic composition of claim 1, further comprising a second polypeptide comprising the amino acid sequence of SEQ ID NO:5 lacking all or at least 8 contiguous amino acid residues of residues 340-363 of SEQ ID NO:5.

14. The immunogenic composition of claim 1, further comprising a second polypeptide comprising the amino acid sequence of SEQ ID NO:4 or the amino acid sequence of SEQ ID NO:4 lacking 1-20 amino acids from the N-terminus, C-terminus, or both.

15. The immunogenic composition of claim 1, further comprising a second polypeptide comprising an amino acid sequence having at least 80% identity to SEQ ID NO:4.

16. The immunogenic composition of claim 1, further comprising a second polypeptide comprising the amino acid sequence of SEQ ID NO:5 or the amino acid sequence of SEQ ID NO:5 lacking 1-20 amino acids from the N-terminus, C-terminus, or both.

17. The immunogenic composition of claim 1, further comprising a second polypeptide comprising an amino acid sequence having at least 80% identity to SEQ ID NO:5.

18. The immunogenic composition of claim 7 or 14, wherein at least one polypeptide is unglycosylated.

19. The immunogenic composition of claim 1, further comprising a second polypeptide comprising the amino acid sequence of SEQ ID NO:3 or the amino acid sequence of SEQ ID NO:3 lacking 1-20 amino acid residues from the N-terminus, C-terminus, or both.

20. The immunogenic composition of claim 1, further comprising a second polypeptide comprising an amino acid sequence having at least 85% identity to SEQ ID NO:3.

21. The immunogenic composition of claim 7 or 14, wherein at least one polypeptide is conjugated to an immunogenic carrier.

22. The immunogenic composition of claim 1, wherein the adjuvant is one or more purified fractions of *quillaja* saponins.

23. The immunogenic composition of claim 22, wherein the adjuvant comprises saponin fraction A and saponin fraction C.

24. The immunogenic composition of claim 23, wherein the adjuvant comprises cholesterol, phosphatidyl choline, saponin fraction A and saponin fraction C.

25. The immunogenic composition of claim 24, wherein the adjuvant is in the form of particles.

26. The immunogenic composition of claim 25, wherein particles comprising saponin fraction A are substantially free of saponin fraction C and particles comprising saponin fraction C are substantially free of saponin fraction A.

27. The immunogenic composition of claim 1, wherein the immunogenic composition comprises 5-200 µg of the polypeptide and 5-200 µg of the adjuvant.

28. The immunogenic composition of claim 7 or 14, wherein at least one polypeptide is conjugated to a tag.

29. The immunogenic composition of claim 1, wherein upon administration to a subject, the immunogenic composition inhibits infection by HSV-1, HSV-2, or HSV-1 and HSV-2 in the subject.

30. The immunogenic composition of claim 1, wherein upon administration to a subject, the immunogenic composition treats infection by HSV-2 in the subject.

31. The immunogenic composition of claim 1, wherein upon administration to a subject infected with HSV-2, the immunogenic composition treats herpes in the subject.

32. The immunogenic composition of claim 31, wherein the herpes is genital herpes.

33. The immunogenic composition of claim 1, wherein the immunogenic composition inhibits herpes symptoms in a subject infected with HSV-2.

34. The immunogenic composition of claim 1, wherein the immunogenic composition inhibits onset of herpes symptoms in a subject infected with HSV-2.

35. The immunogenic composition of claim 1, wherein the immunogenic composition reduces severity of herpes symptoms in a subject infected with HSV-2.

36. The immunogenic composition of claim 1, wherein the immunogenic composition reduces recurrence of outbreaks in a subject infected with HSV-2.

37. The immunogenic composition of claim 1, wherein the immunogenic composition reduces the severity of herpetic lesions in a subject infected with HSV-2.

38. The immunogenic composition of claim 1, wherein the immunogenic composition reduces the number of days a subject experiences herpetic lesions in a subject infected with HSV-2.

39. The immunogenic composition of claim 1, wherein the immunogenic composition reduces the frequency of herpes symptoms in a subject infected with HSV-2.

40. The immunogenic composition of claim 1, wherein the immunogenic composition reduces viral shedding in a subject infected with HSV-2.

41. The immunogenic composition of claim 40, wherein the immunogenic composition reduces viral transmission in a subject infected with HSV-2.

42. The immunogenic composition of claim 1, wherein the immunogenic composition increases the IgG titer to one or more HSV-2 antigens in a subject infected with HSV-2.

43. The immunogenic composition of claim 1, wherein the immunogenic composition activates the T cell response to one or more HSV-2 antigens in a subject infected with HSV-2.

44. The immunogenic composition of claim 1, wherein the immunogenic composition increases the T cell response to one or more HSV-2 antigens in a subject infected with HSV-2.

45. The immunogenic composition of claim 30, wherein the immunogenic composition treats infection by HSV-2 in three or fewer doses.

46. A method of treating a subject suffering from or susceptible to HSV-2 infection, comprising administering to the subject an effective amount of the immunogenic composition according to claim 1, thereby treating the subject.

47. The method of claim 46, wherein administering the immunogenic composition treats infection by HSV-2 in the subject.

48. The method of claim 46, wherein administering the immunogenic composition treats herpes in the subject.

49. The method of claim 48, wherein the herpes is genital herpes.

50. The method of claim 46, wherein administering the immunogenic composition inhibits herpes symptoms.

51. The method of claim 46, wherein administering the immunogenic composition inhibits onset of herpes symptoms.

52. The method of claim 46, wherein administering the immunogenic composition reduces severity of herpes symptoms.

53. The method of claim 46, wherein administering the immunogenic composition reduces recurrence of outbreaks in a subject infected with HSV-2.

54. The method of claim 46, wherein administering the immunogenic composition reduces the severity of herpetic lesions.

55. The method of claim 46, wherein administering the immunogenic composition reduces the number of days a subject experiences herpetic lesions.

56. The method of claim 46, wherein the immunogenic composition reduces the frequency of herpes symptoms.

57. The method of claim 46, wherein administering the immunogenic composition reduces viral shedding.

58. The method of claim 57, wherein administering the immunogenic composition reduces viral transmission.

59. The method of claim 46, wherein administering the immunogenic composition inhibits infection by HSV-2 in an uninfected subject.

60. The method of claim 46, wherein administering the immunogenic composition increases the IgG titer to one or more HSV-2 antigens.

61. The method of claim 46, wherein administering the immunogenic composition activates the T cell response to one or more HSV-2 antigens.

62. The method of claim 46, wherein administering the immunogenic composition increases the T cell response to one or more HSV-2 antigens.

63. The method of claim 46, wherein administering the immunogenic composition treats a subject within a three dose regimen.

64. The method of claim 46, wherein administration of the immunogenic composition occurs prior to, concurrent with, or subsequent to treatment with an antiviral molecule.

65. The method of claim 46, wherein the subject is a human.

66. The immunogenic composition of claim 1, wherein the immunogenic composition inhibits re-activation of the virus in a subject infected with HSV-2.

67. The method of claim 46, wherein administering the immunogenic composition inhibits re-activation of the virus.

68. The immunogenic composition of claim 1, wherein the polypeptide consists of the amino acid sequence of SEQ ID NO:2, or consists of an amino acid sequence of SEQ ID NO:2 lacking 1-20 amino acids from the N-terminus, C-terminus, or both.

69. A method of inhibiting infection by HSV-1, HSV-2, or HSV-1 and HSV-2 in a subject, comprising administering to the subject an effective amount of the immunogenic composition according to claim 1, thereby inhibiting infection.

\* \* \* \* \*